United States Patent
Ogiwara et al.

(10) Patent No.: US 11,730,052 B2
(45) Date of Patent: Aug. 15, 2023

(54) LIGHT-EMITTING DEVICE

(71) Applicant: Idemitsu Kosan Co., Ltd., Tokyo (JP)

(72) Inventors: Toshinari Ogiwara, Sodegaura (JP); Yoshikazu Tanaka, Sodegaura (JP); Keiji Okinaka, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 719 days.

(21) Appl. No.: 14/772,633

(22) PCT Filed: Mar. 18, 2014

(86) PCT No.: PCT/JP2014/057350
§ 371 (c)(1),
(2) Date: Sep. 3, 2015

(87) PCT Pub. No.: WO2014/148493
PCT Pub. Date: Sep. 25, 2014

(65) Prior Publication Data
US 2016/0028025 A1    Jan. 28, 2016

(30) Foreign Application Priority Data
Mar. 18, 2013 (JP) ................... 2013-055735

(51) Int. Cl.
*H01L 51/00* (2006.01)
*H01L 51/50* (2006.01)
(Continued)

(52) U.S. Cl.
CPC ......... *H10K 85/342* (2023.02); *C07D 209/86* (2013.01); *C07D 403/14* (2013.01);
(Continued)

(58) Field of Classification Search
None
See application file for complete search history.

(56) References Cited

U.S. PATENT DOCUMENTS

| 6,872,472 B2 | 3/2005 | Liao et al. |
| 7,663,140 B2 | 2/2010 | Yamazaki et al. |
| (Continued) | | |

FOREIGN PATENT DOCUMENTS

| JP | 2004-039617 A | 2/2004 |
| JP | 2007-173200 A | 7/2007 |
| (Continued) | | |

OTHER PUBLICATIONS

Machine English translation of Kim et al. (WO 2011/139055 A2). Aug. 14, 2018.*

(Continued)

*Primary Examiner* — Jay Yang
(74) *Attorney, Agent, or Firm* — Oblon, McClelland, Maier & Neustadt, L.L.P.

(57) ABSTRACT

A light-emitting apparatus includes an organic electroluminescence device, a first color conversion portion that transmits a first color light, and a second color conversion portion that transmits a second color light. The organic electroluminescence device includes an anode, a cathode, and one or more organic layers interposed between the anode and the cathode. At least one of the organic layer(s) is an emitting layer including a host material and a dopant material that emits light including the first color light and the second color light. A difference $\Delta ST(D)$ between singlet energy $EgS(D)$ of the dopant material and an energy gap $Eg_{77K}(D)$ at 77K of the dopant material satisfies Numerical Formula 1 below, $\Delta ST(D)=EgS(D)-Eg77K(D)<0.3$ (eV)    (Numerical Formula 1).

31 Claims, 2 Drawing Sheets

(51) Int. Cl.
| | | |
|---|---|---|
| *H01L 27/32* | (2006.01) | |
| *H10K 85/30* | (2023.01) | |
| *C07D 413/10* | (2006.01) | |
| *C07D 487/04* | (2006.01) | |
| *C09K 11/06* | (2006.01) | |
| *C07D 403/14* | (2006.01) | |
| *C07D 209/86* | (2006.01) | |
| *H10K 50/11* | (2023.01) | |
| *H10K 50/13* | (2023.01) | |
| *H10K 59/38* | (2023.01) | |
| *H10K 85/60* | (2023.01) | |
| *H10K 101/10* | (2023.01) | |
| *H10K 101/40* | (2023.01) | |
| *H10K 101/30* | (2023.01) | |

(52) U.S. Cl.
CPC ......... *C07D 413/10* (2013.01); *C07D 487/04* (2013.01); *C09K 11/06* (2013.01); *H10K 50/11* (2023.02); *H10K 50/13* (2023.02); *H10K 59/38* (2023.02); *H10K 85/649* (2023.02); *C09K 2211/185* (2013.01); *H10K 85/631* (2023.02); *H10K 85/633* (2023.02); *H10K 85/654* (2023.02); *H10K 85/6572* (2023.02); *H10K 85/6574* (2023.02); *H10K 2101/10* (2023.02); *H10K 2101/30* (2023.02); *H10K 2101/40* (2023.02)

(56) References Cited

U.S. PATENT DOCUMENTS

| | | |
|---|---|---|
| 7,965,034 B2 | 6/2011 | Chae et al. |
| 8,076,671 B2 | 12/2011 | Yamazaki et al. |
| 8,088,901 B2 | 1/2012 | Morishita et al. |
| 8,210,890 B2 | 7/2012 | Chae et al. |
| 8,288,013 B2 | 10/2012 | Morishita |
| 8,299,247 B2 | 10/2012 | Morishita |
| 8,481,177 B2 | 7/2013 | Morishita |
| 8,536,569 B2 | 9/2013 | Yamazaki et al. |
| 8,748,015 B2 | 6/2014 | Morishita et al. |
| 8,847,218 B2 | 9/2014 | Nishimura et al. |
| 8,921,837 B2 | 12/2014 | Seo et al. |
| 8,993,129 B2 | 3/2015 | Endo et al. |
| 2005/0029933 A1 | 2/2005 | Liao et al. |
| 2007/0145887 A1 | 6/2007 | Chae et al. |
| 2008/0135858 A1 | 6/2008 | Yamazaki et al. |
| 2008/0157663 A1* | 7/2008 | Sung ................ H01L 51/5234 313/504 |
| 2009/0315022 A1 | 12/2009 | Morishita et al. |
| 2010/0019659 A1 | 1/2010 | Morishita |
| 2010/0140607 A1 | 6/2010 | Yamazaki et al. |
| 2010/0295445 A1 | 11/2010 | Kuma et al. |
| 2011/0207249 A1 | 8/2011 | Chae et al. |
| 2011/0275814 A1 | 11/2011 | Morishita |
| 2011/0284827 A1 | 11/2011 | Morishita et al. |
| 2012/0104940 A1* | 5/2012 | Shin ................ C09K 11/06 313/504 |
| 2012/0205684 A1 | 8/2012 | Yamazaki et al. |
| 2012/0306362 A1 | 12/2012 | Morishita |
| 2013/0153870 A1 | 6/2013 | Seo et al. |
| 2013/0292664 A1 | 11/2013 | Nishimura et al. |
| 2014/0001461 A1 | 1/2014 | Morishita et al. |
| 2015/0041784 A1* | 2/2015 | Shizu ................ C07D 401/10 257/40 |
| 2015/0166886 A1 | 6/2015 | Endo et al. |

FOREIGN PATENT DOCUMENTS

| | | |
|---|---|---|
| JP | 2011-233536 A | 11/2011 |
| JP | 2013-125746 A | 6/2013 |
| WO | WO 2009/011327 A1 | 1/2009 |
| WO | WO 2009/069717 A1 | 6/2009 |
| WO | WO 2010/064655 A1 | 6/2010 |
| WO | WO-2010/114243 A2 * | 10/2010 |
| WO | WO 2010/134352 A1 | 11/2010 |
| WO | WO 2011/070963 A1 | 6/2011 |
| WO | WO-2011/139055 A2 * | 11/2011 |
| WO | WO 2012/099241 A1 | 7/2012 |
| WO | WO 2013/011955 A1 | 1/2013 |
| WO | WO-2013/172255 A1 * | 11/2013 |

OTHER PUBLICATIONS

C. Adachi, "Expression of Highly-Efficient Thermally-Activated Delayed-Fluorescence and Application Thereof to OLED", Organic EL Symposium, proceeding for the tenth meeting held on Jun. 17 (Thurs.) to 18 (Fri.) in 2010 at National Museum of Emerging Science and Innovation (Mirai CAN Hall), pp. 1-4.

Katumi Tokumaru, "Organic Photochemical Reaction Theory", Tokyo Kagaku Dojin Co., Ltd., (1973), pp. 79-82.

International Search Report corresponding to Application No. PCT/JP2014/057350, dated Jun. 3, 2014.

C. Adachi, "Expression of Highly-Efficient Thermally-Activated Delayed-Fluorescence and Application Thereof to OLED", Organic EL Symposium, proceeding for the tenth meeting held on Jun. 17 (Thurs.) to 18 (Fri.) in 2010 at National Museum of Emerging Science and Innovation (Mirai CAN Hall), pp. 11-12, (with English translation).

* cited by examiner

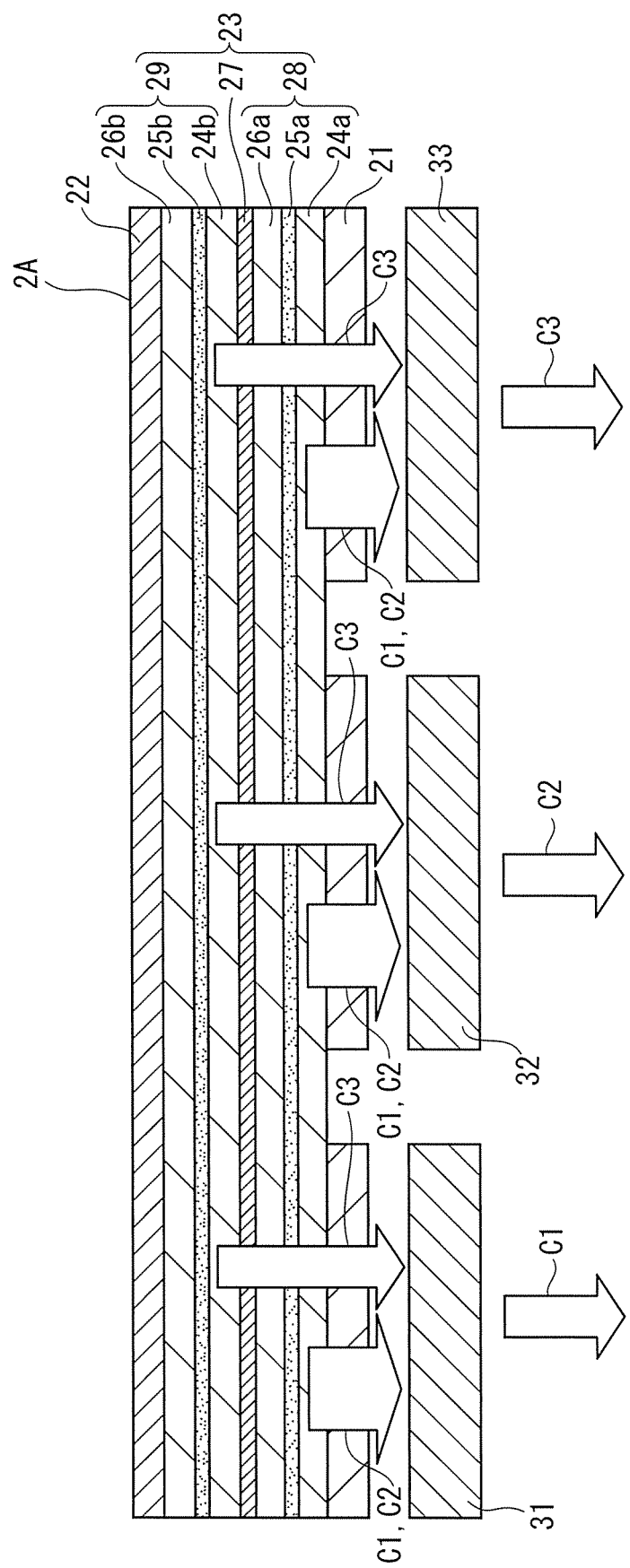

LIGHT-EMITTING DEVICE

TECHNICAL FIELD

The present invention relates to a light-emitting apparatus.

BACKGROUND ART

A liquid crystal display apparatus and the like have been typically used as a light-emitting apparatus used for a display. In recent years, as another light-emitting apparatus, an organic electroluminescent light-emitting apparatus using an organic electroluminescent device (hereinafter, occasionally abbreviated as an "organic EL device") also has been put into practical use. In the organic EL device, a light-emitting unit including an emitting layer is provided between an anode and a cathode and light emission is provided by exciton energy generated by recombination of holes and electrons injected to the emitting layer.

A light-emitting apparatus used for a color display is mainly exemplified by a three-color light-emitting apparatus and a color-filter light-emitting apparatus.

In the three-color light-emitting apparatus, a color display is obtained by forming devices capable of respectively emitting light in three primary colors of red (R), green (G) and blue (B) and controlling a luminous intensity of each of the three colors. However, the three-color light-emitting apparatus requires a high-definition coating using a metal mask when coating, evaporation or the like is performed in order to form emitting layers that emit the respective colors of RGB.

On the other hand, in the color-filter light-emitting apparatus, a white light-emitting device and a color filter are used. White light is converted into three colors of RGB by passing through the color filter. Since the color-filter light-emitting apparatus does not require a high-definition coating, the color-filter light-emitting apparatus can be manufactured more easily than the three-color light-emitting apparatus.

For instance, a light-emitting apparatus disclosed in Patent Literature 1 has an emitting layer between a first anode and a first cathode and another emitting layer between a second anode and a second cathode. The emitting layer between the first anode and the first cathode is provided by laminating a first emitting layer that exhibits emission spectrum having a peak in a blue to blue-green wavelength region and a second emitting layer that exhibits emission spectrum having a peak in a yellow to orange wavelength region. The emitting layer provided between the second anode and the second cathode exhibits emission spectrum having a peak in an orange to red wavelength region. Thus, in the light-emitting apparatus disclosed in Patent Literature 1, three emitting layers exhibiting mutually different emission spectra are laminated to exhibit white emission. The white emission passes through a color filter, whereby RGB light is extracted to the outside.

As a specific method for allowing the emitting layer between the first anode and the first cathode to exhibit the emission spectra having two peaks, Patent Literature 1 only discloses lamination of the emitting layers exhibiting emission spectra having the respective peaks in mutually different wavelength regions. Accordingly, the light-emitting apparatus of Patent Literature 1 is also difficult to manufacture and formation of the emitting layer requires many steps and a large work load.

Moreover, unlike the aforementioned device in which three emitting layers are laminated, Patent Literature 1 also proposes a light-emitting apparatus including: a so-called two-wavelength white emitting device that exhibits a white emission by combining a blue emission and yellow-orange emission; and a color filter.

CITATION LIST

Patent Literature

Patent Literature 1: JP-A-2011-233536

SUMMARY OF THE INVENTION

Problems to be Solved by the Invention

However, since it is difficult to obtain a yellow spectrum having a wide half bandwidth from the two-wavelength white emitting device proposed in Patent Literature 1, a red emission and a green emission needs to be extracted from an outer region away from a peak of a yellow-orange emission spectrum. As a result, the light-emitting apparatus in which the two-wavelength white emitting device is combined with the color filter exhibits a low luminous efficiency.

An object of the invention is to provide a light-emitting apparatus capable of improving a luminous efficiency.

Means for Solving the Problems

According to an aspect of the invention, a light-emitting apparatus includes an organic electroluminescence device, a first color conversion portion that transmits a first color light, and a second color conversion portion that transmits a second color light different from the first color light, in which the organic electroluminescence device includes: an anode; a cathode; and one or more organic layers interposed between the anode and the cathode, at least one of the organic layer(s) is an emitting layer that comprises a host material and a dopant material that emits light comprising the first color light and the second color light, and a difference $\Delta ST(D)$ between singlet energy $EgS(D)$ of the dopant material and an energy gap $Eg_{77K}(D)$ at 77K of the dopant material satisfies a numerical formula (Numerical Formula 1) below, $$\Delta ST(D)=EgS(D)-Eg_{77K}(D)<0.3 \text{ (eV)} \qquad \text{(Numerical Formula 1)}.$$

According to the invention, a light-emitting apparatus capable of improving a luminous efficiency can be provided.

BRIEF DESCRIPTION OF DRAWINGS

FIG. 2 is a cross-sectional view schematically showing an arrangement of a light-emitting device according to a second exemplary embodiment.

DESCRIPTION OF EMBODIMENTS

First Exemplary Embodiment

Figure 1:
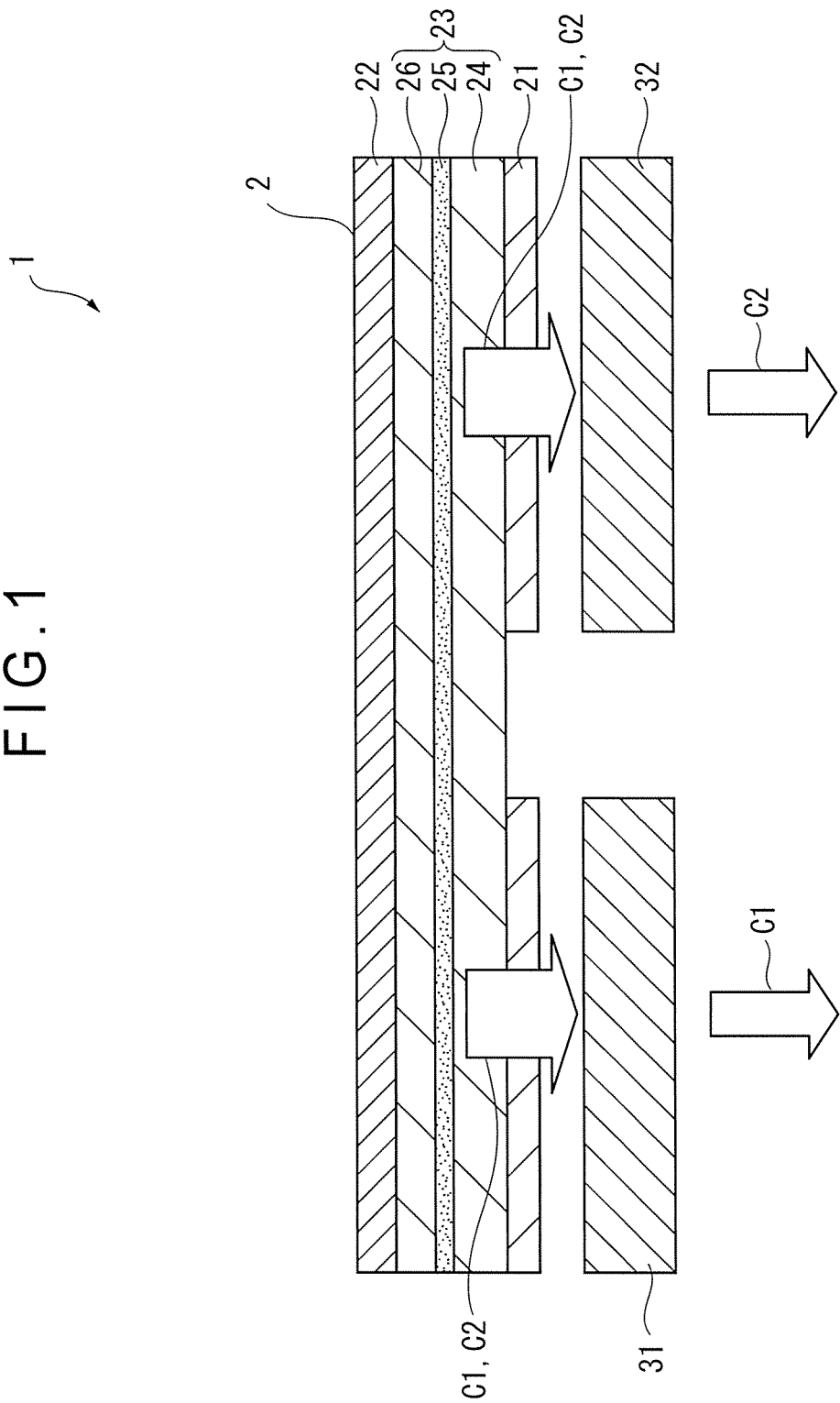
FIG. 1 is a cross-sectional view schematically showing an arrangement of a light-emitting device according to a first exemplary embodiment.

A first exemplary embodiment of the invention will be described below with reference to the drawings.

Arrangement of Light-Emitting Apparatus

FIG. 1 is a cross-sectional view schematically showing an arrangement of a light-emitting device 1 according to the first exemplary embodiment. The light-emitting apparatus 1 includes: an organic EL device 2; a first color conversion portion 31 that transmits a first color light; and a second color conversion portion 32 that transmits a second color light different from the first color light.

Arrangement of Color Conversion Portion

In the first exemplary embodiment, the first color conversion portion 31 and the second color conversion portion 32 are provided near an anode 21 through which light is extracted from the organic EL device 2. In the first exemplary embodiment, light including a first color light C1 and a second color light C2 which are radiated from the emitting layer 25 of the organic EL device 2 is extracted through the anode 21 to pass through the first color conversion portion 31 and the second color conversion portion 32, thereby emitting to the outside of the light-emitting apparatus 1.

The first color conversion portion 31 and the second color conversion portion 32 provide a color converter. The color converter is exemplified by a color filter. The first color conversion portion 31 transmits the first color light C1 and blocks the second color light C2. The second color conversion portion 32 transmits the second color light C2 and blocks the first color light C1. For instance, when light radiated from the emitting layer 25 is a yellow light including a green light and a red light, the first color conversion portion 31 transmits the red light and the second color conversion portion 32 transmits the green light.

In a light-emitting apparatus with the organic EL in which emission from the emitting layer is extracted through an upper electrode, in other words, the emission is extracted toward an opposite from a substrate, a color filter layer is provided on the upper electrode.

The color filter layer may be formed on a sealing film directly provided on the upper electrode. Alternatively, the color filter layer may be formed to a sealing substrate that is provided directly on the upper electrode or is provided on a protective film formed on the upper electrode (see, for instance, JP-A-2007-173200).

In a light-emitting apparatus with the organic EL in which emission from the emitting layer is extracted through a lower electrode, in other words, the emission is extracted through the substrate, the color filter layer is provided underneath the lower electrode.

In this arrangement, the color filter layer may be provided in the substrate on which a thin-film transistor is formed (see, for instance, JP-A-2013-125746), or alternatively, a base material formed with the color filter may be provided to an outside of the substrate.

A typical color filter is used for extracting a white emission produced in the emitting layer in a form of red, green or blue emissions and includes a red filter, a green filter, and a blue filter. The red filter, the green filter, and the blue filter are preferably juxtaposed. The color filter may extract a yellow emission in a form of a red emission or a green emission from components of the white emission. The color filter may also extract a blue-green emission in a form of a blue emission or a green emission. Moreover, in order to enhance visibility, a light shielding member and the like are preferably provided.

A material for the color filter used for the color converter will be described. The material for the color filter is exemplified by the following dyes only and the dyes in a solid state in which the dyes are dissolved or dispersed in a binder resin.

Red (R) Dye

One or a mixture of two or more of a perylene pigment, lake pigment, azo pigment, quinacridone pigment, anthraquinone pigment, anthracene pigment, isoindoline pigment, isoindolinone pigment and the like are usable.

Green (G) Dye

One or a mixture of two or more of a halogen polysubstituted phthalocyanine pigment, halogen polysubstituted copper phthalocyanine pigment, triphenylmethane basic dyes, isoindoline pigment, isoindolinone pigment and the like are usable.

Blue (B) Dye

One or a mixture of two or more of a copper phthalocyanine pigment, indanthrone pigment, indophenol pigment, cyanine pigment, dioxazine pigment and the like are usable.

The binder resin used as the material for the color filter is preferably a transparent material. For instance, a material having light transmittance of 50% or more in a visible light region is preferably used.

Examples of the binder resin used as the material for the color filter include a transparent resin (polymer) such as polymethyl methacrylate, polyacrylate, polycarbonate, polyvinyl alcohol, polyvinyl pyrrolidone, hydroxyethyl cellulose, and carboxymethyl cellulose, among which one or a mixture of two or more are usable.

Arrangement of Organic EL Device

The organic EL device 2 includes: the anode 21; the cathode 22; and an organic layer 23 interposed between the anode 21 and the cathode 22. The organic layer 23 has at least one layer. At least one layer of the organic layer 23 is an emitting layer 25 containing a host material and a dopant material that emits light including the first color light C1 and the second color light C2. In the first exemplary embodiment, preferably, one of the first color light C1 and the second color light C2 is contained in a region ranging from a peak of emission spectrum of the dopant material toward a longer wavelength side of the emission spectrum while the other of the first color light C1 and the second color light C2 is contained in a region ranging from the peak of the emission spectrum of the dopant material toward a shorter wavelength side of the emission spectrum.

Thus, the emitting layer in the first exemplary embodiment is a layer in which a doping system is employed and which is formed of an organic compound including the host material and the dopant material. The host material generally promotes recombination of electrons and holes and transmits exciton energy generated by the recombination to the dopant material. In general, the dopant material receives excitation energy from the host material to exhibit a high emitting performance. The dopant material is preferably a compound having a high quantum yield. The host material and the dopant material will be described in detail later.

In the first exemplary embodiment, the organic layer 23 includes the emitting layer 25, a hole injecting/transporting layer 24 and an electron injecting/transporting layer 26. In the first exemplary embodiment, the hole injecting/transporting layer 24, the emitting layer 25, and the electron injecting/transporting layer 26 are laminated in this order from the anode 21 to provide the organic layer 23. The organic layer 23 is formed of an organic compound, but may further include an inorganic compound.

The hole injecting/transporting (hole injecting•transporting) layer 24 means "at least one of a hole injecting layer and a hole transporting layer" while the electron injecting/transporting (electron injecting•transporting) layer 26 means "at least one of an electron injecting layer and an electron transporting layer."

Herein, when the hole injecting layer and the hole transporting layer are provided, the hole injecting layer is preferably closer to the anode 21. When the electron injecting layer and the electron transporting layer are provided, the electron injecting layer is preferably closer to the cathode 22. Each of the hole injecting layer, hole transporting layer, electron transporting layer and electron injecting layer may be provided by a single layer or a plurality of layers.

Dopant Material

The dopant material contained in the emitting layer 25 has properties below. A difference $\Delta ST(D)$ between singlet energy $EgS(D)$ of the dopant material and an energy gap $Eg_{77K}(D)$ at 77K of the dopant material satisfies a numerical formula (Numerical Formula 1) below, $$\Delta ST(D) = EgS(D) - Eg_{77K}(D) < 0.3 \text{ (eV)} \quad \text{(Numerical Formula 1)}.$$

A compound satisfying Numerical Formula 1 exhibits emission spectrum having a wide half bandwidth. $\Delta ST(D)$ is preferably less than 0.2 eV, more preferably less than 0.15 eV, further preferably less than 0.10 eV.

$\Delta ST$ will be described below.

When a compound having a small energy difference ($\Delta ST$) between the singlet energy $EgS$ and the triplet energy $EgT$ is used as the dopant material, the organic EL device emits at a high efficiency in a high current density region. The above $\Delta ST(D)$ shows $\Delta ST$ of the dopant material.

From quantum chemical viewpoint, a decrease in the energy difference ($\Delta ST$) between the singlet energy $EgS$ and the triplet energy $EgT$ can be achieved by a small exchange interaction therebetween. Physical details of the relationship between $\Delta ST$ and the exchange interaction are described, for instance, in Reference Document 1 and Reference Document 2 below.

Reference Document 1: Organic EL Symposium, proceeding for the tenth meeting edited by Chihaya Adachi et al., S2-5, pp. 11-12

Reference Document 2: Organic Photochemical Reaction Theory edited by Katsumi Tokumaru, Tokyo Kagaku Dojin Co., Ltd. (1973).

Such a material can be synthesized according to molecular design based on quantum calculation. Specifically, the material is a compound in which a LUMO electron orbit and a HOMO electron orbit are localized to avoid overlapping.

Examples of the compound having a small $\Delta ST$ to be used as the dopant material in the first exemplary embodiment are compounds in which a donor element is bonded to an acceptor element in a molecule and $\Delta ST$ is in a range of 0 eV or more and less than 0.3 eV in terms of electrochemical stability (oxidation-reduction stability).

A more preferable compound is such a compound that dipoles formed in the excited state of a molecule interact with each other to form an aggregate having a reduced exchange interaction energy. According to analysis by the inventors, the dipoles are oriented substantially in the same direction in the compound, so that $\Delta ST$ can be further reduced by the interaction of the molecules. In such a case, $\Delta ST$ can be extremely small in a range of 0 eV to 0.2 eV.

TADF Mechanism

When $\Delta ST(D)$ of the organic material is small, inverse intersystem crossing from the triplet energy level of the dopant material to the singlet energy level thereof is easily caused by heat energy given from the outside. An energy state conversion mechanism to perform spin exchange from the triplet state of electrically excited excitons within the organic EL device to the singlet state by inverse intersystem crossing is referred to as TADF (Thermally Activated Delayed Fluorescence) Mechanism.

In the first exemplary embodiment, the compound having $\Delta ST(D)$ satisfying Numerical Formula 1 is used as the dopant material. Accordingly, inverse intersystem crossing from the triplet energy level of the dopant material to the singlet energy level thereof is easily caused by heat energy given from the outside.

Relationship Between EgT and $Eg_{77K}$

The above-described triplet energy EgT is different from a typically defined triplet energy. The difference will be described below.

In general, the triplet energy is obtained by measuring a phosphorescence measurement sample (measurement target) encapsulated in an NMR tube at a low temperature (77K) in terms of phosphorescence spectrum expressed in coordinates of which the ordinate axis indicates the phosphorescence intensity and of which the abscissa axis indicates the wavelength, drawing a tangent to the rise of the phosphorescence spectrum on the shorter wavelength side, and calculating from a predetermined conversion equation based on a wavelength value at an intersection of the tangent and the abscissa axis.

In the first exemplary embodiment, the compound as the dopant material is a compound having $\Delta ST(D)$ satisfying Numerical Formula 1. When $\Delta ST(D)$ is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the first exemplary embodiment, the spectrum is measured by the same method as that for measuring a typical triplet energy, but an amount of the triplet energy measured in the aforementioned manner is referred to as an energy gap $Eg_{77K}$ in order to differentiate the measured energy from a typical triplet energy in a strict meaning. The energy gap $Eg_{77K}$ is the amount of the triplet energy obtained by measuring a phosphorescence measurement sample (measurement target) encapsulated in an NMR tube at a low temperature (77K) in terms of phosphorescence spectrum expressed in coordinates of which the ordinate axis indicates the phosphorescence intensity and of which the abscissa axis indicates the wavelength, drawing a tangent to the rise of the phosphorescence spectrum on the shorter wavelength side, and calculating from a predetermined conversion equation based on a wavelength value at an intersection of the tangent and the abscissa axis. $\Delta ST$ is defined as a difference between the singlet energy $EgS$ and the energy gap $Eg_{77K}$. Accordingly, $\Delta ST(D)$ is represented by Numerical Formula (1) above.

Singlet Energy EgS

In the first exemplary embodiment, the singlet energy EgS is also defined as a value calculated in the same manner as in a typical method. Specifically, a target compound to be measured is deposited on a quartz substrate to prepare a sample. An emission spectrum of the sample is measured at a normal temperature (300K), the spectrum being expressed in coordinates of which the ordinate axis indicates luminous intensity and of which the abscissa axis indicates the wavelength. A tangent is drawn to the rise of the emission spectrum on the short-wavelength side, and a wavelength value at an intersection of the tangent and the abscissa axis is obtained. The singlet energy EgS is calculated from a predetermined conversion equation based on the wavelength value.

The calculation of the singlet energy EgS and the energy gap $Eg_{77K}$ will be described in detail later.

Half Bandwidth

A half bandwidth of the emission spectrum of the dopant material is preferably 60 nm or more, more preferably 70 nm or more, further preferably 80 nm or more.

The dopant material in the first exemplary embodiment only needs to be a compound satisfying Numerical Formula 1 and is preferably a compound represented by a formula (1) below. However, the dopant material is not limited to the compound represented by the formula (1) below.

[Formula 1]

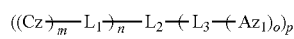
(1)

In the formula (1), Cz is the group derived from the structure represented by the formula (10) below.

[Formula 2]

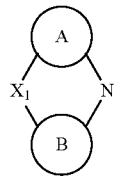
(10)

In the formula (10), $X_1$ represents a single bond, an oxygen atom, a sulfur atom, a carbonyl group, $NR_1$, $CR_2R_3$, $SiR_4R_5$ or $GeR_6R_7$. In other words, the cyclic structure represented by the formula (10) is a cyclic structure selected from the group consisting of cyclic structures represented by formulae (10b) to (10i) below.

[Formula 3]

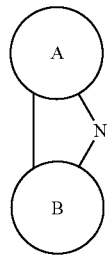
(10b)

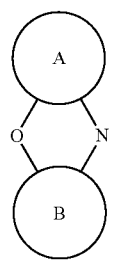
(10c)

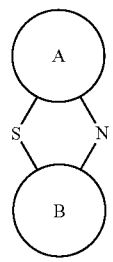
(10d)

(10e)

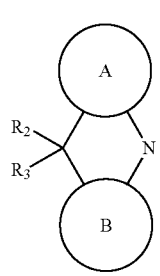

(10f)

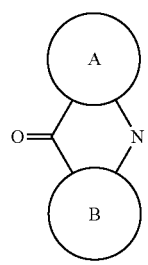

(10g)

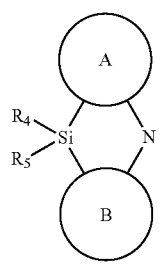

(10h)

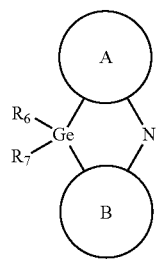

(10i)

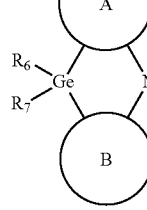

In the formulae (10) and (10b) to (10i), A and B each independently represent a substituted or unsubstituted cyclic structure. When at least one of the cyclic structure A and the cyclic structure B has a plurality of substituents, adjacent ones of the substituents may form a ring. The ring to be formed may be either a saturated ring or an unsaturated ring.

The substituents in at least one of the cyclic structure A and the cyclic structure B are preferably an electron-donating substituent. Moreover, adjacent substituents preferably further form an electron-donating ring.

When at least one of the cyclic structure A and the cyclic structure B has a substituted or unsubstituted heterocyclic structure in the formulae (10) and (10b) to (10i), the heterocyclic structure has a partial structure represented by a formula (11) below.

[Formula 4]

(11)

The group derived from the structure represented by the formula (10) is preferably a group represented by a formula (10-1) below.

[Formula 5]

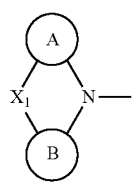
(10-1)

In the formula (10-1), $X_1$ represents the same as $X_1$ of the formula (10). In other words, the group represented by the formula (10-1) is a group selected from the group consisting of groups represented by formulae (10b-1) to (10i-1) below.

[Formula 6]

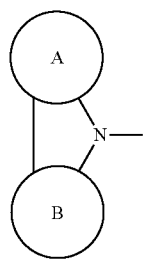
(10b-1)

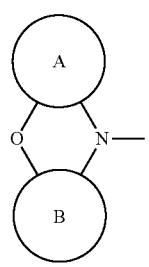
(10c-1)

-continued

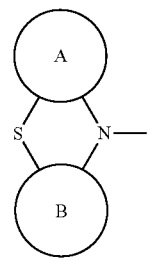
(10d-1)

(10e-1)

(10f-1)

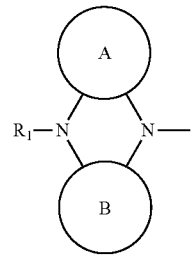

(10g-1)

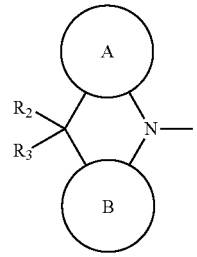

(10h-1)

(10i-1)

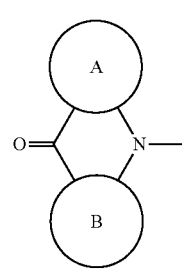

In the formulae (10b-1) to (10i-1), the cyclic structure A and the cyclic structure B respectively independently represent the same as the cyclic structure A and the cyclic structure B in the formulae (10) and (10b) to (10i).

In the formula (1), $L_1$ represents a single bond, a substituted or unsubstituted (m+1)-valent aromatic hydrocarbon group or a substituted or unsubstituted (m+1)-valent heterocyclic group.

$L_2$ represents a single bond, a substituted or unsubstituted (n+p)-valent aromatic hydrocarbon group or a substituted or unsubstituted (n+p)-valent heterocyclic group.

$L_3$ represents a single bond, a substituted or unsubstituted (o+1)-valent aromatic hydrocarbon group or a substituted or unsubstituted (o+1)-valent heterocyclic group;

In the formula (1), $L_1$, $L_2$ and $L_3$ are preferably a single bond. This is because a compound in which $Az_1$ is directly bonded to Cz by a single bond without a linking group tends to have a wider half bandwidth of the emission spectrum than that of a compound in which $Az_1$ is bonded to Cz through a linking group.

In the formula (1), m, n, o and p are each independently an integer of 1 to 6. m, n, o and p are each independently an integer of 1 to 3, more preferably 1 or 2.

When m is 2 or more, a plurality of Cz may be the same or different. When o is 2 or more, a plurality of $Az_1$ may be the same or different. When n is 2 or more, a plurality of moieties represented by $(Cz)_m$-$L_1$-in the formula (1) may be the same or different. When p is 2 or more, a plurality of moieties represented by -$L_3$-$(Az_1)_o$ may be the same or different.

In the first exemplary embodiment, $L_1$ is a linking group of which a valence is determined depending on a value of m. When m is 1, $L_1$ is a divalent linking group. $L_2$ is a linking group of which a valence is determined depending on values of n and p. When both n and p are 1, $L_2$ is a divalent linking group. The same applies to the following linking groups such as $L_3$.

In the formula (1), $Az_1$ is represented by a formula (12) below.

[Formula 7]

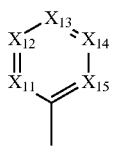

(12)

In the formula (12), $X_{11}$ to $X_{15}$ each independently represent $CR_8$ or a nitrogen atom and at least one of $X_{11}$ to $X_{15}$ is a nitrogen atom. In the formula (12), one to three of $X_{11}$ to $X_{15}$ are preferably nitrogen atom(s). A plurality of $R_8$ may be mutually the same or different. Moreover, in the formula (12), adjacent ones of $R_8$ may be mutually bonded to form a ring.

When one nitrogen atom is present, $X_{11}$ or $X_{15}$ is preferably a nitrogen atom. When two nitrogen atoms are present, $X_{11}$ and $X_{15}$ are preferably nitrogen atoms. When three nitrogen atoms are present, $X_{11}$, $X_{13}$ and $X_{15}$ are preferably nitrogen atoms. Among the above arrangements, a triazine ring in which $X_{11}$, $X_{13}$ and $X_{15}$ are nitrogen atoms is more preferable in the formula (12).

In the formula (12), $X_{11}$ to $X_{15}$ each independently represent $CR_8$ or C-$L_{12}$-CN and at least one of $X_{11}$ to $X_{15}$ may be C-$L_{12}$-CN. A plurality of $R_8$ may be mutually the same or different. Moreover, in the formula (12), adjacent ones of $R_8$ may be mutually bonded to form a ring. $L_{12}$ represents a single bond, a substituted or unsubstituted divalent aromatic hydrocarbon group, or a substituted or unsubstituted divalent heterocyclic group. CN represents a cyano group.

In the formula (1), two or more structures selected from the group consisting of Cz, $L_1$, $L_2$, $L_3$ and $Az_1$ may be mutually bonded to form a ring.

When at least two of $L_1$, $L_2$ and $L_3$ are linking groups, a combination of the linking groups, a combination of substituents of the linking groups and a combination of a substituent of the linking group and a linking group adjacent to the substituent may be bonded to form a ring.

In the formula (1), when $L_1$ is a linking group, a substituent of $L_1$ may be bonded to a substituent of at least one of the cyclic structure A and the cyclic structure B to form a ring, $L_1$ may be bonded to a substituent of at least one of the cyclic structure A and the cyclic structure B to form a ring, or a substituent of $L_1$ may be bonded to at least one of the cyclic structure A and the cyclic structure B to form a ring.

In the formula (1), when $L_1$ is a single bond and $L_2$ is a linking group and when both of $L_1$ and $L_2$ are single bonds and $L_3$ is a linking group, a ring may be formed in the same manner as the above instance where $L_1$ is a linking group.

In the formulae (1) and (10), at least one of $R_1$ to $R_7$ in $X_1$ may be bonded to at least one of the cyclic structure A and the cyclic structure B to form a ring, or at least one of $R_1$ to $R_7$ in $X_1$ may be bonded to at least one of the substituents of the cyclic structure A and the cyclic structure B to form a ring.

In the formula (1), when $L_3$ is a linking group, a substituent of $L_3$ may be bonded to $R_8$ of $CR_8$ in $X_{11}$ to $X_{15}$ to form a ring, $L_3$ may be bonded to $R_8$ to form a ring, or a substituent of $L_3$ may be bonded to a carbon atom C in $X_{11}$ to $X_{15}$ to form a ring.

In the formula (1), when $L_3$ is a single bond and $L_2$ is a linking group and when both of $L_2$ and $L_3$ are single bonds and $L_1$ is a linking group, a ring may be formed in the same manner as the above instance where $L_3$ is a linking group.

The same applies to the following instances where a combination of adjacent substituents, a combination of substituents of adjacent cyclic structures, a combination of substituents of the linking group and the cyclic structure, and the like are mutually bonded to form a ring.

In the formulae (1) and (10) to (12), $R_1$ to $R_8$ are each independently a hydrogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, or a substituted or unsubstituted arylthio group having 6 to 30 ring carbon atoms.

In the first exemplary embodiment, the compound represented by the formula (1) is preferably a compound represented by a formula (13) below.

[Formula 8]

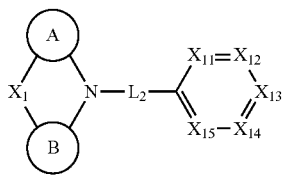

(13)

In the formula (13), $X_1$, a cyclic structure A and a cyclic structure B respectively represent the same as $X_1$, the cyclic structure A and the cyclic structure B of the formula (10).

In the formula (13), $L_2$ represents the same as $L_2$ of the formula (1).

In the formula (13), $X_{11}$ to $X_{15}$ each independently represent the same as $X_{11}$ to $X_{15}$ of the formula (12).

Among the compound represented by the formula (13), compounds represented by formulae (13a) to (13c) below are preferable and the compound represented by the formula (13c) is more preferable.

[Formula 9]

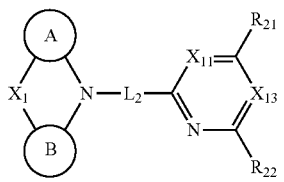

(13a)

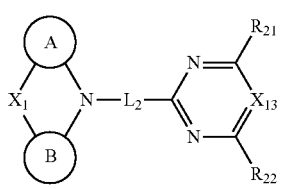

(13b)

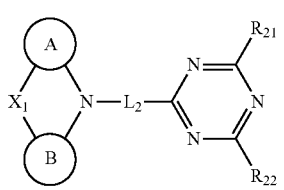

(13c)

In the formulae (13a) to (13c), $X_1$, a cyclic structure A and a cyclic structure B respectively represent the same as $X_1$, the cyclic structure A and the cyclic structure B of the formula (10).

In the formulae (13a) to (13c), $L_2$ represents the same as $L_2$ of the formula (1).

$X_{11}$ and $X_{13}$ of the formula (13a) and $X_{13}$ of the formula (13b) each independently represent the same as $X_{11}$ to $X_{15}$ of the formula (12).

In the formulae (13a) to (13c), $R_{21}$ and $R_{22}$ each independently represent the same as $R_1$ to $R_8$ described above.

In the formulae (1), (10), (10b) to (10i), (10b-1) to (10i-1), (10-1), (13) and (13a) to (13c), at least one of the cyclic structure A and the cyclic structure B preferably has at least one substituent selected from the group consisting of a substituted or unsubstituted aryl group having 6 to 30 ring carbon atoms, a substituted or unsubstituted heterocyclic group having 5 to 30 ring atoms, and a substituted or unsubstituted amino group, more preferably has at least one substituent selected from the group consisting of a substituted or unsubstituted heterocyclic group having 5 to 30 ring atoms and a substituted or unsubstituted amino group.

In the first exemplary embodiment, the compound represented by the formula (1) is preferably a compound represented by a formula (100) below.

[Formula 10]

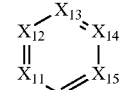

(100)

In the formula (100), $L_2$, a cyclic structure A, a cyclic structure B, $X_1$ and $X_{11}$ to $X_{15}$ respectively represent the same as $L_2$, the cyclic structure A, the cyclic structure B, $X_1$ and $X_{11}$ to $X_{15}$ of the formulae (1), (10) and (12).

In the formula (100), $R_{51}$ to $R_{54}$ each independently represent the same as $R_1$ to $R_8$ described above. $R_{51}$ and $R_{52}$ may be mutually bonded to form a ring. $R_{53}$ and $R_{54}$ may be mutually bonded to form a ring. In the formula (100), $R_{51}$ to $R_{54}$ are preferably each independently a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

In the formula (100), y and z are each independently an integer of 1 to 4. When y and z are an integer of 2 or more, an amino group to be bonded to the cyclic structure A may be mutually the same or different and an amino group to be bonded to the cyclic structure B may also be mutually the same or different.

In the formula (100), a nitrogen atom bonded with $R_{51}$ and $R_{52}$ is further bonded to an atom forming the cyclic structure B and a nitrogen atom bonded with $R_{53}$ and $R_{54}$ is further bonded to an atom forming the cyclic structure A.

In the compound represented by the formula (100), it is preferable that $R_{51}$ and $R_{52}$ are mutually bonded to form a ring and $R_{53}$ and $R_{54}$ are mutually bonded to form a ring. In this arrangement, a compound represented by a formula (101) below is preferable among the compound represented by the formula (100).

[Formula 11]

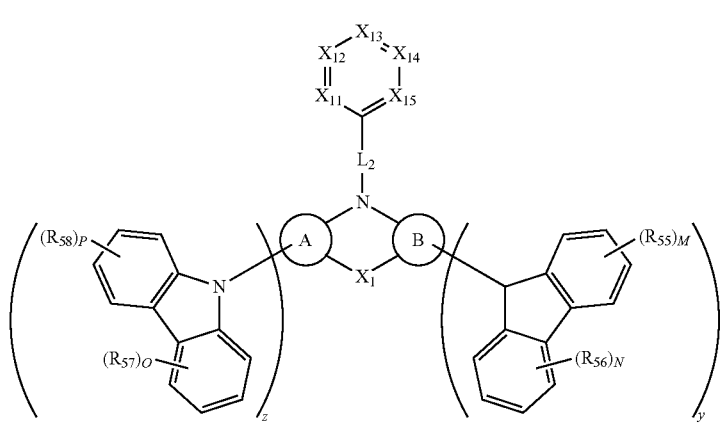

(101)

In the formula (101), $L_2$, a cyclic structure A, a cyclic structure B, $X_1$ and $X_{11}$ to $X_{15}$ respectively represent the same as $L_2$, the cyclic structure A, the cyclic structure B, $X_1$ and $X_{11}$ to $X_{15}$ of the formulae (1), (10) and (12).

In the formula (101), $R_{55}$ to $R_58$ each independently represent the same as $R_1$ to $R_8$ described above. Adjacent ones of $R_{55}$ may be mutually bonded to form a ring, adjacent ones of $R_{56}$ may be mutually bonded to form a ring, adjacent ones of $R_{57}$ may be mutually bonded to form a ring, and adjacent ones of $R_{58}$ may be mutually bonded to form a ring. $R_{55}$ to $R_{58}$ are respectively bonded to carbon atoms forming the six-membered ring of a carbazole ring.

In the formula (101), M, N, O and P are 4.

In the formula (101), an N-carbozolyl group is bonded to an atom forming the cyclic structure A or the cyclic structure B.

In the formula (101), y and z are each independently an integer of 1 to 4. When y and z are an integer of 2 or more, the N-carbozolyl group to be bonded to the cyclic structure A may be mutually the same or different and the N-carbozolyl group to be bonded to the cyclic structure B may also be mutually the same or different.

In the formula (101), y and z are preferably 1. In this arrangement, the compound represented by the formula (101) is represented by a formula (102) below.

[Formula 12]

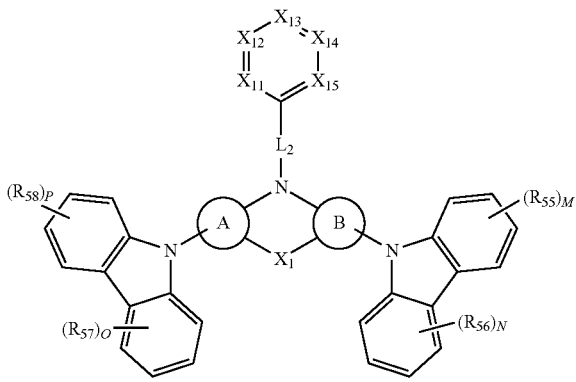

(102)

In the formula (102), $L_2$, a cyclic structure A, a cyclic structure B, $X_1$, $X_{11}$ to $X_{15}$, $R_{55}$ to $R_{58}$, M, N, O and P respectively represent the same as $L_2$, the cyclic structure A, the cyclic structure B, $X_1$, $X_{11}$ to $X_{15}$, $R_{55}$ to $R_{58}$, M, N, O and P of the formulae (101).

In the first exemplary embodiment, the compound represented by the formula (100) is preferably a compound represented by a formula (103) below.

[Formula 13]

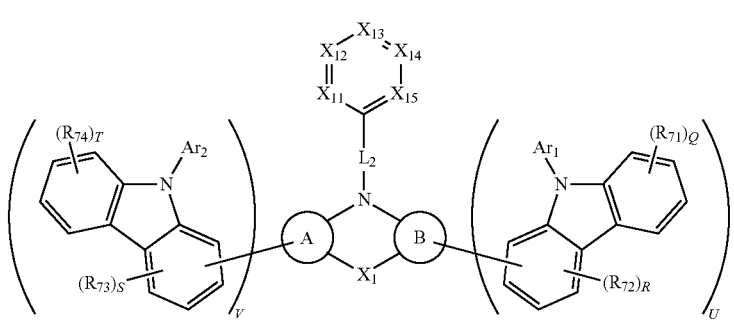

(103)

In the formula (103), $L_2$, a cyclic structure A, a cyclic structure B, $X_1$ and $X_{11}$ to $X_{15}$ respectively represent the same as $L_2$, the cyclic structure A, the cyclic structure B, $X_1$ and $X_{11}$ to $X_{15}$ of the formulae (1), (10) and (12).

In the formula (103), $R_{71}$ to $R_{74}$ each independently represent the same as $R_1$ to $R_8$ described above. Adjacent ones of $R_{71}$ may be mutually bonded to form a ring, adjacent ones of $R_{72}$ may be mutually bonded to form a ring, adjacent ones of $R_{73}$ may be mutually bonded to form a ring, and adjacent ones of $R_{74}$ may be mutually bonded to form a ring. $R_{71}$ to $R_{74}$ are respectively bonded to carbon atoms forming the six-membered ring of a carbazole ring.

In the formula (103), Q and T are 4 and R and S are 3.

In the formula (103), $Ar_1$ and $Ar_2$ each independently represent a substituted or unsubstituted aryl group having 6 to 30 ring carbon atoms or a substituted or unsubstituted heterocyclic group having 5 to 30 ring atoms. However, when $Ar_1$ is a substituted or unsubstituted six-membered nitrogen-containing heterocyclic group, the nitrogen-containing heterocyclic group may directly be bonded by a single bond to a nitrogen atom at a position 9 of the carbazole ring substituted with $R_{71}$ and $R_{72}$, or alternatively, may be bonded thereto through a linking group. The linking group provided between $Ar_1$ and the nitrogen atom at the position 9 of the carbazole ring substituted with $R_{71}$ and $R_{72}$ represents the same as $L_2$ of the formula (1). The same applies to bonding between $Ar_2$ and the carbazole ring. $Ar_1$ and $Ar_2$ are preferably a substituted or unsubstituted aryl group having 6 to 30 ring carbon atoms. Specific examples of $Ar_1$ and $Ar_2$ include a phenyl group, biphenyl group, terphenyl group, naphthyl group, phenanthryl group, triphenylyl group, dibenzofuranyl group, dibenzothiophenyl group and carbazolyl group.

In the formula (103), one of carbon atoms of the six-membered rings forming the carbazole ring substituted with $R_{71}$ and $R_{72}$ is bonded to an atom forming the cyclic structure B and one of carbon atoms of the six-membered rings forming the carbazole ring substituted with $R_{73}$ and $R_{74}$ is bonded to an atom forming the cyclic structure A.

In the formula (103), U and V are each independently an integer of 1 to 4. When U and V are an integer of 2 or more, the carbazolyl group to be bonded to the cyclic structure A may be mutually the same or different and the carbazolyl group to be bonded to the cyclic structure B may also be mutually the same or different.

In the formula (103), U and V are preferably 1.

In the first exemplary embodiment, the compound represented by the formula (1) is preferably a compound represented by a formula (104) below.

[Formula 14]

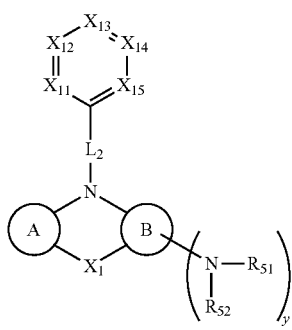

(104)

In the formula (104), $L_2$, a cyclic structure A, a cyclic structure B, $X_1$ and $X_{11}$ to $X_{15}$ respectively represent the same as $L_2$, the cyclic structure A, the cyclic structure B, $X_1$ and $X_{11}$ to $X_{15}$ of the formulae (1), (10) and (12).

In the formula (104), $R_{51}$ and $R_{52}$ each independently represent the same as $R_1$ to $R_8$ described above. $R_{51}$ and $R_{52}$ may be mutually bonded to form a ring.

In the formula (104), y is an integer of 1 to 4. In the formula (104), when y is an integer of 2 or more, an amino group to be bonded to the cyclic structure B may be mutually the same or different.

In the formula (104), a nitrogen atom bonded with $R_{51}$ and $R_{52}$ is bonded to an atom forming the cyclic structure B.

In the compound represented by the formula (104), it is preferable that $R_{51}$ and $R_{52}$ are mutually bonded to form a ring. In this arrangement, a compound represented by a formula (105) below is preferable among the compound represented by the formula (104).

[Formula 15]

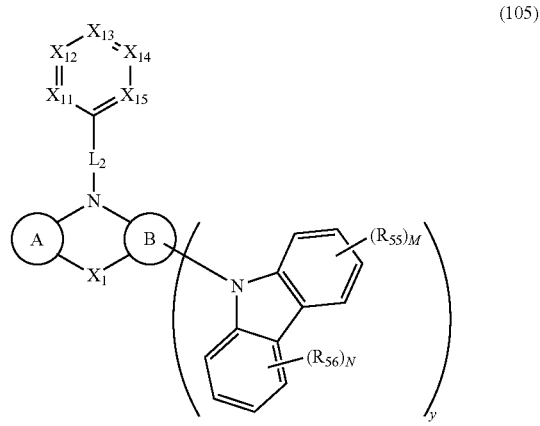

(105)

In the formula (105), $L_2$, a cyclic structure A, a cyclic structure B, $X_1$ and $X_{11}$ to $X_{15}$ respectively represent the same as $L_2$, the cyclic structure A, the cyclic structure B, $X_1$ and $X_{11}$ to $X_{15}$ of the formulae (1), (10) and (12).

In the formula (105), $R_{55}$ and $R_{56}$ each independently represent the same as $R_1$ to $R_8$ described above. Adjacent ones of $R_{55}$ may be mutually bonded to form a ring and adjacent ones of $R_{56}$ may be mutually bonded to form a ring. $R_{55}$ and $R_{56}$ are respectively bonded to carbon atoms forming the six-membered ring of a carbazole ring.

In the formula (105), M and N are 4.

In the formula (105), an N-carbozolyl group is bonded to an atom forming the cyclic structure B.

In the formula (105), y is an integer of 1 to 4. When y is an integer of 2 or more, the N-carbozolyl group to be bonded to the cyclic structure B may be mutually the same or different.

In the formula (105), y is preferably 1. In this arrangement, the compound represented by the formula (105) is represented by a formula (106) below.

[Formula 16]

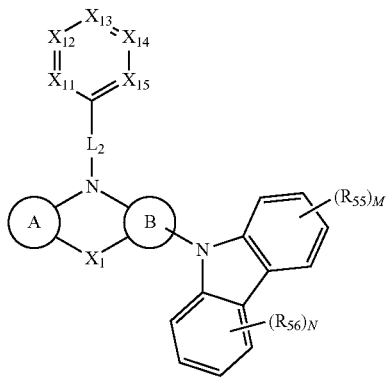

(106)

In the formula (106), $L_2$, a cyclic structure A, a cyclic structure B, $X_1$, $X_{11}$ to $X_{15}$, $R_{55}$, $R_{56}$, M and N respectively represent the same as $L_2$, the cyclic structure A, the cyclic structure B, $X_1$, $X_{11}$ to $X_{15}$, $R_{55}$, $R_{56}$, M and N of the formulae (105).

In the first exemplary embodiment, the compound represented by the formula (1) is preferably a compound represented by a formula (107) below.

[Formula 17]

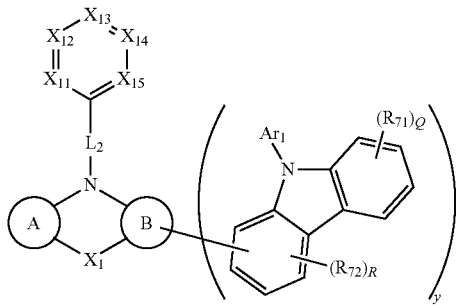

(107)

In the formula (107), $L_2$, a cyclic structure A, a cyclic structure B, $X_1$ and $X_{11}$ to $X_{15}$ respectively represent the same as $L_2$, the cyclic structure A, the cyclic structure B, $X_1$ and $X_{11}$ to $X_{15}$ of the formulae (1), (10) and (12).

In the formula (107), $R_{71}$ and $R_{72}$ each independently represent the same as $R_1$ to $R_8$ described above. Adjacent ones of $R_{71}$ may be mutually bonded to form a ring and adjacent ones of $R_{72}$ may be mutually bonded to form a ring. $R_{71}$ and $R_{72}$ are respectively bonded to carbon atoms forming the six-membered ring of a carbazole ring.

In the formula (107), Q is 4 and R is 3.

In the formula (107), $Ar_1$ represents the same as $Ar_1$ of the formula (103).

In the formula (107), one of carbon atoms of the six-membered ring forming the carbazole group substituted with $R_{71}$ and $R_{72}$ is bonded to an atom forming the cyclic structure B.

In the formula (107), y is an integer of 1 to 4. When y is an integer of 2 or more, the carbozolyl group to be bonded to the cyclic structure B may be mutually the same or different.

In the formulae (1), (10), (10b) to (10i), (10b-1) to (10i-1), (10-1), (13), (13a) to (13c) and (101) to (107), examples of the cyclic structure A and the cyclic structure B include a saturated or unsaturated five-membered ring and a saturated or unsaturated six-membered ring, among which a benzene ring or an azine ring (unsaturated six-membered ring) is preferable and the benzene ring is more preferable.

In the first exemplary embodiment, Cz of the formula (1) is preferably represented by the formula (10b). Further, both of the cyclic structure A and the cyclic structure B are preferably a substituted or unsubstituted benzene ring. The substituent in this arrangement is the same as described above.

In the formula (10b), when at least one of the cyclic structure A and the cyclic structure B is a heterocycle, the heterocycle preferably has the partial structure represented by the formula (11), specifically, the cyclic structure A and the cyclic structure B in the formula (10b) are preferably a six-membered heterocycle having the partial structure represented by the formula (11).

In the first exemplary embodiment, the compound represented by the formula (1) is preferably a compound represented by a formula (14) below.

[Formula 18]

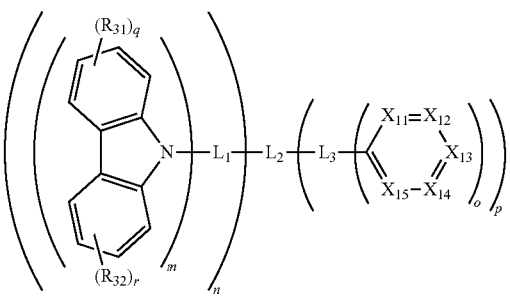

(14)

In the formula (14), $L_1$, $L_2$, $L_3$, m, n, o and p respectively represent the same as $L_1$, $L_2$, $L_3$, m, n, o and p of the formula (1). In the formula (14), $L_1$, $L_2$ and $L_3$ are preferably a single bond.

In the formula (14), $X_{11}$ to $X_{15}$ each independently represent the same as $X_{11}$ to $X_{15}$ of the formula (12).

In the formula (14), $R_{31}$ and $R_{32}$ each independently represent the same as $R_1$ to $R_8$ described above. $R_{31}$ to $R_{32}$ are respectively bonded to carbon atoms forming the six-membered ring of a carbazole ring. Adjacent ones of $R_{31}$ may be mutually bonded to form a ring and adjacent ones of $R_{32}$ may be mutually bonded to form a ring. Alternatively, $R_{31}$ or a substituent thereof may be bonded to at least one of $L_1$, $L_2$ and $L_3$ or a substituent thereof to form a ring in the same manner as the above. $R_{32}$ or a substituent thereof may be bonded to at least one of $L_1$, $L_2$ and $L_3$ or a substituent thereof to form a ring in the same manner as the above.

In the formula (14), q and r are 4.

In the first exemplary embodiment, the compound represented by the formula (1) is preferably a compound represented by a formula (15) below. Specifically, in the compound represented by the formula (14), $L_1$ and $L_3$ are preferably a single bond and n, o and p are preferably 1.

[Formula 19]

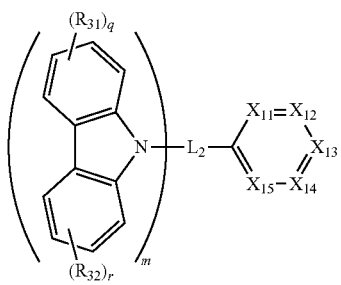

(15)

In the formula (15), $L_2$ and m respectively represents the same as $L_2$ and m of the formula (1).

In the formula (15), $X_{11}$ to $X_{15}$ each independently represent the same as $X_{11}$ to $X_{15}$ of the formula (12).

In the formula (15), $R_{31}$ and $R_{32}$ each independently represent the same as $R_1$ to $R_8$ described above. Adjacent ones of $R_{31}$ may be mutually bonded to form a ring and adjacent ones of $R_{32}$ may be mutually bonded to form a ring.

In the formula (15), q and r are 4.

In the formula (15), $R_{31}$ to $R_{32}$ are respectively bonded to carbon atoms forming the six-membered ring of a carbazole ring.

In the first exemplary embodiment, the compound represented by the formula (15) is preferably a compound represented by a formula (16) below.

[Formula 20]

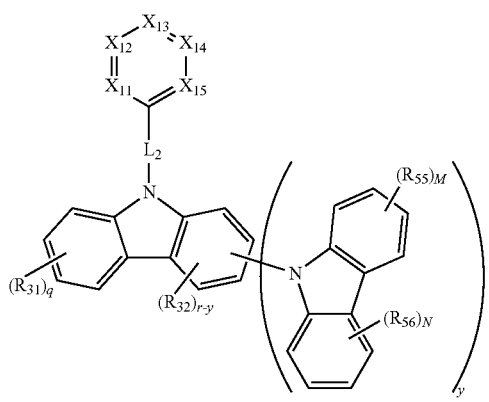

(16)

In the formula (16), $L_2$ represents the same as $L_2$ of the formula (1).

In the formula (16), $X_{11}$ to $X_{15}$ represent the same as $X_{11}$ to $X_{15}$ of the formula (12).

In the formula (16), $R_{31}$, $R_{32}$, $R_{55}$ and $R_{56}$ each independently represent the same as $R_1$ to $R_8$ described above. Adjacent ones of $R_{31}$ may be mutually bonded to form a ring, adjacent ones of $R_{32}$ may be mutually bonded to form a ring, adjacent ones of $R_{55}$ may be mutually bonded to form a ring, and adjacent ones of $R_{56}$ may be mutually bonded to form a ring. $R_{31}$, $R_{32}$, $R_{55}$ and $R_{56}$ are respectively bonded to carbon atoms forming the six-membered ring of a carbazole ring.

In the formula (16), M and N are 4.

In the formula (16), q and r are 4 and y is an integer of 1 to 3. When y is an integer of 2 or more, a plurality of N-carbozolyl groups substituted with $R_{55}$ and $R_{56}$ may be mutually the same or different.

In the formula (16), a nitrogen atom of the N-carbozolyl group substituted with $R_{55}$ and $R_{56}$ is bonded to one of carbon atoms forming a six-membered ring substituted with $R_{32}$.

In the first exemplary embodiment, y is preferably 1 in the formula (16). In this arrangement, the compound represented by the formula (16) is preferably a compound represented by a formula (17) below, more preferably a compound represented by a formula (18) below.

[Formula 21]

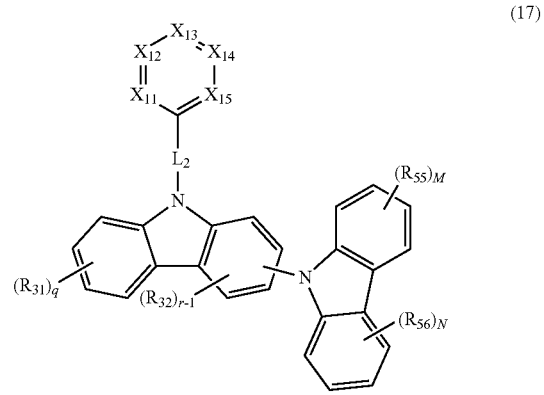

(17)

In the formula (17), $L_2$, $X_{11}$ to $X_{15}$, $R_{31}$, $R_{32}$, $R_{55}$, $R_{56}$, M, N, q and r represent the same as $L_2$, $X_{11}$ to $X_{15}$, $R_{31}$, $R_{32}$, $R_{55}$, $R_{56}$, M, N, q and r in the formula (16).

[Formula 22]

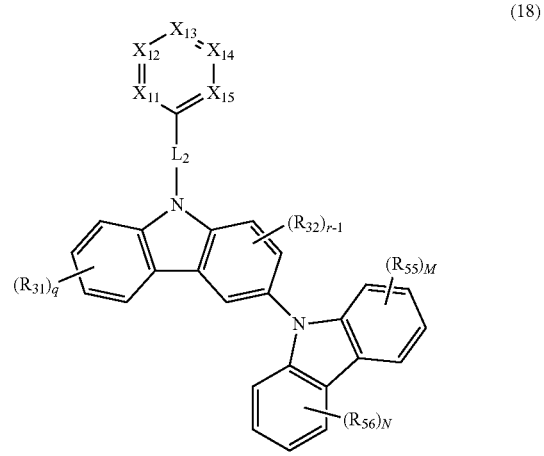

(18)

In the formula (18), $L_2$, $X_{11}$ to $X_{15}$, $R_{31}$, $R_{32}$, $R_{55}$, $R_{56}$, M, N, q and r represent the same as $L_2$, $X_{11}$ to $X_{15}$, $R_{31}$, $R_{32}$, $R_{55}$, $R_{56}$, M, N, q and r in the formula (16).

In the first exemplary embodiment, the compound represented by the formula (14) is preferably a compound represented by a formula (19) below.

[Formula 23]

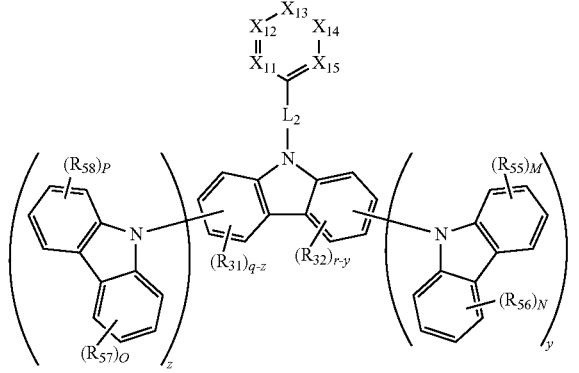

(19)

In the formula (19), $L_2$ represents the same as $L_2$ of the formula (1).

In the formula (19), $X_{11}$ to $X_{15}$ represent the same as $X_{11}$ to $X_{15}$ of the formula (12).

In the formula (19), $R_{31}$, $R_{32}$ and $R_{55}$ to $R_{58}$ each independently represent the same as $R_1$ to $R_8$ described above. Adjacent ones of $R_{31}$ may be mutually bonded to form a ring, adjacent ones of $R_{32}$ may be mutually bonded to form a ring, adjacent ones of $R_{55}$ may be mutually bonded to form a ring, adjacent ones of $R_{56}$ may be mutually bonded to form a ring, adjacent ones of $R_{57}$ may be mutually bonded to form a ring, and adjacent ones of $R_{58}$ may be mutually bonded to form a ring. $R_{31}$, $R_{32}$ and $R_{55}$ to $R_{58}$ are respectively bonded to carbon atoms forming the six-membered ring of a carbazole ring.

In the formula (19), M, N, O and P are 4.

In the formula (19), q and r are 4 and y and z are each independently an integer of 1 to 3. When y is an integer of 2 or more, a plurality of N-carbozolyl groups substituted with $R_{55}$ and $R_{56}$ may be mutually the same or different. When z is an integer of 2 or more, a plurality of N-carbozolyl groups substituted with $R_{57}$ and $R_{58}$ may be mutually the same or different.

In the formula (19), a nitrogen atom of the N-carbozolyl group substituted with $R_{55}$ and $R_{56}$ is bonded to one of carbon atoms forming a six-membered ring substituted with $R_{32}$. In the formula (19), a nitrogen atom of the N-carbozolyl group substituted with $R_{57}$ and $R_{58}$ is bonded to one of carbon atoms forming a six-membered ring substituted with $R_{31}$.

In the first exemplary embodiment, the compound represented by the formula (19) in which y and z are 1 is preferable. A compound represented by a formula (19a) below is more preferable.

[Formula 24]

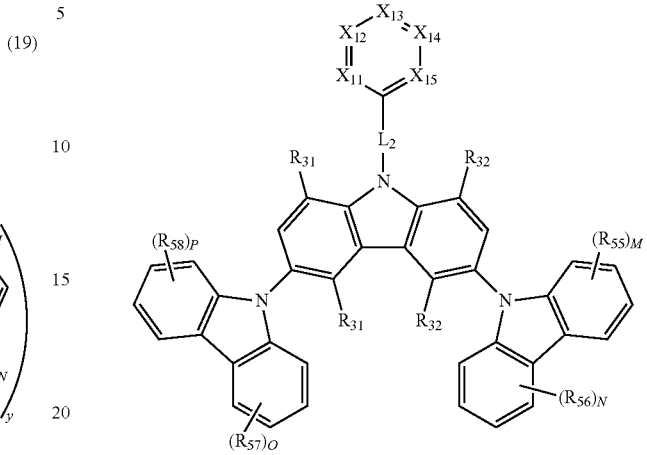

(19a)

In the formula (19a), $L_2$, $X_{11}$ to $X_{15}$, $R_{31}$, $R_{32}$, $R_{55}$ to $R_{58}$, M, N, O and P represent the same as $L_2$, $X_{11}$ to $X_{15}$, $R_{31}$, $R_{32}$, $R_{55}$ to $R_{58}$, M, N, O and P in the formula (19).

In the first exemplary embodiment, the compound represented by the formula (1) is preferably a compound represented by a formula (5) below. Specifically, in the compound represented by the formula (15), m is preferably 1 and one of four $R_{32}$ is preferably a carbazolyl group.

[Formula 25]

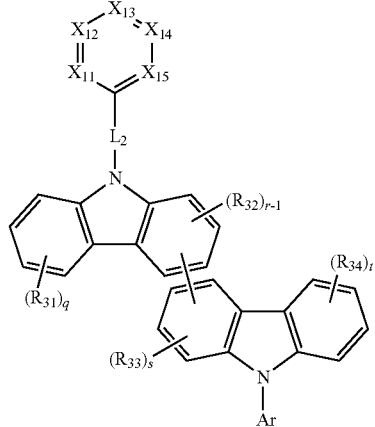

(5)

In the formula (5), $L_2$ represents the same as $L_2$ of the formula (1).

In the formula (5), $X_1$ to $X_5$ represent the same as $X_{11}$ to $X_{15}$ of the formula (12).

In the formula (5), $R_{31}$ to $R_{34}$ each independently represent the same as $R_1$ to $R_8$. q and r are 4. s is 3. t is 4. $R_{31}$ to $R_{34}$ are respectively bonded to carbon atoms forming the six-membered ring of a carbazole ring.

In the formula (5), Ar represents a substituted or unsubstituted aryl group having 6 to 30 ring carbon atoms or a substituted or unsubstituted heterocyclic group having 5 to 30 ring atoms. However, when Ar is a substituted or unsubstituted six-membered nitrogen-containing heterocyclic group, the nitrogen-containing heterocyclic group may directly be bonded by a single bond to a nitrogen atom at a position 9 of the carbazole ring substituted with $R_{33}$ and $R_{34}$, or alternatively, may be bonded through a linking group. The linking group provided between Ar and the nitrogen atom at the position 9 of the carbazole ring substituted with $R_{33}$ and $R_{34}$ represents the same as $L_2$ of the formula (1). Ar is preferably a substituted or unsubstituted aryl group having 6 to 30 ring carbon atoms. Specific examples of Ar include a phenyl group, biphenyl group, terphenyl group, naphthyl group, phenanthryl group, triphenylyl group, dibenzofuranyl group, dibenzothiophenyl group and carbazolyl group.

In the formula (5), one of carbon atoms of the six-membered ring forming the carbazole group substituted with $R_{32}$ is bonded to one of carbon atoms forming the carbazole ring substituted with $R_{33}$.

The compound represented by the formula (5) is preferably a compound represented by a formula (5A) or (5B) below.

[Formula 26]

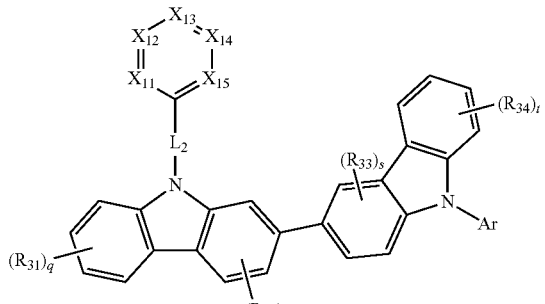

(5A)

[Formula 27]

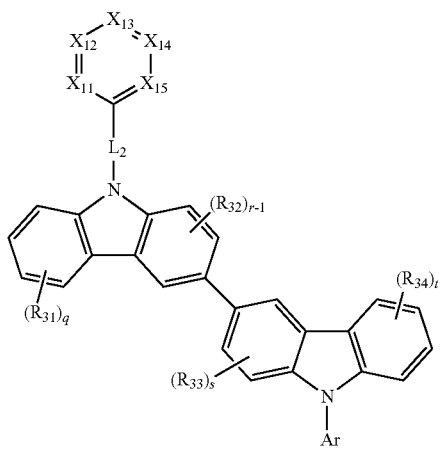

(5B)

In the formula (5A) or (5B), $L_2$, $X_{11}$ to $X_{15}$, $R_{31}$ to $R_{34}$, q, r, s, t and Ar represent the same as $L_2$, $X_{11}$ to $X_{15}$, $R_{31}$ to $R_{34}$, q, r, s, t and Ar in the formula (5).

In the first exemplary embodiment, in the group represented by the formula (10), it is preferable that the cyclic structure A is a substituted or unsubstituted benzene ring and the cyclic structure B is a cyclic structure in which any ones of a plurality of five-membered rings and six-membered rings are mutually fused. In this arrangement, any one of the cyclic structures may have a substituent. In the first exemplary embodiment, the compound represented by the formula (1) is preferably a compound represented by a formula (31) below.

[Formula 28]

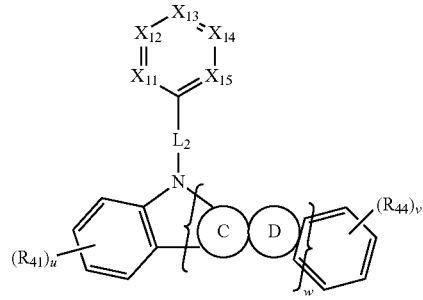

(31)

In the formula (31), $L_2$ represents the same as $L_2$ of the formula (1).

In the formula (31), $X_{11}$ to $X_{15}$ each independently represent the same as $X_{11}$ to $X_{15}$ of the formula (12).

In the formula (31), $R_{41}$ and $R_{44}$ each independently represent the same as $R_1$ to $R_8$ described above. A plurality of $R_{41}$ may be mutually the same or different. A plurality of $R_{44}$ may be mutually the same or different. Adjacent ones of $R_{41}$ may form a ring and adjacent ones of $R_{44}$ may form a ring. In the formula (31), $R_{41}$ and $R_{44}$ are respectively bonded to carbon atoms forming the six-membered ring.

In the formula (31), u and v are 4.

In the formula (31), C represents a cyclic structure represented by a formula (32) below and D represents a cyclic structure represented by a formula (33) below. Each of a cyclic structure C and a cyclic structure D is fused to an adjacent cyclic structure at any position.

In the formula (31), w is an integer of 1 to 4. w is a repeating unit of a linking cyclic structure in which the cyclic structure C and the cyclic structure D are fused.

[Formula 29]

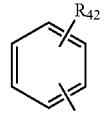

(32)

[Formula 30]

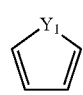

(33)

In the formula (32), $R_{42}$ and $R_{43}$ each independently represent the same as $R_1$ to $R_8$ of the formula (1). When $R_{42}$ and $R_{43}$ are substituents at adjacent positions, $R_{42}$ and $R_{43}$ may form a ring. In the formula (32), $R_{42}$ and $R_{43}$ are respectively bonded to carbon atoms forming the six-membered ring.

in the formula (33): $Y_1$ represents $CR_{45}R_{46}$, $NR_{47}$, a sulfur atom, or an oxygen atom; and $R_{45}$ to $R_{47}$ each independently represent the same as $R_1$ to $R_8$ described above.

In the formula (31), w is preferably 1. In this arrangement, the compound represented by the formula (31) is represented by a formula (31a) below.

[Formula 31]

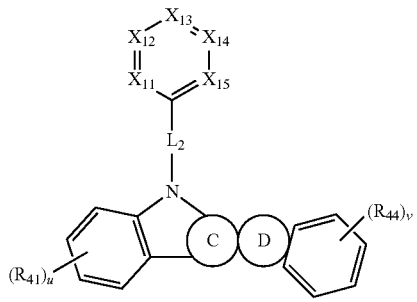
(31a)

In the formula (31a), $L_2$ represents the same as $L_2$ of the formula (1).

In the formula (31a), $X_{11}$ to $X_{15}$ each independently represent the same as $X_{11}$ to $X_{15}$ of the formula (12).

In the formula (31a), $R_{41}$ and $R_{44}$ each independently represent the same as $R_1$ to $R_8$ described above. Adjacent ones of $R_{41}$ may form a ring and adjacent ones of $R_{44}$ may form a ring. In the formula (31a), $R_{41}$ and $R_{44}$ are respectively bonded to carbon atoms forming the six-membered ring.

In the formula (31a), u and v are 4.

In the formula (31a), C represents the cyclic structure represented by the formula (32) and D represents the cyclic structure represented by the formula (33). Each of the cyclic structure C and the cyclic structure D is fused to an adjacent cyclic structure at any position.

In the first exemplary embodiment, Cz represented by the formula (1) is preferably a group selected from the group consisting of groups represented by formulae (110) to (115) below.

[Formula 32]

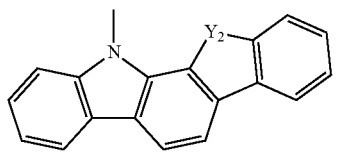
(110)

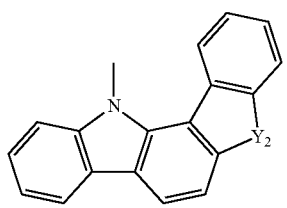
(111)

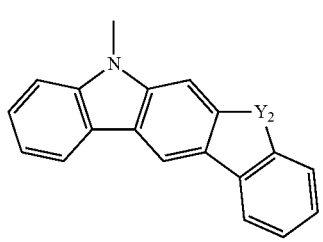
(112)

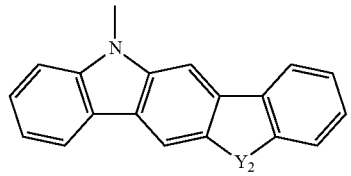
(113)

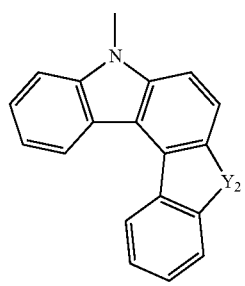
(114)

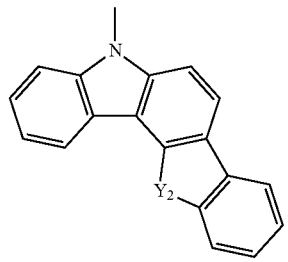
(115)

In the formulae (110) to (115), $Y_2$ represents $CR_{48}R_{49}$, $NR_{50}$, a sulfur atom, or an oxygen atom. $R_{48}$ to $R_{50}$ each independently represent the same as $R_1$ to $R_8$ described above. The groups represented by the formulae (110) to (115) may further have a substituent.

In the formulae (110) to (115), $Y_2$ is preferably an oxygen atom.

The compounds including the groups represented by the formulae (110) to (115) are preferably compounds represented by the formulae (31b) to (31g).

[Formula 33]

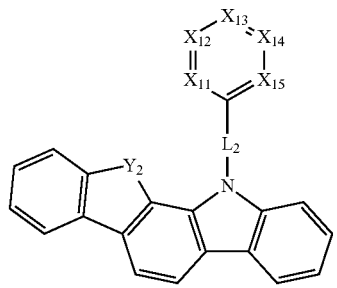
(31b)

(31c)

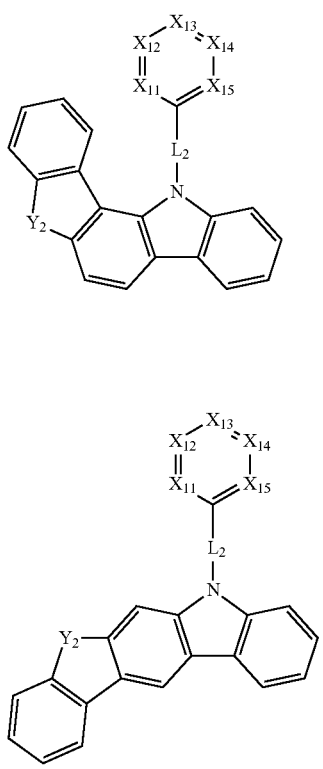

(31d)

(31e)

(31f)

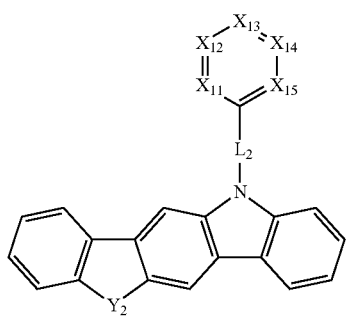

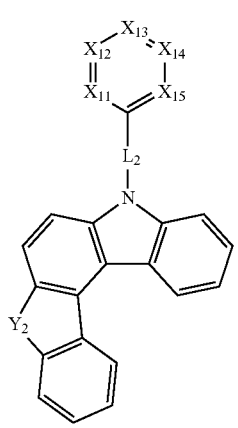

(31g)

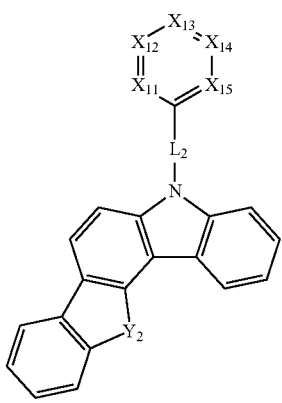

In the formulae (31b) to (31g), $L_2$ represents the same as $L_2$ of the formula (1).

In the formulae (31b) to (31g), $X_{11}$ to $X_{15}$ each independently represent the same as $X_{11}$ to $X_{15}$ of the formula (12).

In the formulae (31b) to (31g), $Y_2$ represents $CR_{48}R_{49}$, $NR_{50}$, a sulfur atom, or an oxygen atom. $R_{48}$ to $R_{50}$ each independently represent the same as $R_1$ to $R_8$ described above.

In the formulae (31b) to (31g), $Y_2$ is preferably an oxygen atom.

In the first exemplary embodiment, Cz of the formula (1) may be a group selected from the group consisting of groups derived from structures represented by formulae (116) to (119) below.

[Formula 34]

(116)

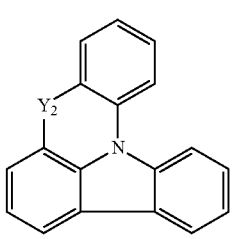

(117)

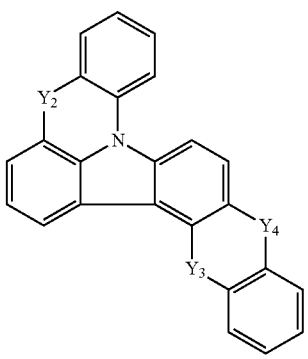

-continued

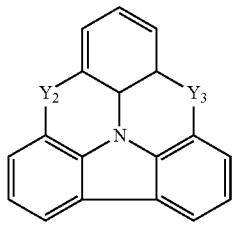
(118)

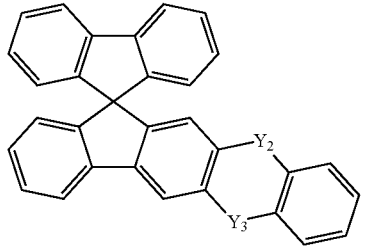
(119)

In the formulae (116) to (119), $Y_2$, $Y_3$ and $Y_4$ each independently represent $CR_{48}R_{49}$, $NR_{50}$, a sulfur atom, or an oxygen atom. $R_{48}$ to $R_{50}$ each independently represent the same as $R_1$ to $R_8$ described above. The group derived from the structure represented by the formulae (116) to (119) has a hand(s) at any positions and is bonded to $L_2$ in the formula (1). The groups derived from the structures represented by the formulae (116) to (119) may further have a substituent.

In the formulae (5), (5A), (5B), (13), (13a) to (13c), (15) to (19), (19a), (31), (31a) to (31g) and (100) to (107), $L_2$ is preferably a single bond.

When $L_2$ is a divalent linking group, $L_2$ is preferably a substituted or unsubstituted divalent aromatic hydrocarbon group. Moreover, in the exemplary embodiment, when $L_2$ is a divalent linking group, $L_2$ preferably has a divalent six-membered ring structure, more preferably a divalent six-membered ring structure represented by a formula (3), (3a) or (3b) below, further preferably a divalent six-membered ring structure represented by the formula (3) below.

[Formula 35]

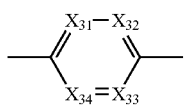
(3)

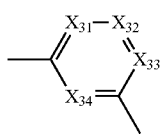
(3a)

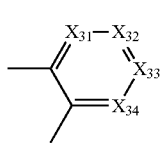
(3b)

In the formulae (3), (3a) and (3b), $X_{31}$ to $X_{34}$ each independently represent $CR_{101}$ or a nitrogen atom. $R_{101}$ each independently represents the same as $R_1$ to $R_8$ in the formula (1). In the exemplary embodiment, $X_{31}$ to $X_{34}$ are preferably each independently $CR_{101}$, in which $R_{101}$ is more preferably a hydrogen atom, alkyl group, alkoxy group, aryloxy group, cyano group, halogen atom and silyl group.

In the exemplary embodiment, examples of the aryl group having 6 to 30 ring carbon atoms include a phenyl group, biphenyl group, terphenyl group, naphthyl group, anthryl group, phenanthryl group, fluorenyl group, pyrenyl group, chrysenyl group, fluoranthenyl group, benzo[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

The aryl group in the exemplary embodiment preferably has 6 to 20 ring carbon atoms, more preferably 6 to 12 ring carbon atoms. Among the above aryl group, a phenyl group, biphenyl group, naphthyl group, phenanthryl group, terphenyl group, and fluorenyl group are particularly preferable. A carbon atom at a position 9 of each of 1-fluorenyl group, 2-fluorenyl group, 3-fluorenyl group and 4-fluorenyl group is preferably substituted by a substituted or unsubstituted alkyl group having 1 to 30 carbon atoms later described in the exemplary embodiment.

Examples of the heterocyclic group having 5 to 30 ring atoms in the exemplary embodiment include a pyridyl group, pyrimidinyl group, pyrazinyl group, pyridazynyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazole group, benzofuranyl group, benzothiophenyl group, benzoxazolyl group, benzothiazolyl group, benzisoxazolyl group, benzisothiazolyl group, benzoxadiazolyl group, benzothiadiazolyl group, dibenzofuranyl group, dibenzothiophenyl group, piperidinyl group, pyrrolidinyl group, piperazinyl group, morpholyl group, phenazinyl group, phenothiazinyl group, and phenoxazinyl group.

The heterocyclic group in the exemplary embodiment preferably has 5 to 20 ring atoms, more preferably 5 to 14 ring atoms. Among the above heterocyclic group, a 1-dibenzofuranyl group, 2-dibenzofuranyl group, 3-dibenzofuranyl group, 4-dibenzofuranyl group, 1-dibenzothiophenyl group, 2-dibenzothiophenyl group, 3-dibenzothiophenyl group, 4-dibenzothiophenyl group, 1-carbazolyl group, 2-carbazolyl group, 3-carbazolyl group, 4-carbazolyl group, and 9-carbazolyl group are particularly preferable. A nitrogen atom at a position 9 of each of 1-carbazolyl group, 2-carbazolyl group, 3-carbazolyl group and 4-carbazolyl group is preferably substituted by a substituted or unsubstituted aryl group having 6 to 30 ring carbon atoms or a substituted or unsubstituted heterocyclic group having 5 to 30 ring atoms in the exemplary embodiment.

The alkyl group having 1 to 30 carbon atoms in the exemplary embodiment is preferably linear, branched or cyclic. Examples of the linear or branched alkyl group include: a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear or branched alkyl group in the exemplary embodiment preferably has 1 to 10 carbon atoms, more preferably 1 to 6 carbon atoms. Among the linear or branched alkyl group, a methyl group, ethyl group, propyl group, isopropyl group, n-butyl group, s-butyl group, isobutyl group, t-butyl group, n-pentyl group, n-hexyl group, amyl group, isoamyl group, and neopentyl group are particularly preferable.

Examples of the cycloalkyl group in the exemplary embodiment include a cyclopropyl group, cyclobutyl group, cyclopentyl group, cyclohexyl group, 4-methylcyclohexyl group, adamantyl group and norbornyl group. The cycloalkyl group preferably has 3 to 10 ring carbon atoms, more preferably 5 to 8 ring carbon atoms. Among the above cycloalkyl group, a cyclopentyl group and a cyclohexyl group are particularly preferable.

The halogenated alkyl group provided by substituting the alkyl group with a halogen atom is exemplified by a halogenated alkyl group obtained by substituting the alkyl group having 1 to 30 carbon atoms with one or more halogen atoms. Specific examples of the halogenated alkyl group includes a fluoromethyl group, difluoromethyl group, trifluoromethyl group, fluoroethyl group, trifluoromethylmethyl group, trifluoroethyl group, and pentafluoroethyl group.

The alkylsilyl group having 3 to 30 carbon atoms in the exemplary embodiment is exemplified by a trialkylsilyl group having the above alkyl group having 1 to 30 carbon atoms. Specific examples of the trialkylsilyl group include a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyldimethylsilyl group, propyldimethylsilyl group and triisopropylsilyl group. Three alkyl groups in the trialkylsilyl group may be mutually the same or different.

Examples of the arylsilyl group having 6 to 30 ring carbon atoms in the exemplary embodiment include a dialkylarylsilyl group, alkyldiarylsilyl group and triarylsilyl group.

The dialkylarylsilyl group is exemplified by a dialkylarylsilyl group including two of the alkyl group listed as the examples of the alkyl group having 1 to 30 carbon atoms and one of the aryl group listed as the examples of the aryl group having 6 to 30 ring carbon atoms. The dialkylarylsilyl group preferably has 8 to 30 carbon atoms.

The alkyldiarylsilyl group is exemplified by an alkyldiarylsilyl group including one of the alkyl group listed as the examples of the alkyl group having 1 to 30 carbon atoms and two of the aryl group listed as the examples of the aryl group having 6 to 30 ring carbon atoms. The alkyldiarylsilyl group preferably has 13 to 30 carbon atoms.

The triarylsilyl group is exemplified by a triarylsilyl group having three of the above aryl group having 6 to 30 ring carbon atoms. The triarylsilyl group preferably has 18 to 30 carbon atoms.

The alkoxy group having 1 to 30 carbon atoms in the exemplary embodiment is represented by $-OZ_1$. $-OZ_1$ is exemplified by the above alkyl group having 1 to 30 carbon atoms. Examples of the alkoxy group include a methoxy group, ethoxy group, propoxy group, butoxy group, pentyloxy group and hexyloxy group.

The halogenated alkoxy group provided by substituting the alkoxy group with a halogen atom is exemplified by a halogenated alkoxy group obtained by substituting the alkoxy group having 1 to 30 carbon atoms with one or more halogen atoms.

The aryloxy group having 6 to 30 ring carbon atoms in the exemplary embodiment is represented by $-OZ_2$. $Z_2$ is exemplified by the above aryl group having 6 to 30 ring carbon atoms. The aryloxy group is exemplified by a phenoxy group.

The alkylamino group having 2 to 30 carbon atoms is represented by $-NHR_V$ or $-N(R_V)_2$. $R_V$ is exemplified by the above alkyl group having 1 to 30 carbon atoms.

The arylamino group having 6 to 60 ring carbon atoms is represented by $-NHR_W$ or $-N(R_W)_2$. $R_W$ is exemplified by the above aryl group having 6 to 30 ring carbon atoms.

The alkylthio group having 1 to 30 carbon atoms is represented by $-SR_V$. $R_V$ is exemplified by the above alkyl group having 1 to 30 carbon atoms.

The arylthio group having 6 to 30 ring carbon atoms is represented by $-SR_W$. $R_W$ is exemplified by the above aryl group having 6 to 30 ring carbon atoms.

In the invention, "carbon atoms forming a ring (ring carbon atoms)" mean carbon atoms forming a saturated ring, an unsaturated ring, or an aromatic ring. "Atoms forming a ring (ring atoms)" mean carbon atoms and hetero atoms forming a hetero ring including a saturated ring, unsaturated ring, or aromatic ring.

In the invention, a hydrogen atom includes isotope having different numbers of neutrons, specifically, protium, deuterium and tritium.

Examples of the substituents in the first exemplary embodiment such as the substituent meant by "substituted or unsubstituted," the substituent in the linking group for $L_1$ to $L_3$, and the substituent in the cyclic structures A and B are an alkenyl group, alkynyl group, aralkyl group, halogen atom, cyano group, hydroxyl group, nitro group and carboxy group, in addition to the above-described aryl group, heterocyclic group, alkyl group (linear or branched alkyl group, cycloalkyl group and haloalkyl group), alkylsilyl group, arylsilyl group, alkoxy group, aryloxy group, alkylamino group, arylamino group, alkylthio group, and arylthio group.

Among the above substituents, an aryl group, heterocyclic group, alkyl group, halogen atom, alkylsilyl group, arylsilyl group and cyano group are preferable. More preferable substituents are the preferable substituents specifically described for each substituent.

In $L_1$ to $L_3$ as the linking group and the like, the aromatic hydrocarbon group is exemplified by a group derived from the aryl group having 6 to 30 ring carbon atoms and the heterocyclic group is exemplified by a group derived from the heterocyclic group having 5 to 30 ring atoms.

The alkenyl group is preferably an alkenyl group having 2 to 30 carbon atoms, which may be linear, branched or cyclic. Examples of the alkenyl group include a vinyl group, propenyl group, butenyl group, oleyl group, eicosapentaenyl group, docosahexaenyl group, styryl group, 2,2-diphenylvinyl group, 1,2,2-triphenylvinyl group, 2-phenyl-2-propenyl group, cyclopentadienyl group, cyclopentenyl group, cyclohexenyl group, and cyclohexadienyl group.

The alkynyl group is preferably an alkynyl group having 2 to 30 carbon atoms, which may be linear, branched or cyclic. Examples of the alkynyl group include ethynyl, propynyl, and 2-phenylethynyl.

The aralkyl group is preferably an aralkyl group having 6 to 30 ring carbon atoms and is represented by —$Z_3$-$Z_4$. $Z_3$ is exemplified by an alkylene group derived from the above alkyl group having 1 to 30 carbon atoms. $Z_4$ is exemplified by the above aryl group having 6 to 30 ring carbon atoms. This aralkyl group is preferably an aralkyl group having 7 to 30 carbon atoms, in which an aryl moiety has 6 to 30 carbon atoms, preferably 6 to 20 carbon atoms, more preferably 6 to 12 carbon atoms and an alkyl moiety has 1 to 30 carbon atoms, preferably 1 to 20 carbon atoms, more preferably 1 to 10 carbon atoms, further preferably 1 to 6 carbon atoms. Examples of the aralkyl group include a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthylisopropyl group, and 2-β-naphthylisopropyl group.

Examples of the halogen atom are fluorine, chlorine, bromine and iodine, among which a fluorine atom is preferable.

"Unsubstituted" in "substituted or unsubstituted" herein means that a group is not substituted by the above-described substituents but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of a substituent(s) of the substituted ZZ group.

The same description as the above applies to "substituted or unsubstituted" in the following compound or a partial structure thereof.

Specific examples of the compound represented by the formula (1) are shown below, but the invention is not limited thereto.

[Formula 36]

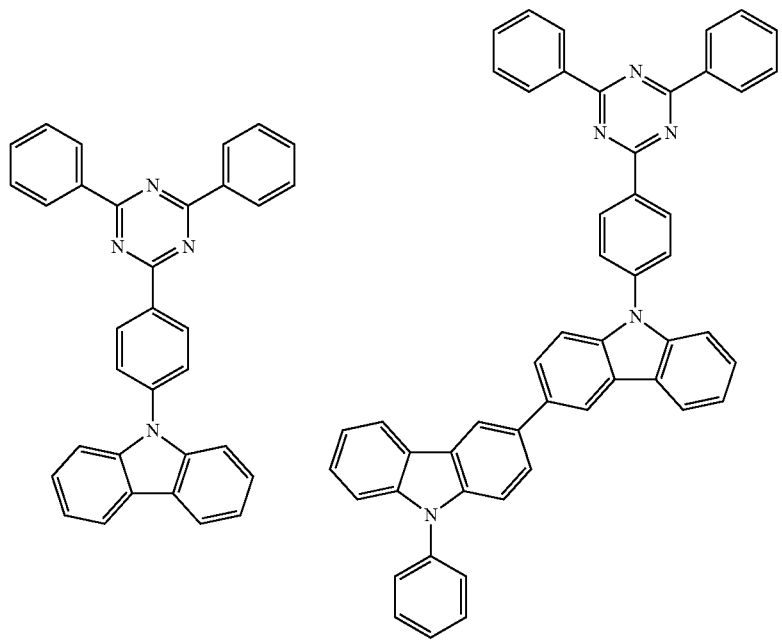

-continued
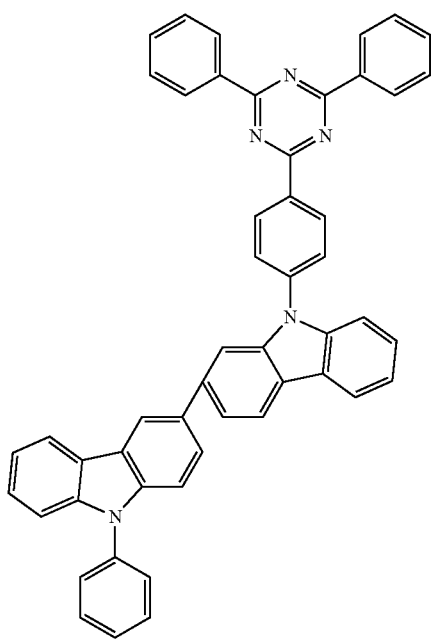
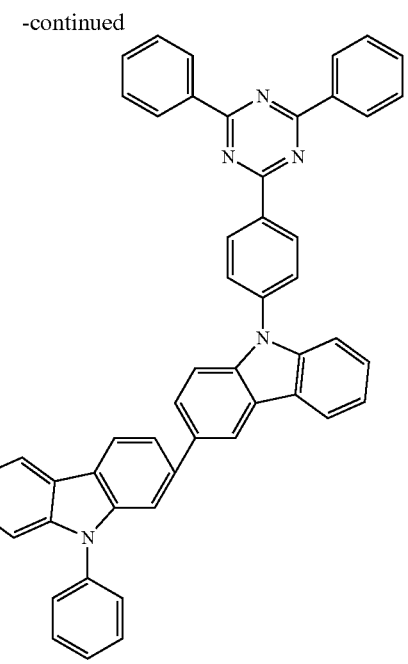
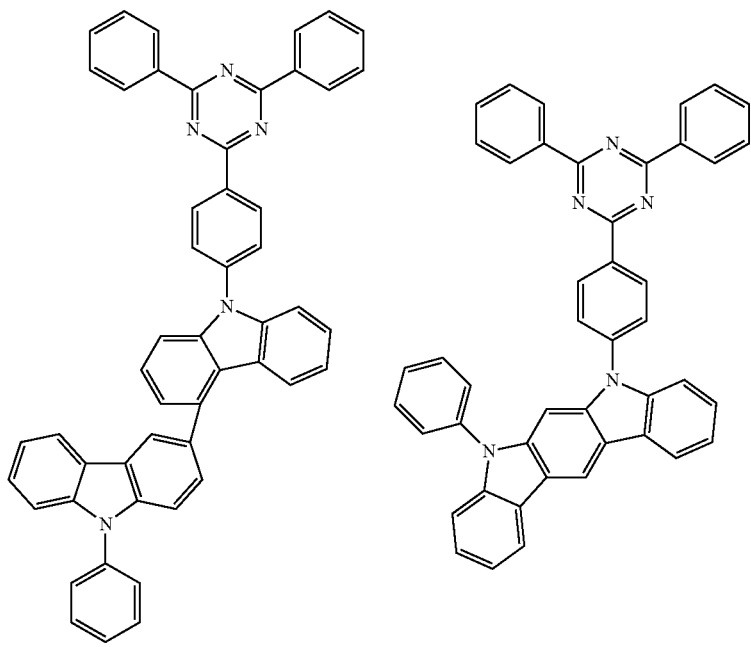

[Formula 37]
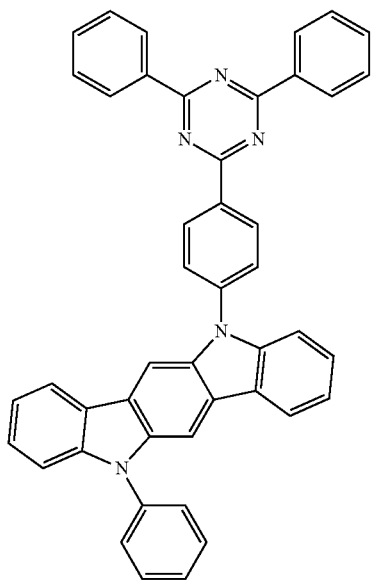
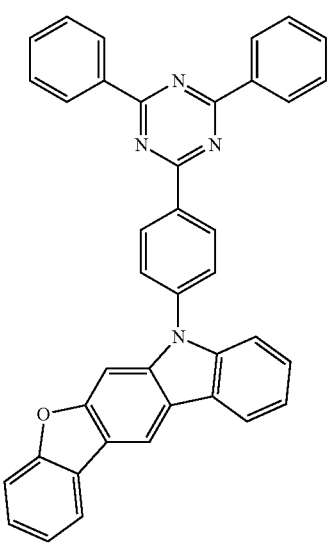
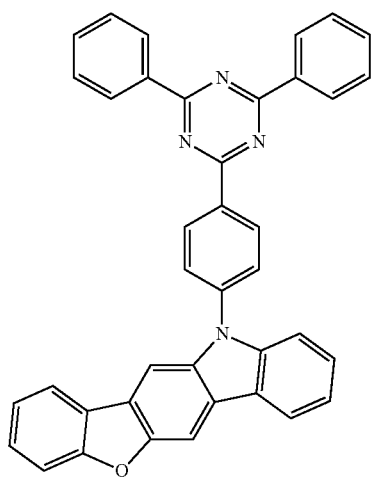
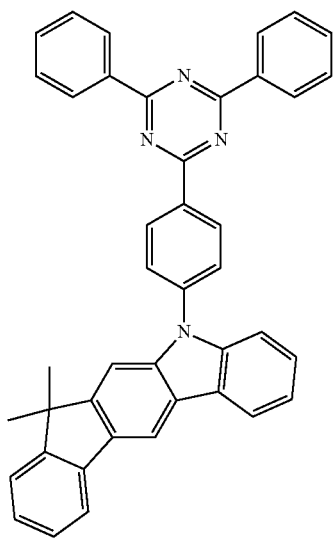

[Formula 38]
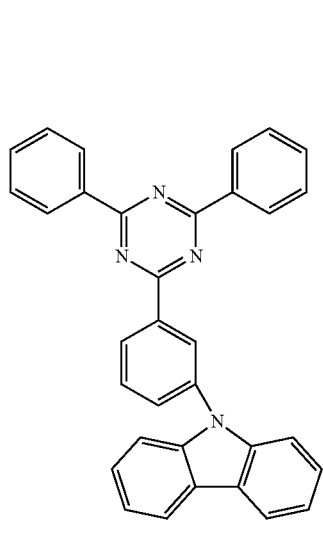
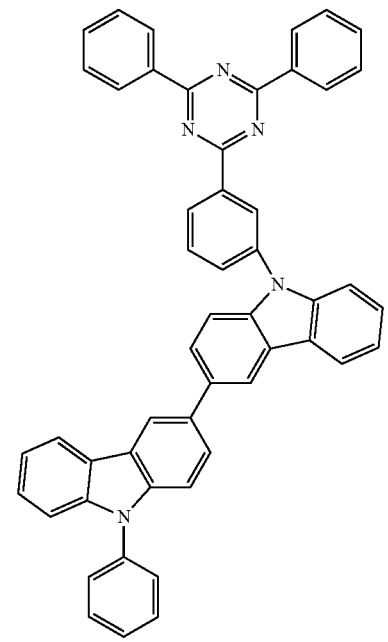
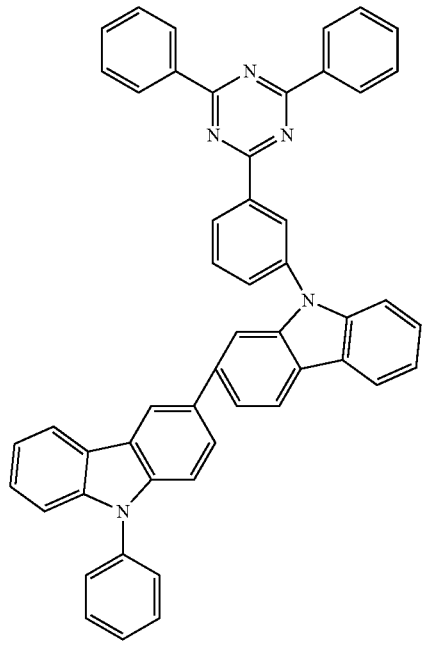
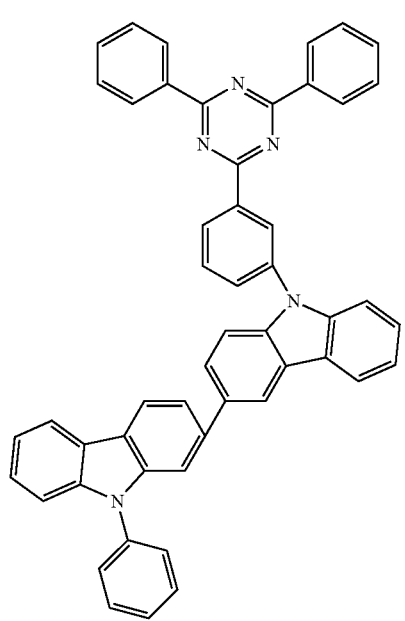
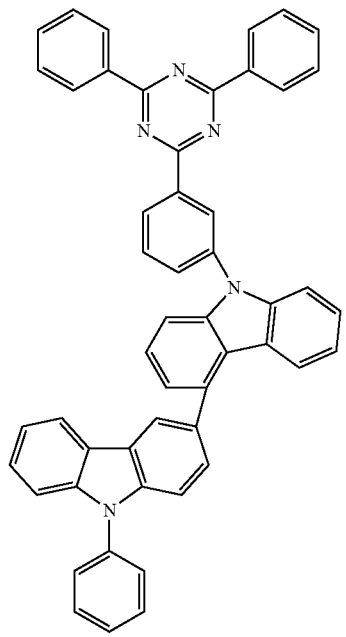
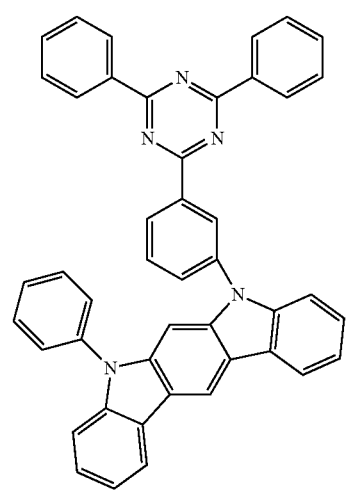

[Formula 39]
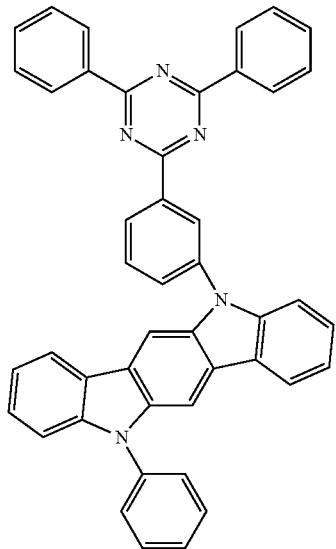 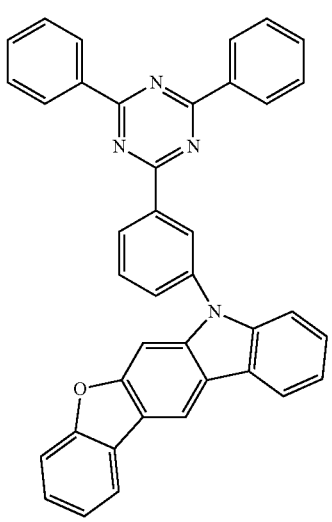 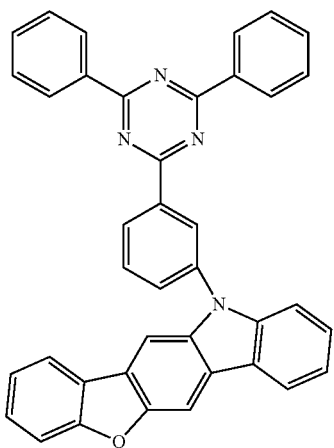
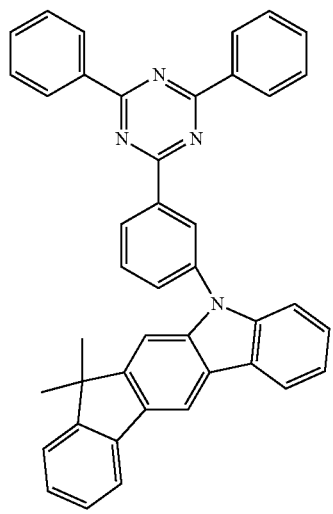

-continued
[Formula 40]
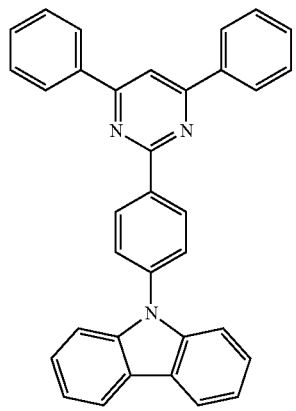
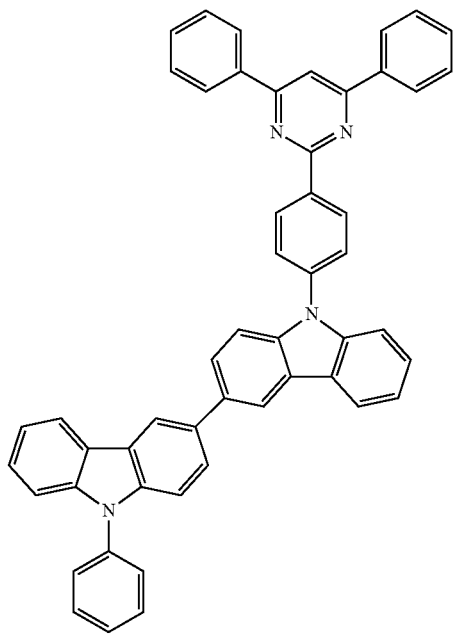
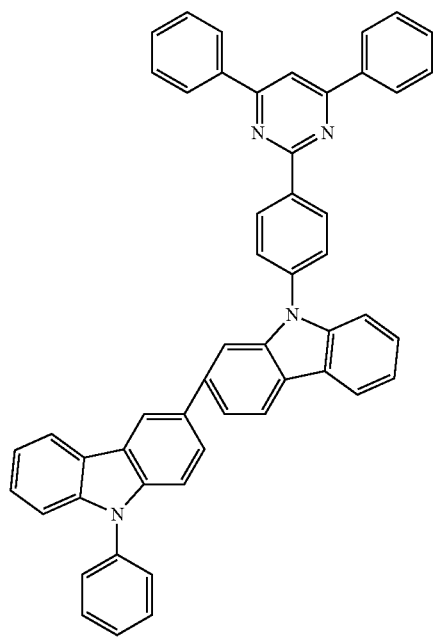
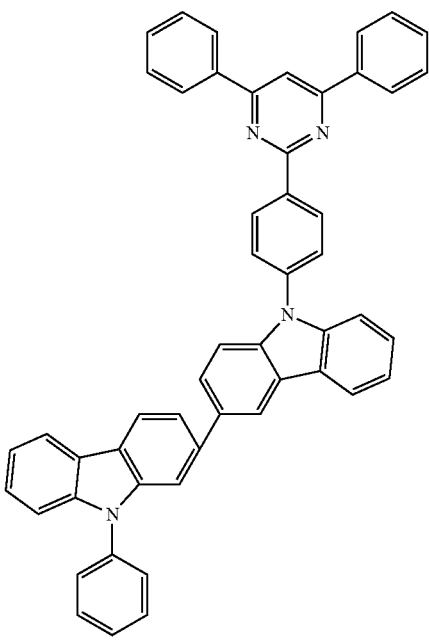

-continued
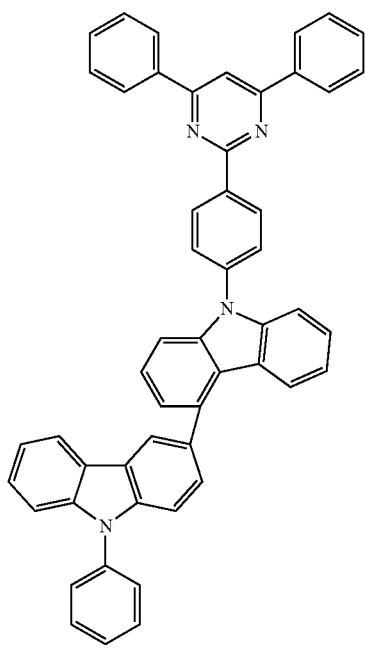
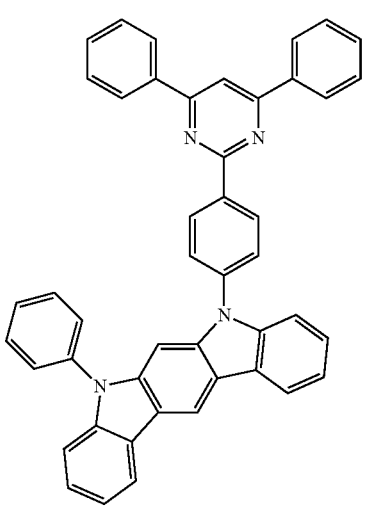
[Formula 41]
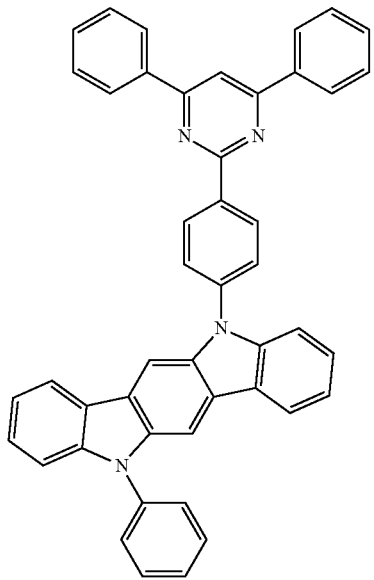
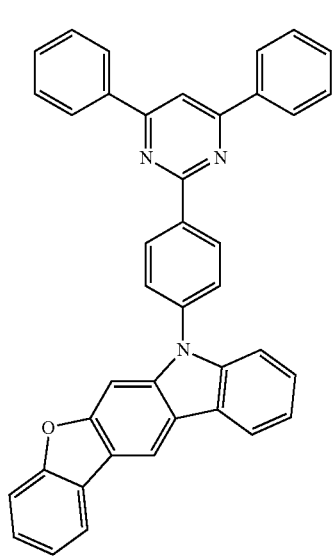
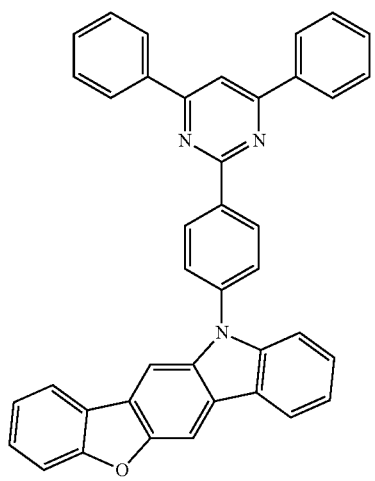

-continued
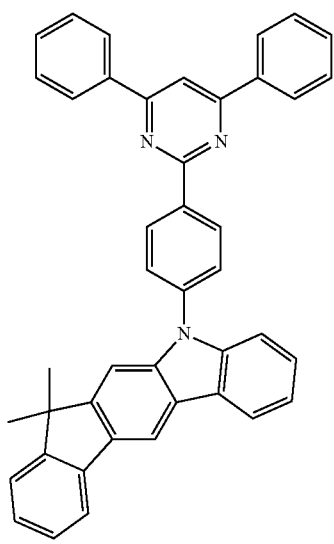
[Formula 42]
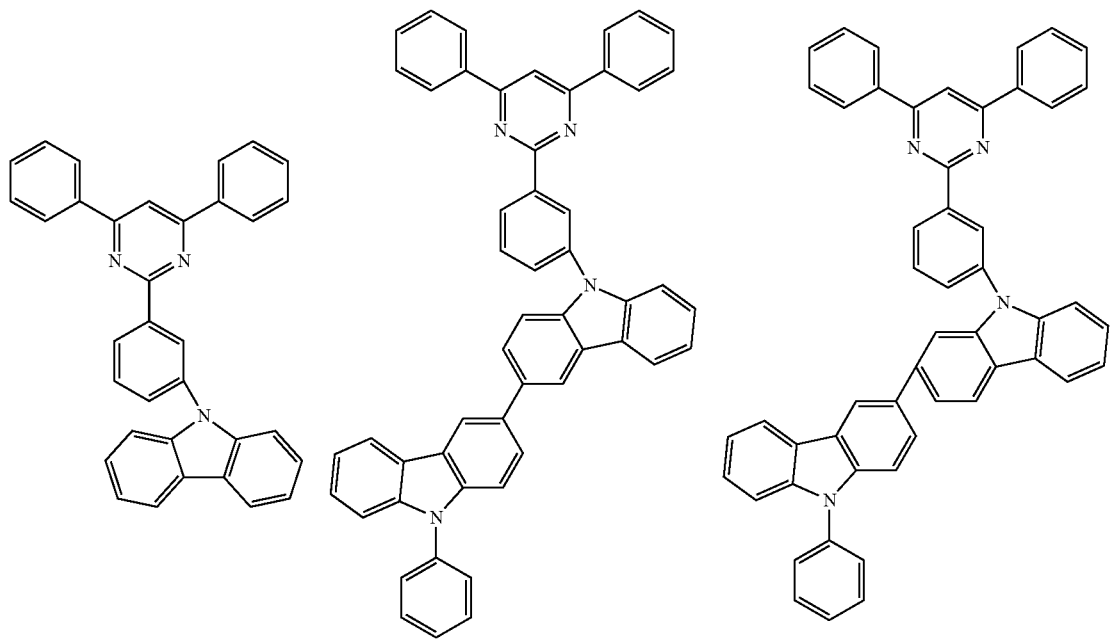

51
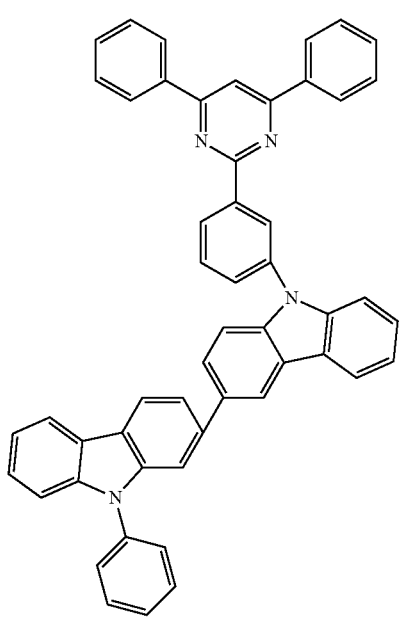
-continued
52
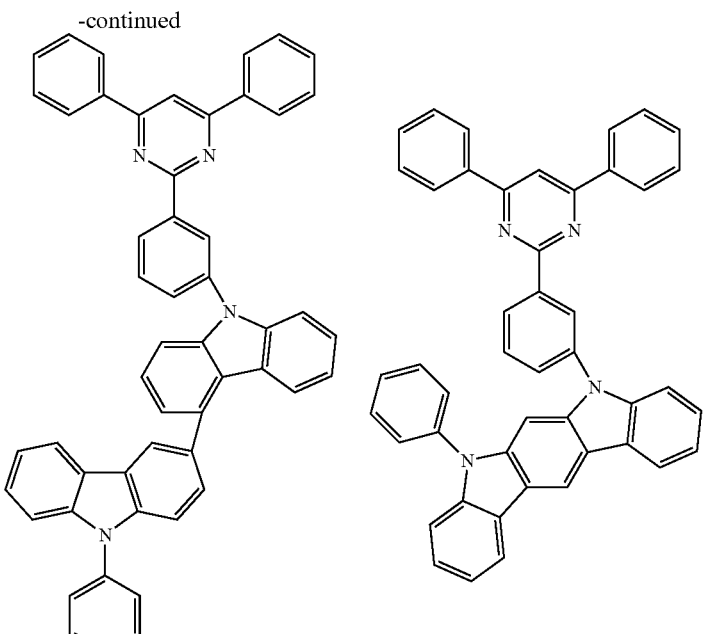
[Formula 43]
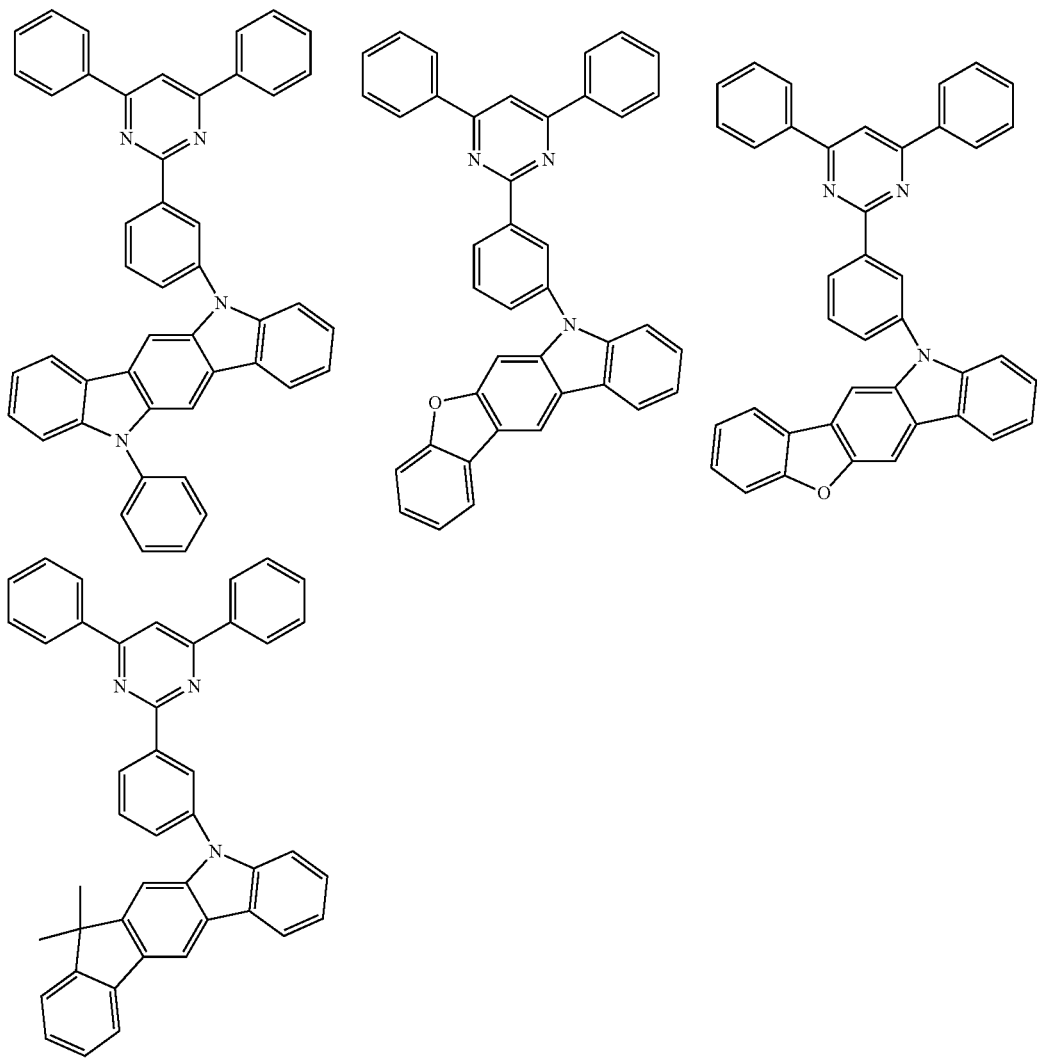

[Formula 44]
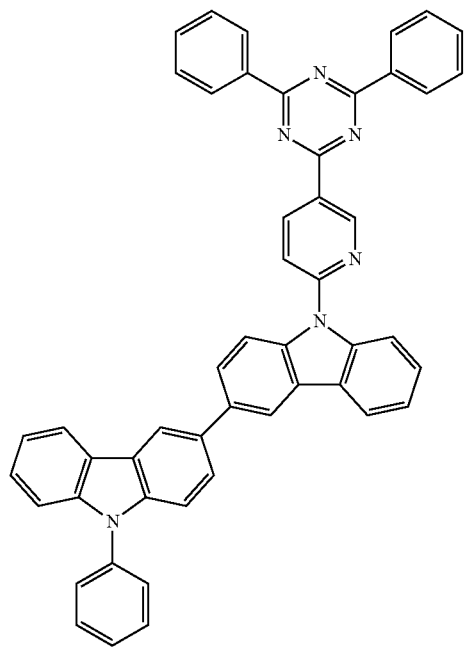 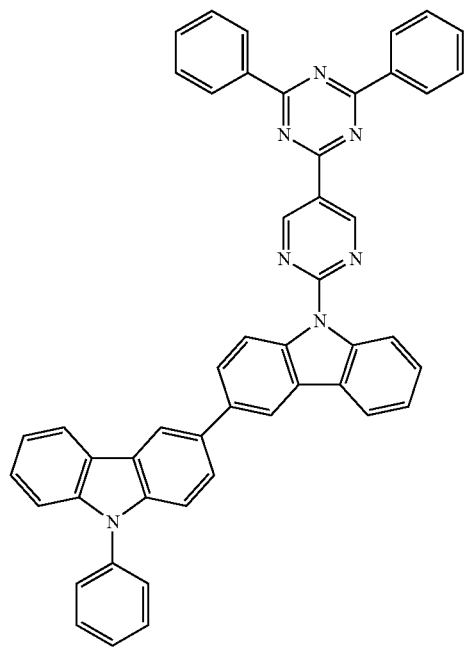
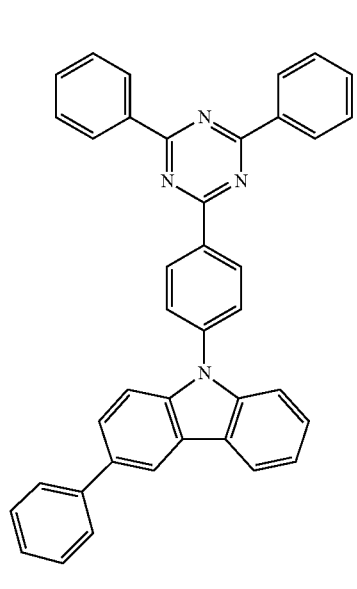 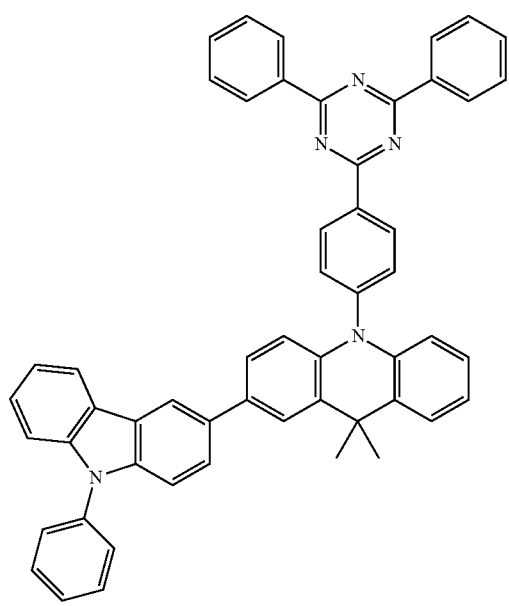

-continued
55
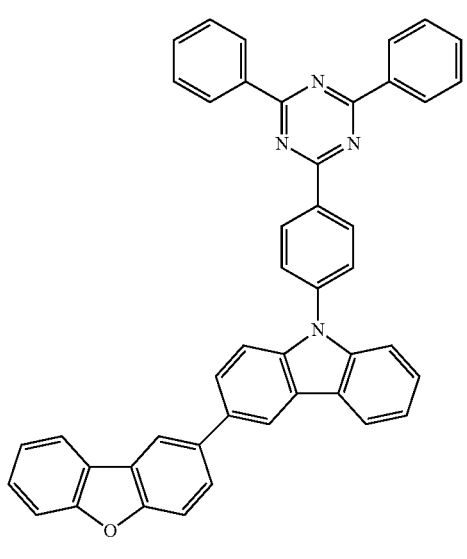
56
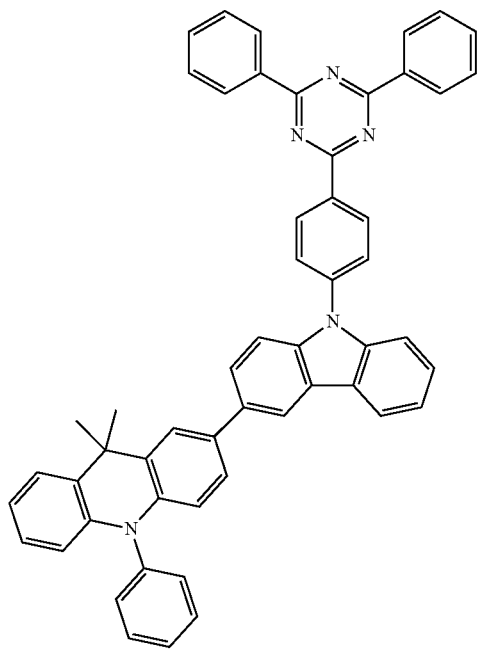
[Formula 45]
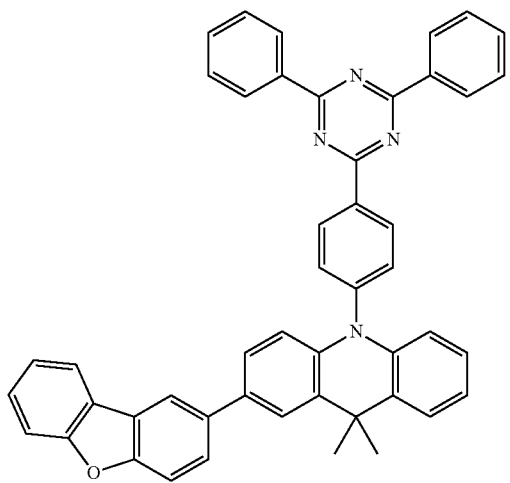
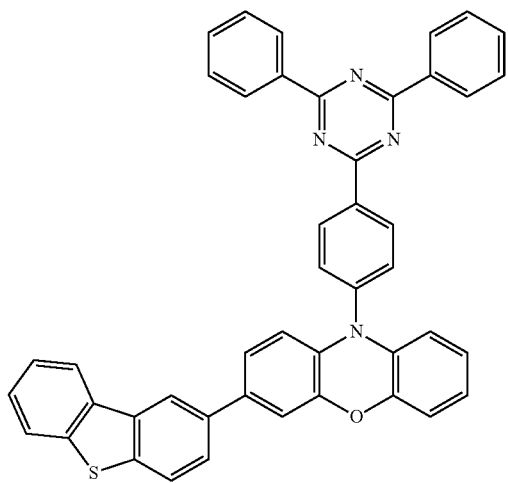

-continued
57
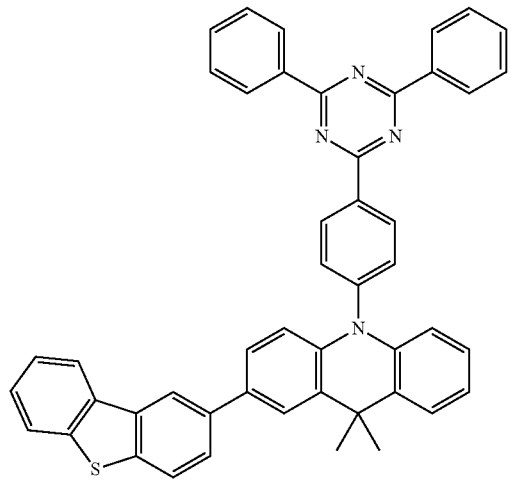
58
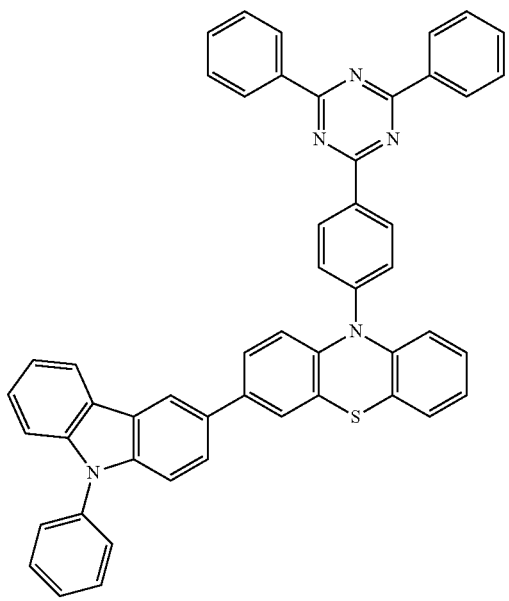
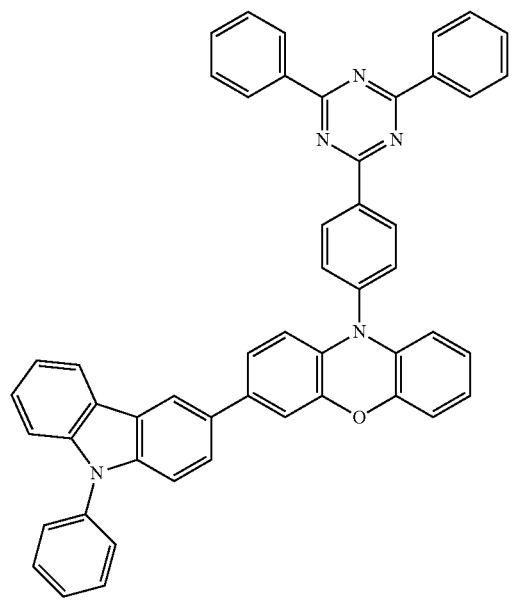
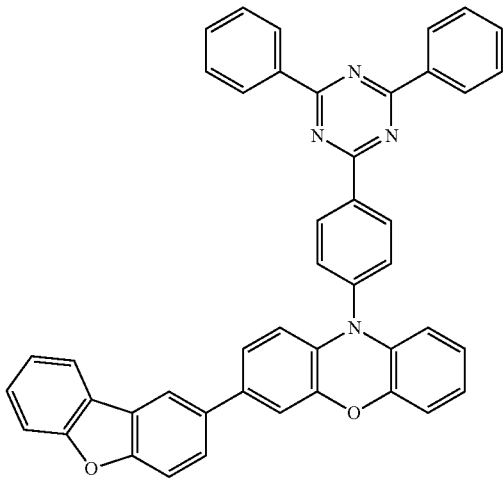

-continued
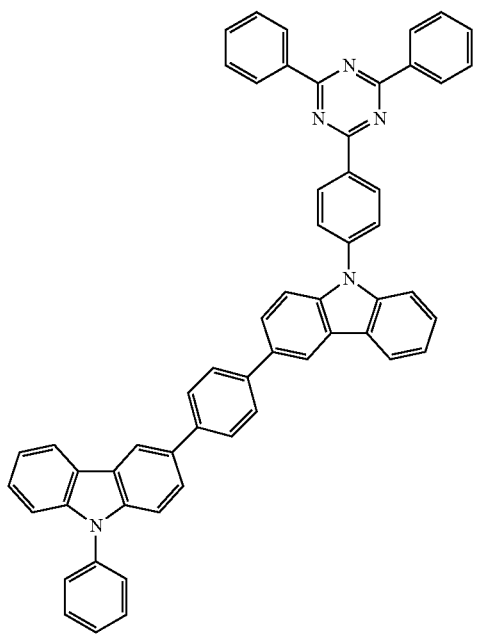
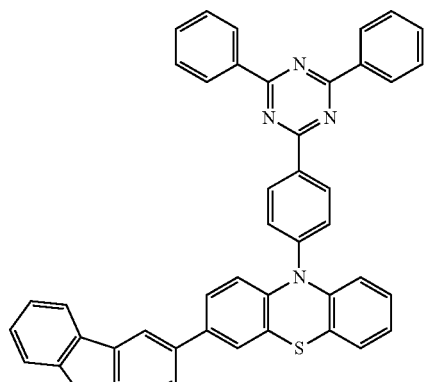
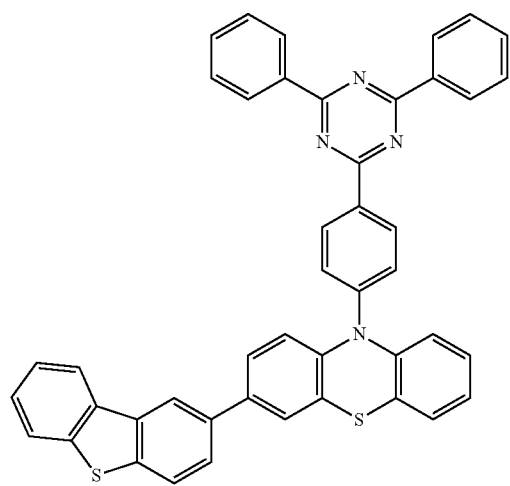

{Formula 46]
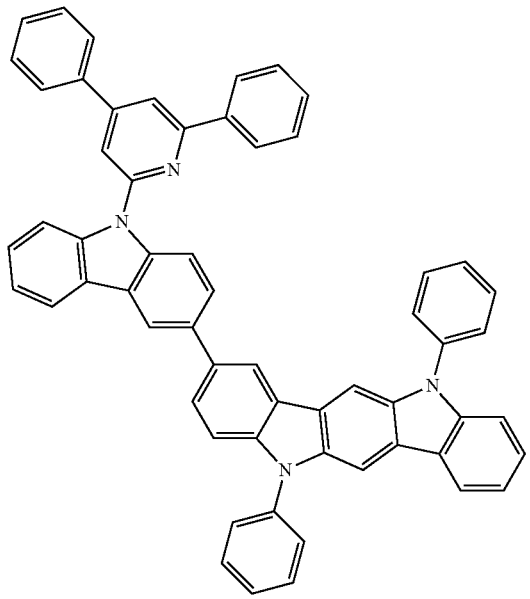
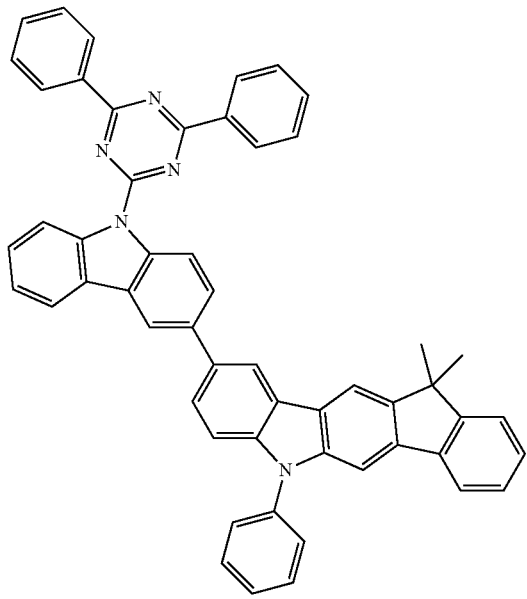
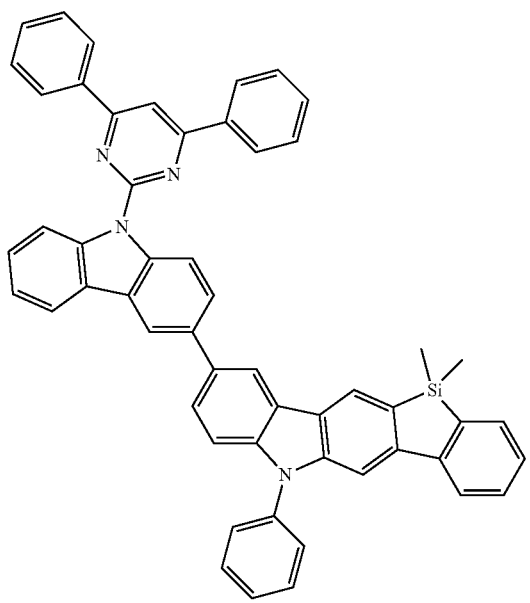
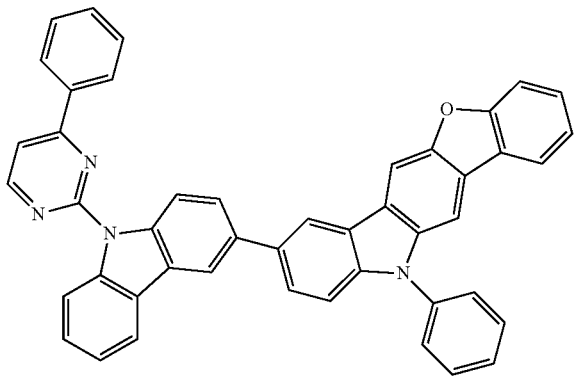

-continued
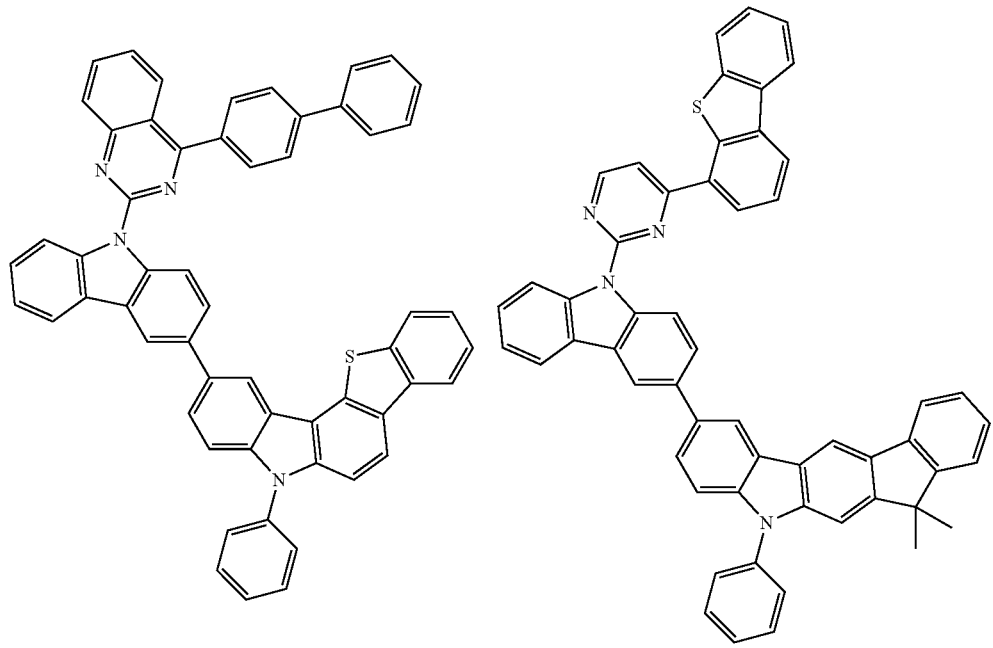
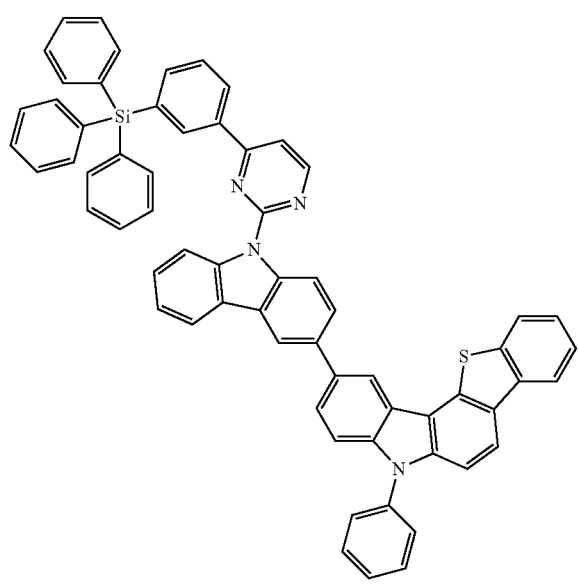

[Formula 47]
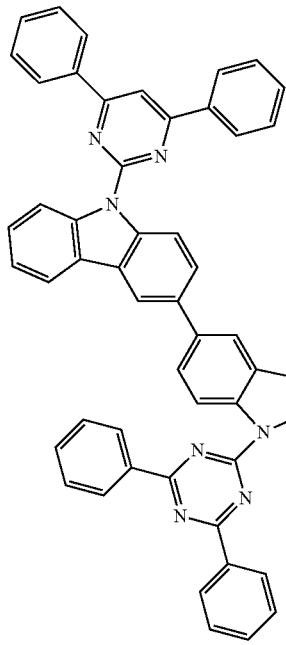
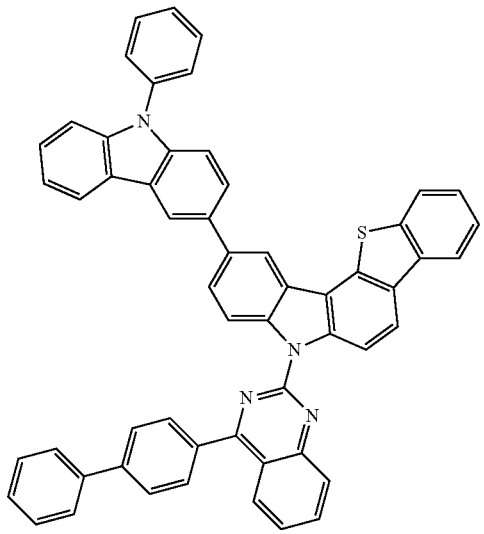
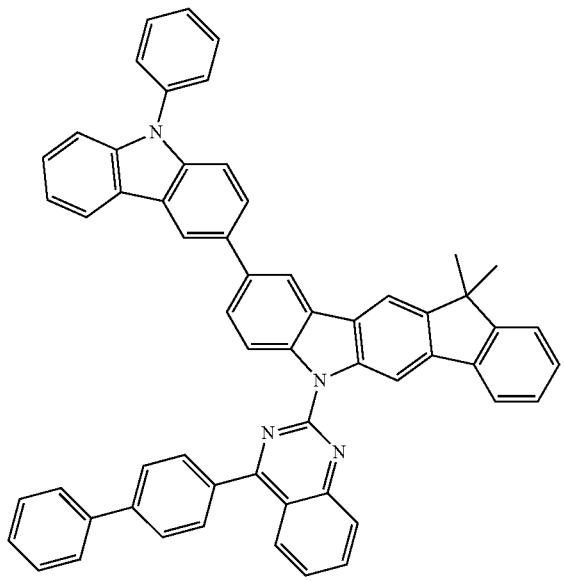

{Formula 48]
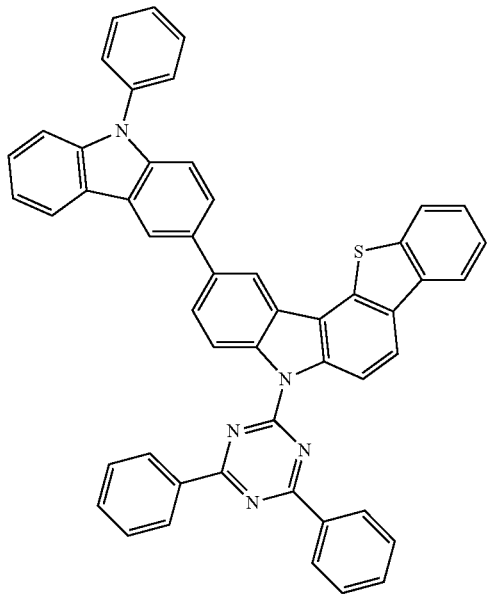
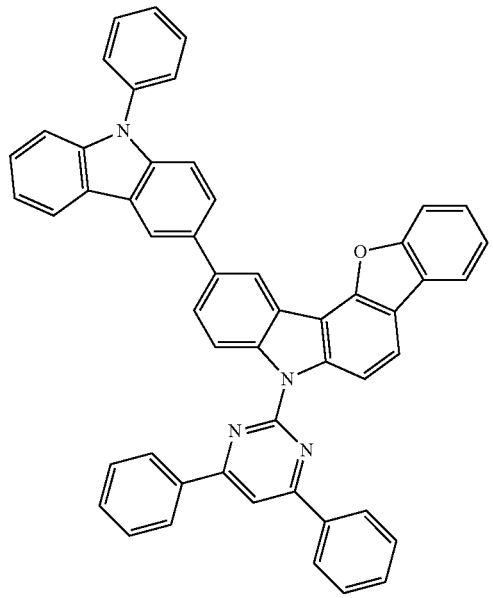
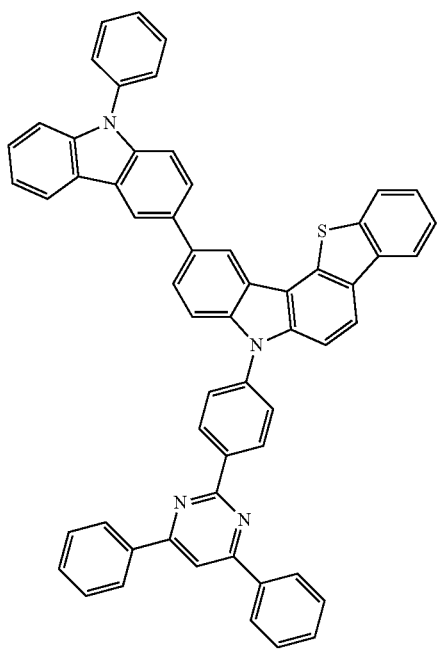

{Formula 49]
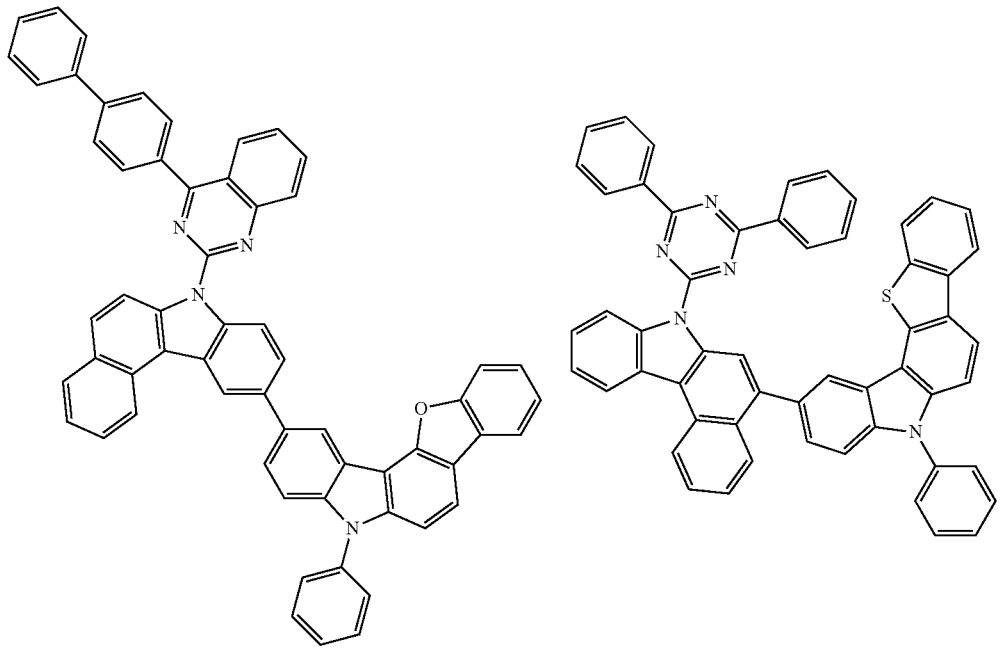
[Formula 50]
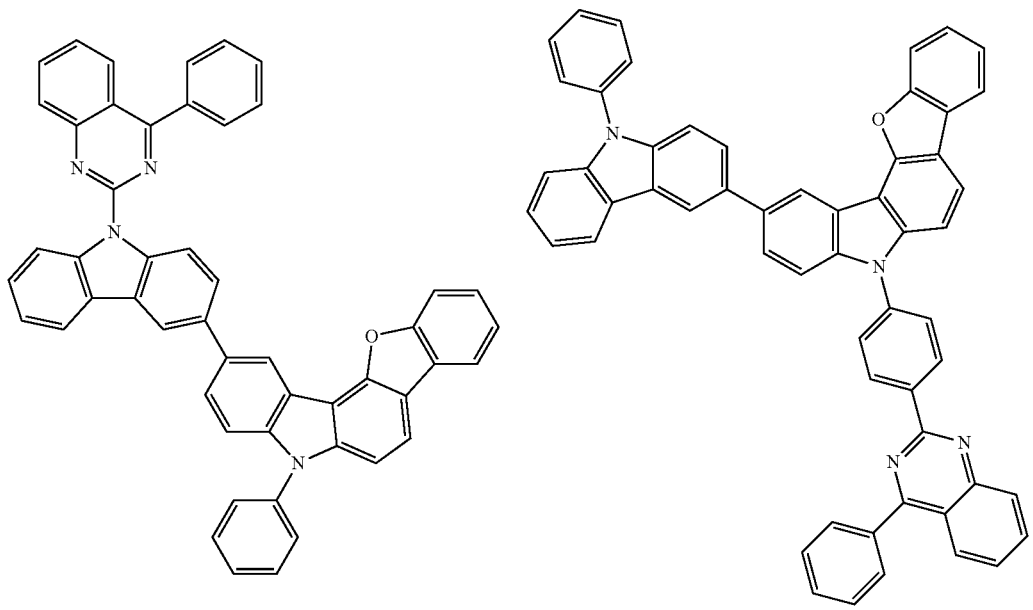

71 72
-continued
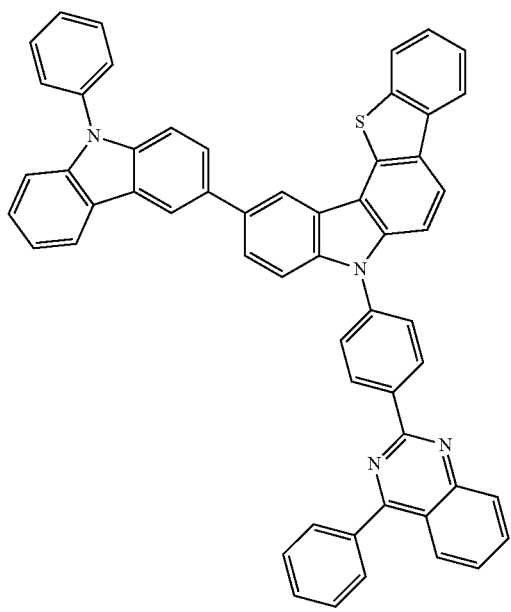
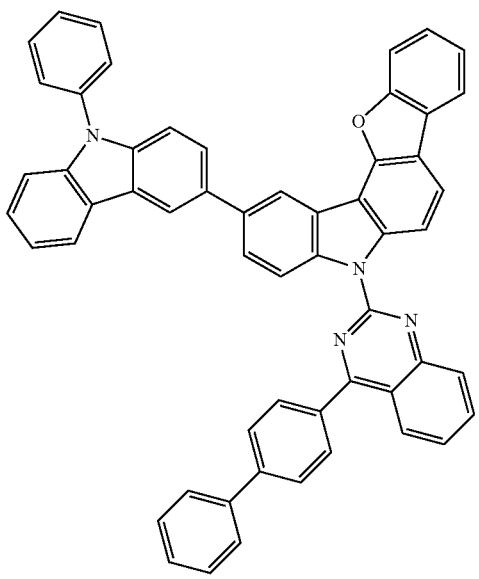
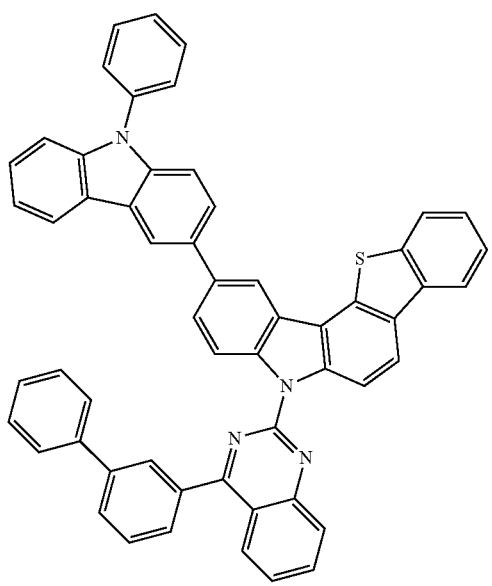
[Formula 51]
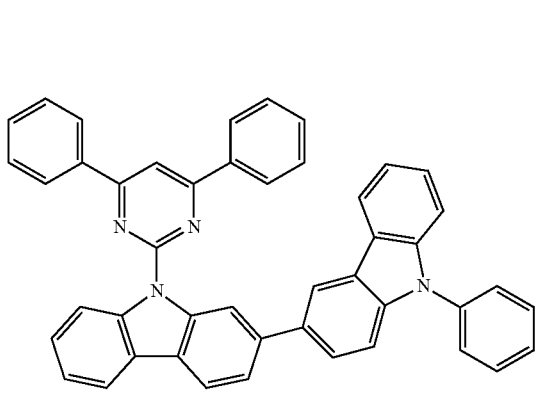
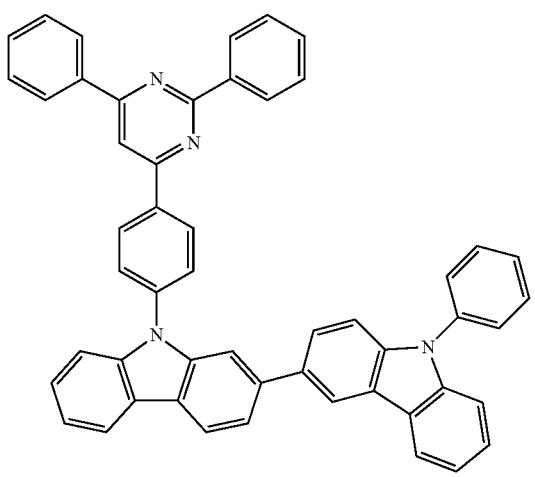

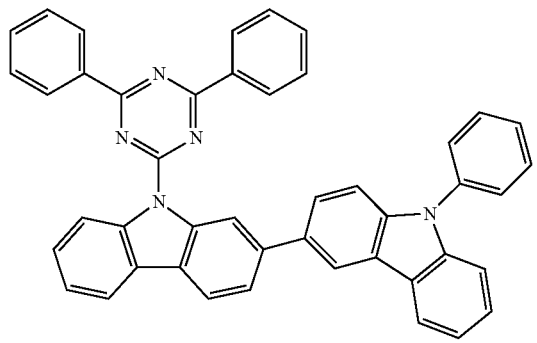
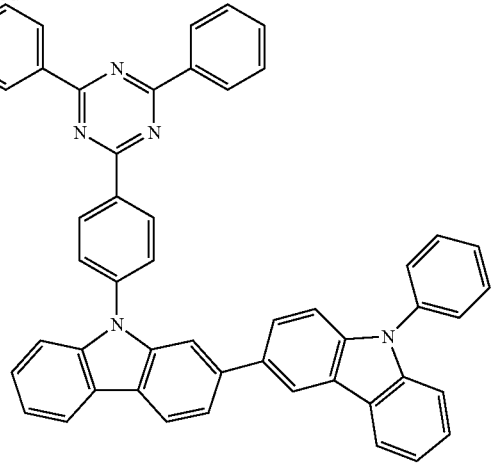
[Formula 52]
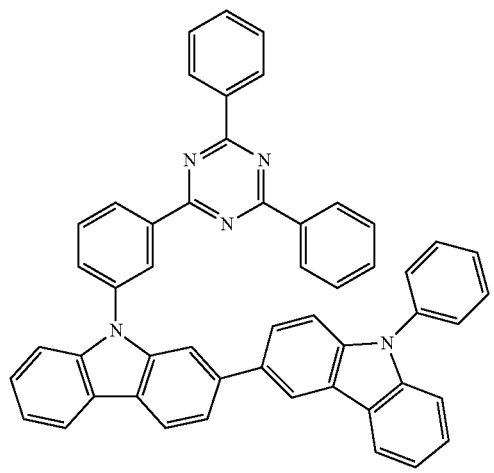
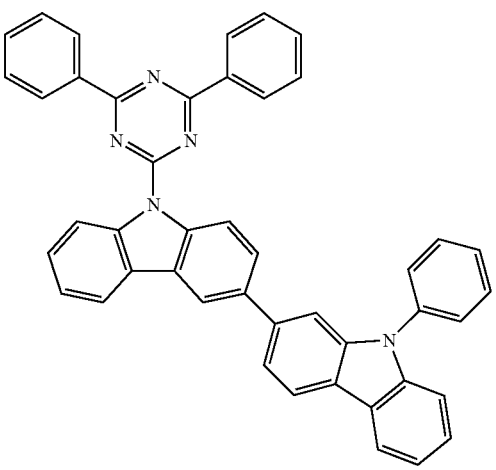
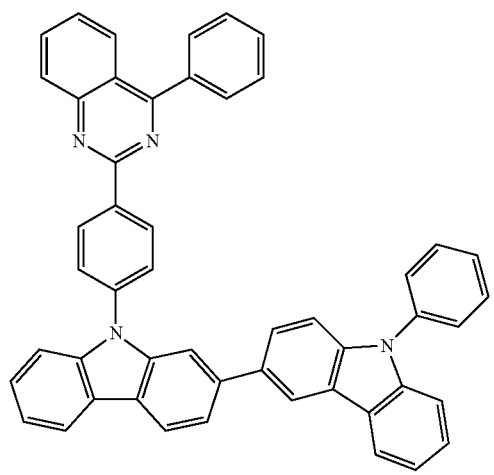

[Formula 53]
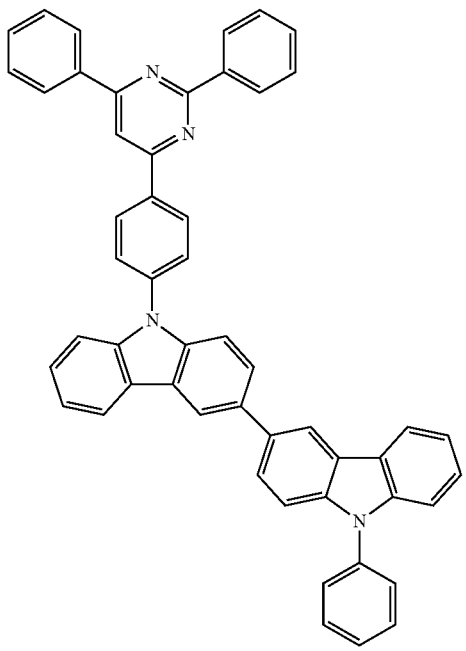
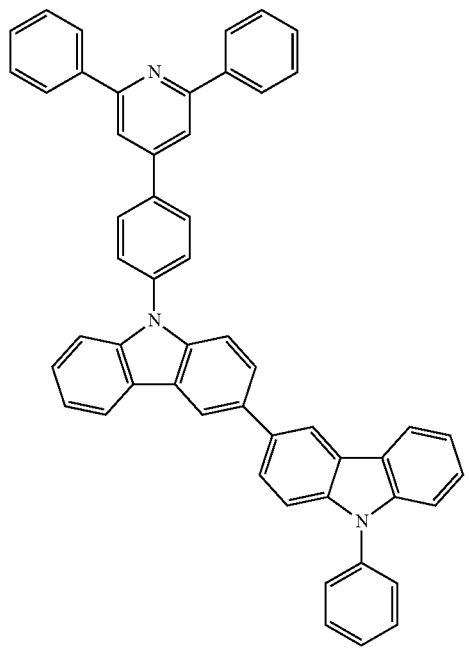
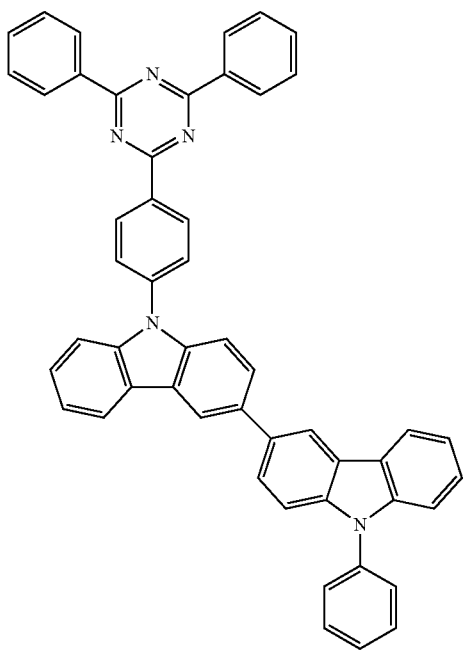

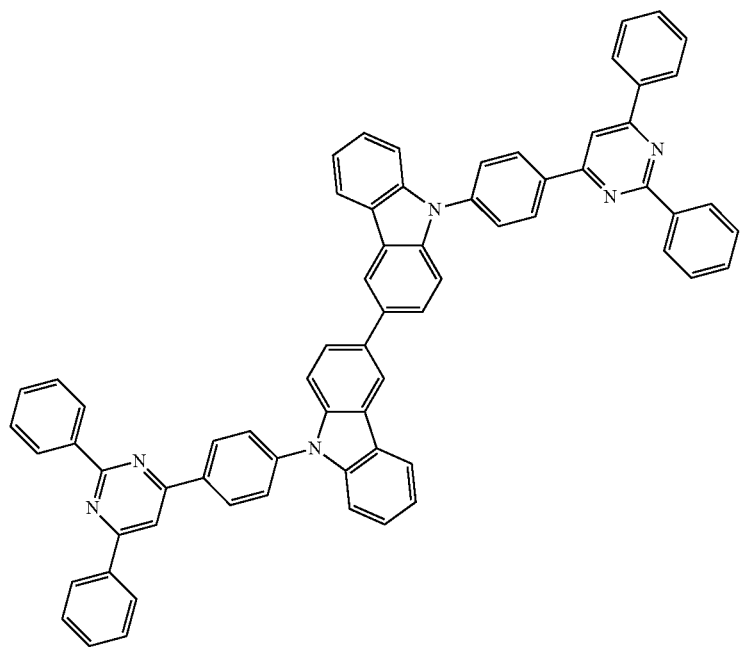
[Formula 54]
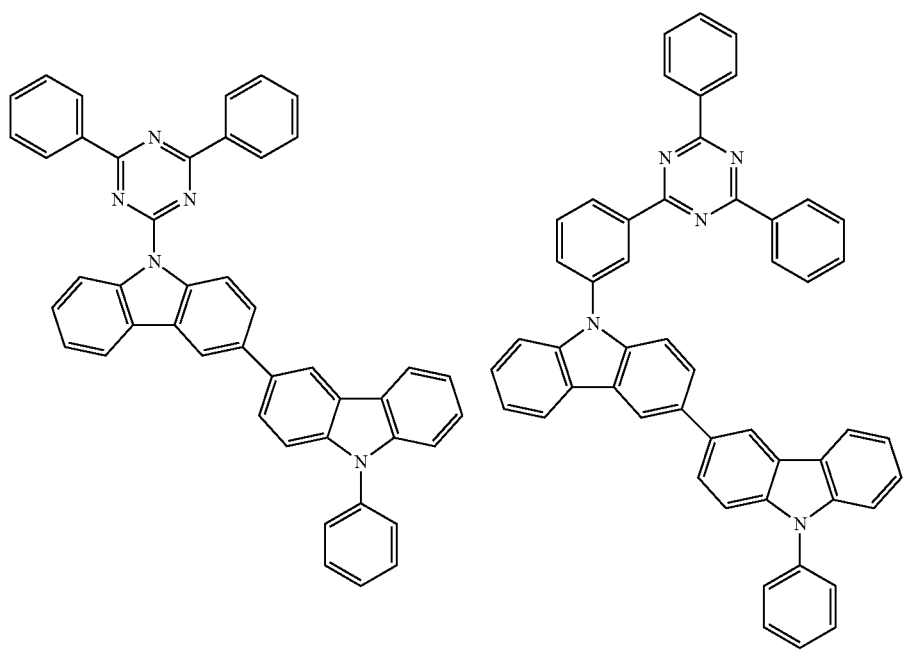

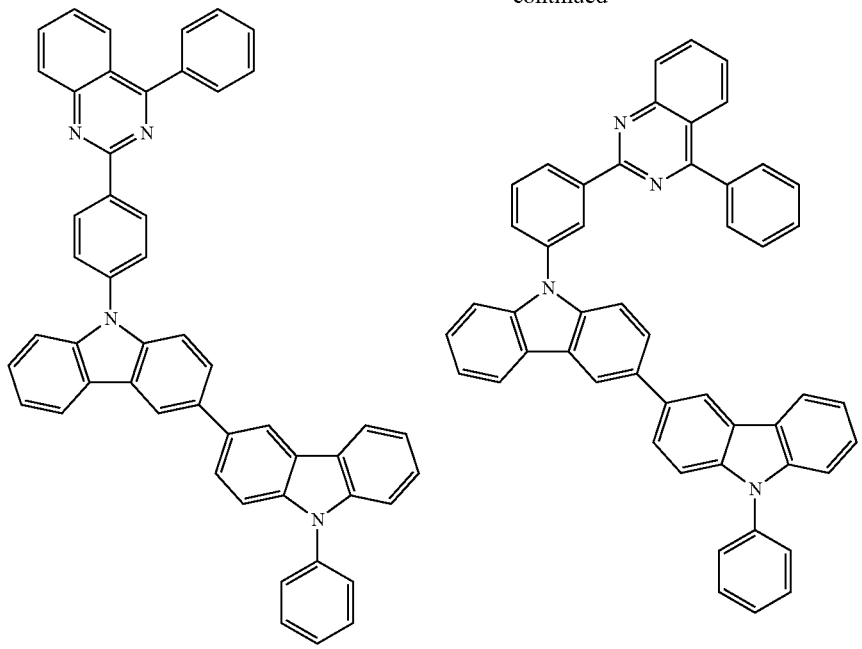
[Formula 55]
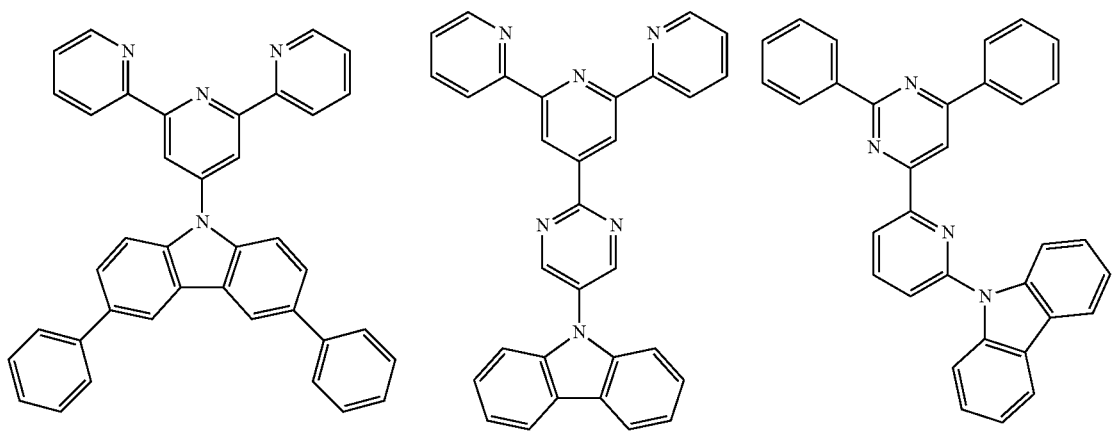
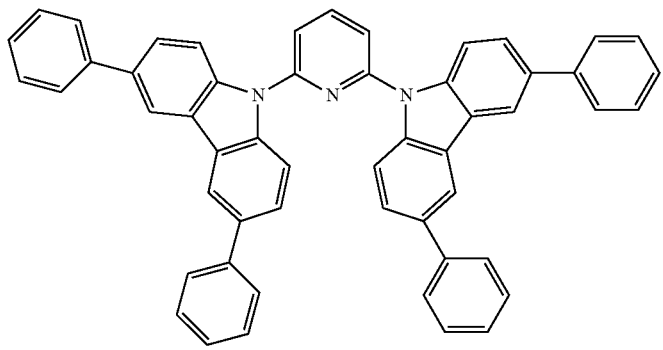

-continued
[Formula 56]
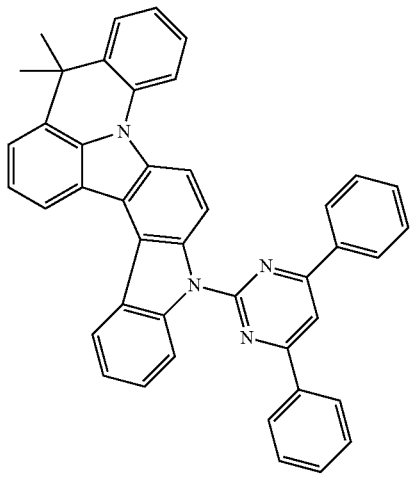
[Formula 57]
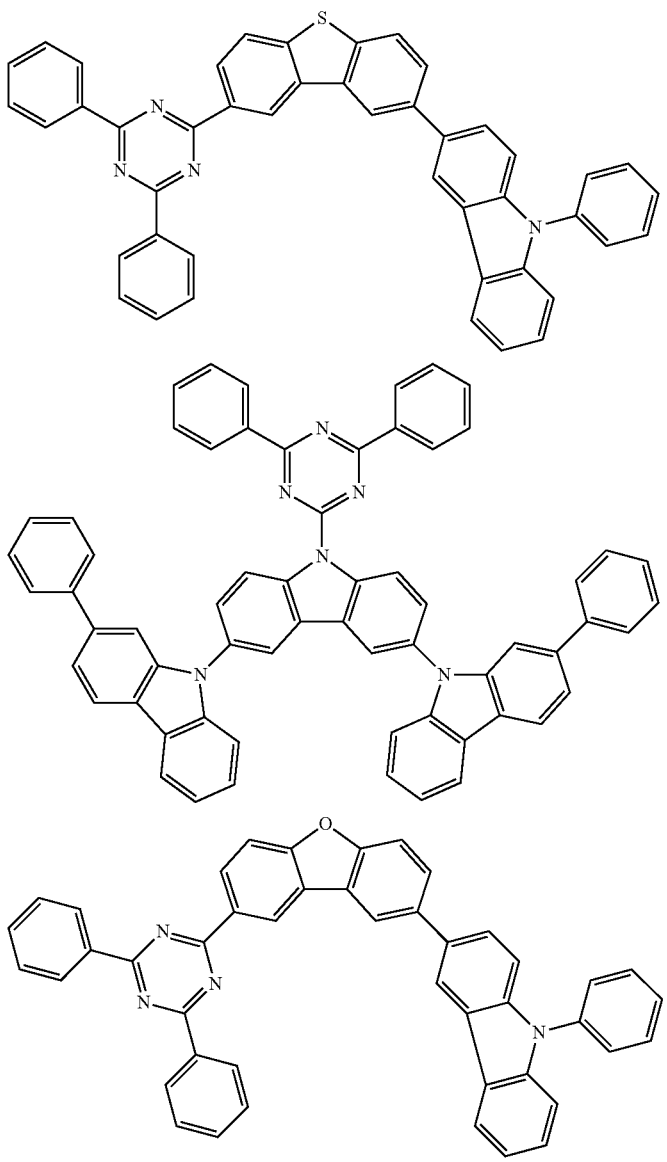

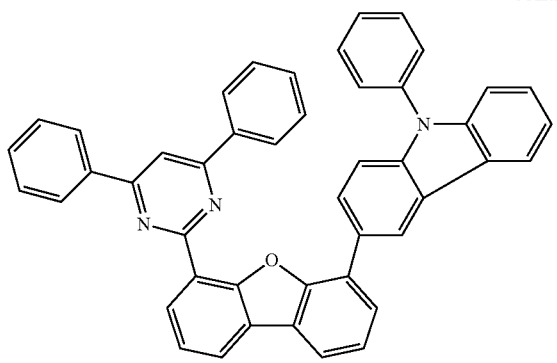
[Formula 58]
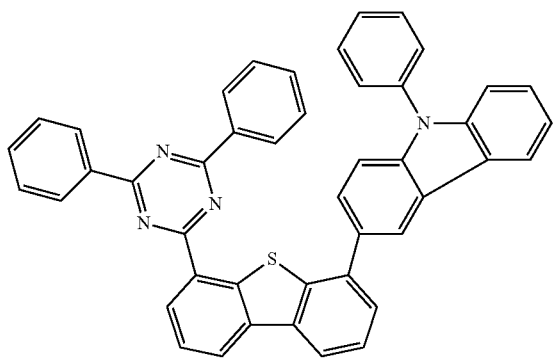
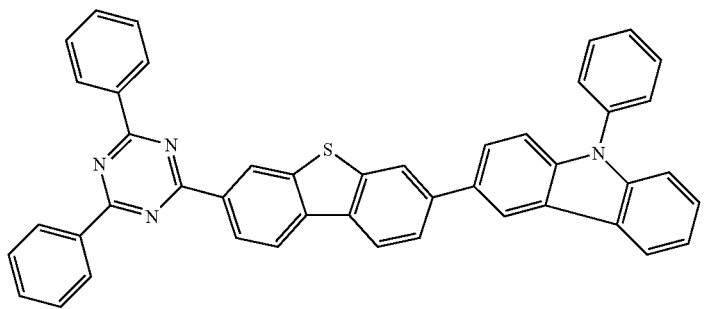
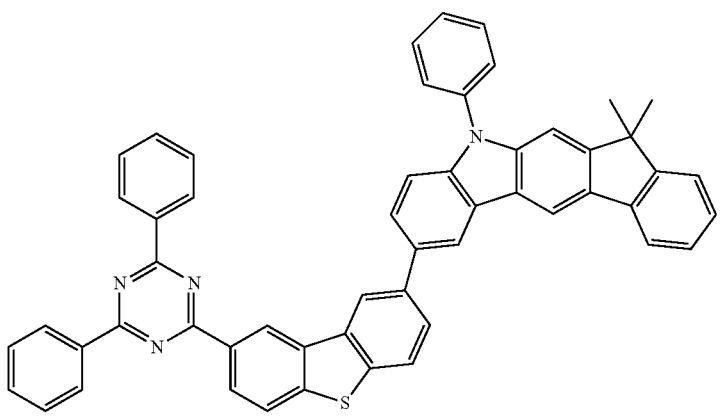

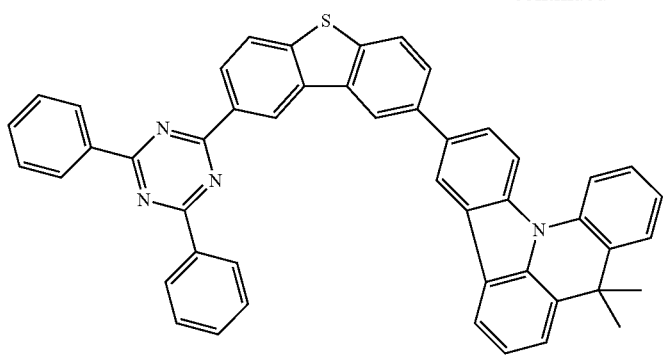
[Formula 59]
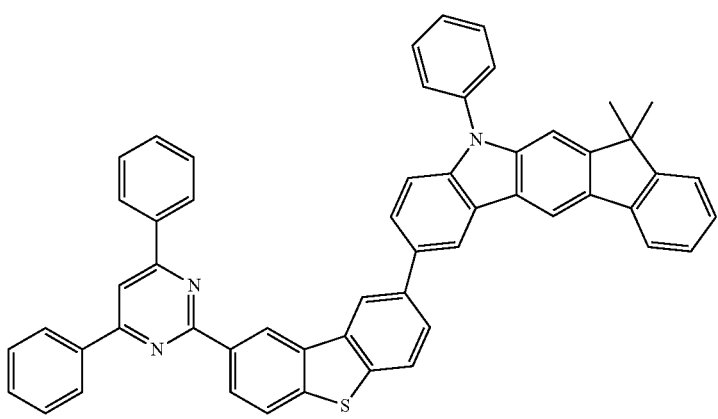
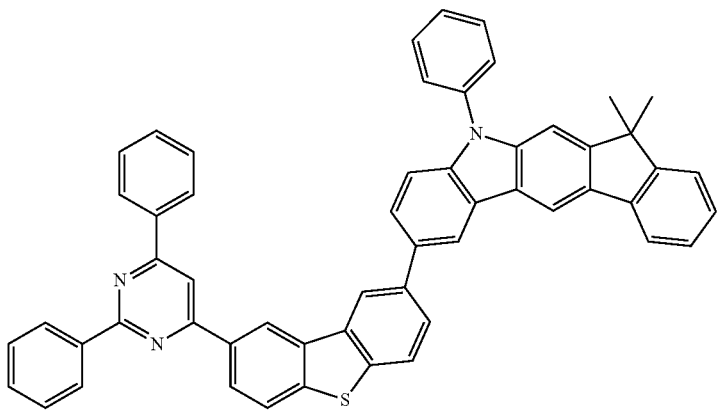

-continued
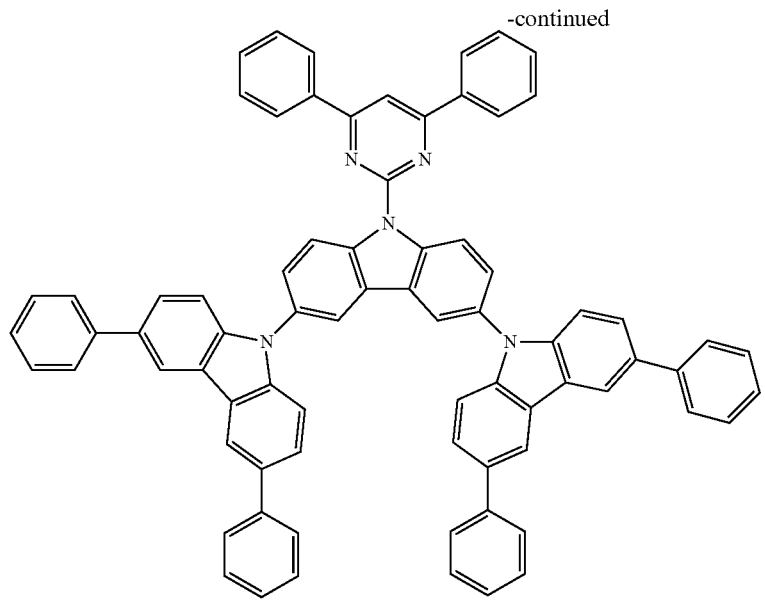
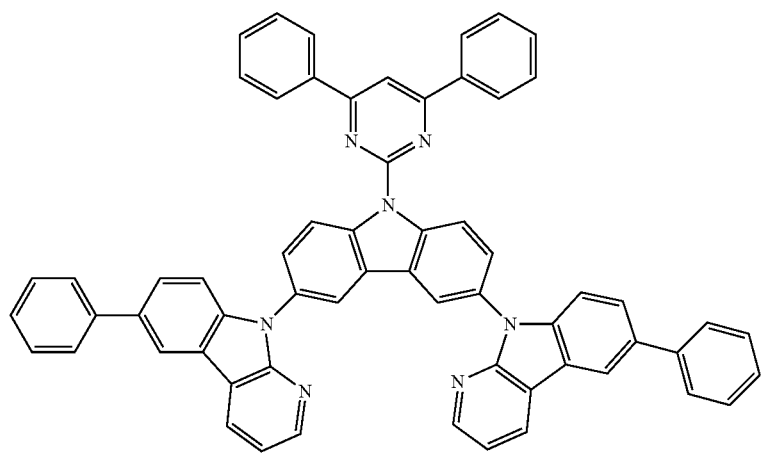
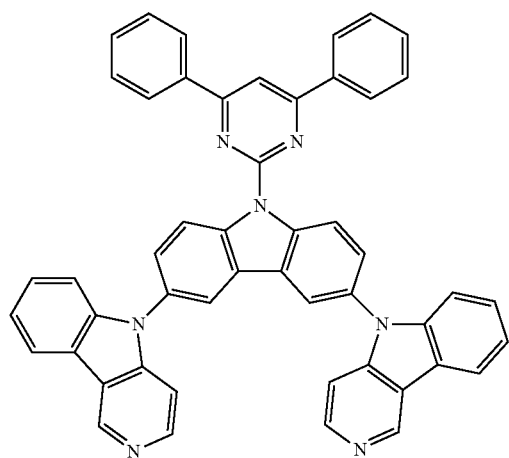

[Formula 60]
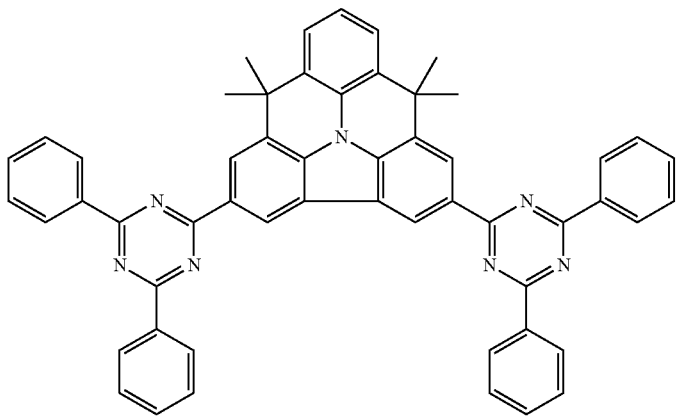
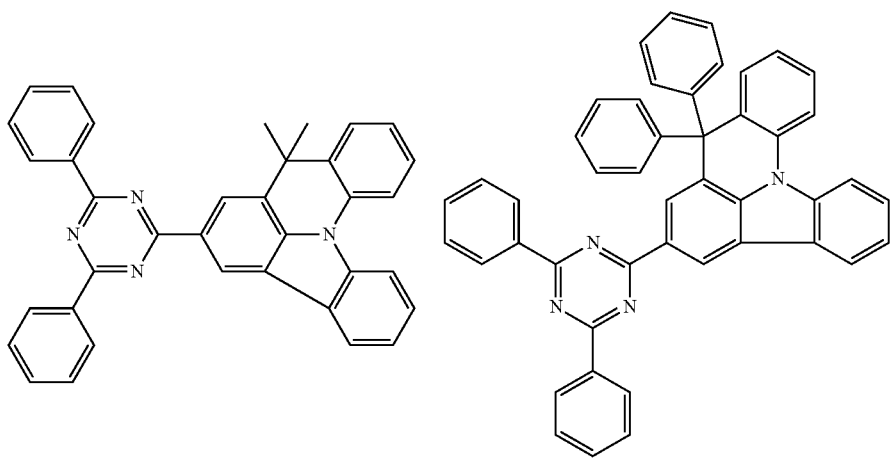
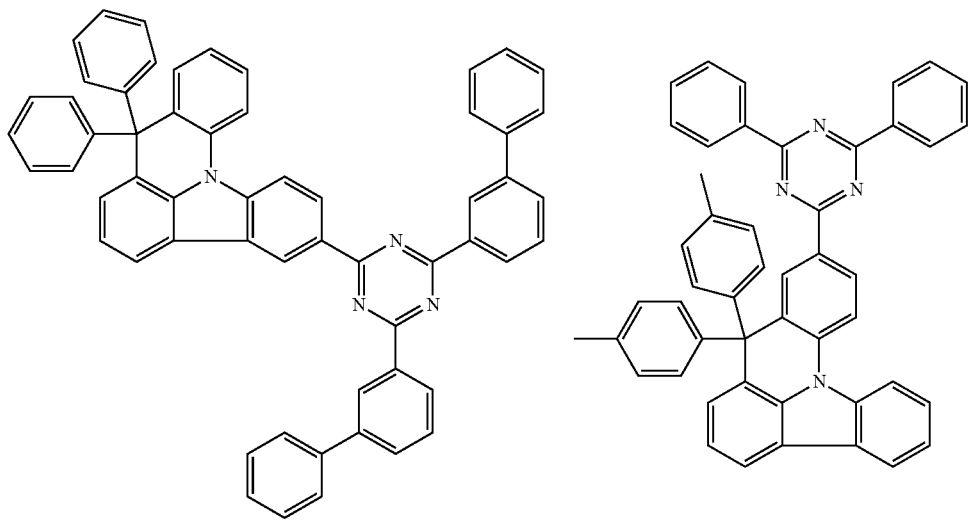

91 92
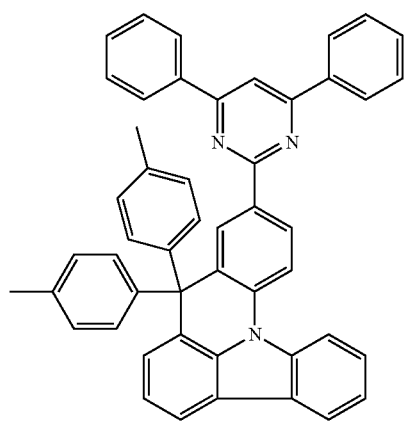
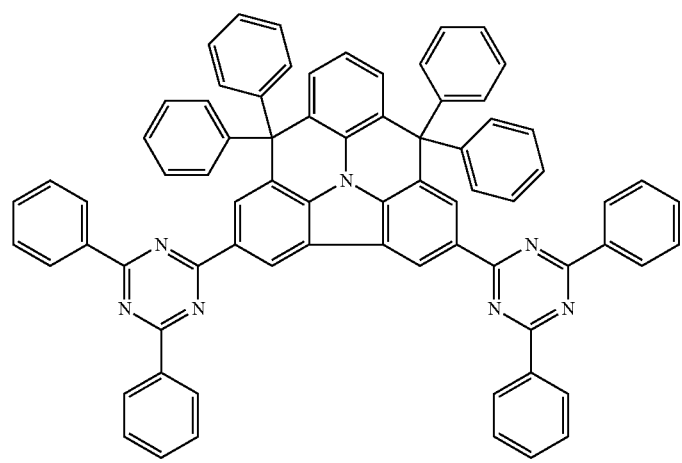
[Formula 61]
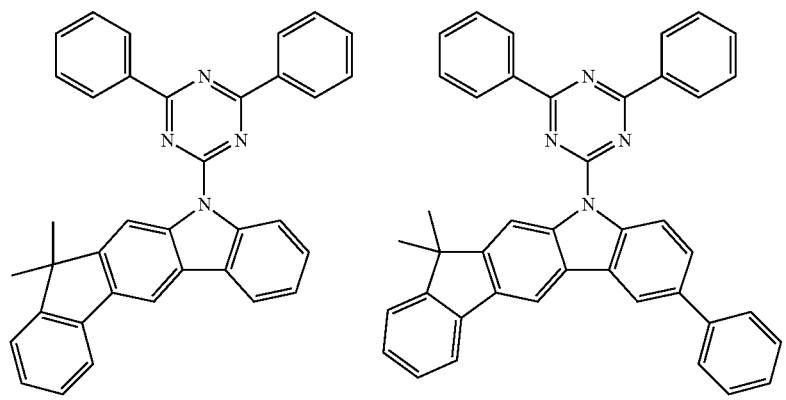
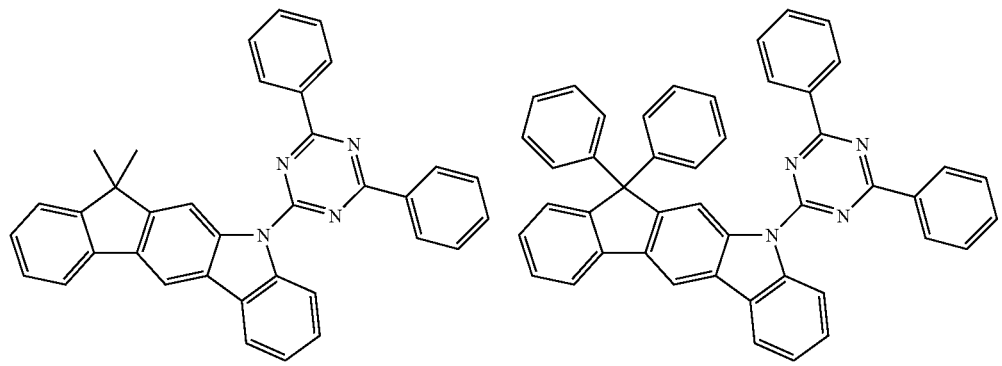
[Formula 62]
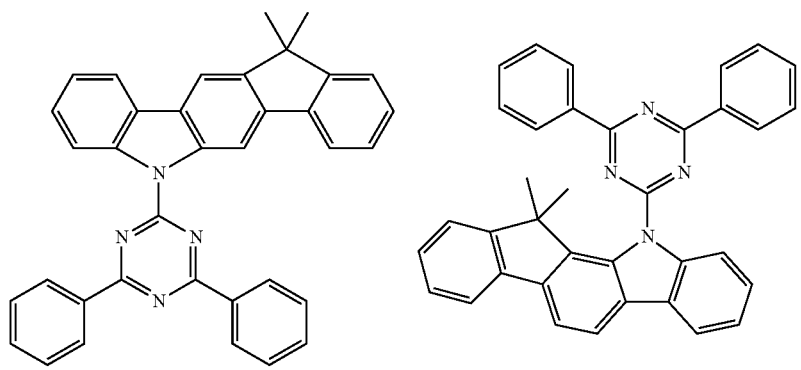

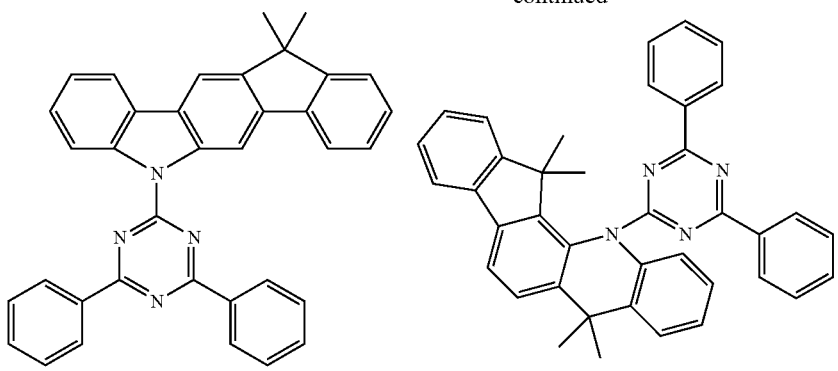
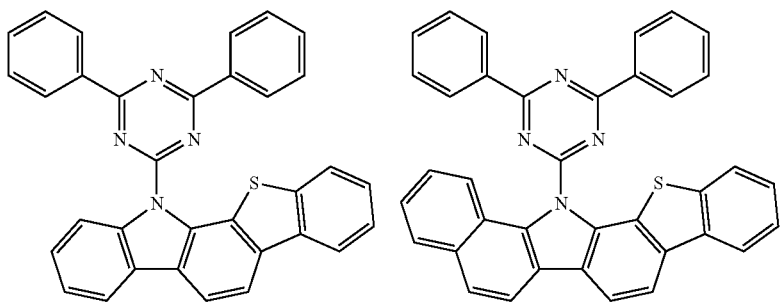
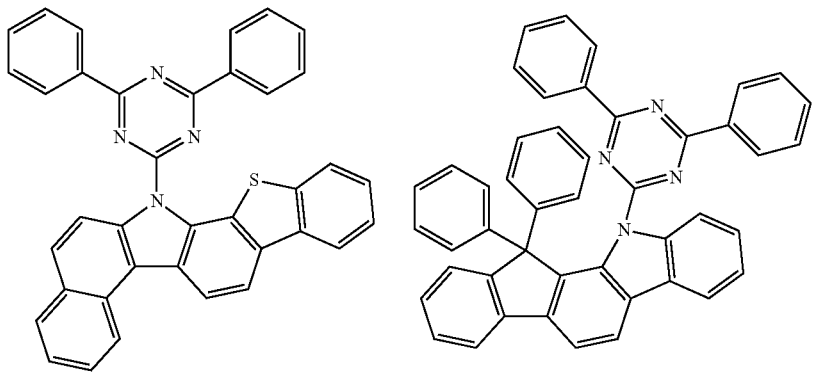
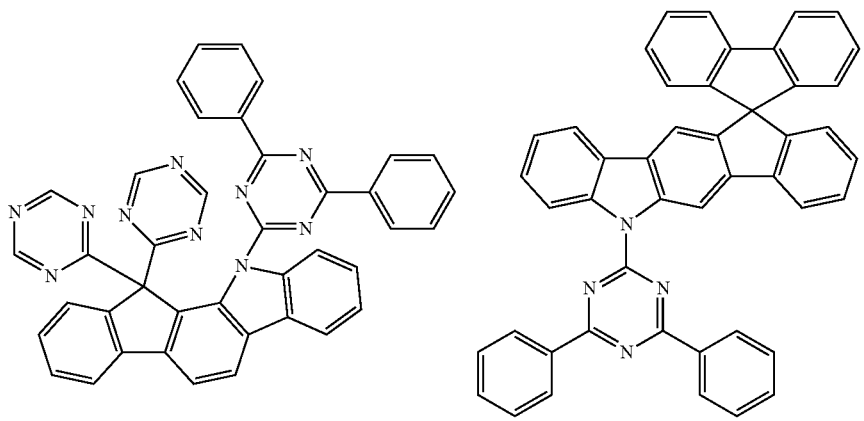

-continued
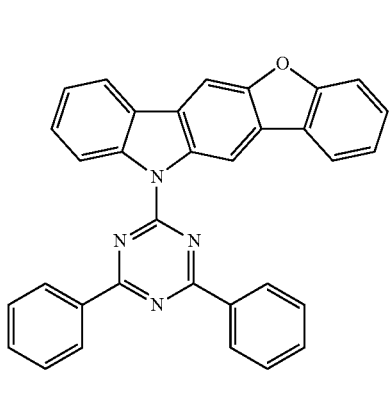
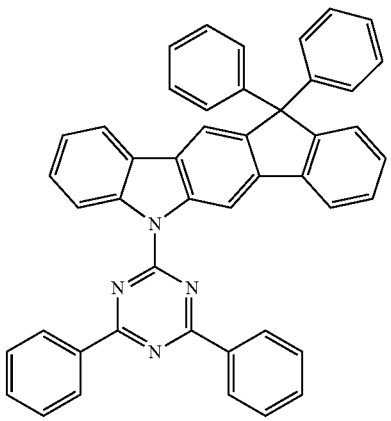
[Formula 63]
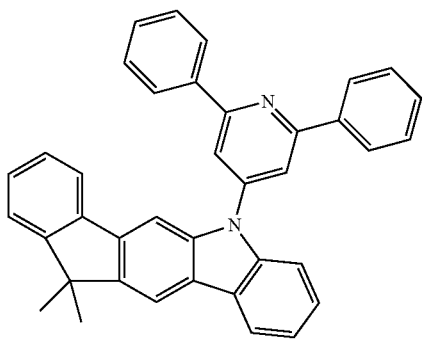
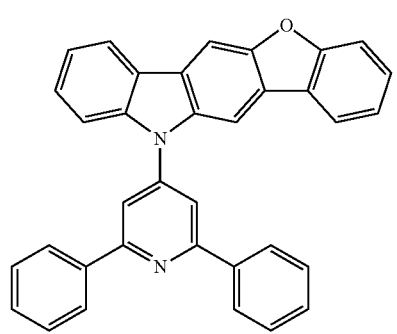
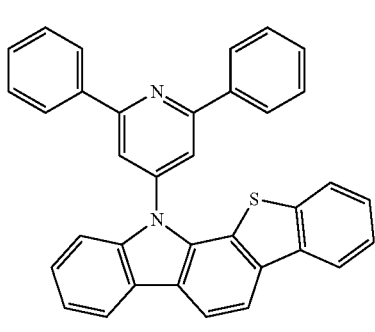
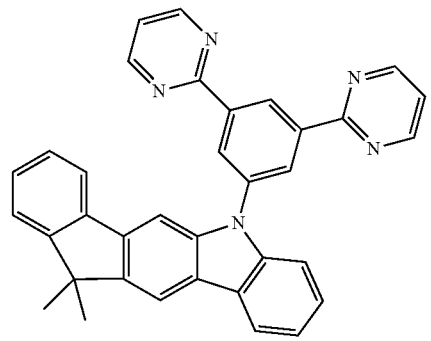
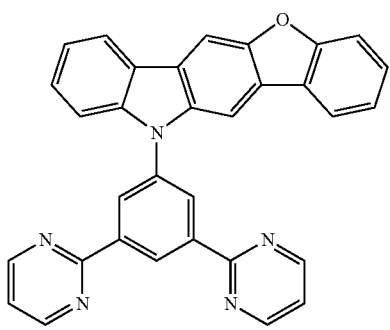
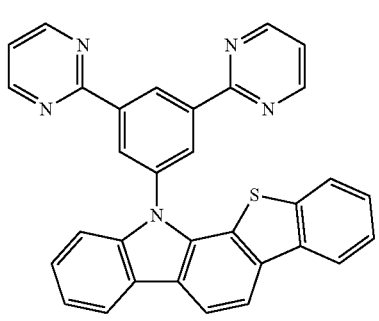

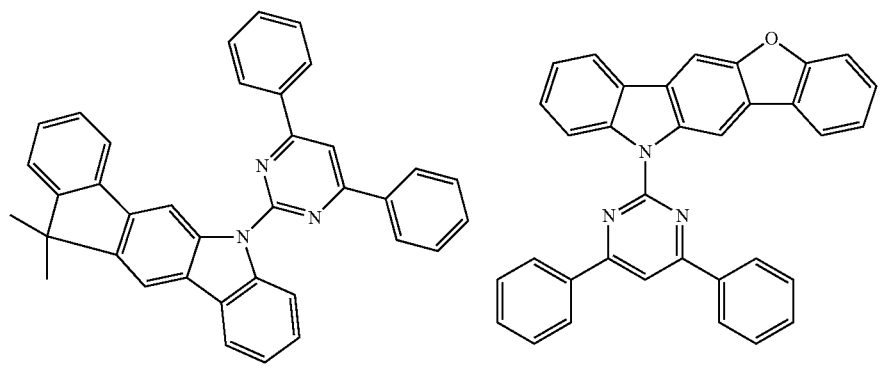
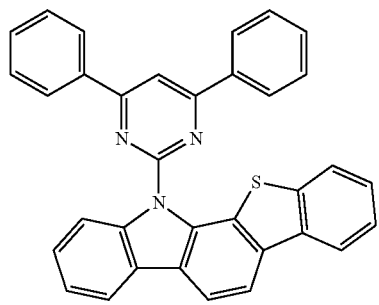
[Formula 64]
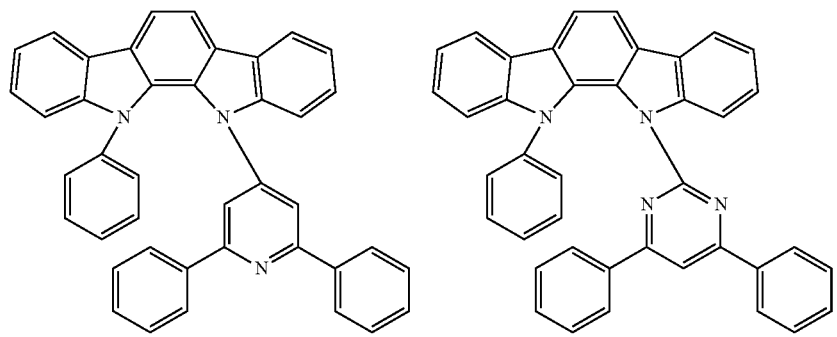
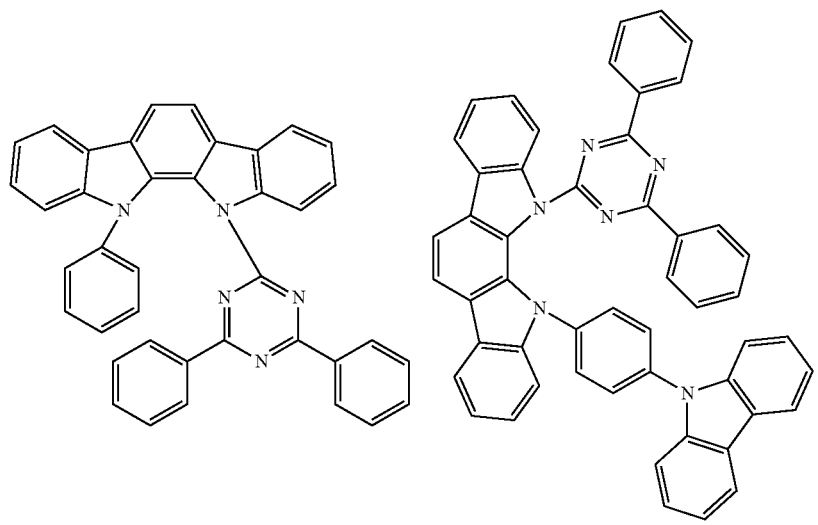

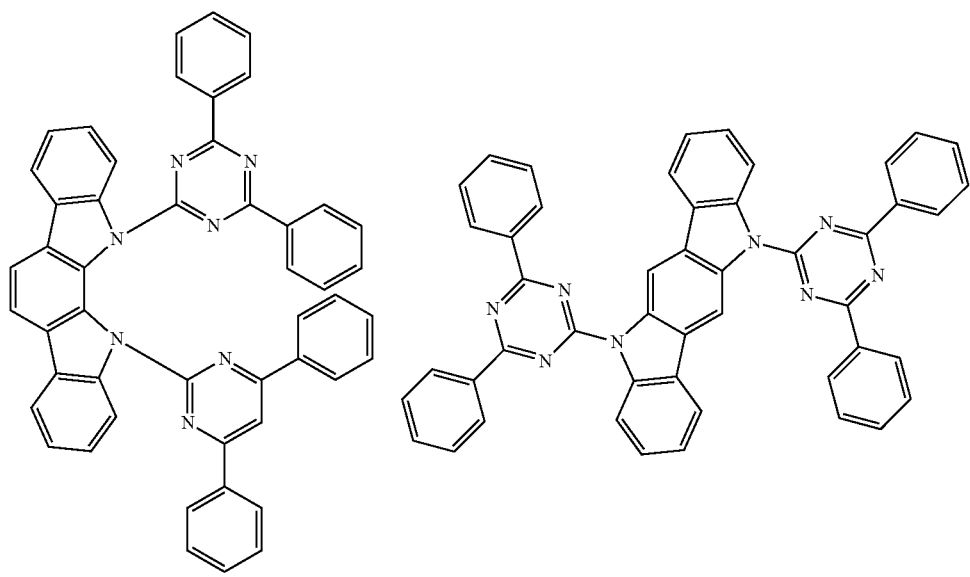
[Formula 65]
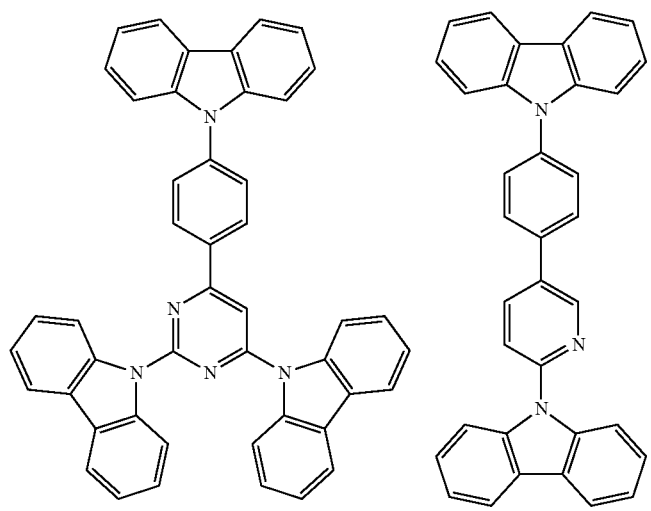
[Formula 66]
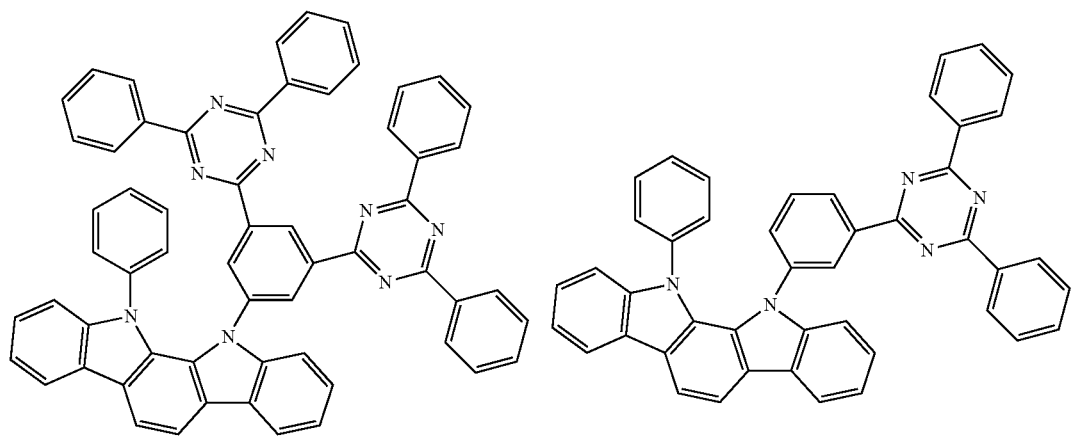

-continued
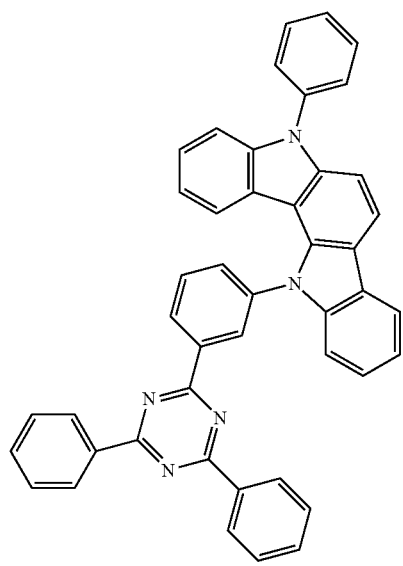
[Formula 67]
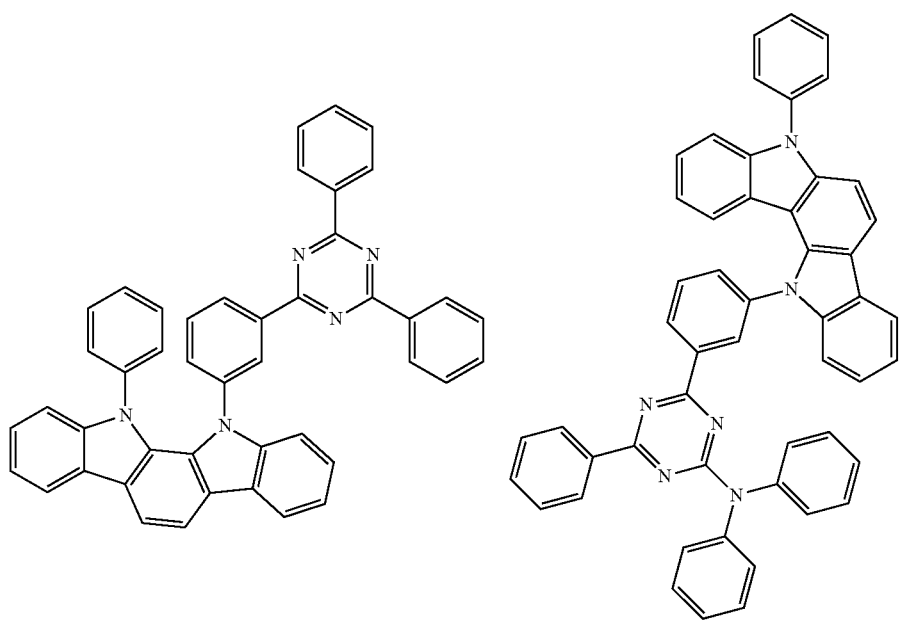
[Formula 68]
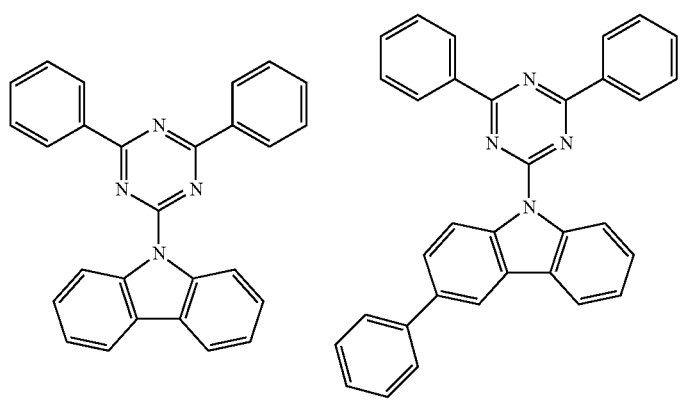

[Formula 69]
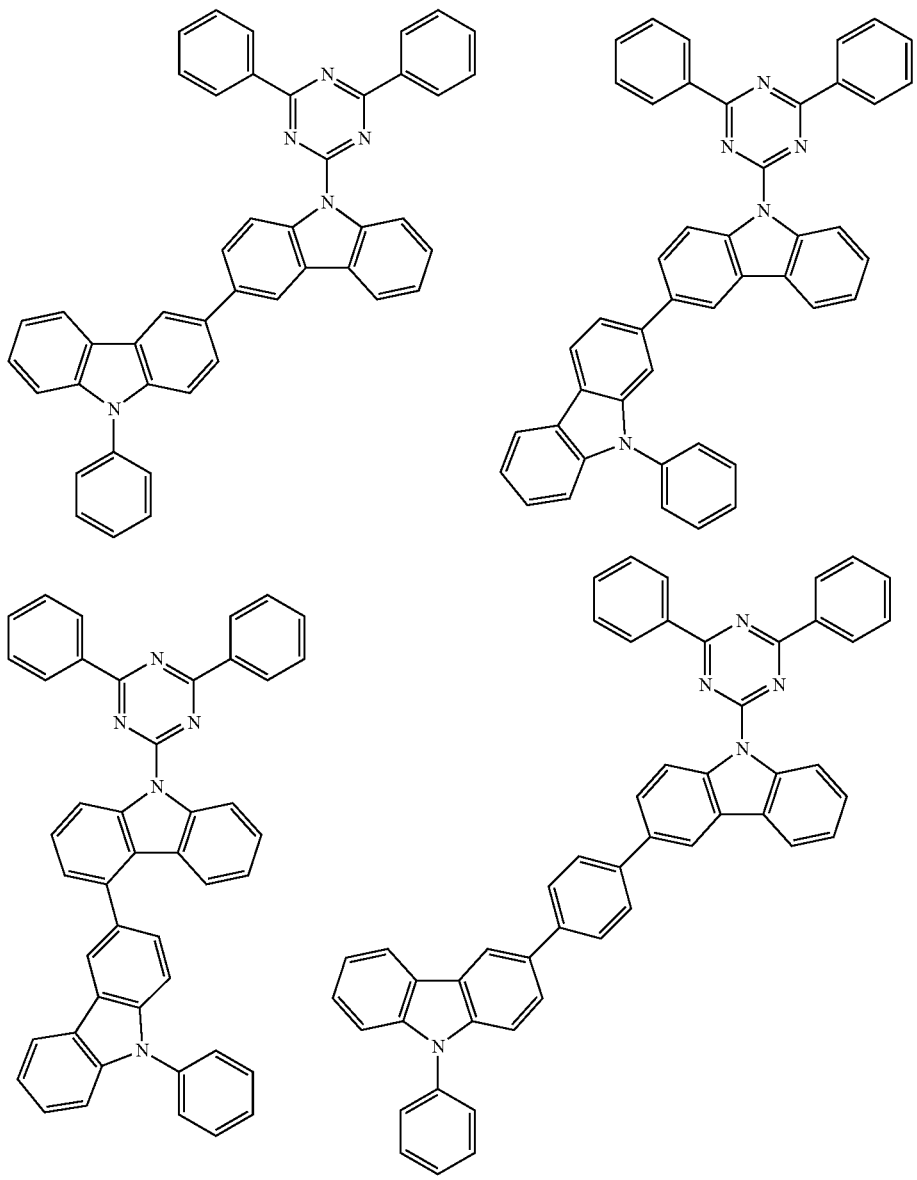
[Formula 70]
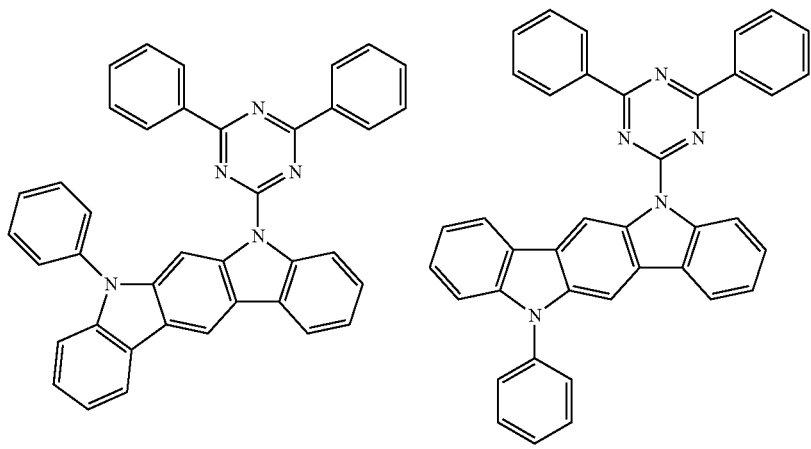

-continued
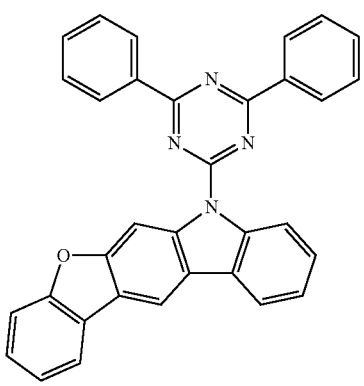
[Formula 71]
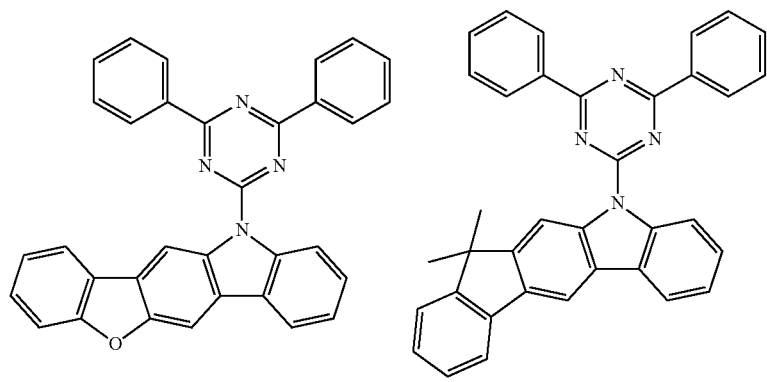
[Formula 72]
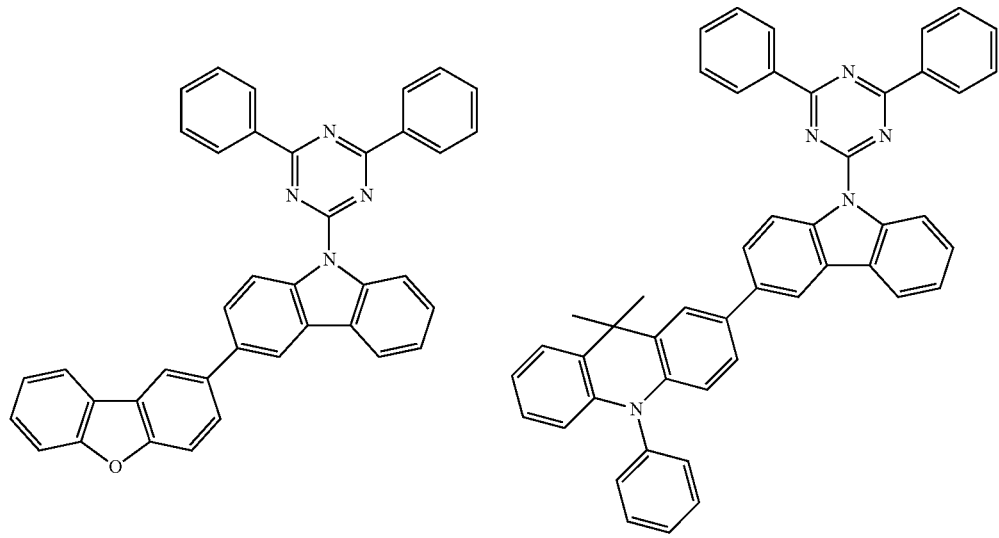

[Formula 73]
-continued
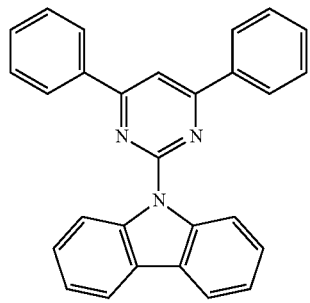
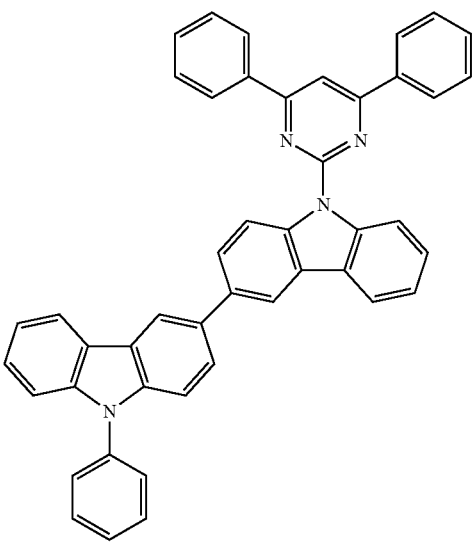
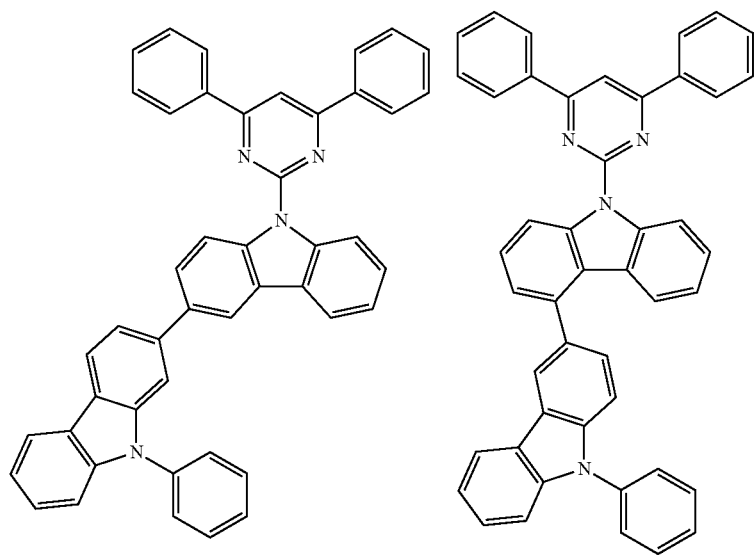
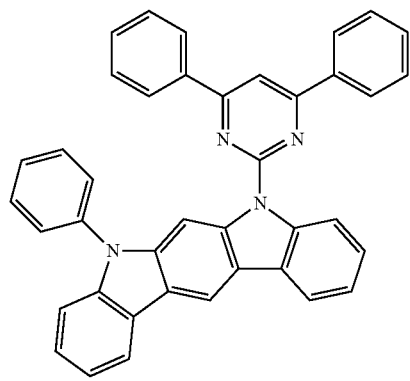

[Formula 74]

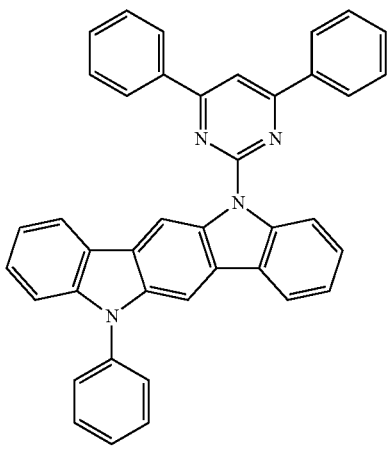
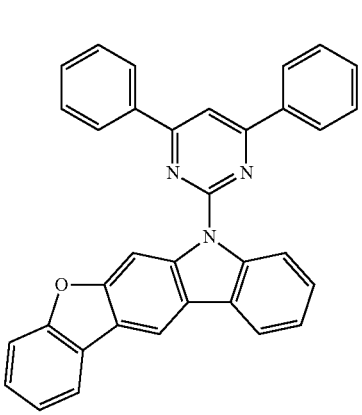
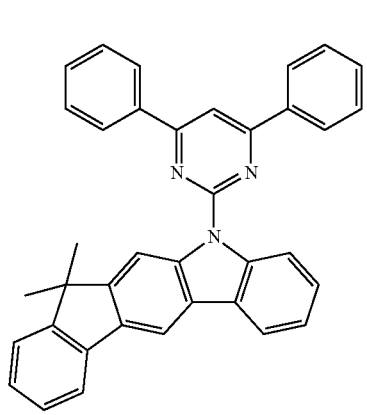

The dopant material in the first exemplary embodiment may be a second compound having a partial structure represented by a formula (30) below and a partial structure represented by a formula (31) below in a molecule.

[Formula 75]

(30)

[Formula 76 area]

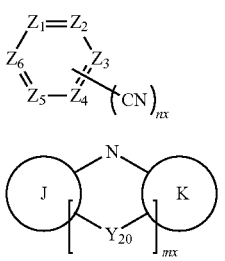

(31)

In the formula (30), CN is a cyano group.

nx is an integer of 1 or more. nx is preferably an integer of 1 to 5, more preferably an integer of 2 to 4.

$Z_1$ to $Z_6$ are each independently a nitrogen atom, a carbon atom to be bonded to CN, or a carbon atom to be bonded to another atom in the molecule of the second compound. For instance, when $Z_1$ is a carbon atom to be bonded to CN, at least one of the other five ($Z_2$ to $Z_6$) is a carbon atom to be bonded to another atom in the molecule of the second compound. The another atom may be an atom in the partial structure represented by the formula (31) or an atom forming a linking group between the partial structures or a substituent.

The second compound in the first exemplary embodiment may have a six-membered ring consisting of $Z_1$ to $Z_6$ or may have a fused ring in which a ring is further fused to the six-membered ring.

In the formula (31), J and K each independently represent a cyclic structure. The cyclic structure J and the cyclic structure K are preferably a five-membered ring or a six-membered ring, in which the five-membered ring or the six-membered ring is preferably an unsaturated ring and the six-membered ring is more preferably an unsaturated ring. The cyclic structure J and the cyclic structure K may be unsubstituted or substituted. mx is 0 or 1. When mx is 1, $Y_{20}$ represents a single bond, an oxygen atom, a sulfur atom, a selenium atom, a carbon atom, silicon atom, or a germanium atom.

The formula (31) is preferably represented by a formula (31a) below.

[Formula 76]

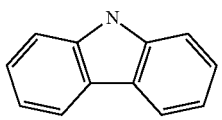

(31a)

The second compound preferably has a structure represented by a formula (31e) below in a molecule.

[Formula 77]

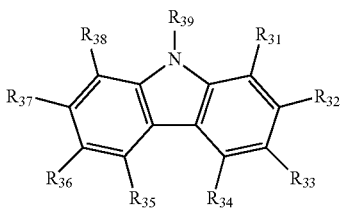

(31e)

In the formula (31e), $R_{31}$ to $R_{39}$ are each independently a hydrogen atom, a halogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted alkoxy group having 1 to 30 carbon atoms, a substituted or unsubstituted aryloxy group having 6 to 30 ring carbon atoms, a substituted or unsubstituted alkylamino group having 2 to 30 carbon atoms, a substituted or unsubstituted arylamino group having 6 to 60 ring carbon atoms, a substituted or unsubstituted alkylthio group having 1 to 30 carbon atoms, a substituted or unsubstituted arylthio group having 6 to 30 ring carbon atoms, or a single bond to be bonded to another atom in a molecule of the second compound. Note that at least one of $R_{31}$ to $R_{39}$ is a single bond to be bonded to another atom in the molecule of the second compound.

In the formula (31e), at least one of combinations of substituents selected from $R_{31}$ to $R_{39}$ may be mutually bonded to form a cyclic structure. Specifically, in the formula (31e), in carbon atoms of the six-membered ring or a nitrogen atom of the five-membered ring to which $R_{31}$ to $R_{39}$ are bonded, substituents selected from $R_{31}$ to $R_{38}$, which are respectively bonded to adjacent carbon atoms, and $R_{39}$ bonded to the nitrogen atom of the five-membered ring can form a cyclic structure. Specifically, in the formula (31e), at least one of combinations of substituents, namely, a combination of $R_{31}$ and $R_{32}$, a combination of $R_{32}$ and $R_{33}$, a combination of $R_{33}$ and $R_{34}$, a combination of $R_{34}$ and $R_{35}$, a combination of $R_{35}$ and $R_{36}$, a combination of $R_{36}$ and $R_{37}$, a combination of $R_{37}$ and $R_{38}$, a combination of $R_{38}$ and a combination of $R_{39}$, and $R_{31}$ can be mutually bonded to form a cyclic structure. In the first exemplary embodiment, the cyclic structure formed by bonding the substituents is preferably a fused ring. For instance, when the cyclic structure is formed in the formula (31e), the formed structure is preferably a fused six-membered cyclic structure.

The dopant material of the first exemplary embodiment can be synthesized by a known synthesizing method.

Host Material

The host material of the first exemplary embodiment is exemplified by any host material applicable to the organic EL device without specific limitation.

In the first exemplary embodiment, a difference $\Delta ST(H)$ between singlet energy $EgS(H)$ of the host material and an energy gap $Eg_{77K}(H)$ at 77K of the host material satisfies a numerical formula (Numerical Formula 2) below, $$\Delta ST(H)=EgS(H)-Eg_{77K}(H)<0.3 \text{ (eV)} \quad \text{(Numerical Formula 2).}$$

In the first exemplary embodiment, the energy gap $Eg_{77K}(H)$ at 77K of the host material is preferably larger than the energy gap $Eg_{77K}(D)$ at 77K of the dopant material. $\Delta ST(H)$ is preferably less than 0.2 eV.

In the first exemplary embodiment, the singlet energy $EgS(D)$ of the dopant material and the singlet energy $EgS(H)$ of the host material satisfy a numerical formula (Numerical Formula 3) below, $$EgS(H)>EgS(D) \quad \text{(Numerical Formula 3).}$$

In the first exemplary embodiment, the energy gap $Eg_{77K}(H)$ at 77K of the host material is preferably larger than the energy gap $Eg_{77K}(D)$ at 77K of the compound used as the dopant material.

The host material of the first exemplary embodiment is preferably a compound represented by a formula (2) below. However, the dopant material is not limited to the compound represented by the formula (2) below.

[Formula 78]

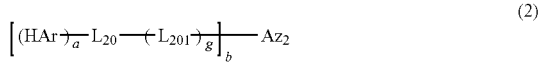

(2)

In the formula (2), $L_{20}$ represents a single bond, a substituted or unsubstituted (a+1)-valent aromatic hydrocarbon group or a substituted or unsubstituted (a+1)-valent heterocyclic group.

In the formula (2), $L_{201}$ is a substituted or unsubstituted divalent aromatic hydrocarbon group or a substituted or unsubstituted divalent heterocyclic group.

In the formula (2), a is an integer of 1 to 6 and b is an integer of 1 to 6. a and b are each independently preferably an integer of 1 to 3, more preferably 1 or 2. When a is 2 or more, HAr bonded to $L_{20}$ is 2 or more and may be mutually the same or different.

In the formula (2), g is an integer of 0 to 2, preferably 0 or 1. When g is from 1 to 2, $L_{20}$ and $L_{201}$ may independently be the same or different. When g is 2, two $L_{201}$ may independently be the same or different. When b is 2 or more, a plurality of moieties represented by a formula (2-1) to be bonded to $Az_2$ may be mutually the same or different.

[Formula 79]

(2-1)

In the formula (2), HAr is a group derived from a structure represented by a formula (20) below.

[Formula 80]

(20)

In the formula (20), $X_{20}$ represents a single bond, an oxygen atom, a sulfur atom, a carbonyl group, $NR_9$, $CR_{10}R_{11}$, $SiR_{12}R_{13}$ or $GeR_{14}R_{15}$. $R_9$ to $R_{15}$ each independently represent the same as $R_1$ to $R_8$ described above. In the formula (20), $X_{20}$ is preferably an oxygen atom, a sulfur atom, a carbonyl group, $NR_9$, $CR_{10}R_{11}$, $SiR_{12}R_{13}$ or $GeR_{14}R_{15}$.

The cyclic structure represented by the formula (20) is a cyclic structure selected from the group consisting of cyclic structures represented by formulae (20b) to (20i) below.

[Formula 81]

(20b)

(20c)

(20d)
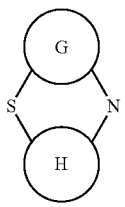

(20e)

(20f)

(20g)

(20h)
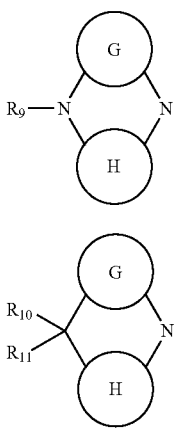

(20i)
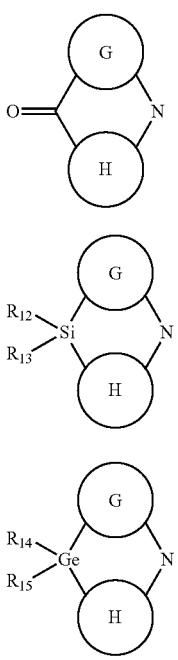

In the formulae (20), (20b) to (20i), G and H each independently represent a substituted or unsubstituted cyclic structure. When at least one of the cyclic structure G and the cyclic structure H have a plurality of substituents, adjacent ones of the substituents may be mutually bonded to form a ring. The ring to be formed may be either a saturated ring or an unsaturated ring.

The substituent at this time is preferably an electron-donating substituent. Moreover, adjacent substituents preferably further form an electron-donating ring.

When at least one of the cyclic structure A and the cyclic structure B has a substituted or unsubstituted heterocyclic structure in the formulae (20) and (20b) to (20i), the heterocyclic structure has a partial structure represented by a formula (20-2) below.

[Formula 82]

 (20-2)

The group derived from the structure represented by the formula (20) is preferably a group represented by a formula (20-1) below.

[Formula 83]

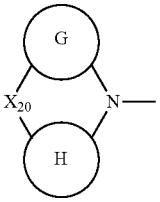 (20-1)

In the formula (20-1), $X_{20}$ represents the same as $X_{20}$ of the formula (20). In other words, the group represented by the formula (20-1) is a group selected from the group consisting of groups represented by formulae (20b-1) to (20i-1) below.

[Formula 84]

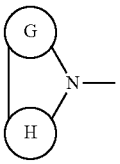 (20b-1)

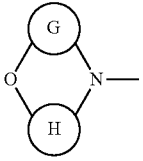 (20c-1)

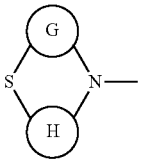 (20d-1)

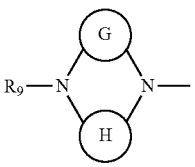 (20e-1)

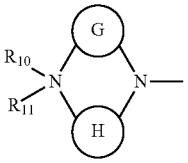 (20f-1)

-continued

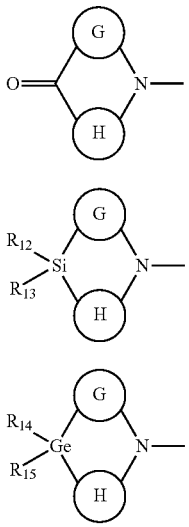
(20g-1)

(20h-1)

(20i-1)

In the formulae (20b-1) to (20i-1), the cyclic structure G and the cyclic structure H respectively represent the same as the cyclic structure G and the cyclic structure H in the formulae (20) and (20b) to (20i).

In the exemplary embodiment, HAr of the formula (2) is preferably a group derived from a structure represented by a formula (2B) below.

[Formula 85]

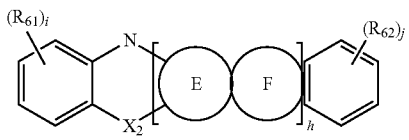
(2B)

In the formula (2B), $X_2$ represents the same as $X_{20}$ of the formula (20). $X_2$ is preferably an oxygen atom, a sulfur atom, a carbonyl group, $NR_9$, $CR_{10}R_{11}$, $SiR_{12}R_{13}$ or $GeR_{14}R_{15}$.

In the formula (2B), $R_{61}$ and $R_{62}$ each independently represent the same as $R_1$ to $R_8$ described above. A plurality of $R_{61}$ may be mutually the same or different. A plurality of $R_{62}$ may be mutually the same or different. Adjacent ones of $R_{61}$ may be mutually bonded to form a ring and adjacent ones of $R_{62}$ may be mutually bonded to form a ring. In the formula (2B), $R_{61}$ to $R_{62}$ are respectively bonded to carbon atoms forming the six-membered ring.

In the formula (2B), i and j are 4.

In the formula (2B), E represents a cyclic structure represented by a formula (2h) below and F represents a cyclic structure represented by a formula (2i) or (2j) below. Each of the cyclic structure E and the cyclic structure F is fused to an adjacent cyclic structure at any position. In the formula (2B), h is an integer of 0 to 4. Note that h is a repeating unit of a linking cyclic structure in which the cyclic structure E and the cyclic structure F are fused to each other. When h is 2 or more, a plurality of cyclic structures E and F may be the same or different.

[Formula 86]

(2h)

[Formula 87]

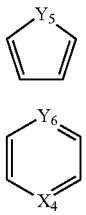
(2i)

(2j)

In the formula (2h), when $R_{63}$ and $R_{64}$ are substituents at adjacent positions, $R_{63}$ and $R_{64}$ may be bonded to form a ring. In the formula (2h), $R_{63}$ and $R_{64}$ are respectively bonded to carbon atoms forming the six-membered ring.

$Y_5$ of the formula (2i) and $Y_6$ of the formula (2j) each independently represent $CR_{65}R_{66}$, $NR_{67}$, a sulfur atom, an oxygen atom or a nitrogen atom to be bonded to $L_{20}$.

$X_4$ of the formula (2j) represents the same as $X_{20}$ of the formula (20). However, $X_4$ is not a single bond.

$R_{63}$ to $R_{67}$ each independently represent the same as $R_1$ to $R_8$ described above.

In the first exemplary embodiment, h of the formula (2B) is preferably 0 or 1.

In the formula (2B), when h is 0, HAr is preferably a group represented by a formula (2b) or (2bx) below.

[Formula 88]

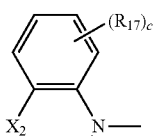
(2b)

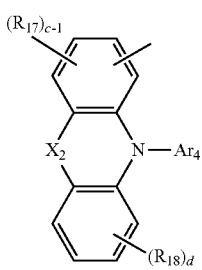
(2bx)

In the formulae (2b) and (2bx), $X_2$ represents a single bond, an oxygen atom, a sulfur atom, a carbonyl group, $NR_9$, $CR_{10}R_{11}$, $SiR_{12}R_{13}$ or $GeR_{14}R_{15}$. In other words, the group represented by the formula (2b) is a group selected from the group consisting of groups represented by formulae (2b-1) to (2b-8) below.

[Formula 89]

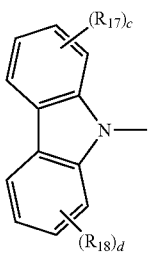
(2b-1)

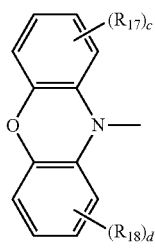
(2b-2)

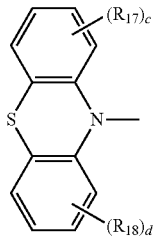
(2b-3)

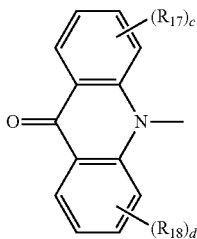
(2b-4)

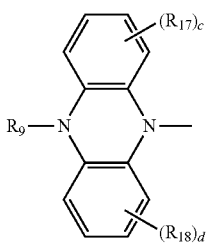
(2b-5)

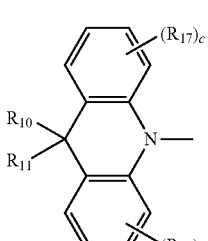
(2b-6)

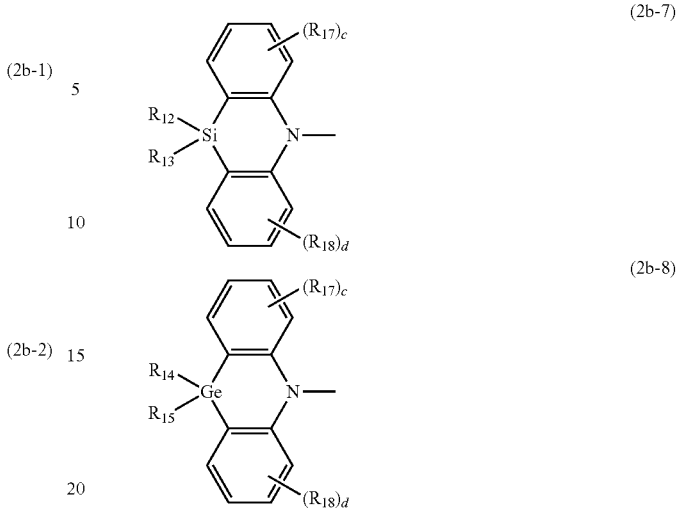

In the formulae (2b), (2bx) and (2b-1) to (2b-8), c and d are 4.

In the formulae (2b), (2bx) and (2b-1) to (2b-8), $R_9$ to $R_{15}$, $R_{17}$ and $R_{18}$ each independently represent the same as $R_1$ to $R_8$ described above. A plurality of $R_{17}$ may be mutually the same or different. A plurality of $R_{18}$ may be mutually the same or different. Adjacent ones of $R_{17}$ may be mutually bonded to form a ring and adjacent ones of $R_{18}$ may be mutually bonded to form a ring. In the formulae (2) and (20), at least one of $R_9$ to $R_{15}$ in $X_{20}$ may be bonded to at least one of $R_{17}$ and $R_{18}$ to form a ring. In the formulae (2b), (2bx) and (2b-1) to (2b-8), $R_{17}$ and $R_{18}$ are respectively bonded to carbon atoms forming the six-membered ring.

In the formula (2bx), $Ar_4$ represents the same as $R_1$ to $R_8$ described above. $Ar_4$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_4$ is preferably a phenyl group, biphenyl group, terphenyl group, naphthyl group, phenanthryl group, triphenylyl group, dibenzofuranyl group, dibenzothiophenyl group, carbazolyl group and the like.

In the first exemplary embodiment, $Az_2$ of the formula (2) is preferably represented by a formula (2d) below.

[Formula 90]

(2d)

In the formula (2d), $X_{21}$ to $X_{26}$ each independently represent $CR_{16}$ or a nitrogen atom. At least one of $X_{21}$ to $X_{26}$ is a nitrogen atom and b of $X_{21}$ to $X_{26}$ is a carbon atom to be bonded to $L_{20}$ or $L_{201}$. Since b is an integer of 1 to 3 as described above, one to three of $X_{21}$ to $X_{26}$ are carbon atom(s) to be bonded to $L_{20}$. In the formula (2d), adjacent ones of $R_{16}$ optionally form a ring. In the formula (2d), $R_{16}$ represents the same as $R_1$ to $R_8$ described above.

In the formula (2d), one to three of $X_{21}$ to $X_{26}$ are preferably nitrogen atom(s). For instance, when $X_{26}$ is a carbon atom bonded to $L_{20}$ and one of $X_{21}$ to $X_{25}$ is a nitrogen atom, $X_{21}$ or $X_{25}$ is preferably a nitrogen atom. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms. A triazine ring in which $X_{21}$, $X_{23}$ and $X_{25}$ are nitrogen atoms is preferable in the formula (2d).

In the formula (2), two or more structures selected from the group consisting of HAr, $L_{20}$, $L_{201}$ and $Az_2$ may be mutually bonded to form a ring.

In the formula (2), when g is 1 or 2, $L_{20}$ and $L_{201}$ may form a ring, the respective substituents of $L_{20}$ and $L_{201}$ may form a ring, or one of $L_{20}$ and $L_{201}$ and a substituent of the other of $L_{20}$ and $L_{201}$ may form a ring.

In the formulae (2) and (20), a substituent of $L_{20}$ may be bonded to at least one of the substituents of the cyclic structure G and the cyclic structure H to form a ring, $L_{20}$ may be bonded to a substituent of at least one of the cyclic structure G and the cyclic structure H to form a ring, or a substituent of $L_{20}$ may be bonded to at least one of the cyclic structure G and the cyclic structure H.

In the formulae (2) and (20), at least one of $R_9$ to $R_{15}$ in $X_{20}$ may be bonded to at least one of the cyclic structure G and the cyclic structure H to form a ring, or at least one of $R_9$ to $R_{15}$ in $X_{20}$ may be bonded to at least one of the substituents of the cyclic structure G and the cyclic structure H to form a ring.

In the formulae (2) and (2d), when g is 1 or 2, a substituent of $L_{201}$ may be bonded to $R_{16}$ of $CR_{16}$ in $X_{21}$ to $X_{25}$ to form a ring, $L_{201}$ may be bonded to $R_{16}$ to form a ring, or a substituent of $L_{201}$ may be bonded to a carbon atom C in $X_{21}$ to $X_{25}$ to form a ring.

In the formulae (2) and (2d), when g is 0, $L_{20}$ or a substituent thereof may be bonded to $R_{16}$ of $CR_{16}$ or a carbon atom C in $X_{21}$ to $X_{25}$ to form a ring in the same manner as described above.

In the first exemplary embodiment, it is preferable that a and b are 1 and g is 0 in the formula (2) and $X_{26}$ is a carbon atom to be bonded to $L_{20}$ in formula (2d) and HAr is represented by the formula (2b). Among compounds in this arrangement, a compound represented by a formula (21) below is preferable.

[Formula 91]

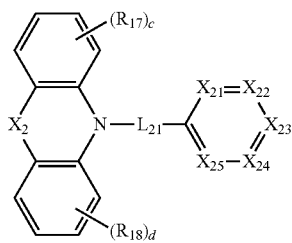

(21)

In the formula (21), $X_2$ represents the same as $X_2$ of the formula (2b).

In the formula (21), L21 is a substituted or unsubstituted divalent aromatic hydrocarbon group or a substituted or unsubstituted divalent heterocyclic group.

In the formula (21), $X_{21}$ to $X_{25}$ each independently represent $CR_{16}$ or a nitrogen atom and at least one of $X_{21}$ to $X_{25}$ is a nitrogen atom. When one of $X_{21}$ to $X_{25}$ is a nitrogen atom, $X_{21}$ or $X_{25}$ is preferably a nitrogen atom. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms.

In the formula (21), c and d are 4 and $R_{17}$ and $R_{18}$ each independently represent the same as $R_1$ to $R_8$ described above. A plurality of $R_{17}$ may be mutually the same or different. A plurality of $R_{18}$ may be mutually the same or different. In the formula (21), $R_{17}$ and $R_{18}$ are respectively bonded to carbon atoms forming the six-membered ring.

In the first exemplary embodiment, the compound represented by the formula (2) is preferably the compound represented by the formula (21), in which $X_2$ is preferably an oxygen atom.

In the first exemplary embodiment, it is preferable that a is 2 and b is 1 in the formula (2) and $X_{26}$ is a carbon atom to be bonded to $L_{20}$ in formula (2d) and HAr is represented by the formula (2b). In other words, the compound represented by the formula (2) is preferably a compound represented by a formula (22) below.

[Formula 92]

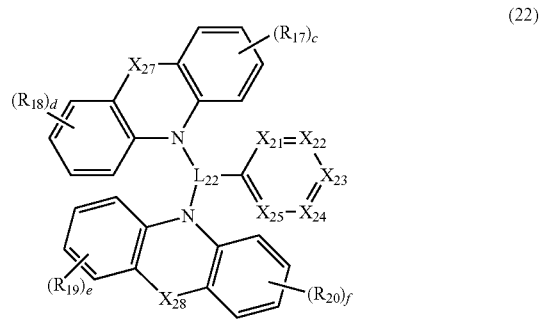

(22)

In the formula (22), $X_{27}$ and $X_{28}$ each independently represent the same as $X_2$ of the formula (2b), in which $X_{27}$ and $X_{28}$ may be mutually the same or different.

In the formula (22), $L_{22}$ is a substituted or unsubstituted trivalent aromatic hydrocarbon group or a substituted or unsubstituted trivalent heterocyclic group.

In the formula (22), $X_{21}$ to $X_{25}$ each independently represent $CR_{16}$ or a nitrogen atom and at least one of $X_{21}$ to $X_{25}$ is a nitrogen atom. When one of $X_{21}$ to $X_{25}$ is a nitrogen atom, $X_{21}$ or $X_{25}$ is preferably a nitrogen atom. When two of $X_{21}$ to $X_{25}$ are nitrogen atoms, $X_{21}$ and $X_{25}$ are preferably nitrogen atoms. When three of $X_{21}$ to $X_{25}$ are nitrogen atoms, $X_{21}$, $X_{23}$ and $X_{25}$ are preferably nitrogen atoms.

In the formula (22), c, d, e and f are each 4 and $R_{17}$ to $R_{20}$ each independently represent the same as $R_1$ to $R_8$ described above. A plurality of $R_{17}$ may be mutually the same or different. A plurality of $R_{18}$ may be mutually the same or different. A plurality of $R_{19}$ may be mutually the same or different. Adjacent ones of $R_{17}$ may be mutually bonded to form a ring, adjacent ones of $R_{18}$ may be mutually bonded to form a ring, adjacent ones of $R_{19}$ may be mutually bonded to form a ring, and adjacent ones of $R_{20}$ may be mutually bonded to form a ring. In the formula (22), $R_{17}$ to $R_{20}$ are respectively bonded to carbon atoms forming the six-membered ring.

In the first exemplary embodiment, the compound represented by the formula (2) is preferably the compound represented by the formula (22), in which $X_{27}$ and $X_{28}$ are preferably oxygen atoms.

In the first exemplary embodiment, it is preferable that a is 1, b is 2, and g is 0 in the formula (2) and $X_{24}$ and $X_{26}$ are carbon atoms to be bonded to $L_{20}$, HAr is represented by the formula (2b) and $X_{21}$, $X_{23}$ and $X_{25}$ are nitrogen atoms in formula (2d). In other words, the compound represented by the formula (2) is preferably a compound represented by a formula (23) below.

[Formula 93]

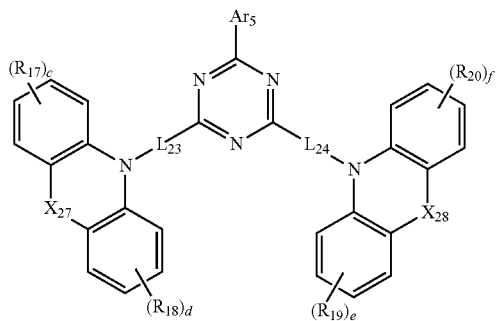

(23)

In the formula (23), $X_{27}$ and $X_{28}$ each independently represent the same as $X_2$ of the formula (2b).

In the formula (23), $L_{23}$ and $L_{24}$ each independently represent a substituted or unsubstituted divalent aromatic hydrocarbon group or a substituted or unsubstituted divalent heterocyclic group.

In the formula (23), $Ar_5$ represents the same as $R_1$ to $R_8$ described above. $Ar_5$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_5$ is preferably a phenyl group, biphenyl group, terphenyl group, naphthyl group, phenanthryl group, triphenylyl group, dibenzofuranyl group, dibenzothiophenyl group, carbazolyl group and the like.

In the formula (23), c, d, e and f are each 4 and $R_{17}$ to $R_{20}$ each independently represent the same as $R_1$ to $R_8$ described above. Adjacent ones of $R_{17}$ may be mutually bonded to form a ring, adjacent ones of $R_{18}$ may be mutually bonded to form a ring, adjacent ones of $R_{19}$ may be mutually bonded to form a ring, and adjacent ones of $R_{20}$ may be mutually bonded to form a ring. In the formula (23), $R_{17}$ to $R_{20}$ are respectively bonded to carbon atoms forming the six-membered ring.

In the first exemplary embodiment, the compound represented by the formula (2) is preferably the compound represented by the formula (23), in which $X_{27}$ and $X_{28}$ are preferably oxygen atoms.

In the first exemplary embodiment, in the compound represented by the formula (2), it is preferable that HAr is the group represented by the formula (2b), $L_{20}$ is a substituted or unsubstituted divalent heterocyclic group, and g is 1. In this arrangement, $L_{20}$ is more preferably a substituted or unsubstituted divalent carbazolyl group. Further, the compound represented by the formula (2) is preferably a compound represented by a formula (24) below.

[Formula 94]

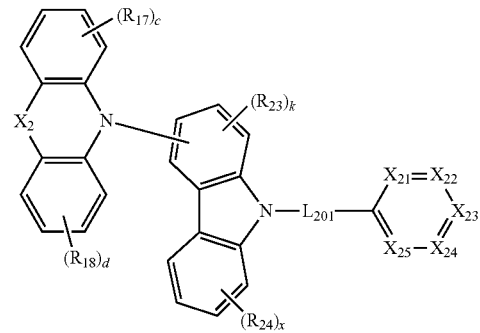

(24)

In the formula (24), $X_{21}$ to $X_{25}$ represent the same as $X_{21}$ to $X_{25}$ of the formula (21).

In the formula (24), $R_{17}$ to $R_{18}$ and $R_{23}$ to $R_{24}$ each independently represent the same as $R_1$ to $R_8$ described above. Adjacent ones of $R_{17}$ may be mutually bonded to form a ring, adjacent ones of $R_{18}$ may be mutually bonded to form a ring, adjacent ones of $R_{23}$ may be mutually bonded to form a ring, and adjacent ones of $R_{24}$ may be mutually bonded to form a ring. In the formula (24), $R_{17}$ to $R_{18}$ and $R_{23}$ to $R_{24}$ are respectively bonded to carbon atoms forming the six-membered ring.

In the formula (24), $L_{201}$ represents the same as $L_{201}$ of the formula (2).

In the formula (24), c, d and x are 4 and k is 3.

In the formula (2B), when h is 1 and the cyclic structure F is represented by the formula (2i), the structure of the formula (2B) is represented by any one of formulae (2B-1) to (2B-6) below.

[Formula 95]

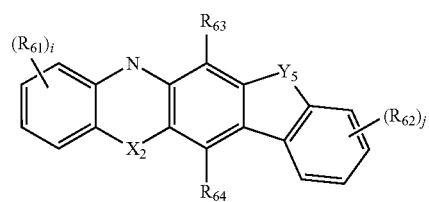

(2B-1)

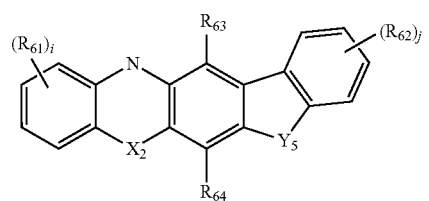

(2B-2)

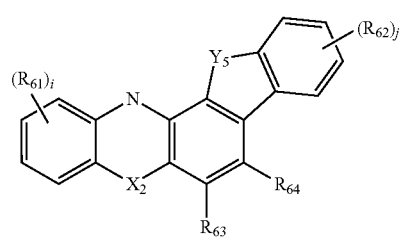

(2B-3)

-continued (2B-4)
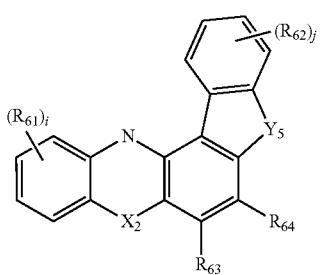

(2B-5)
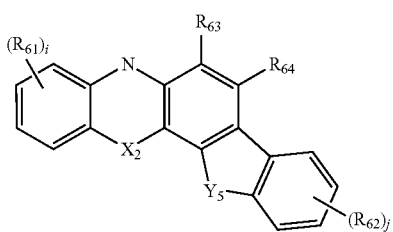

(2B-6)
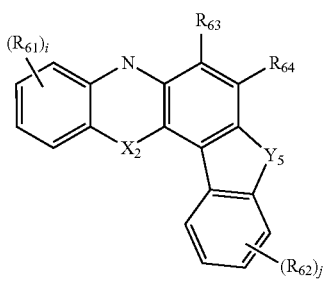

In the formulae (2B-1) to (2B-6), $X_2$ represents the same as $X_2$ of the formula (2b).

In the formulae (2B-1) to (2B-6), $R_{61}$ to $R_{64}$ each independently represent the same as $R_1$ to $R_8$ described above. A plurality of $R_{61}$ may be mutually the same or different. A plurality of $R_{62}$ may be mutually the same or different. Adjacent ones of $R_{61}$ may be mutually bonded to form a ring and adjacent ones of $R_{62}$ may be mutually bonded to form a ring. Adjacent $R_{63}$ and $R_{64}$ may be mutually bonded to form a ring. In the formulae (2B-1) to (2B-6), $R_{61}$ to $R_{62}$ are respectively bonded to carbon atoms forming the six-membered ring.

In the formulae (2B-1) to (2B-6), $Y_5$ represents the same as $Y_5$ of the formula (2i).

In the formulae (2B-1) to (2B-6), i and j are 4.

Groups derived from the structure represented by the formulae (2B-1) to (2B-6) are preferably groups represented by formulae (2B-7) to (2B-18) below.

[Formula 96]

(2B-7)
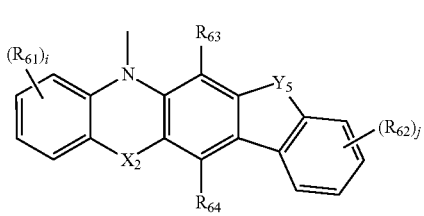

-continued (2B-8)
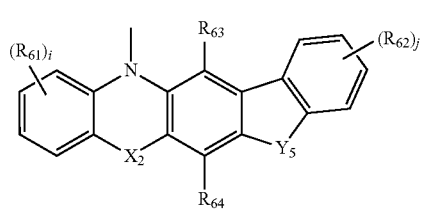

(2B-9)
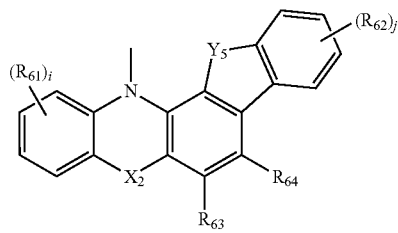

(2B-10)
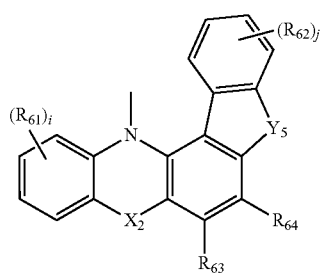

(2B-11)
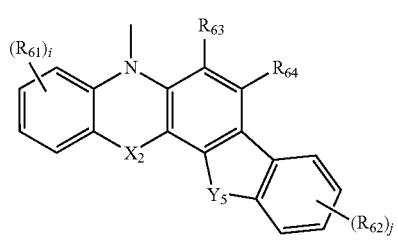

(2B-11)
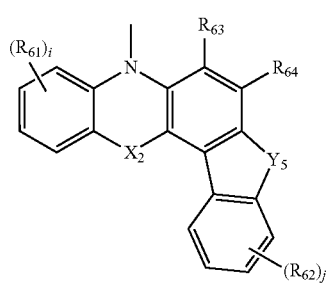

[Formula 97]

(2B-13)
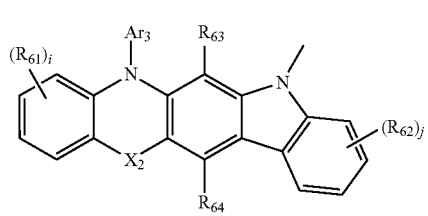

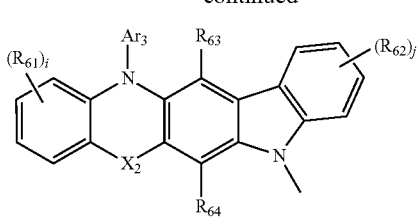

(2B-14)

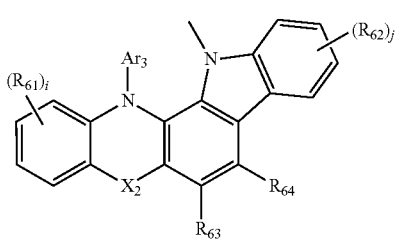

(2B-15)

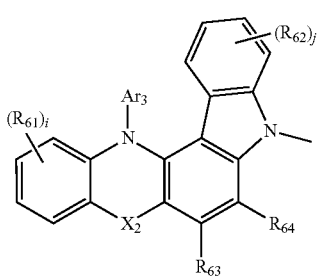

(2B-16)

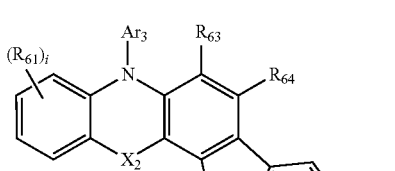

(2B-17)

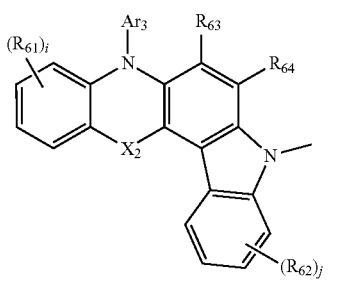

(2B-18)

In the formulae (2B-7) to (2B-12), $X_2$ represents the same as $X_2$ of the formula (2b), among which $X_2$ is preferably an oxygen atom.

In the formulae (2B-7) to (2B-12), $R_{61}$ to $R_{64}$ each independently represent the same as $R_1$ to $R_8$ described above. A plurality of $R_{61}$ may be mutually the same or different. A plurality of $R_{62}$ may be mutually the same or different. Adjacent ones of $R_{61}$ may be mutually bonded to form a ring and adjacent ones of $R_{62}$ may be mutually bonded to form a ring. Adjacent $R_{63}$ and $R_{64}$ may be mutually bonded to form a ring. In the formulae (2B-7) to (2B-12), $R_{61}$ to $R_{62}$ are respectively bonded to carbon atoms forming the six-membered ring.

In the formulae (2B-7) to (2B-12), $Y_5$ represents the same as $Y_5$ of the formula (2i), among which $Y_5$ is preferably $NR_{67}$. $R_{67}$ represents the same as $R_1$ to $R_8$ described above and is preferably a substituted or unsubstituted aryl group having 6 to 30 ring carbon atoms.

In the formulae (2B-7) to (2B-12), i and j are 4.

In the formulae (2B-13) to (2B-18), $X_2$ represents the same as $X_2$ of the formula (2b), among which $X_2$ is preferably an oxygen atom.

In the formulae (2B-13) to (2B-18), $R_{61}$ to $R_{64}$ each independently represent the same as $R_1$ to $R_8$ described above. A plurality of $R_{61}$ may be mutually the same or different. A plurality of $R_{62}$ may be mutually the same or different. Adjacent ones of $R_{61}$ may be mutually bonded to form a ring and adjacent ones of $R_{62}$ may be mutually bonded to form a ring. Adjacent $R_{63}$ and $R_{64}$ may be mutually bonded to form a ring.

In the formulae (2B-13) to (2B-18), $Ar_3$ represents the same as $R_1$ to $R_8$ described above. $Ar_3$ is preferably a substituted or unsubstituted aryl group having 6 to 30 ring carbon atoms or a substituted or unsubstituted heterocyclic group having 5 to 30 ring atoms, more preferably a substituted or unsubstituted aryl group having 6 to 30 ring carbon atoms. $Ar_3$ is preferably a phenyl group, biphenyl group, terphenyl group, naphthyl group, phenanthryl group, triphenylyl group, dibenzofuranyl group, dibenzothiophenyl group, carbazolyl group and the like.

In the formulae (2B-13) to (2B-18), i and j are 4.

In the formula (2B), when h is 1 and the cyclic structure F is represented by the formula (2j), the structure of the formula (2B) is represented by any one of formulae (2B-19) to (2B-20) below.

[Formula 98]

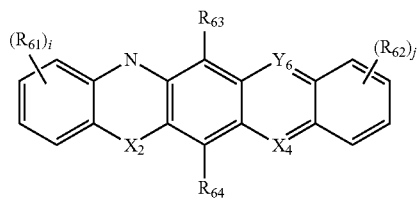

(2B-19)

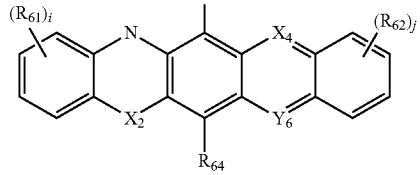

(2B-20)

In the formulae (2B-19) to (2B-20), $X_2$ and $X_4$ represent the same as $X_2$ of the formula (2B). However, $X_4$ is not a single bond.

In the formulae (2B-19) to (2B-20), $R_{61}$ to $R_{64}$ each independently represent the same as $R_1$ to $R_8$ described above. Adjacent ones of $R_{61}$ may be mutually bonded to form a ring and adjacent ones of $R_{62}$ may be mutually bonded to form a ring. Adjacent $R_{63}$ and $R_{64}$ may be mutually bonded to form a ring. In the formulae (2B-19) to (2B-20), $R_{61}$ to $R_{62}$ are respectively bonded to carbon atoms forming the six-membered ring.

In the formulae (2B-19) to (2B-20), $Y_6$ represents the same as $Y_6$ of the formula (2j).

In the formulae (2B-19) to (2B-20), i and j are 4.

Groups derived from the structure represented by the formulae (2B-19) to (2B-20) are preferably groups represented by formulae (2B-21) to (2B-22) below.

[Formula 99]

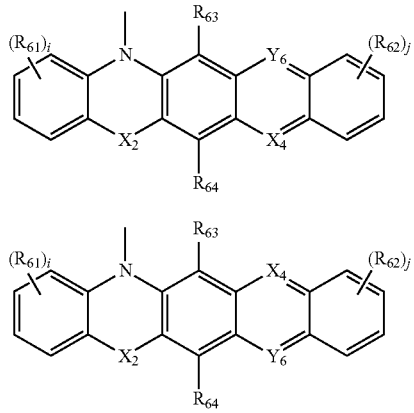

(2B-21)

(2B-22)

In the formulae (2B-21) to (2B-22), $X_2$, $X_4$, $R_{61}$ to $R_{64}$, $Y_6$, i and j respectively represent the same as $X_2$, $X_4$, $R_{61}$ to $R_{64}$, $Y_6$, i and j of the formulae (2B-19) to (2B-20).

In the first exemplary embodiment, when $L_{20}$ to $L_{24}$ and $L_{201}$ are divalent linking groups to be bonded to $Az_2$, $L_{20}$ to $L_{24}$ and $L_{201}$ are each preferably a substituted or unsubstituted divalent aromatic hydrocarbon group. When g is 1 or more in the formula (2), not $L_{20}$ but $L_{201}$ is a divalent linking group to be bonded to $Az_2$.

Moreover, in the exemplary embodiment, when $L_{20}$ to $L_{24}$ and $L_{201}$ are divalent linking groups to be bonded to $Az_2$, $L_{20}$ to $L_{24}$ and $L_{201}$ each preferably have a divalent six-membered ring structure, more preferably a divalent six-membered ring structure represented by a formula (2e), (2f) or (2g) below, further preferably a divalent six-membered ring structure represented by the formula (2e) below.

[Formula 100]

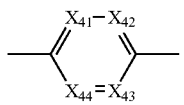

(2e)

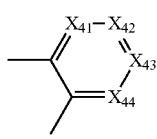

(2f)

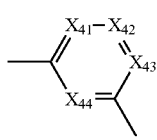

(2g)

In the formulae (2e) to (2g), $X_{41}$ to $X_{44}$ each independently represent $CR_{102}$ or a nitrogen atom, wherein $R_{102}$ each independently represents the same as $R_1$ to $R_8$ described above.

In the first exemplary embodiment, $X_{41}$ to $X_{44}$ of the formulae (2e) to (2g) are each independently preferably $CR_{102}$, in which $R_{102}$ is more preferably a hydrogen atom, alkyl group, alkoxy group, aryloxy group, cyano group, halogen atom and silyl group.

When g is 1 in the formula (2), $L_{201}$ preferably has a divalent six-membered ring structure represented by the formula (2e) and $L_{20}$ is preferably a heterocyclic group having 5 to 30 ring atoms. In this arrangement, the heterocyclic group is preferably a carbazolyl group, in which a nitrogen atom at a position 9 of the carbazolyl group is preferably bonded to $L_{201}$. Further preferably, at least one of the structures represented by the formulae (2b) and (2bx) is bonded to the carbazolyl group.

Moreover, $L_{21}$ of the formula (21), $L_{22}$ of the formula (22), $L_{23}$ and $L_{24}$ of the formula (23) and $L_{201}$ of the formula (24) each preferably have a divalent six-membered ring structure represented by the formula (2e).

In the first exemplary embodiment, the compound represented by the formula (2) is preferably a compound represented by a formula (25) below. Specifically, the compound represented by the formula (2) is preferably represented by a formula (25) below in which HAr is represented by the formula (2b), $L_{20}$ is a single bond, g is 0 and HAr is directly bonded to $Az_2$ by a single bond.

[Formula 101]

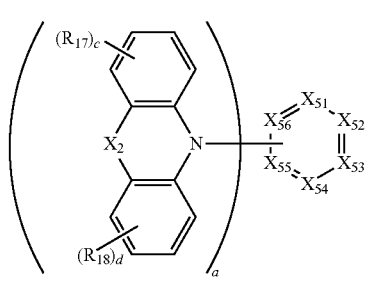

(25)

In the formula (25), $X_{51}$ to $X_{56}$ each independently represent $CR_{81}$, a nitrogen atom, a cyano group or a carbon atom to be bonded to a nitrogen atom of the partial structure represented by the formula (2b). At least one of $X_{51}$ to $X_{56}$ is a nitrogen atom and least one of $X_{51}$ to $X_{56}$ is a cyano group. $R_{81}$ represents the same as $R_1$ to $R_8$ described above.

In the formula (25), $X_2$ represents a single bond, an oxygen atom, a sulfur atom, a carbonyl group, $NR_9$, $CR_{10}R_{11}$, $SiR_{12}R_{13}$ or $GeR_{14}R_{15}$.

In the formula (25), $R_{17}$ and $R_{18}$ represent the same as $R_1$ to $R_8$ described above.

In the formula (25), a is an integer of 1 to 5, preferably an integer of 1 to 4. In the formula (25), c and d are 4.

In the formula (25), $X_2$ is preferably a single bond. In this arrangement, the compound represented by the formula (25) is represented by a formula (26) below.

[Formula 102]
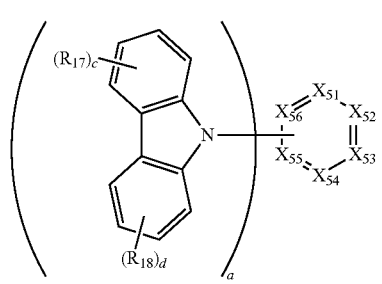
(26)
In the formula (26), $X_{51}$ to $X_{56}$, $R_{17}$, $R_{18}$, a, c and d represent the same as $X_{51}$ to $X_{56}$, $R_{17}$, $R_{18}$, a, c and d of the formula (25).
Specific examples of the compound represented by the formula (2) are shown below, but the invention is not limited thereto.
[Formula 103]
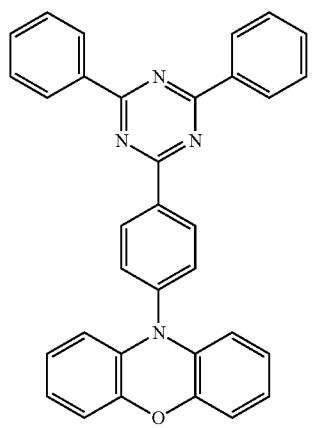
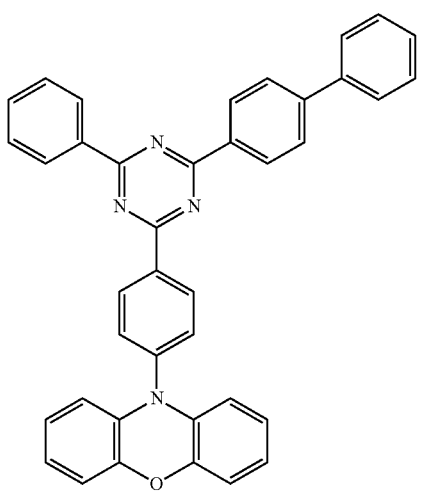
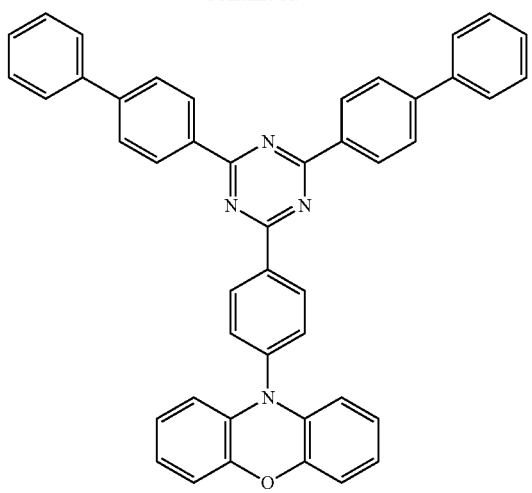
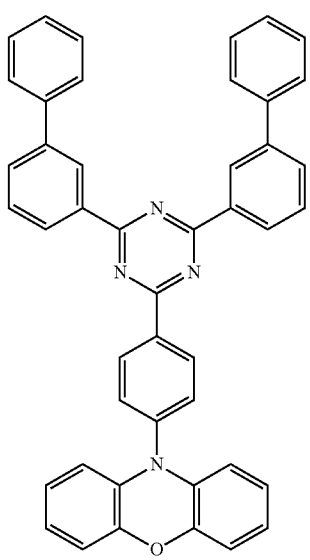
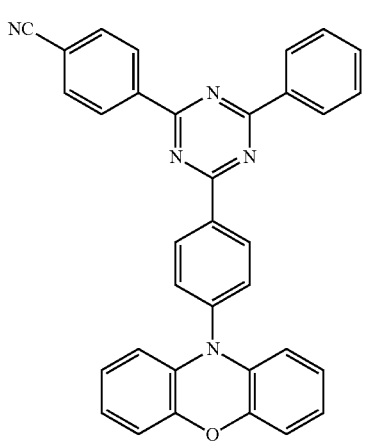

131
-continued
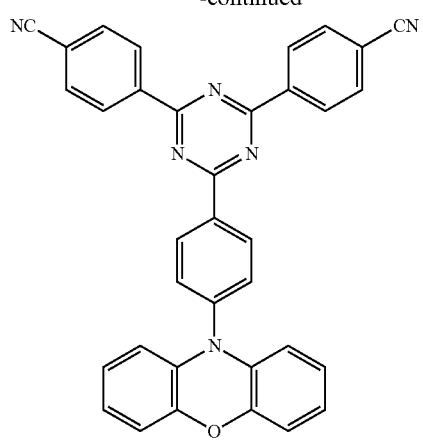
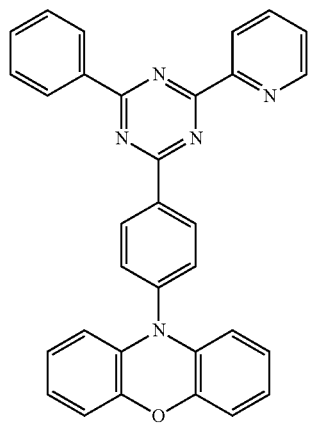
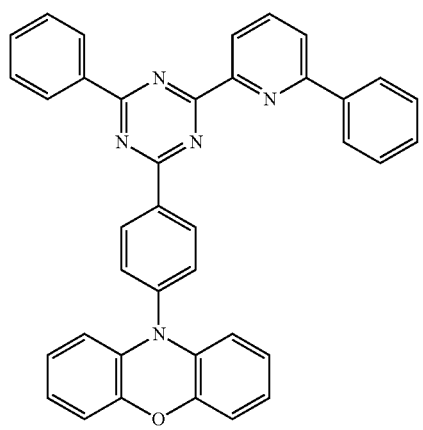
132
-continued
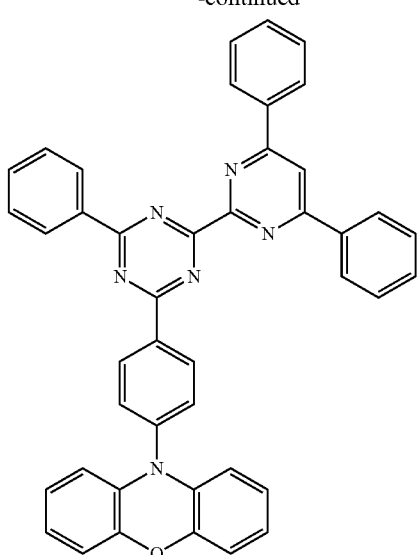
[Formula 104]
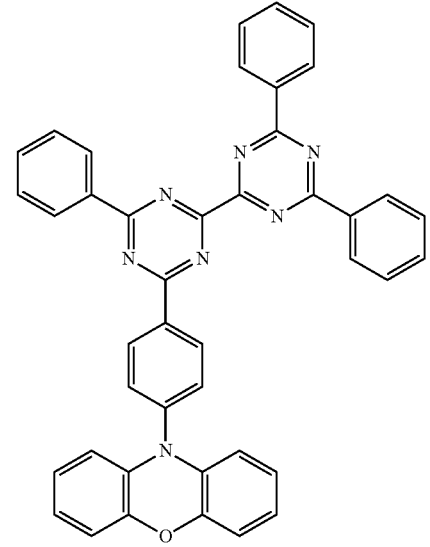
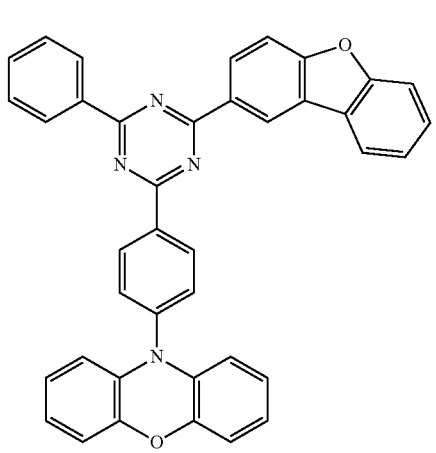

133
-continued
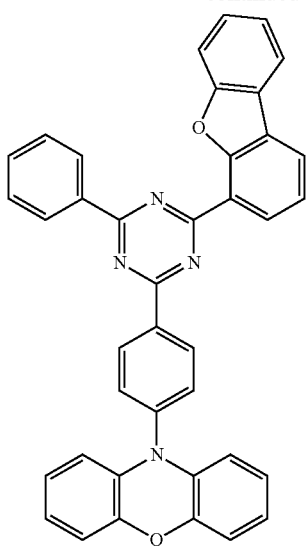
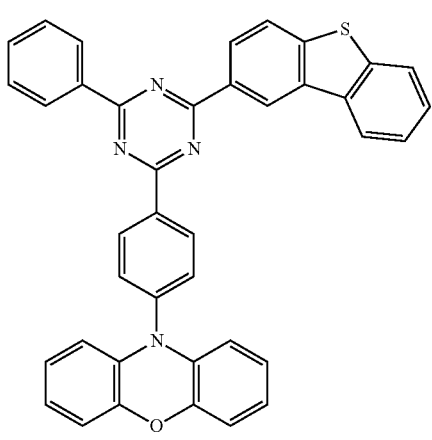
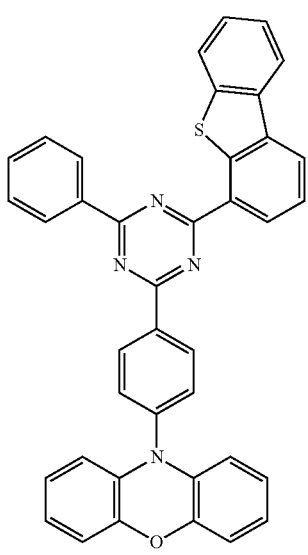
134
-continued
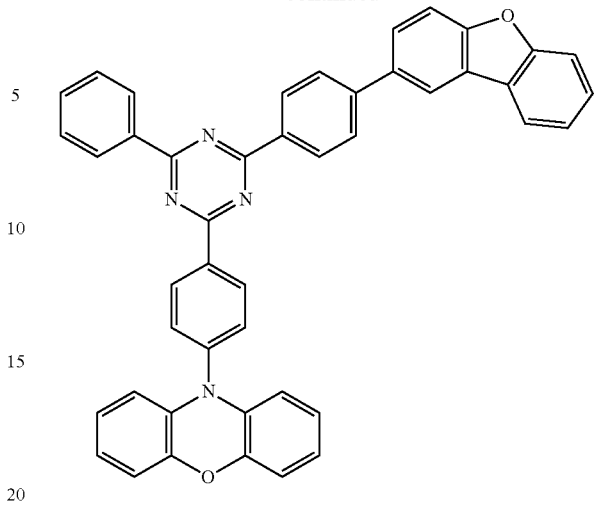
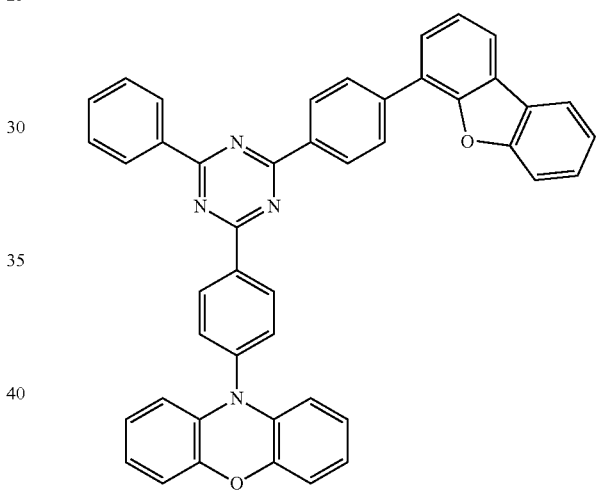
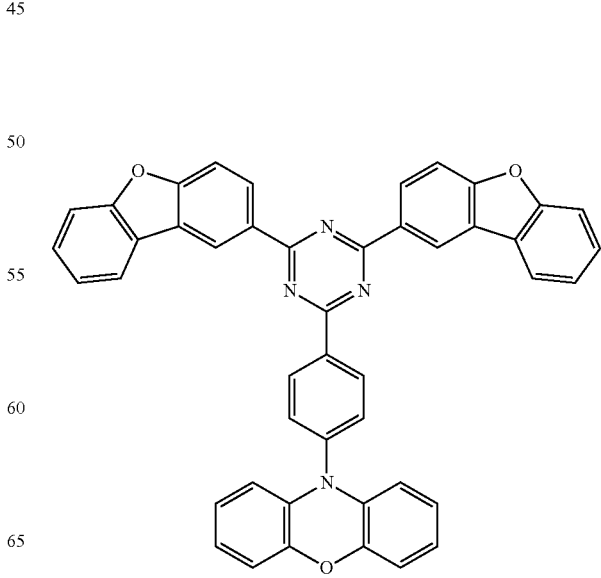

[Formula 105]
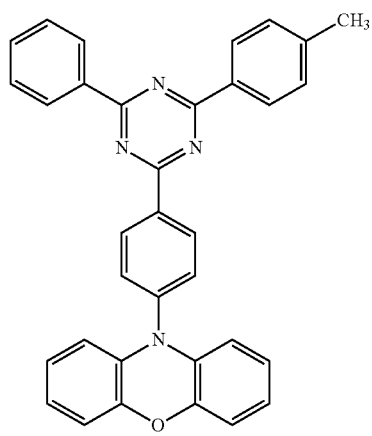
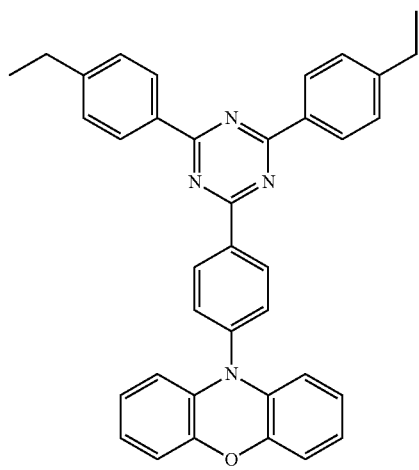
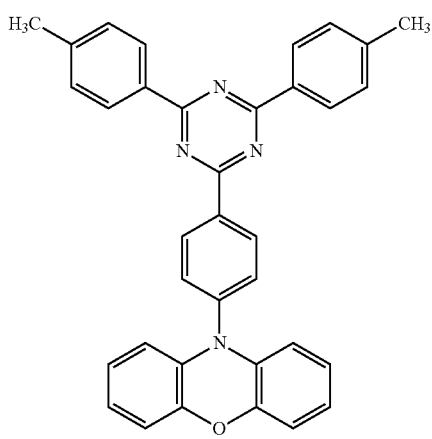
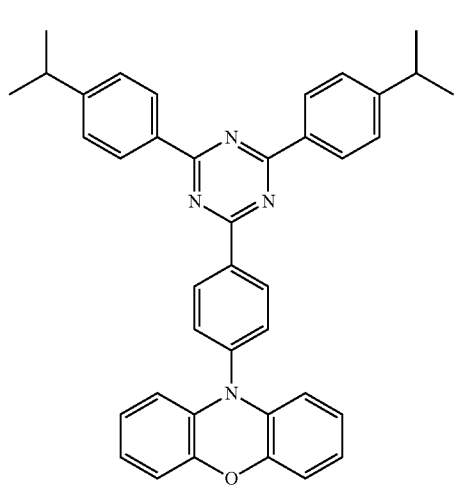
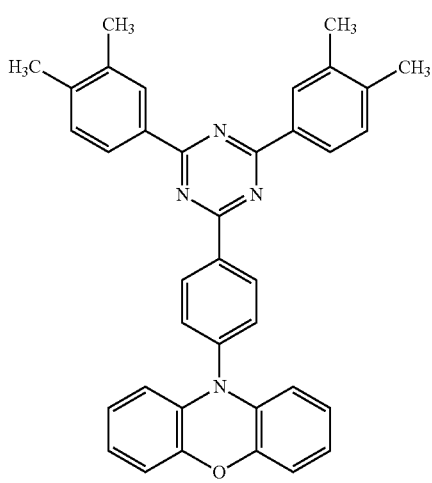
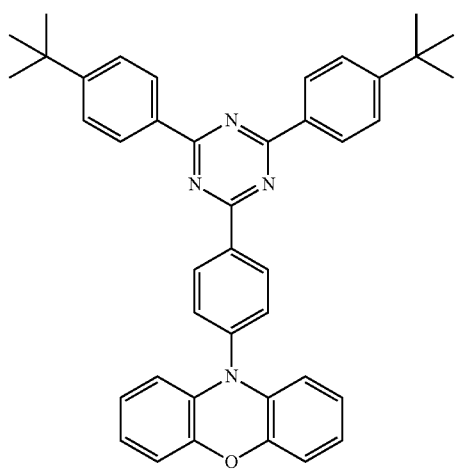

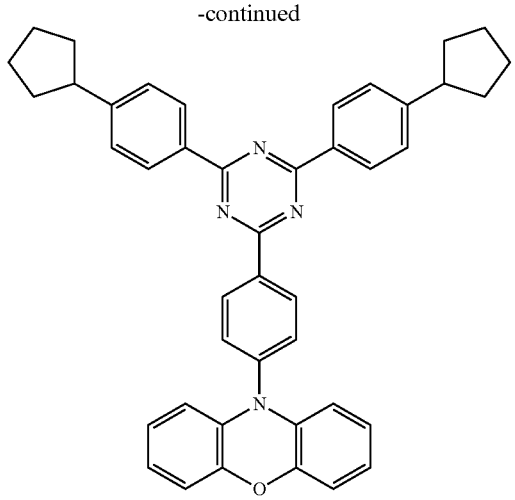
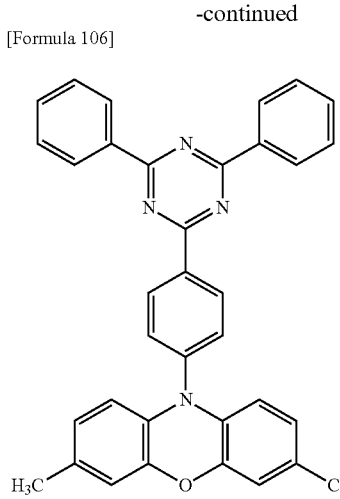
[Formula 106]
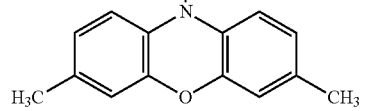
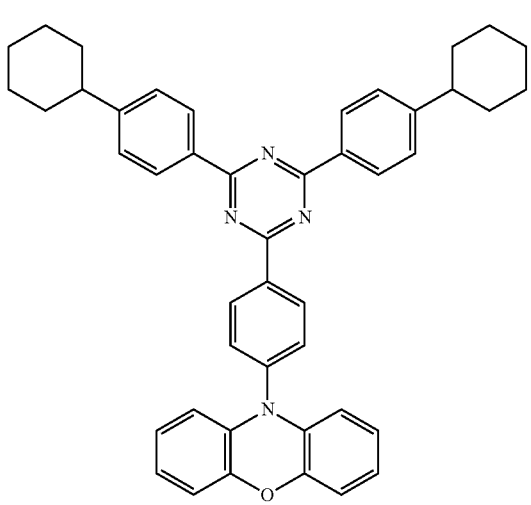
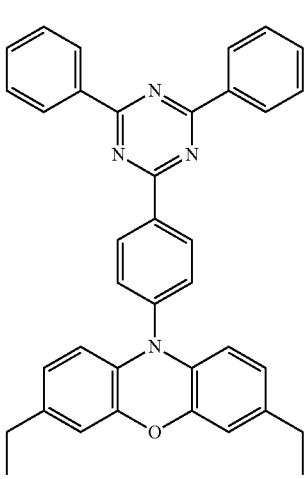
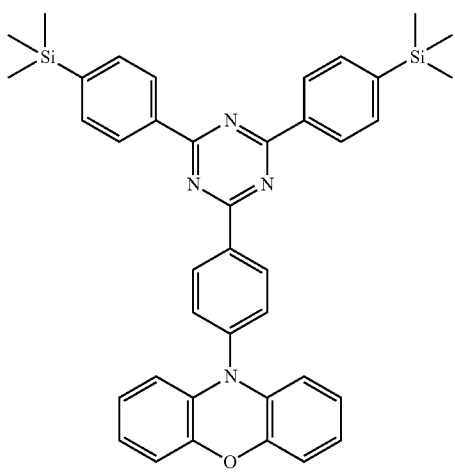
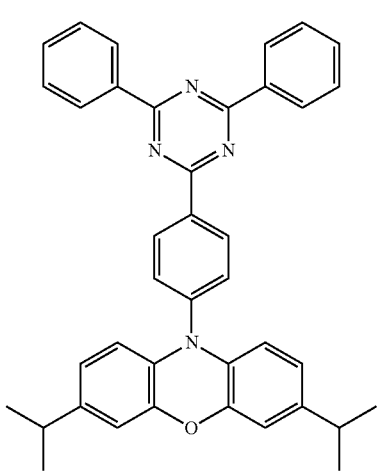

139
-continued
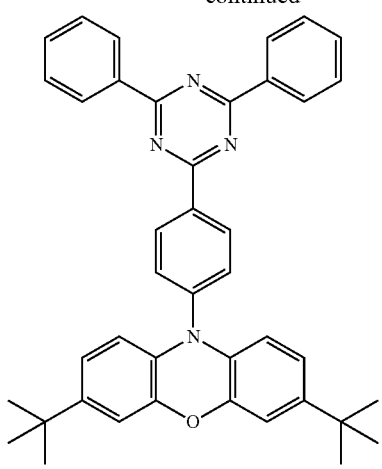
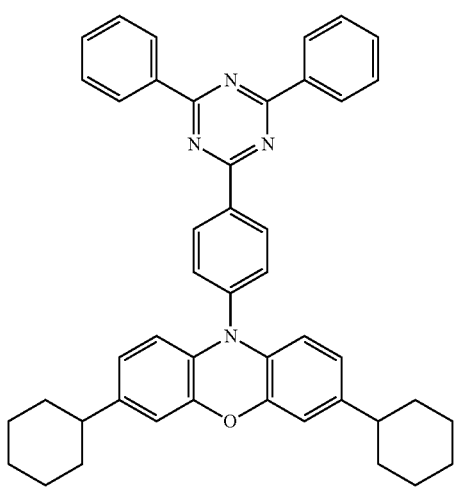
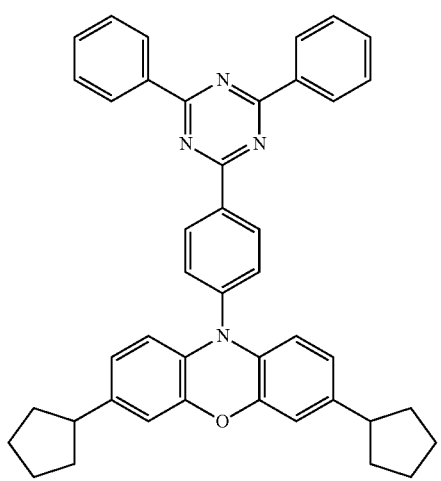
140
-continued
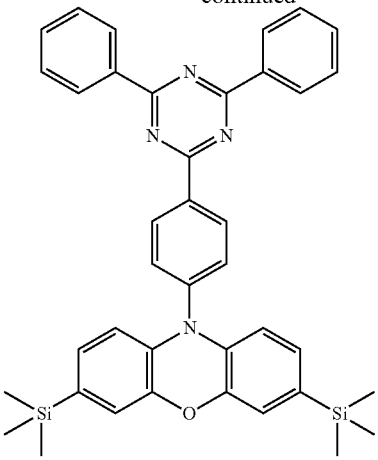
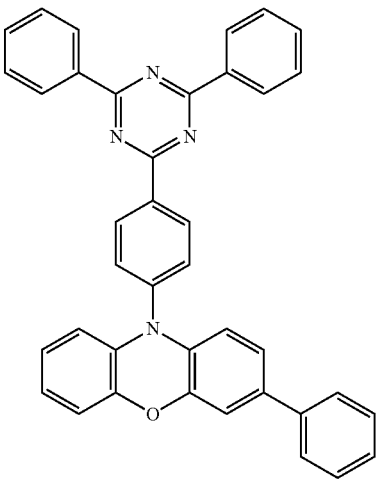
[Formula 107]

141
-continued
142
-continued
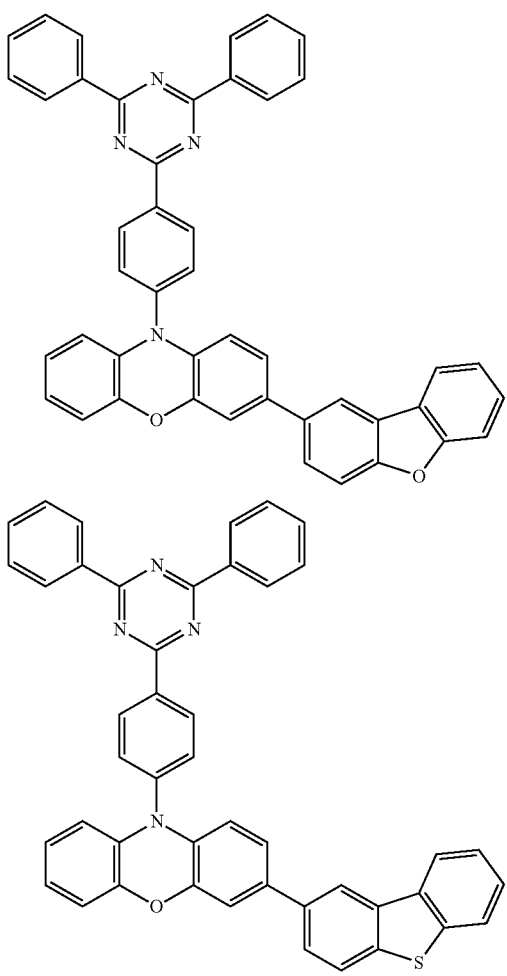
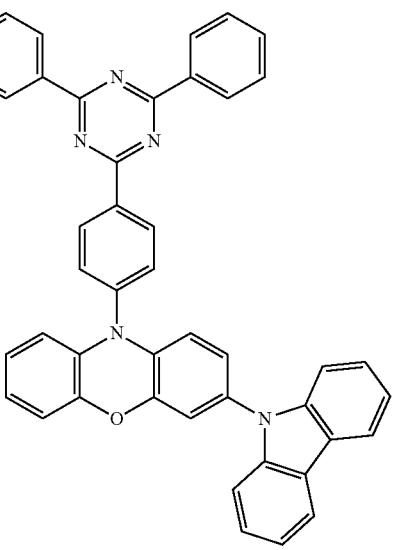
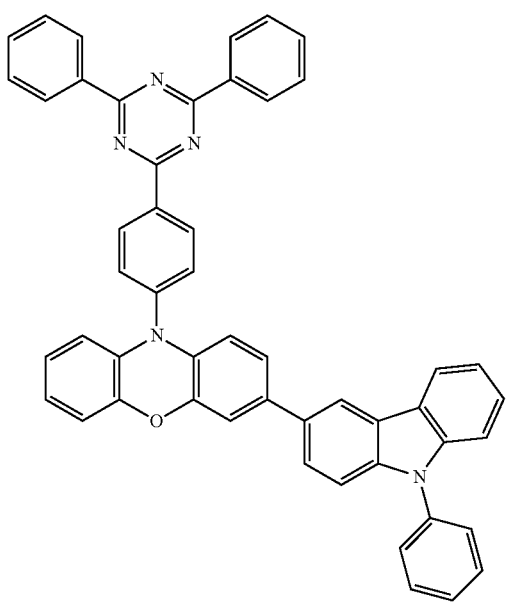
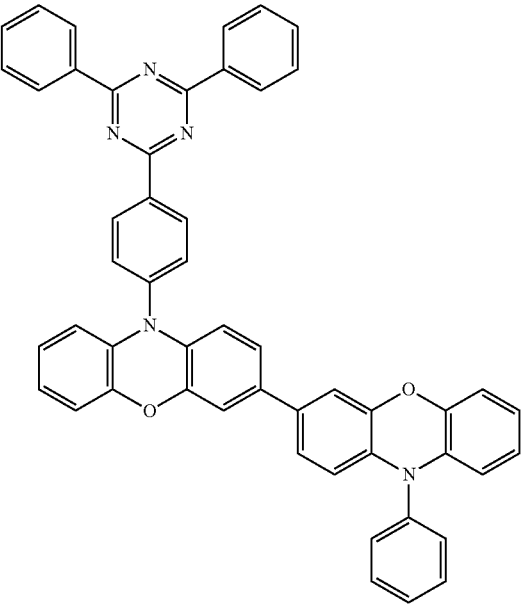

143
-continued
144
-continued
[Formula 108]
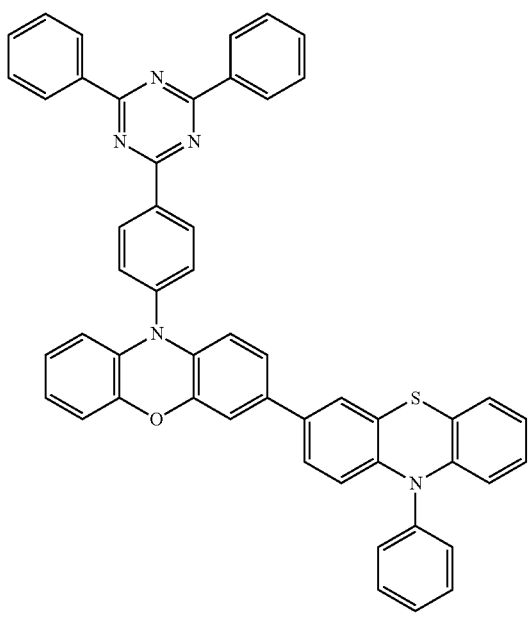
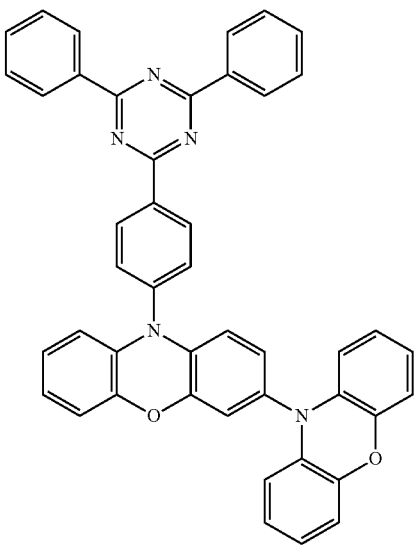

145
-continued
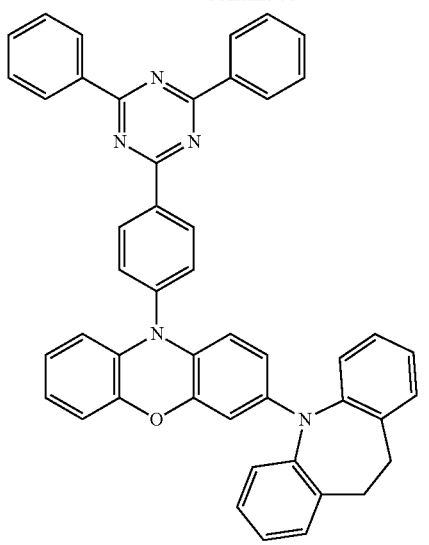
146
-continued
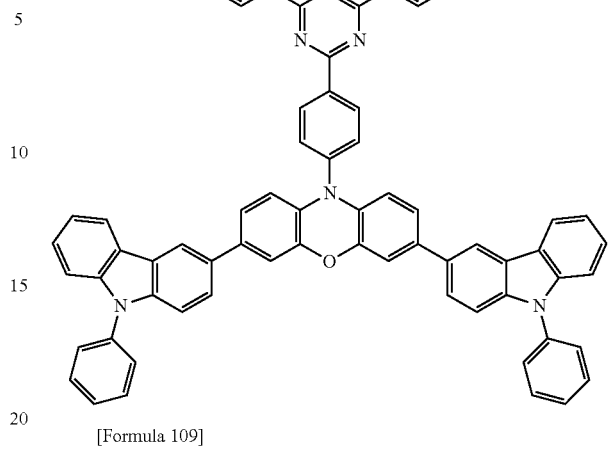
[Formula 109]
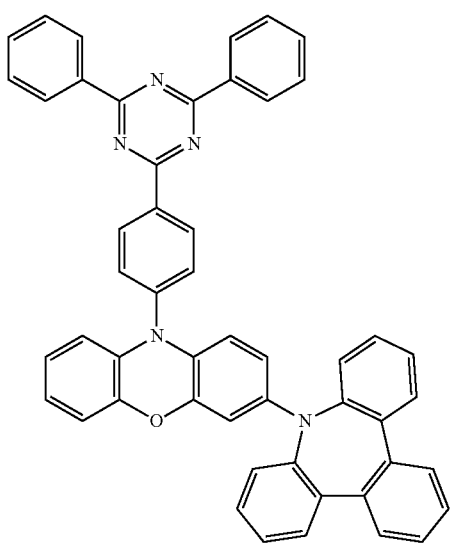
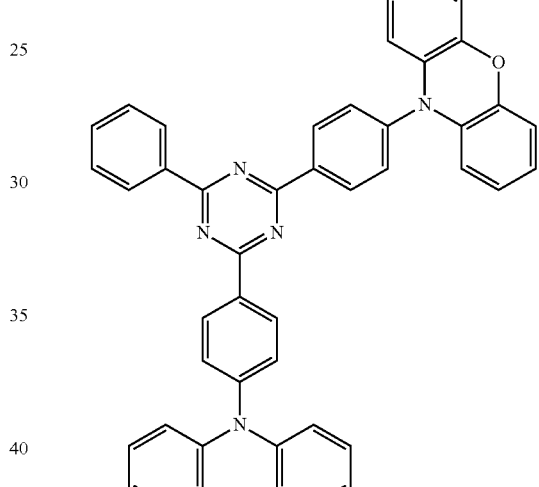
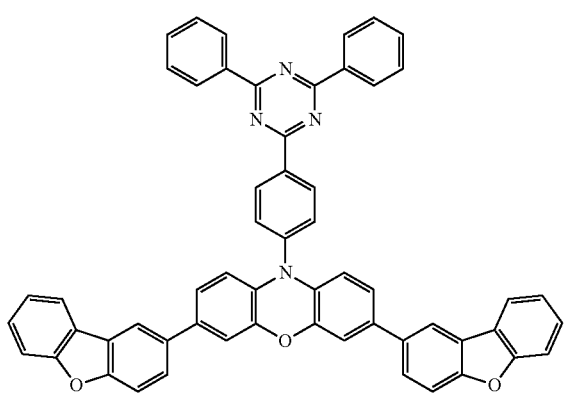
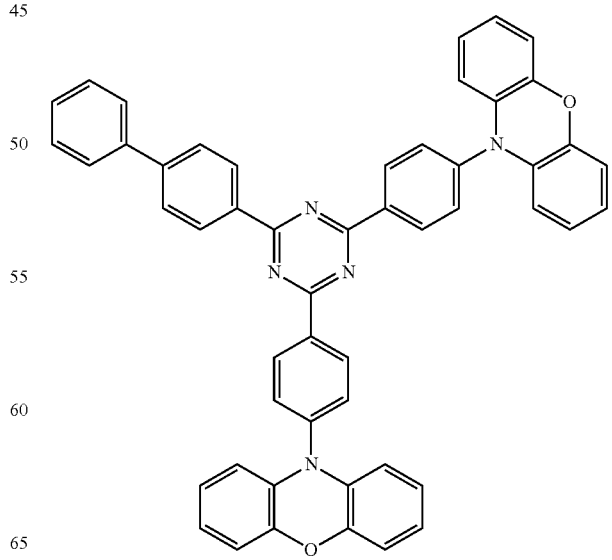

147
-continued
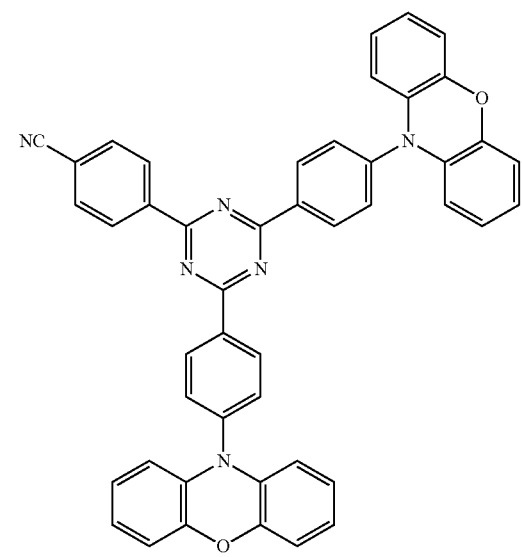
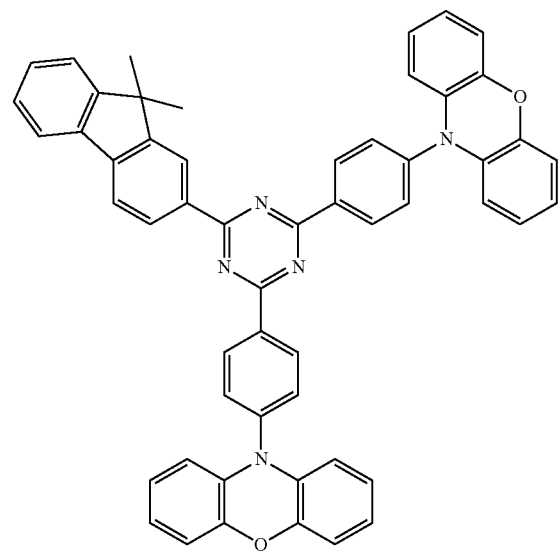
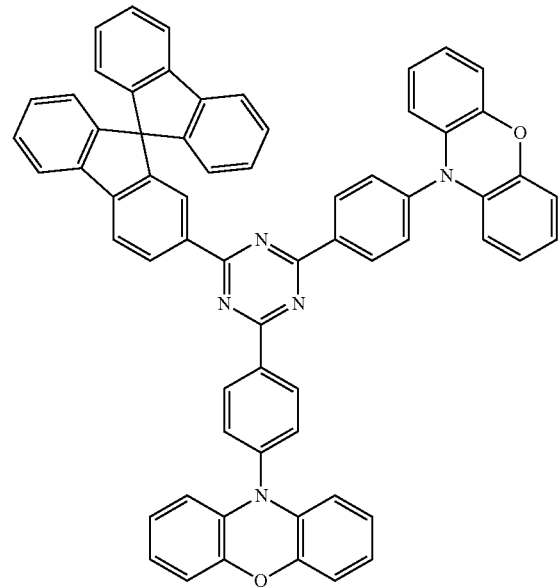
148
-continued
[Formula 110]
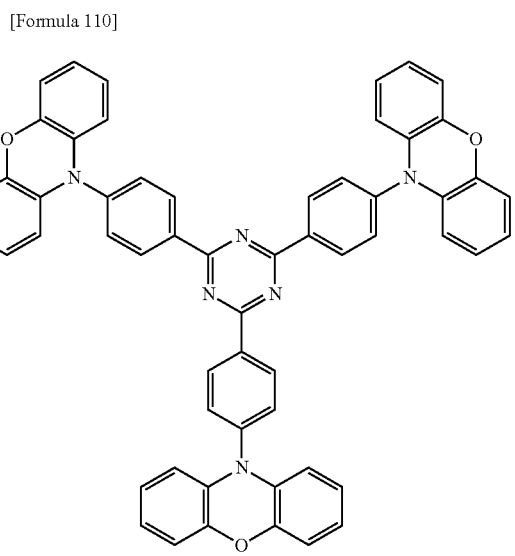
[Formula 111]
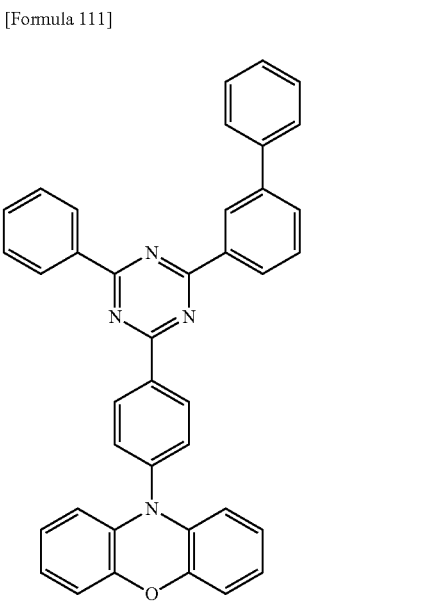
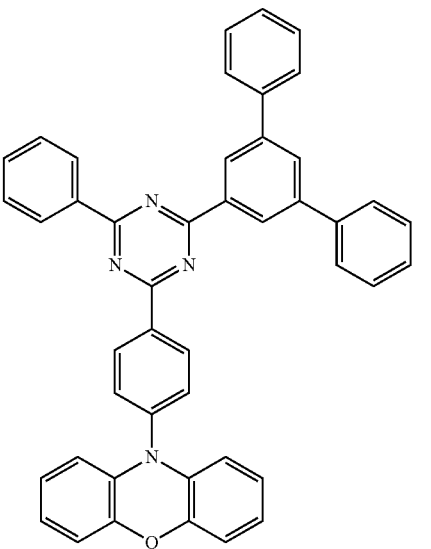

-continued
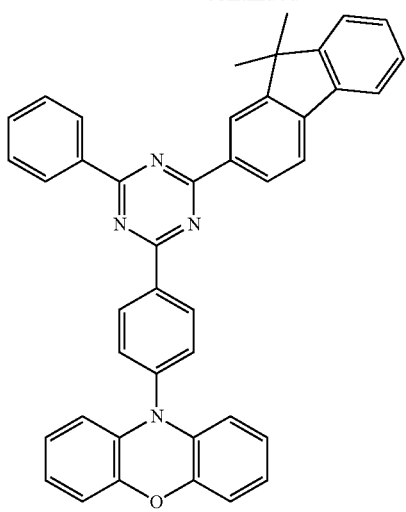
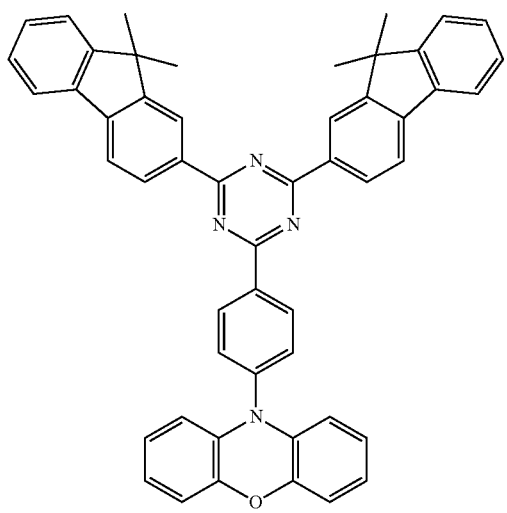
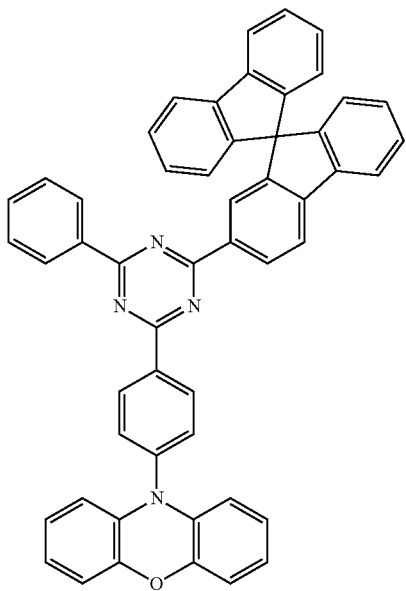
-continued
[Formula 112]
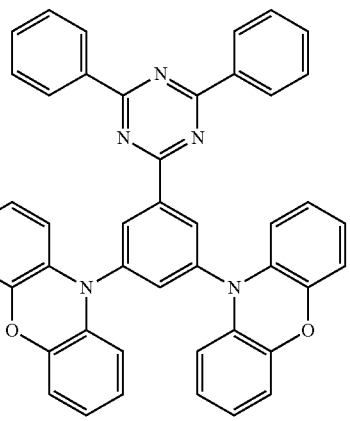
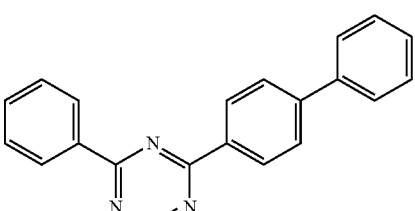
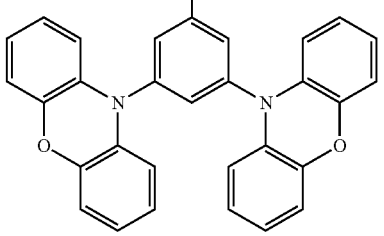
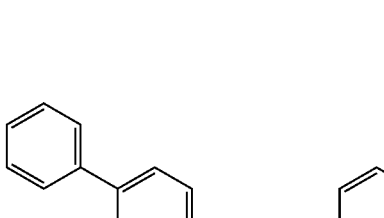

151
-continued
[Formula 113]
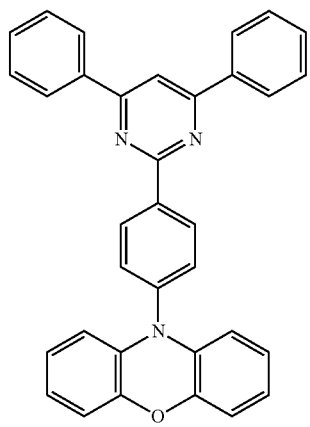
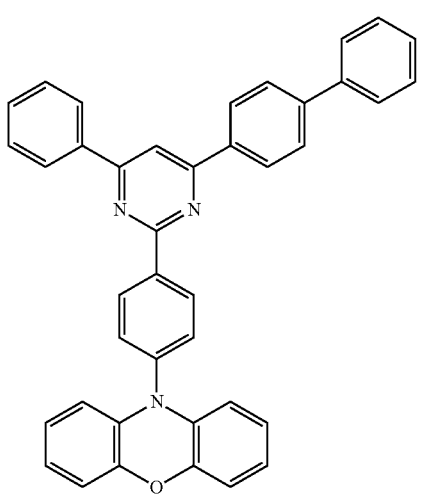
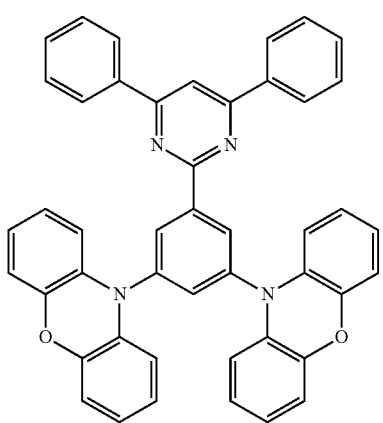
152
-continued
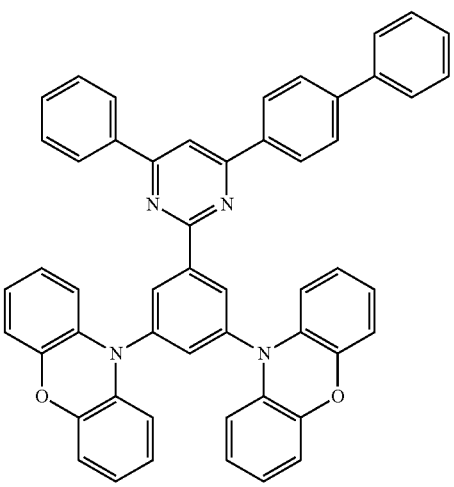
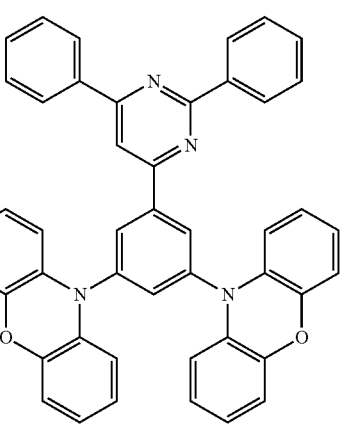
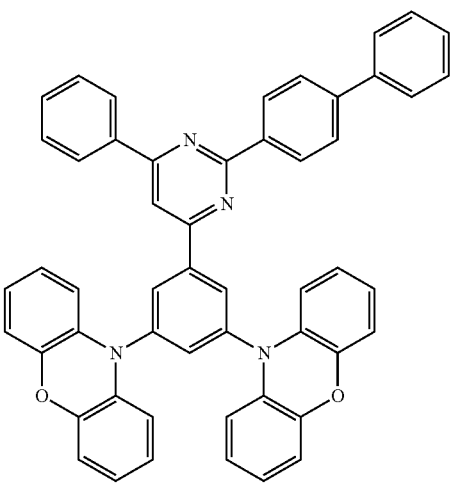

153
-continued
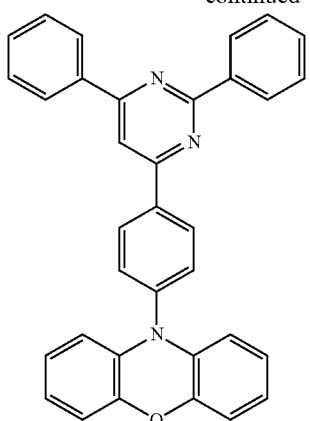
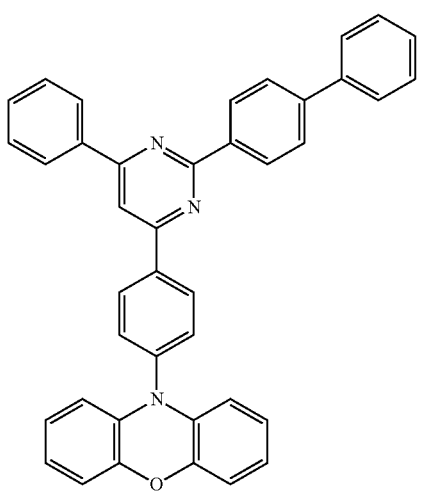
[Formula 114]
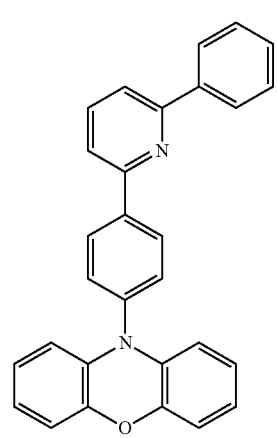
154
-continued
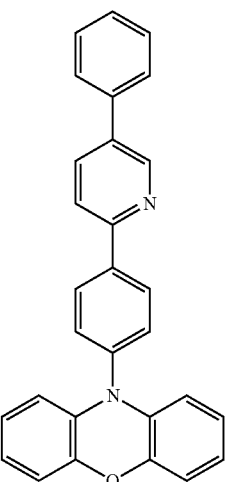
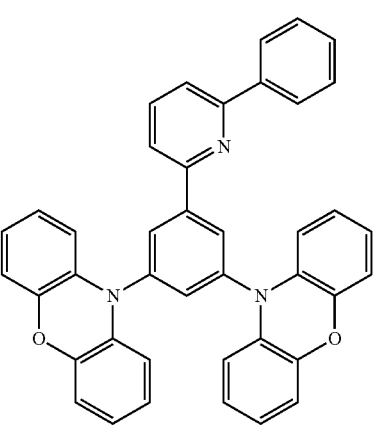
[Formula 15]
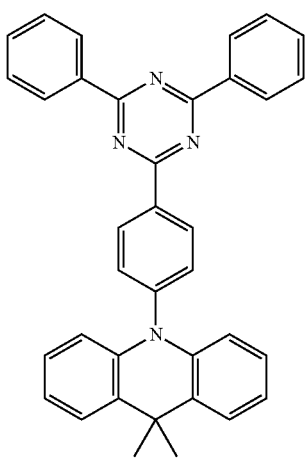

155
-continued
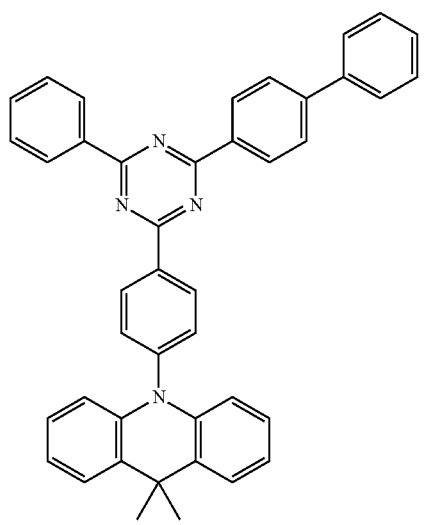
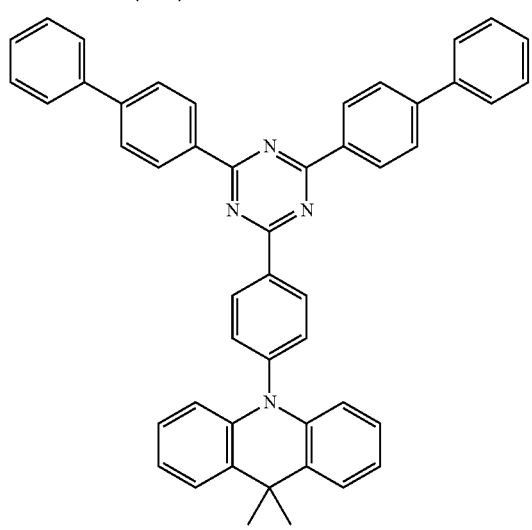
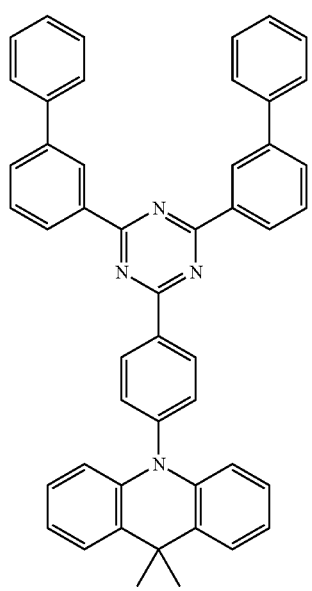
156
-continued
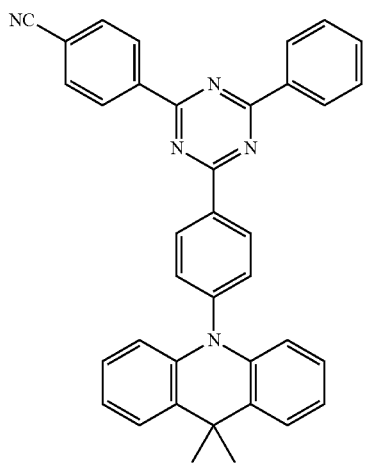
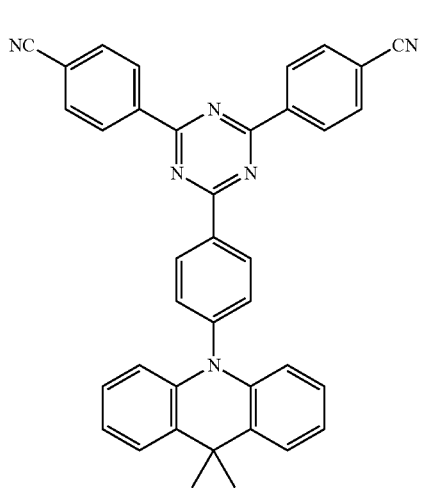
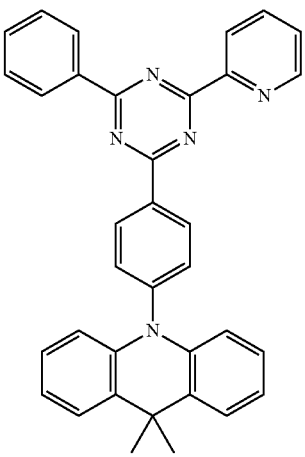

157
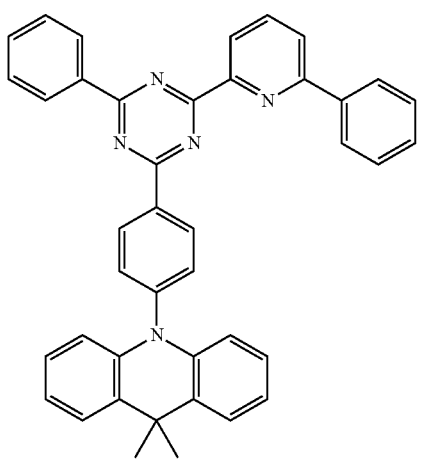
[Formula 116]
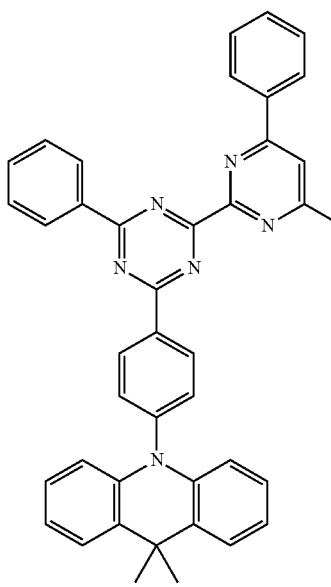
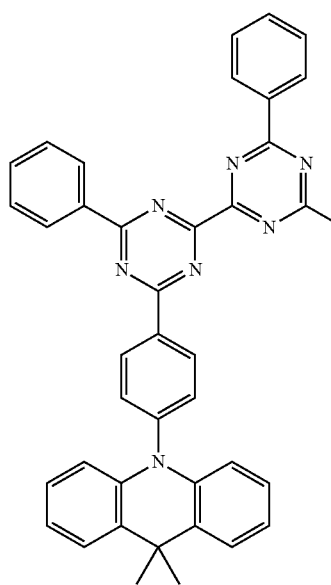
158
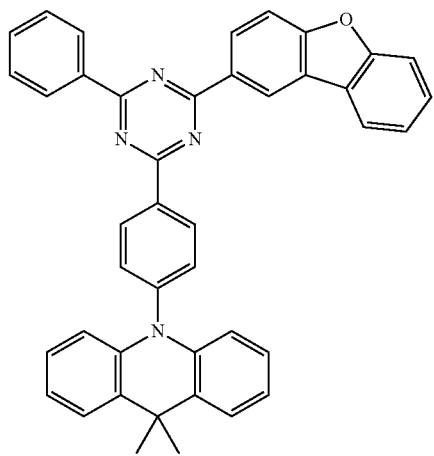
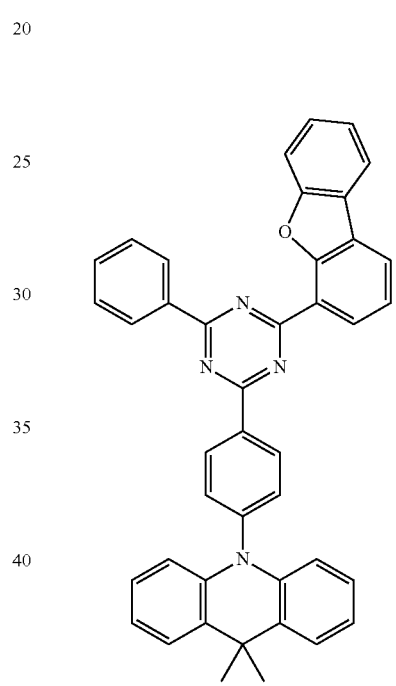
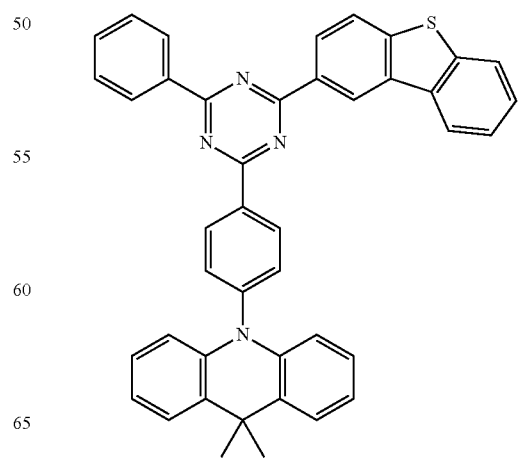

159
-continued
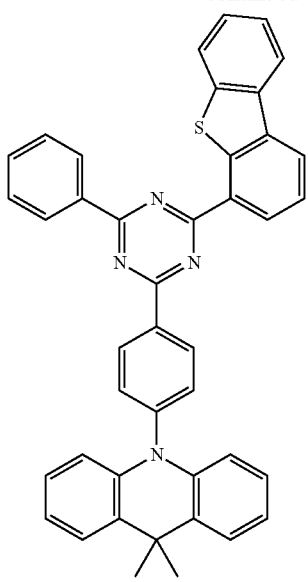
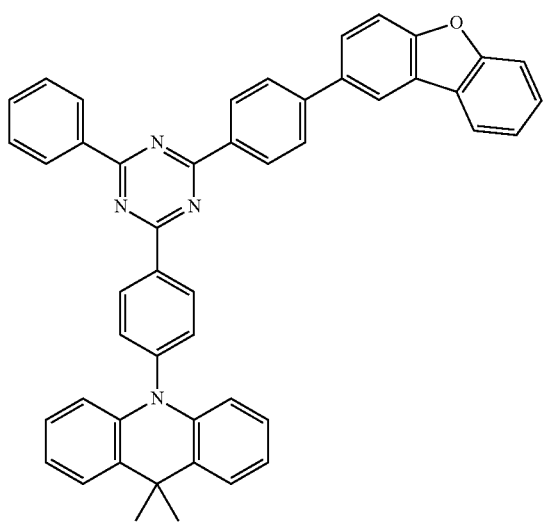
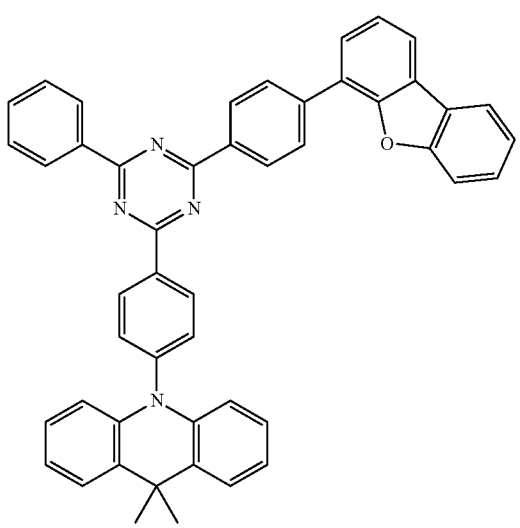
160
-continued
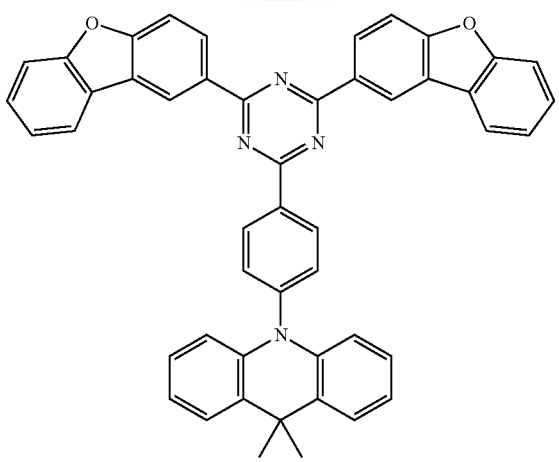
[Formula 117]
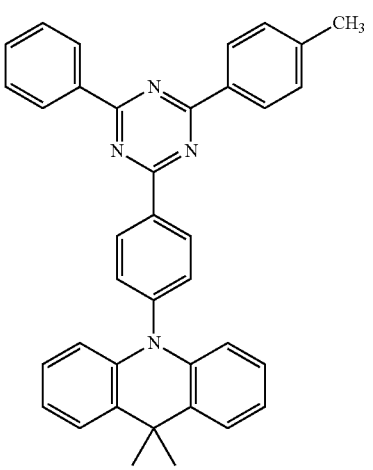
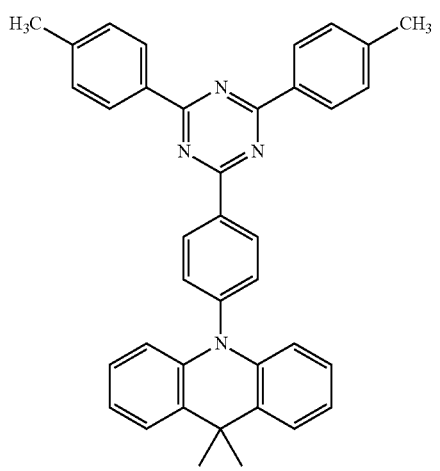

161
-continued
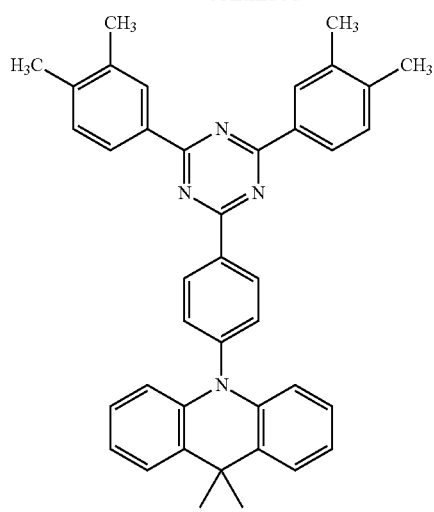
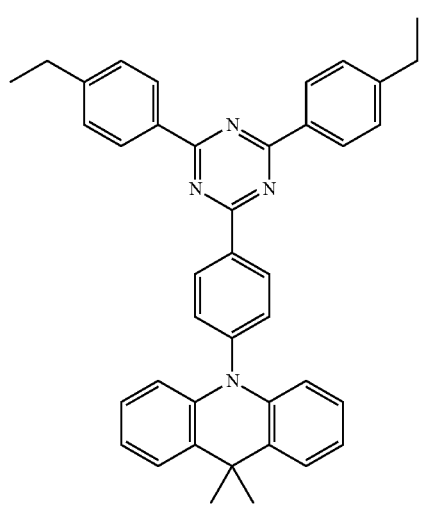
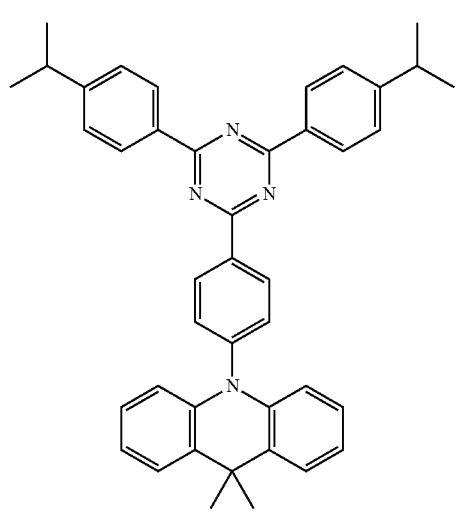
162
-continued
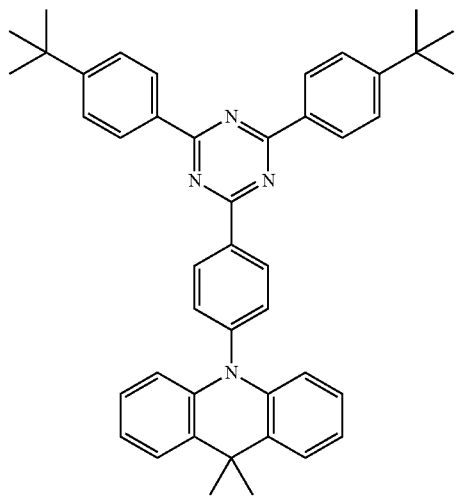
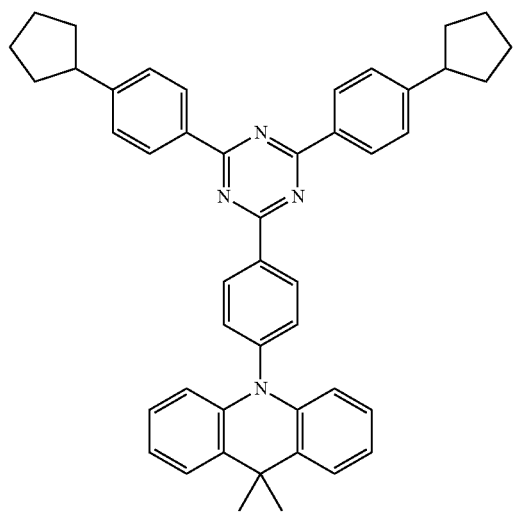
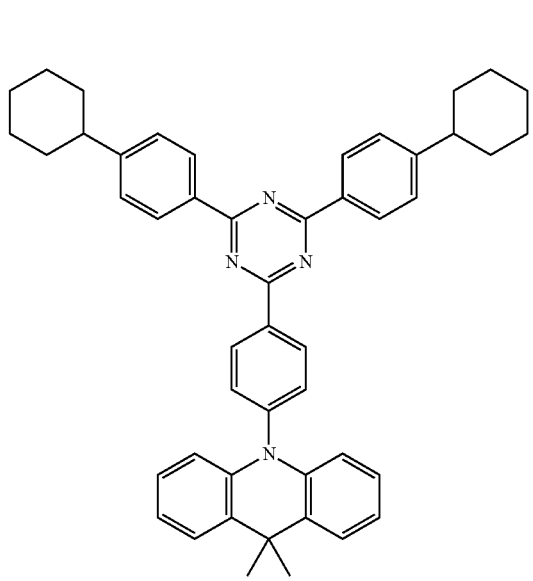

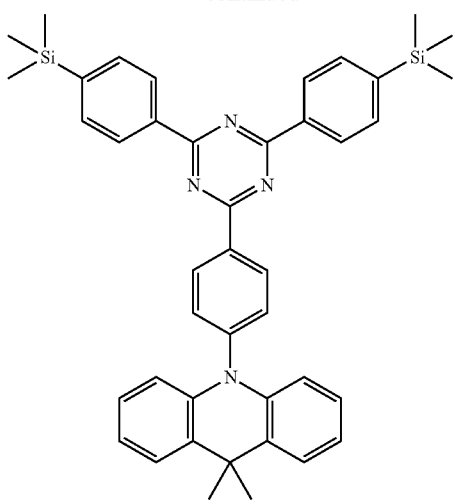
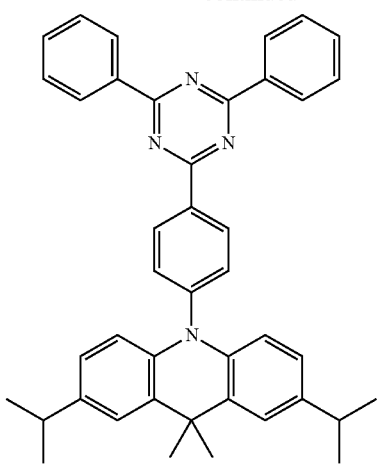
[Formula 118]
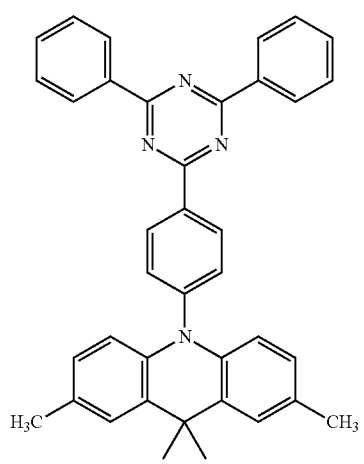
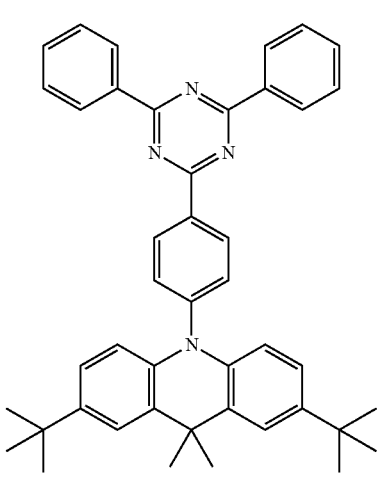
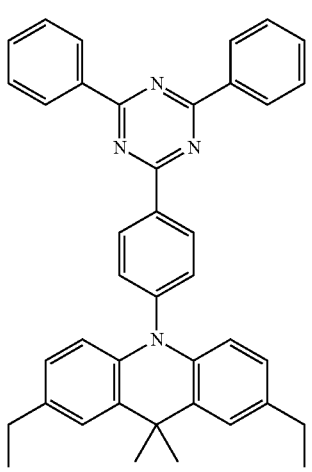
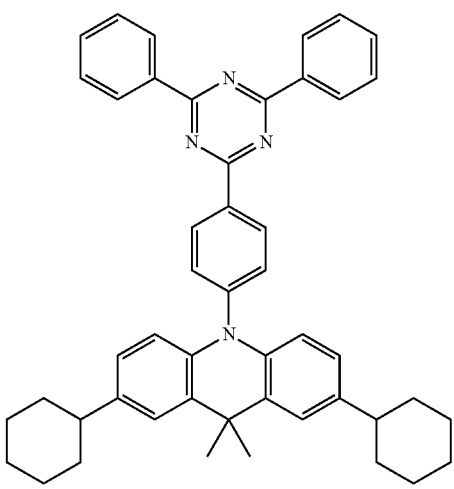

165
-continued
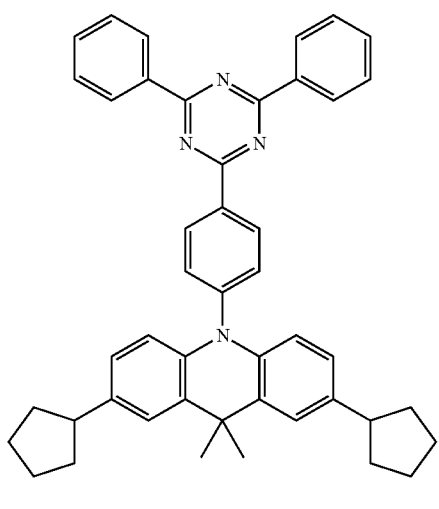
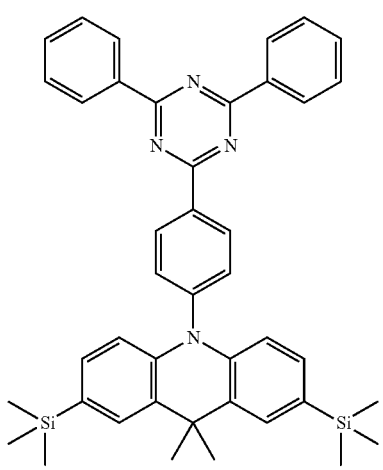
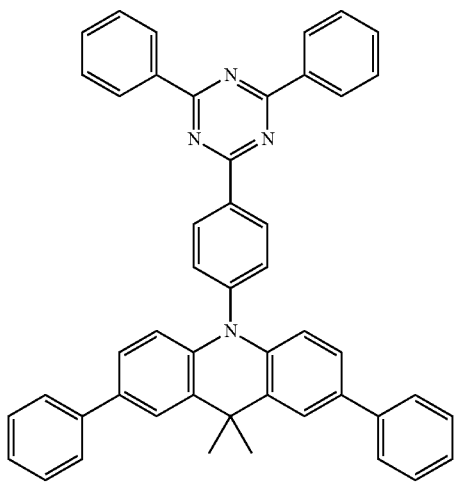
166
-continued
[Formula 119]
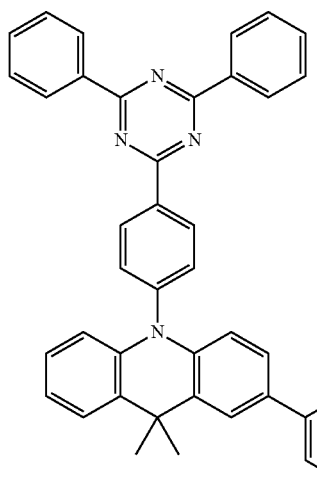
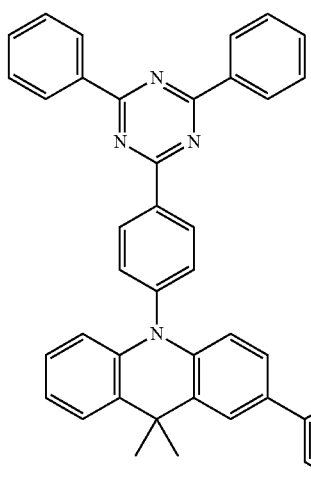
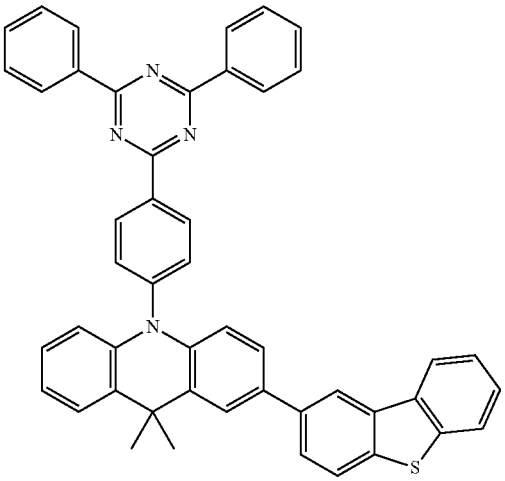

167
-continued
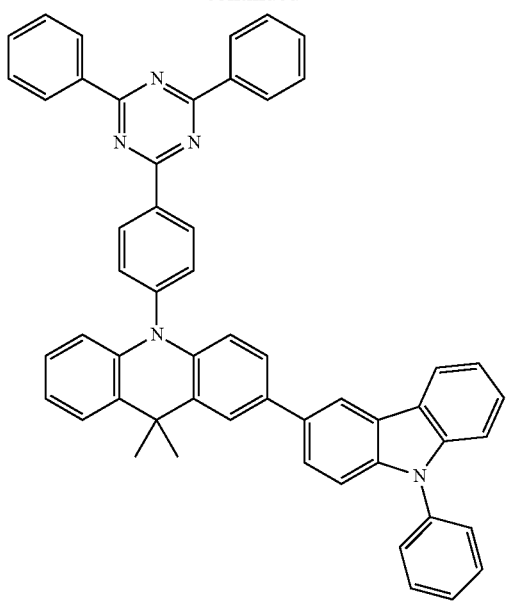
168
-continued
[Formula 120]
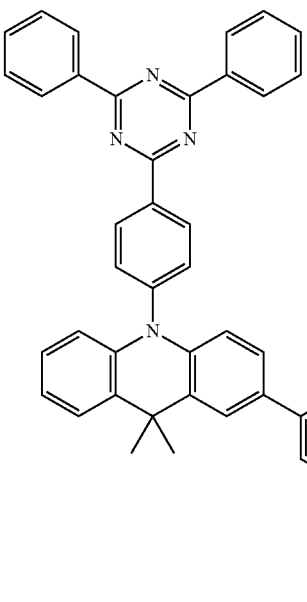
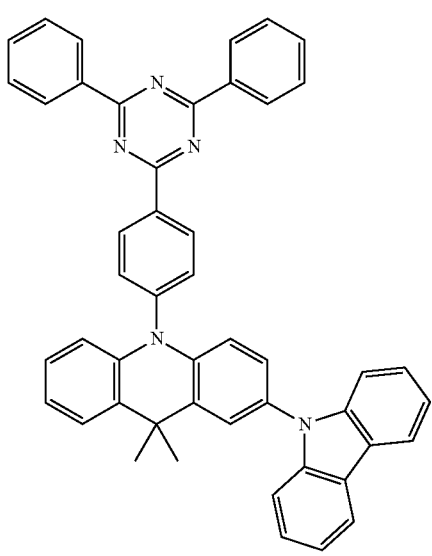
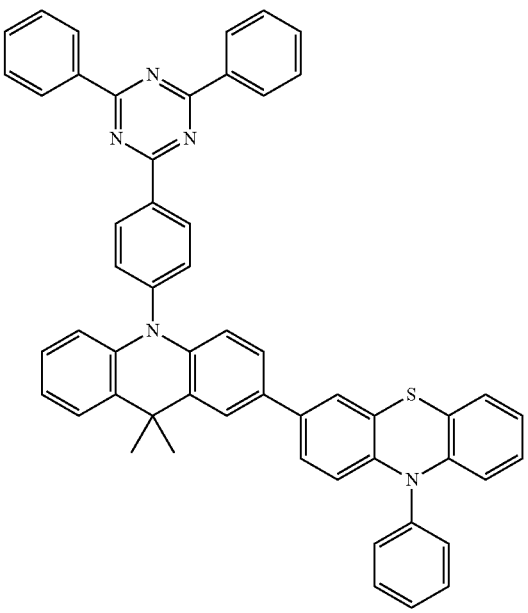

169
-continued
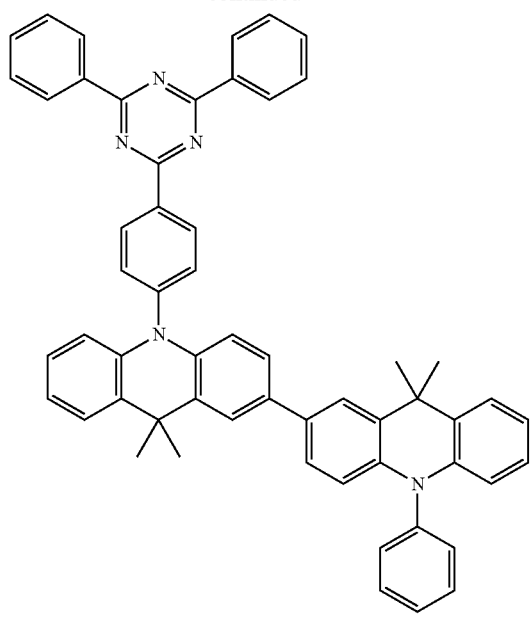
170
-continued
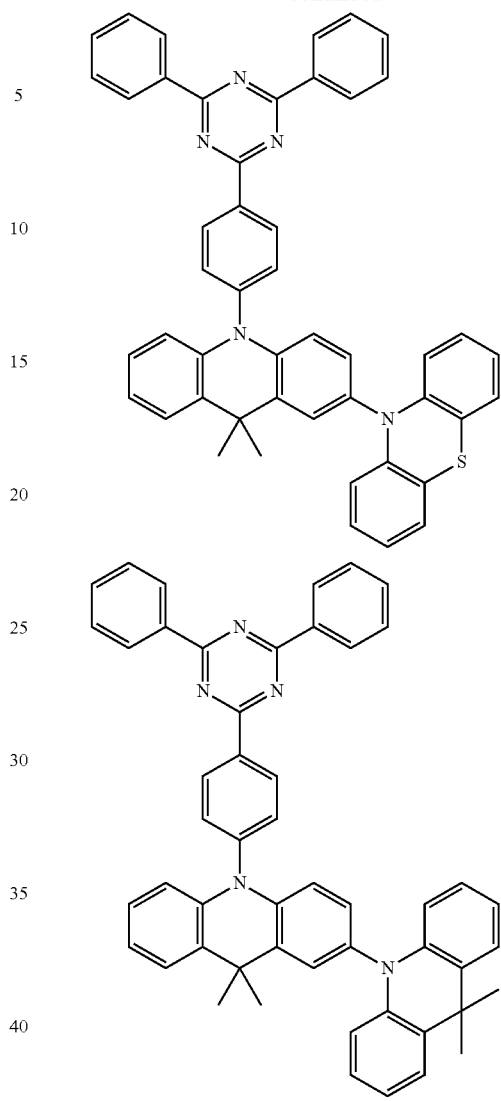
[Formula 121]
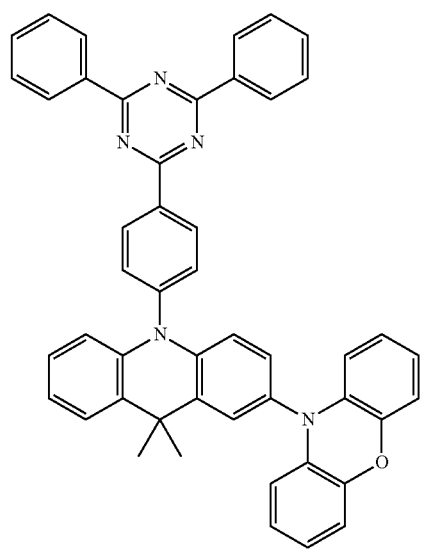
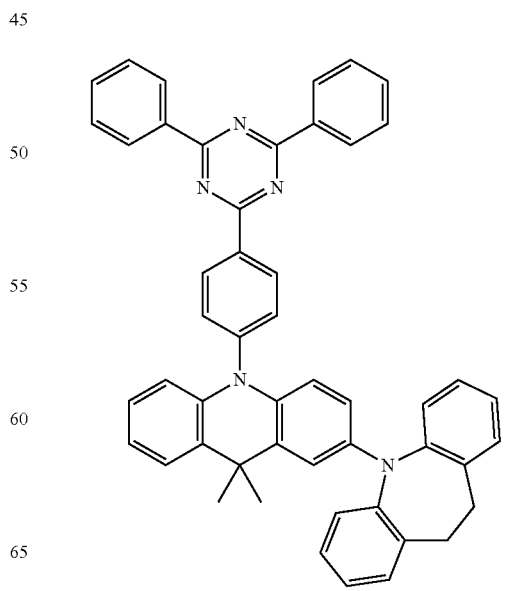

171
-continued
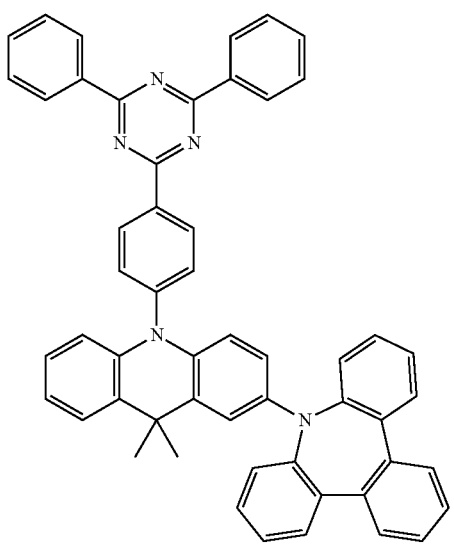
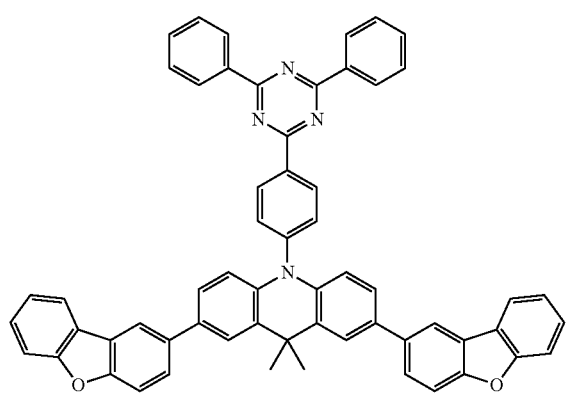
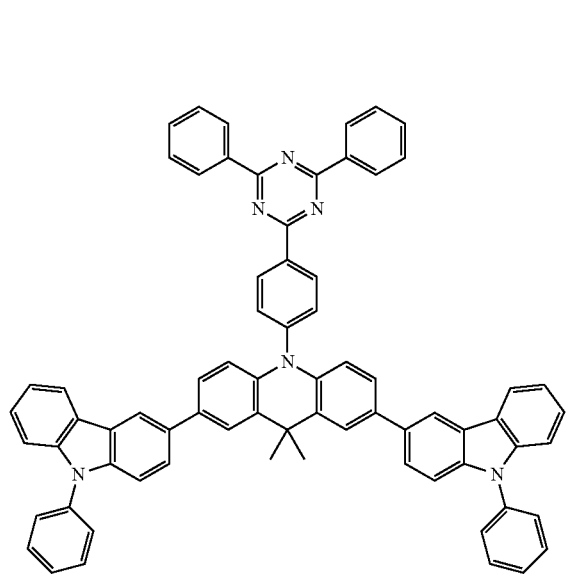
172
-continued
[Formula 122]
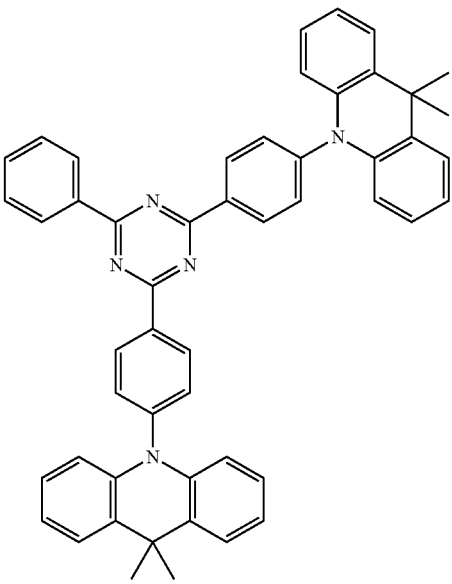
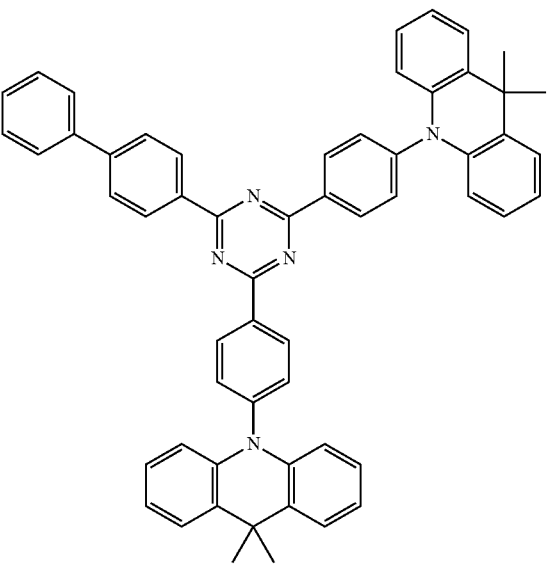

173
-continued
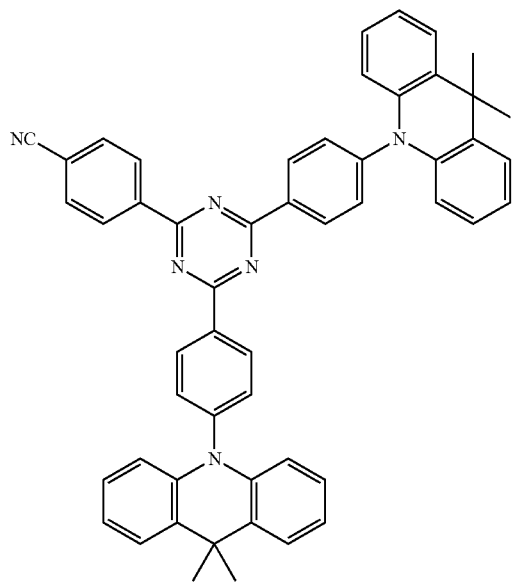
174
-continued
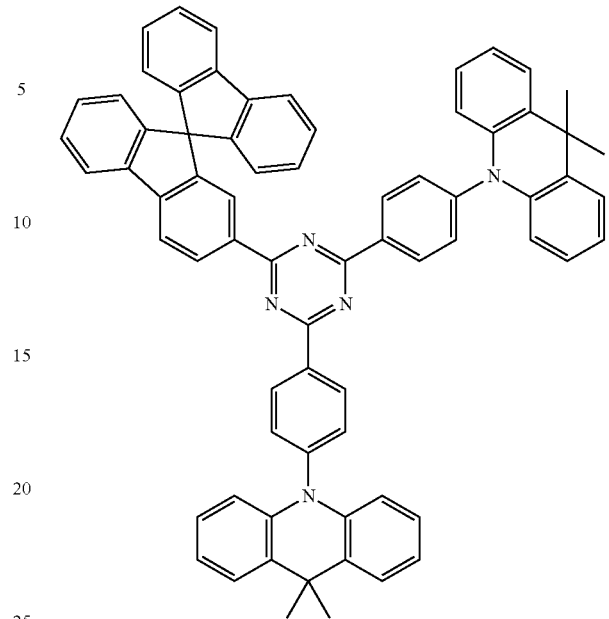
[Formula 123]
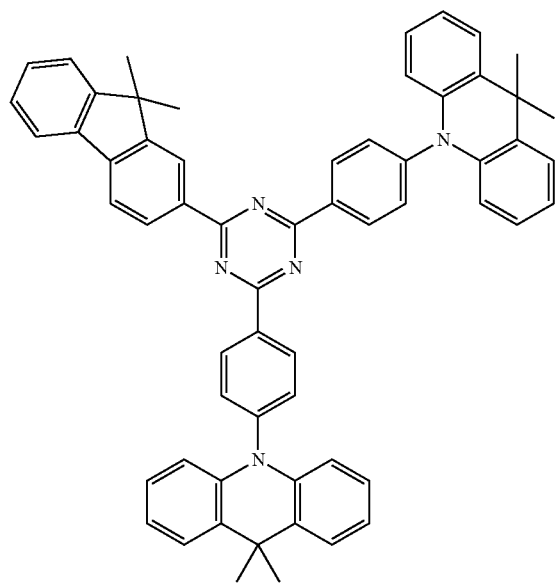
[Formula 124]
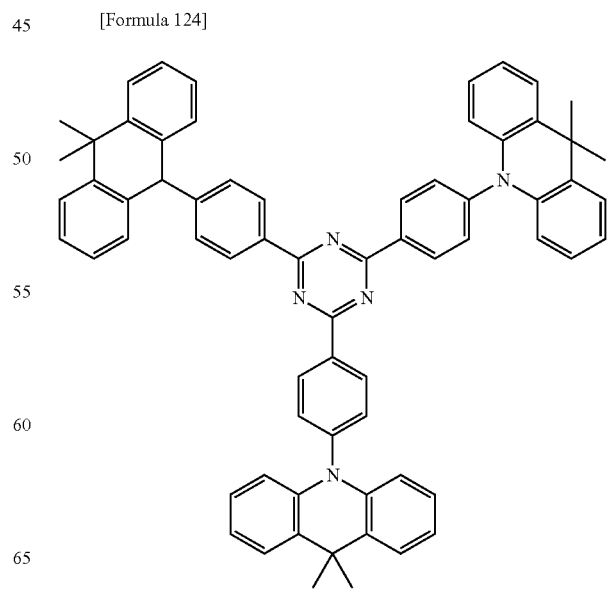

-continued
[Formula 125]
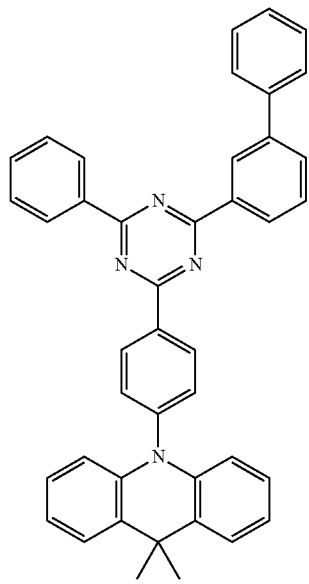
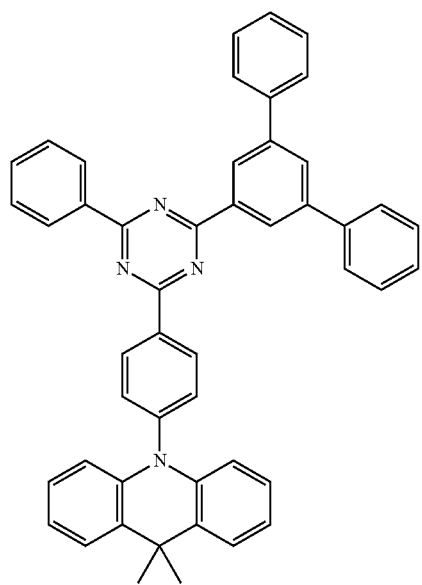
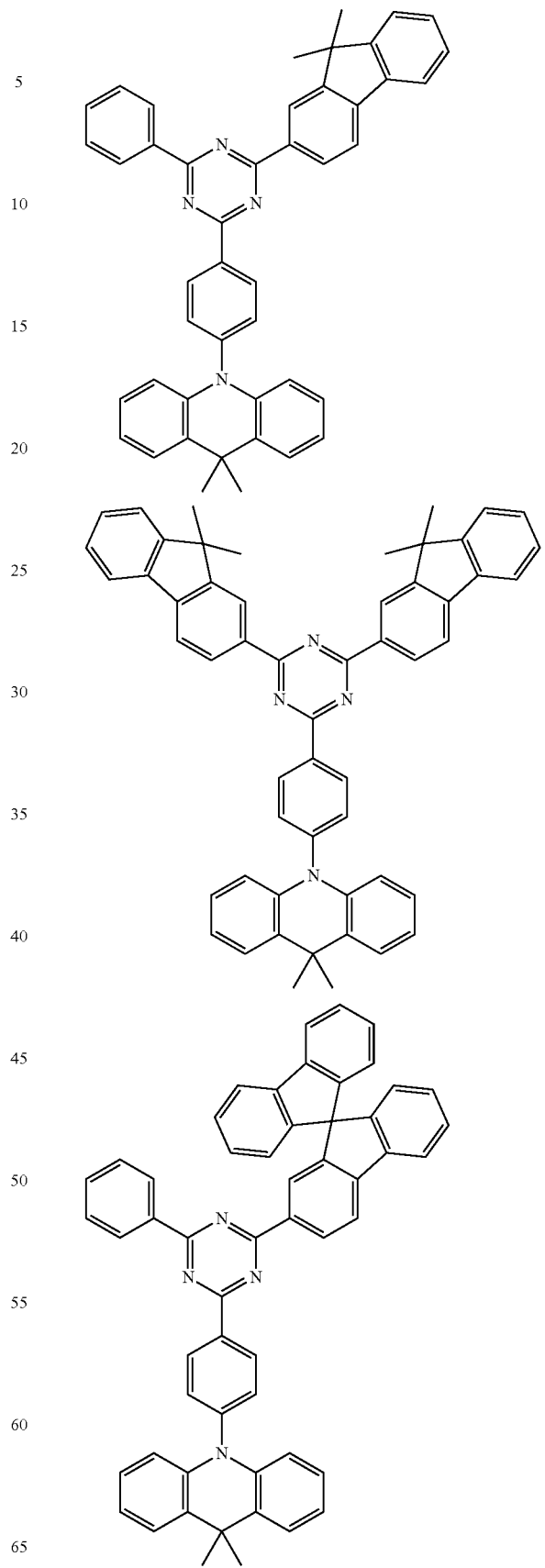

[Formula 126]
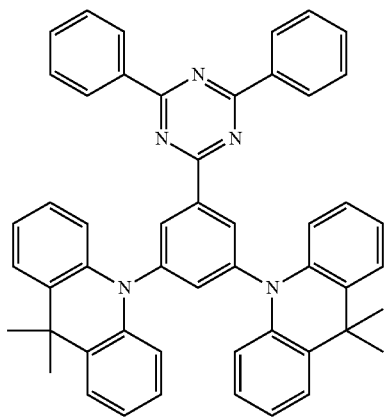
[Formula 127]
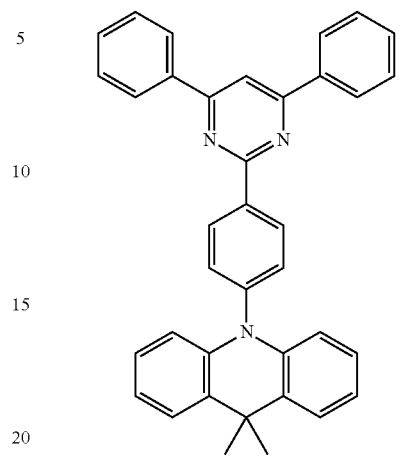
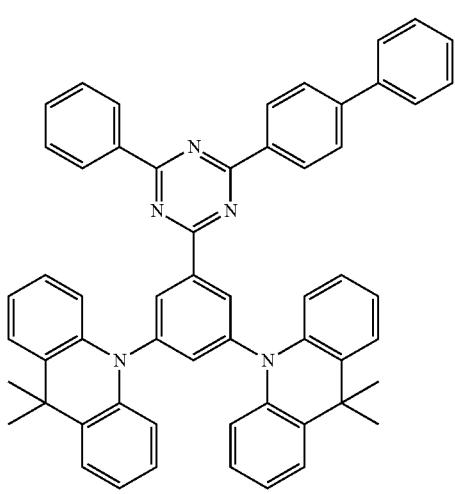
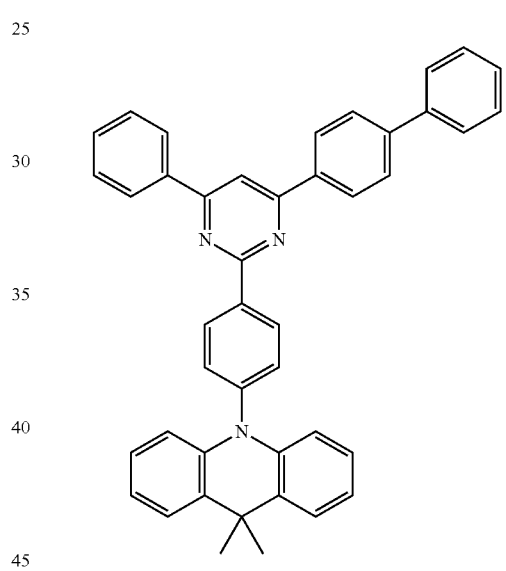
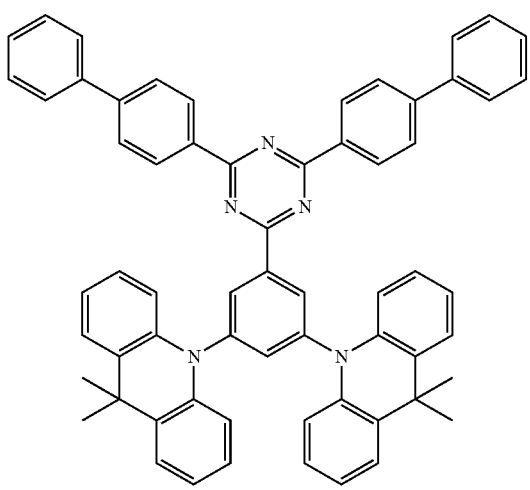
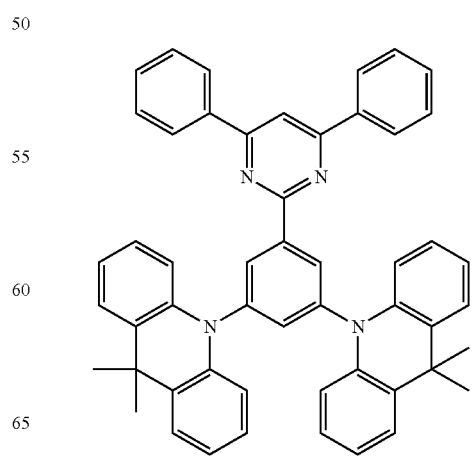

179
-continued
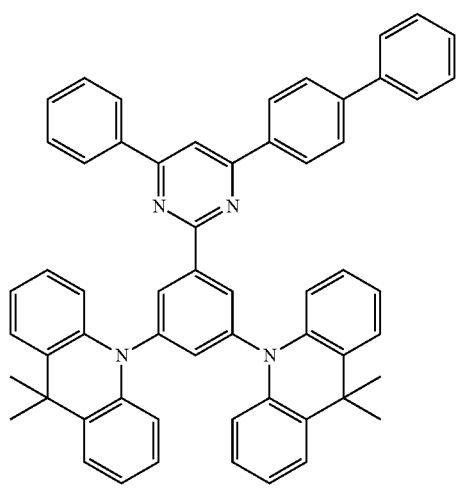
180
-continued
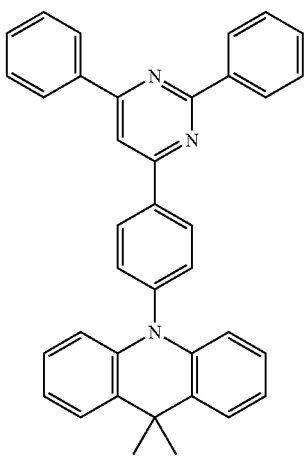
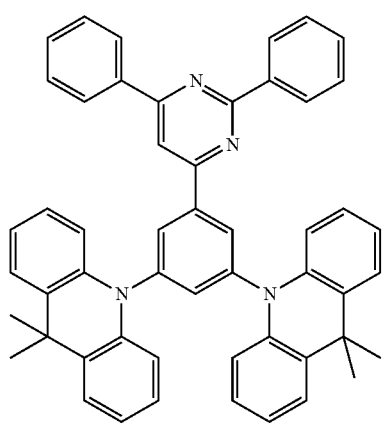
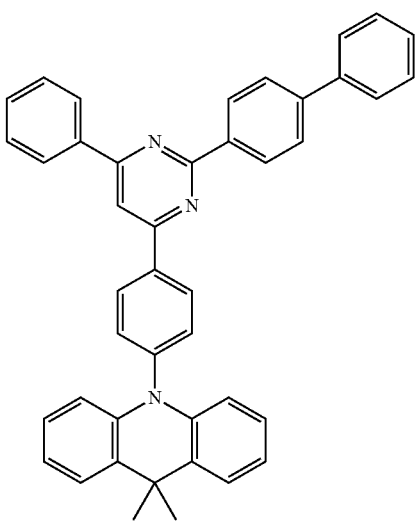
[Formula 128]
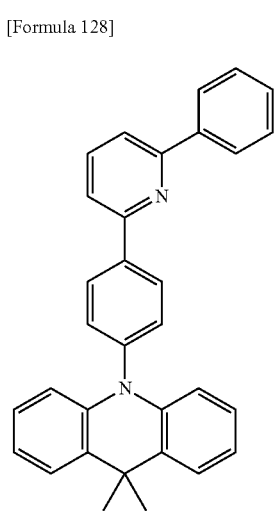

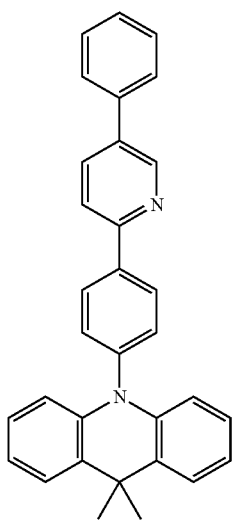
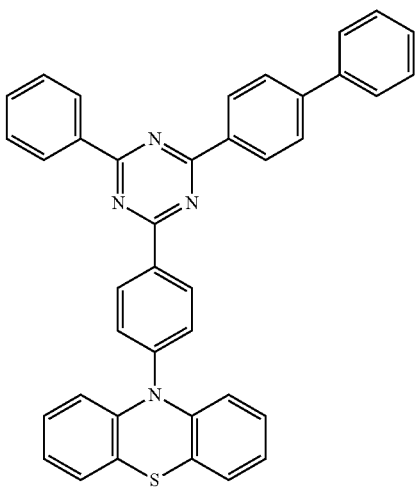
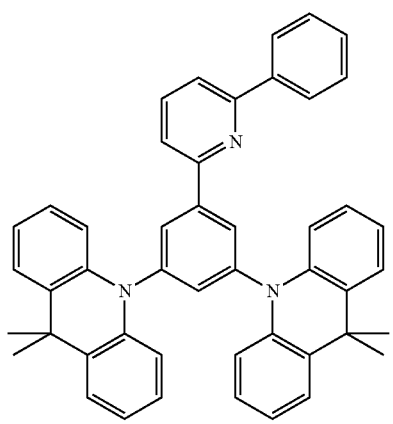
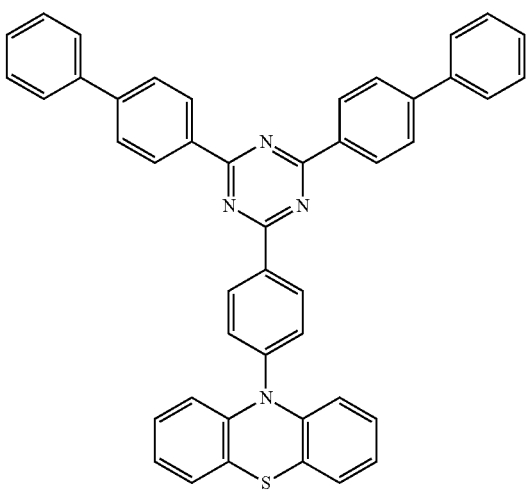
[Formula 129]
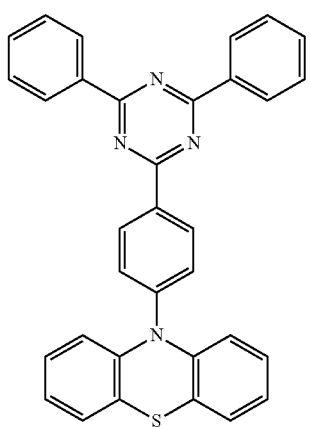

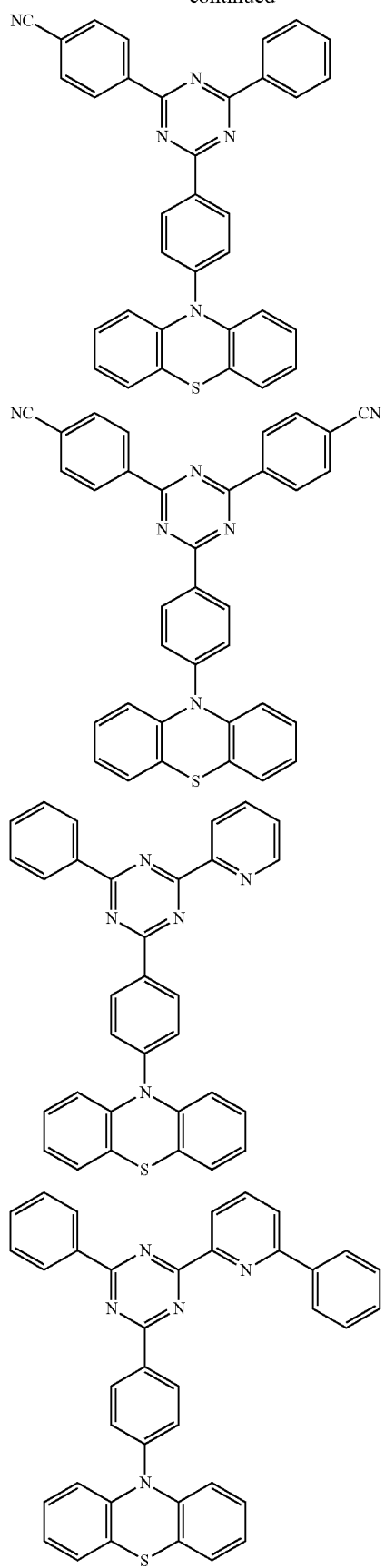
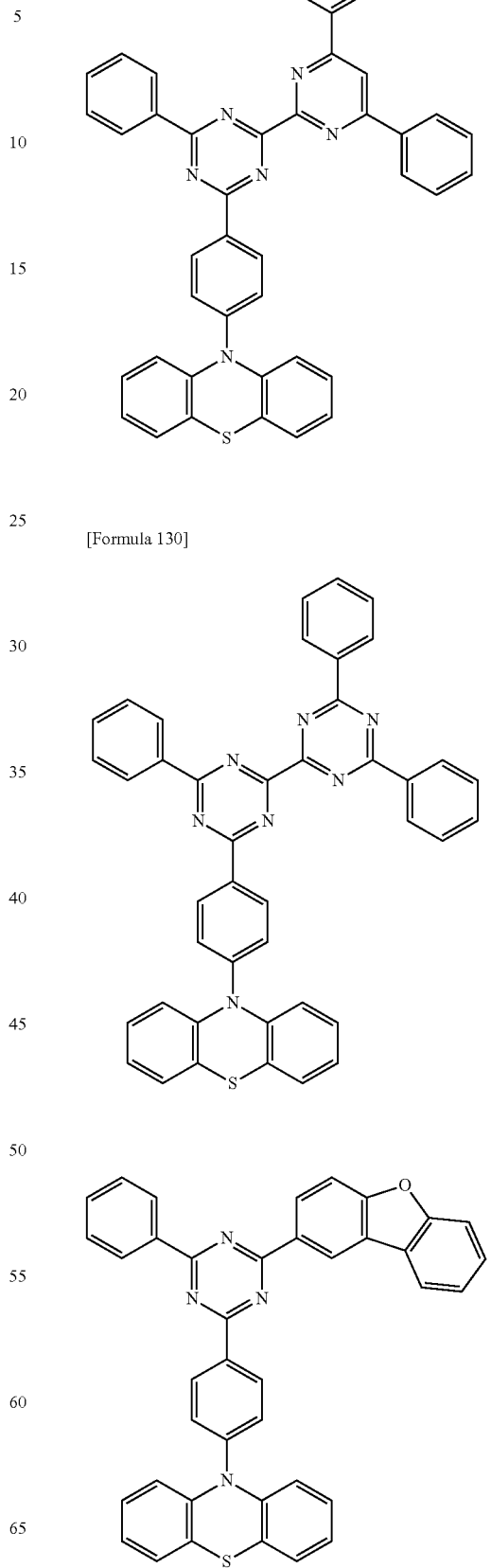
[Formula 130]

185
-continued
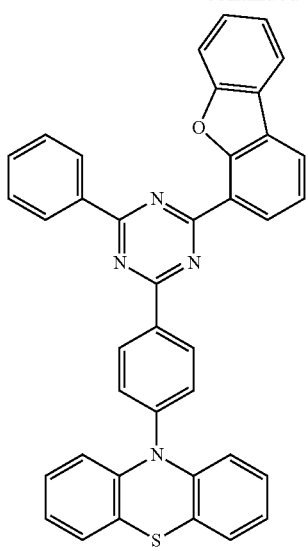
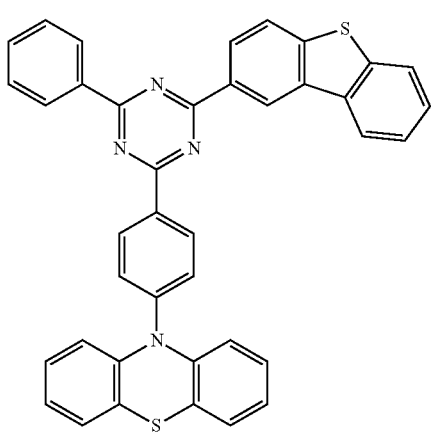
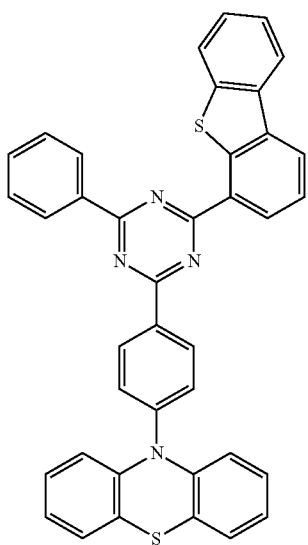
186
-continued
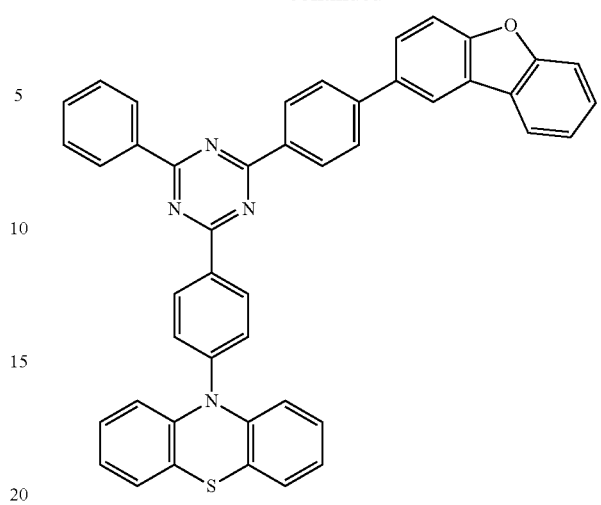
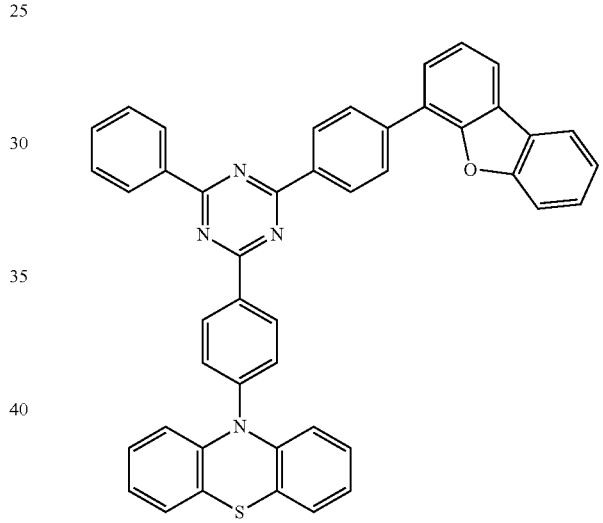
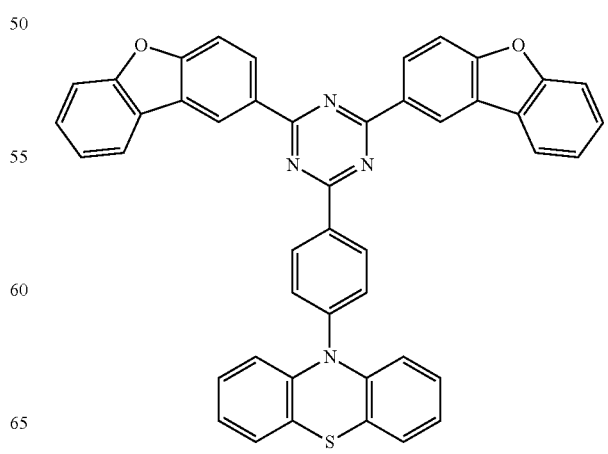

-continued
[Formula 131]
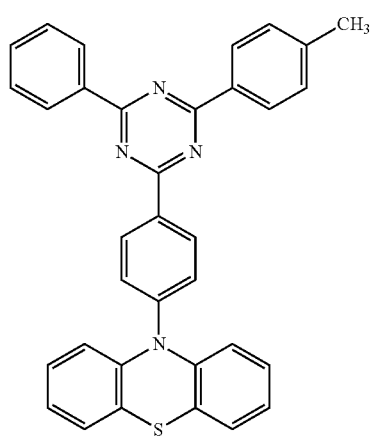
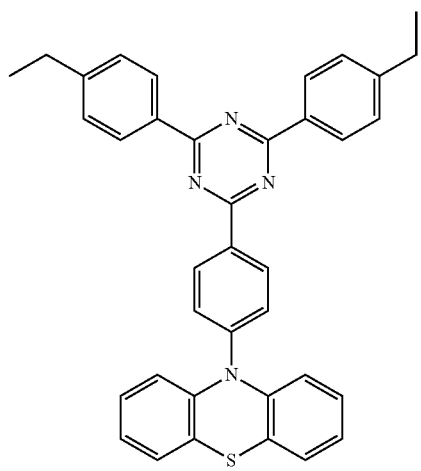
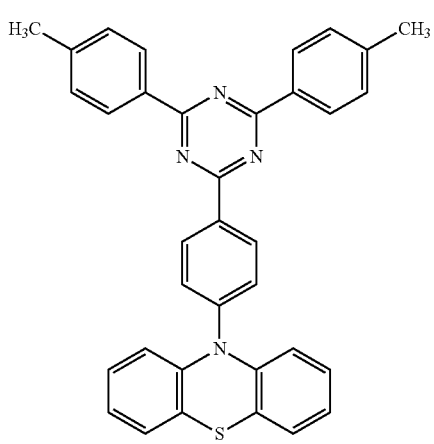
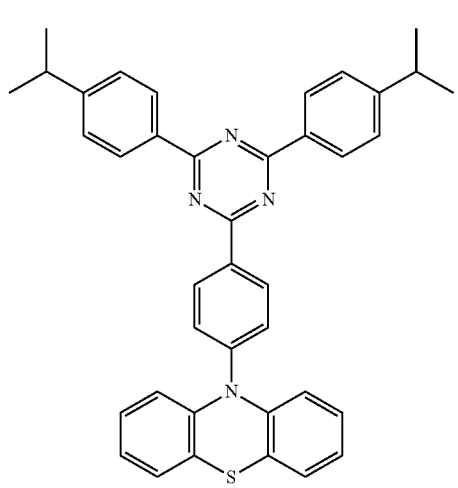
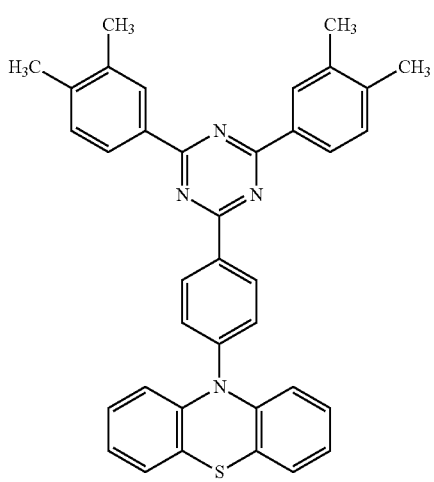
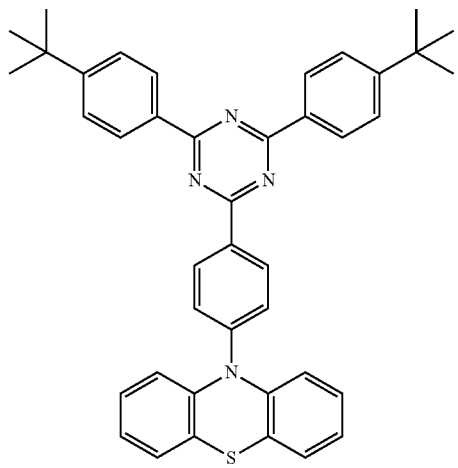

[Formula 132]
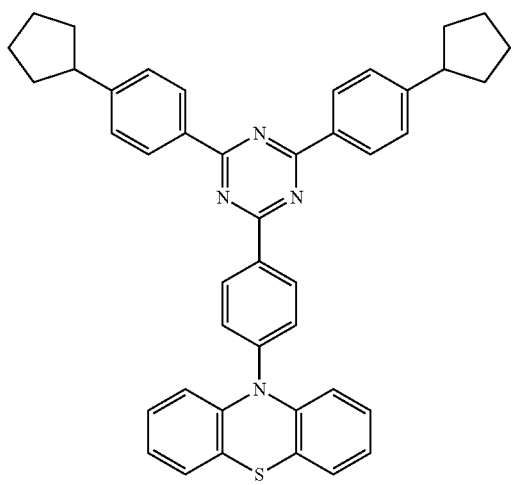
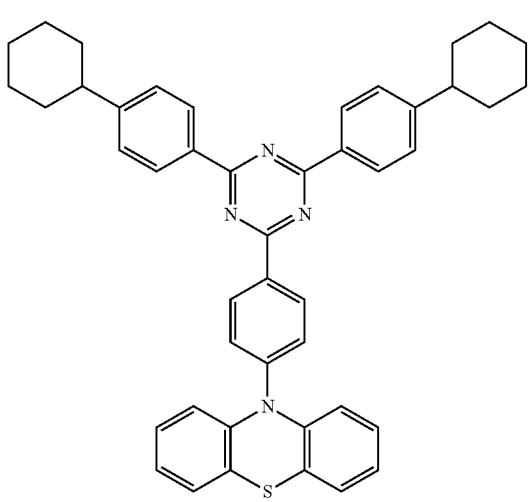
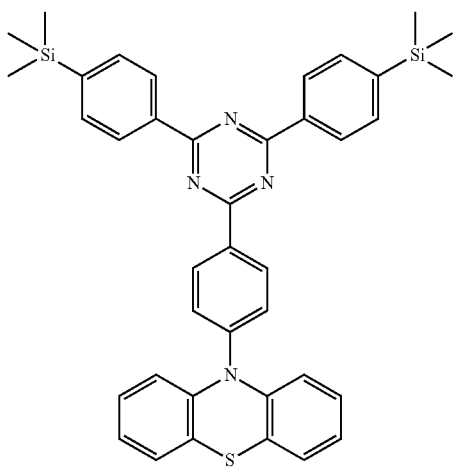
[Formula 133]
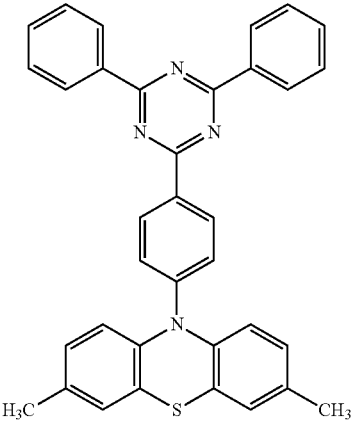
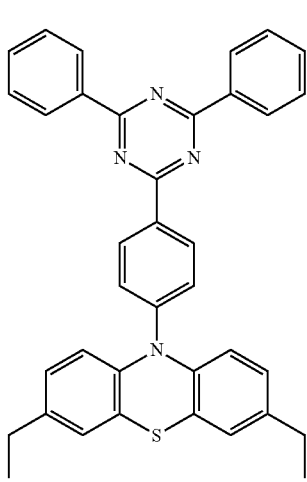
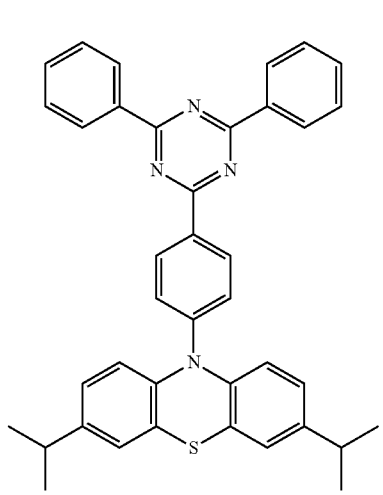

191
-continued
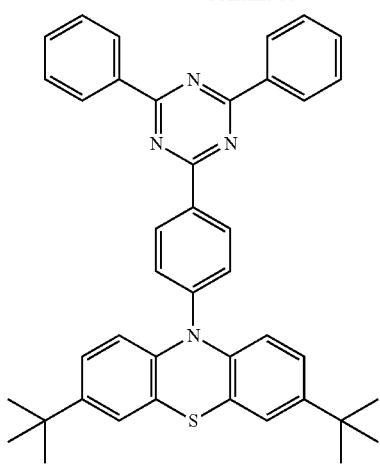
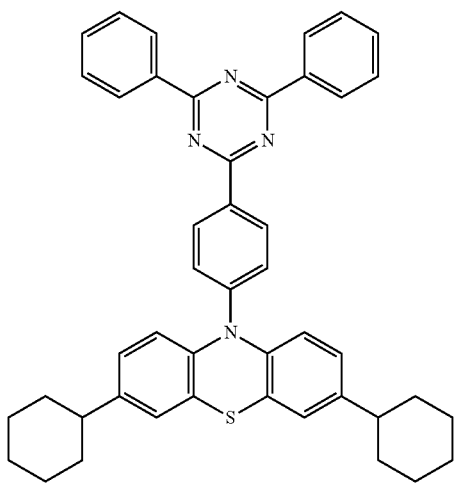
192
-continued
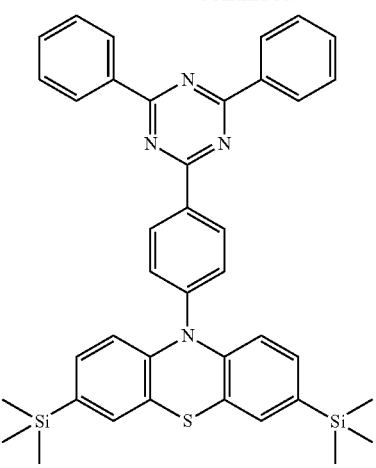
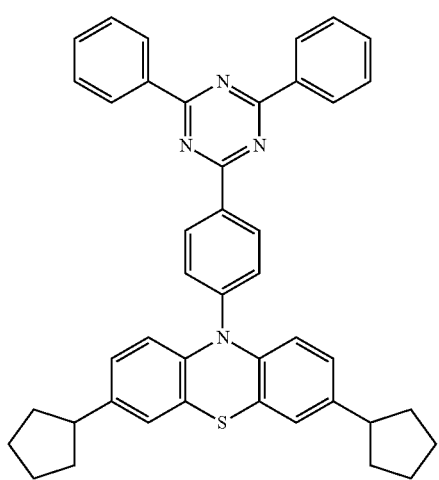
[Formula 134]
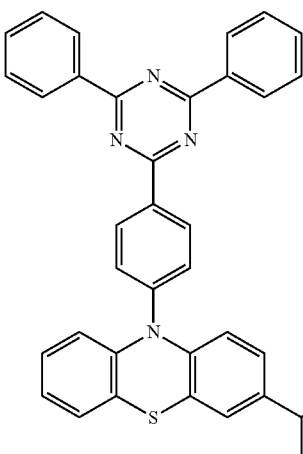

193
-continued
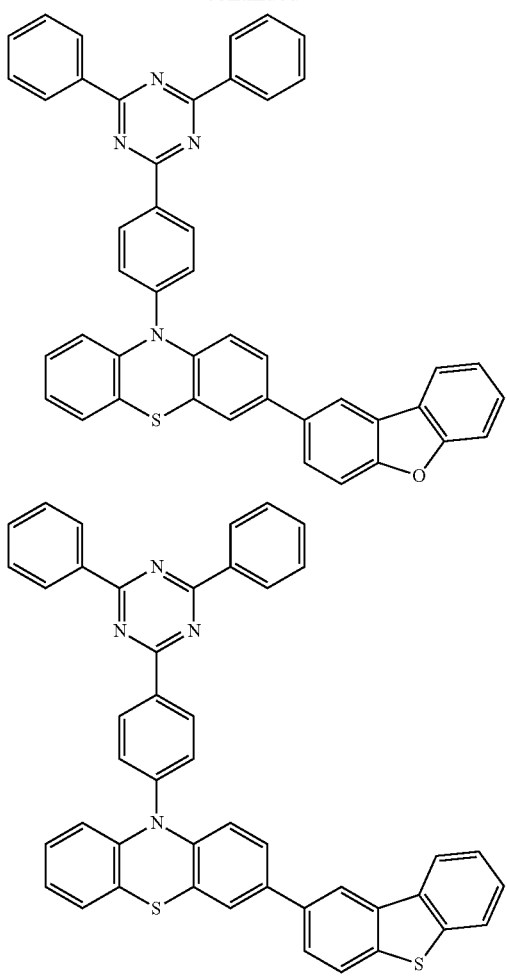
194
-continued
[Formula 135]
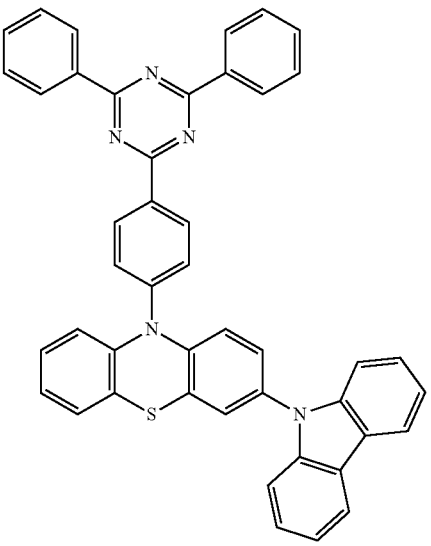
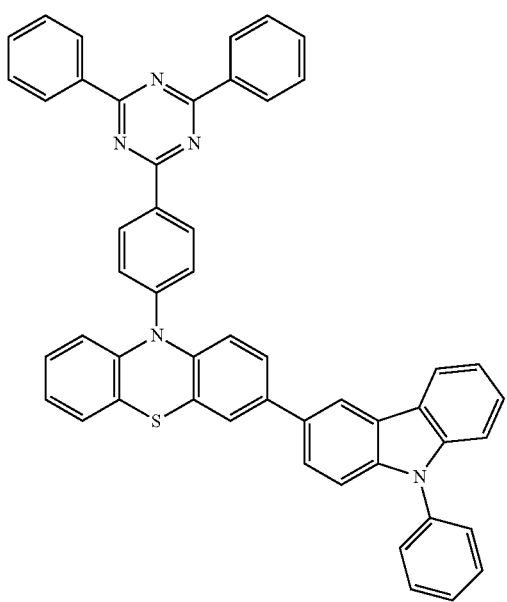
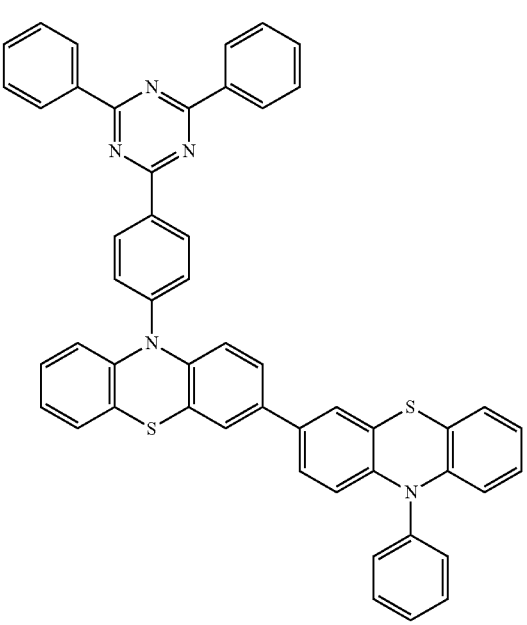

195
-continued
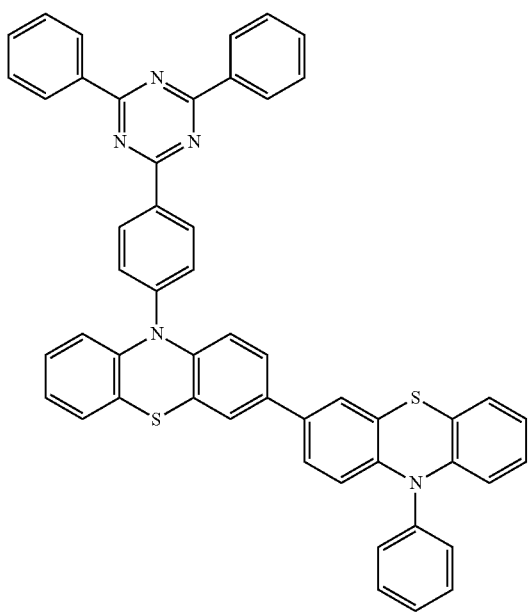
196
-continued
[Formula 136]
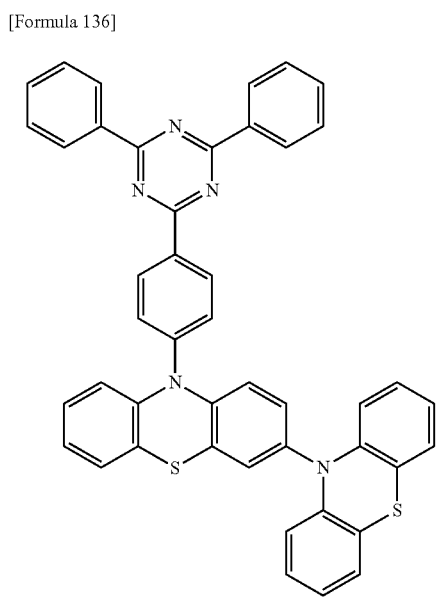
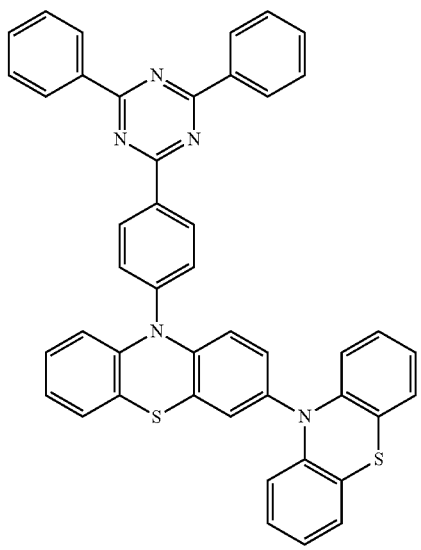
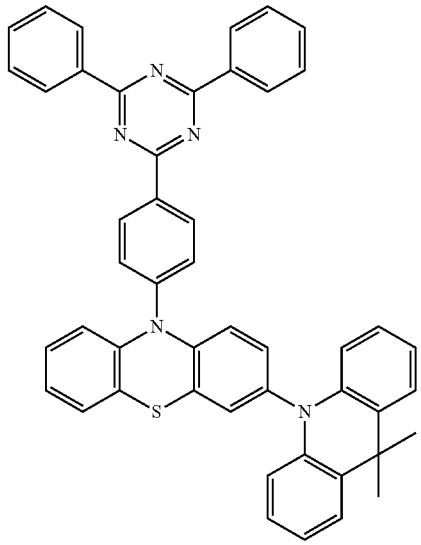

197
-continued
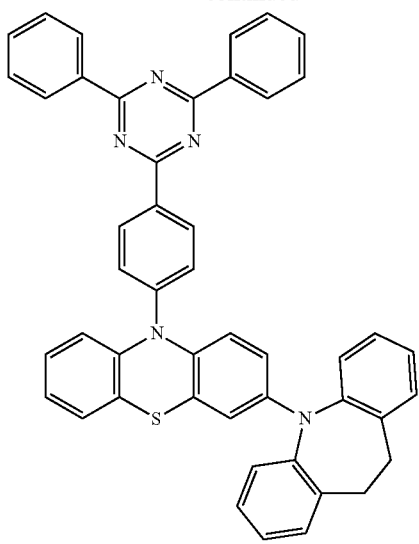
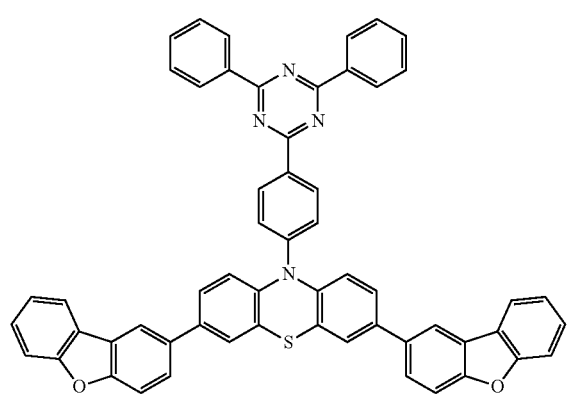
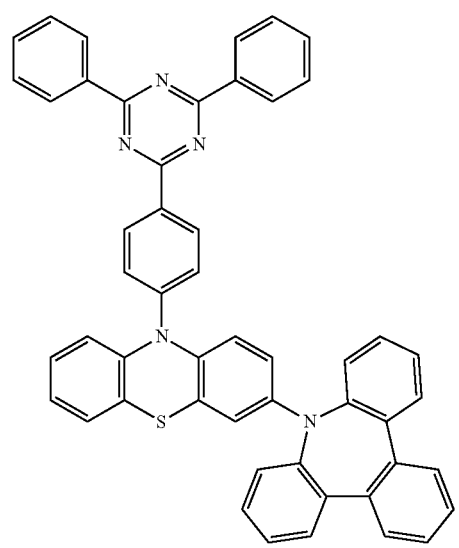
198
-continued
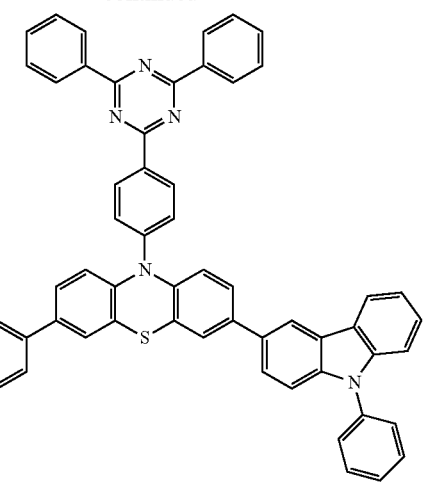
[Formula 137]
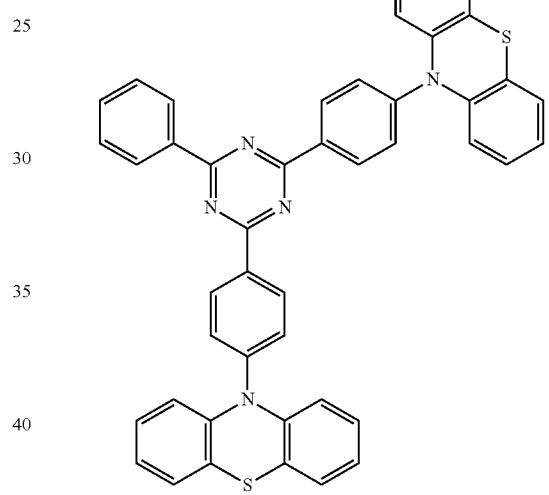
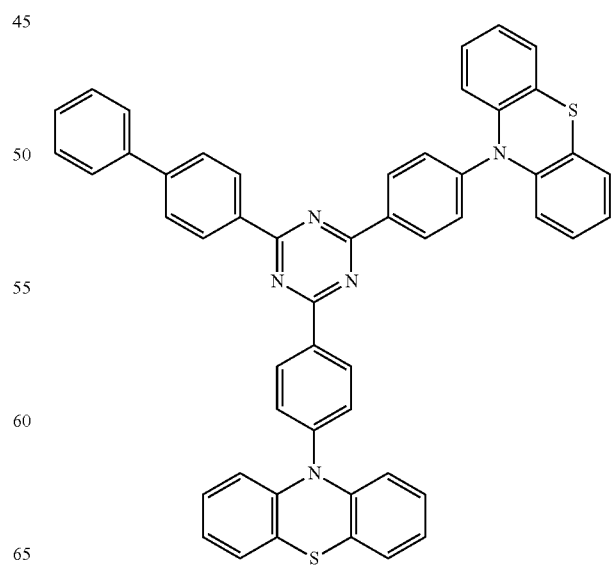

199
-continued
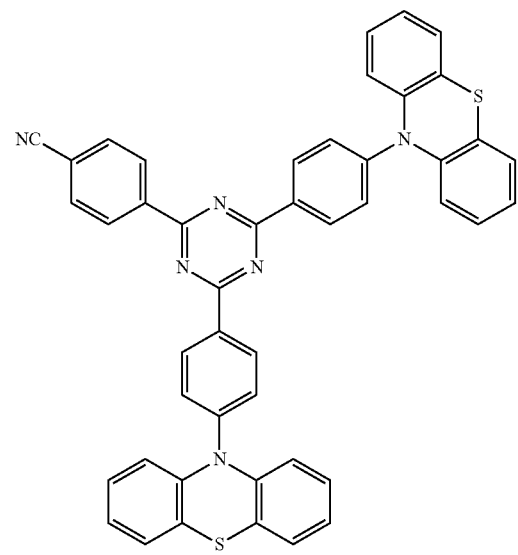
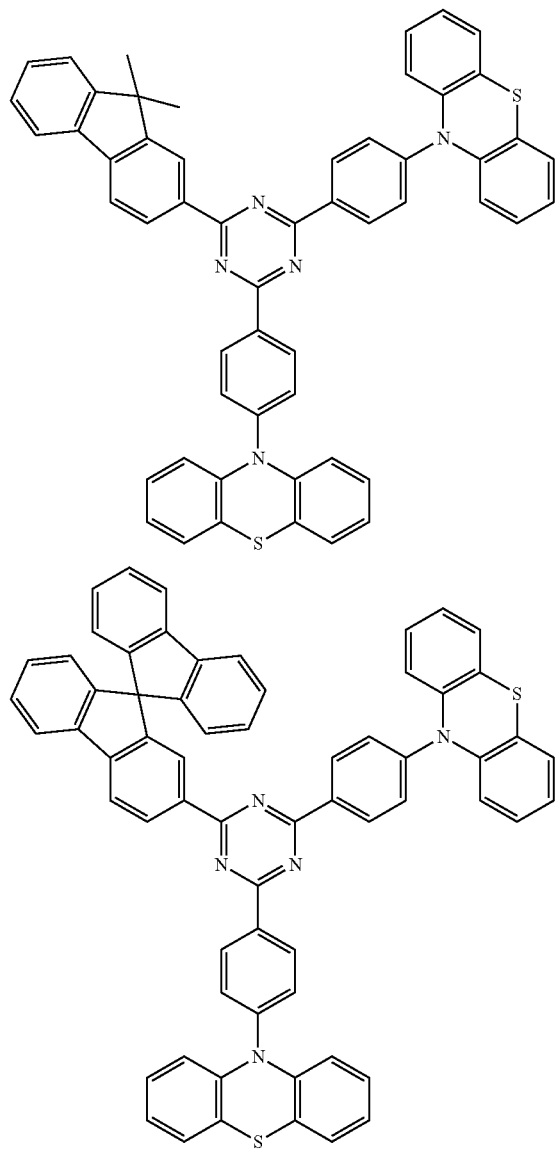
200
-continued
[Formula 138]
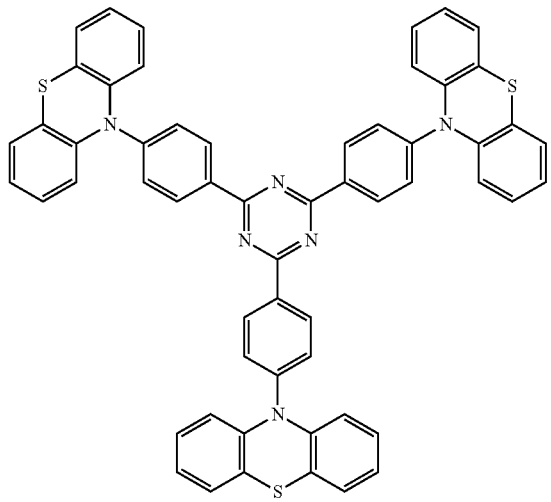
[Formula 139]
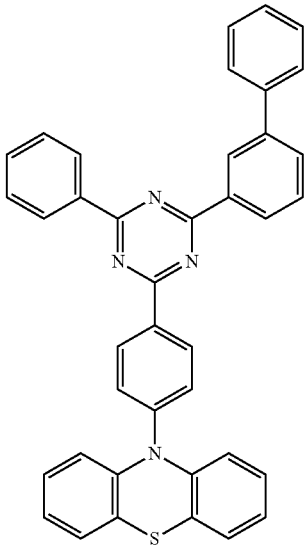
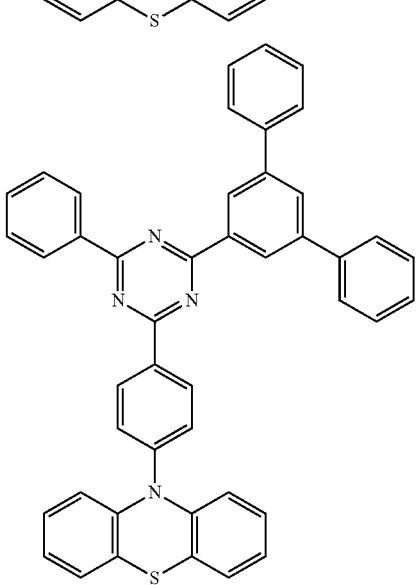

-continued
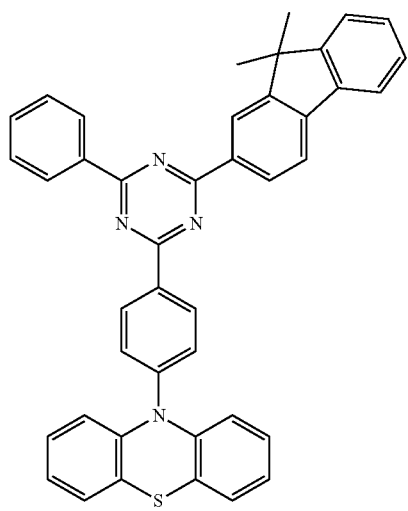
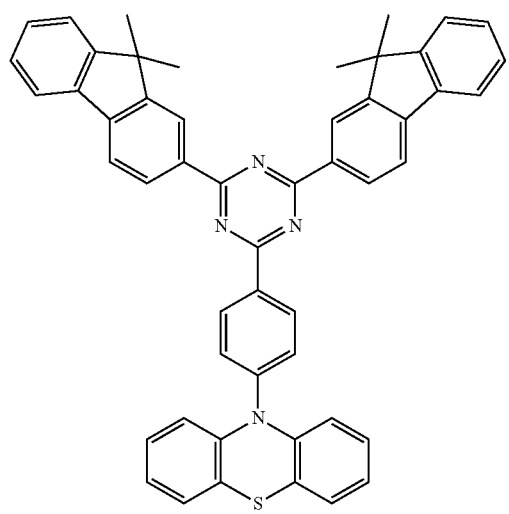
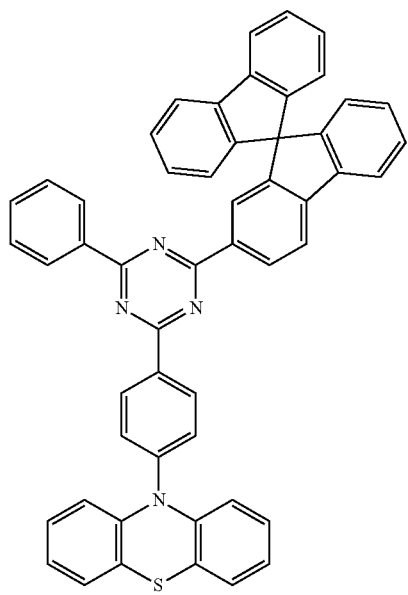
-continued
[Formula 140]
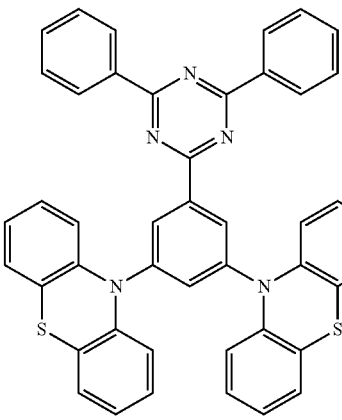
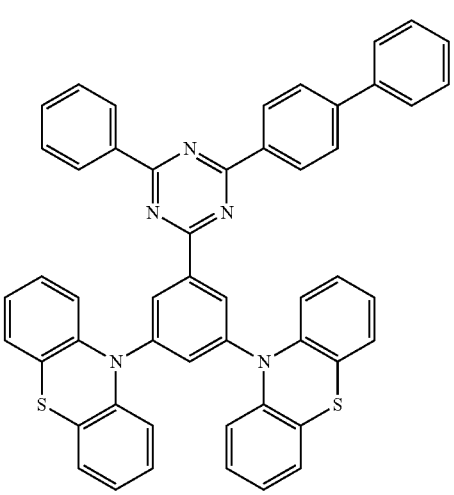
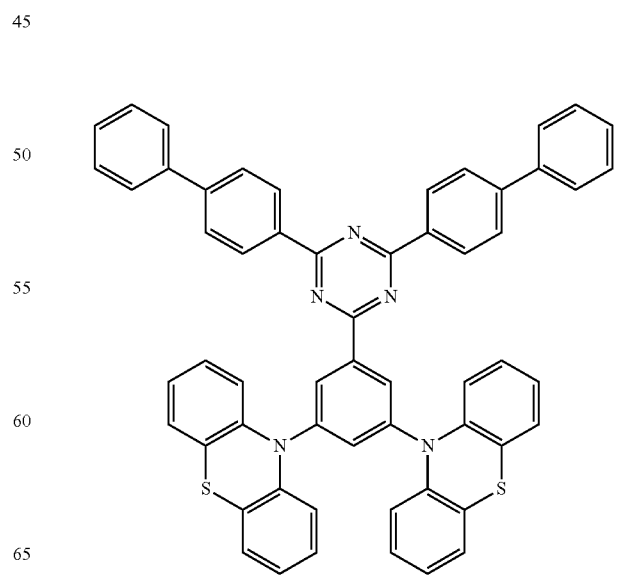

-continued
[Formula 141]
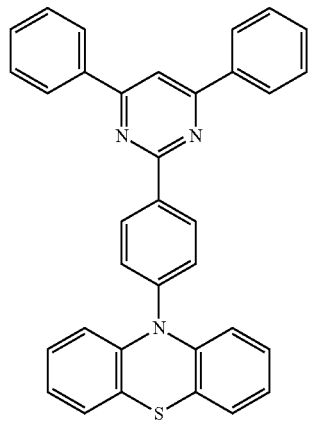
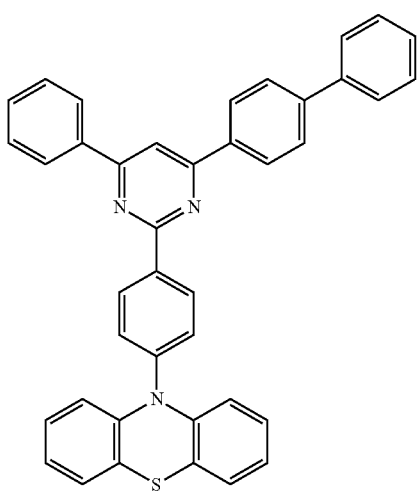
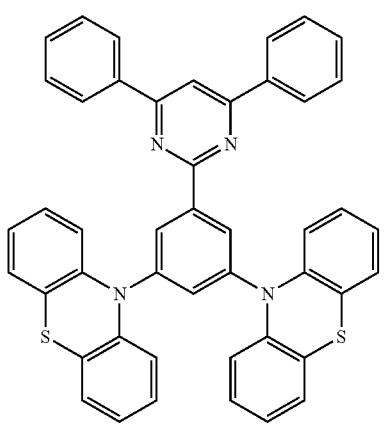
-continued
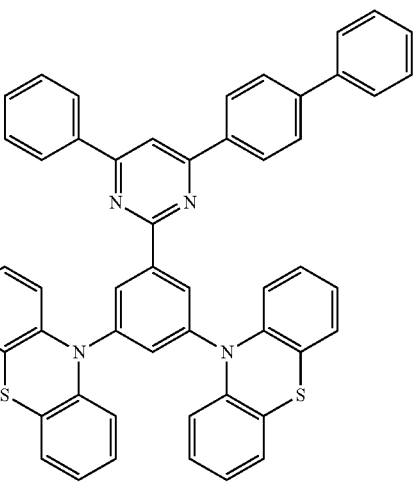
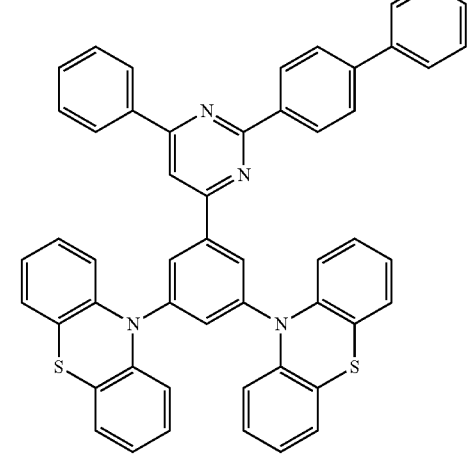

205
-continued
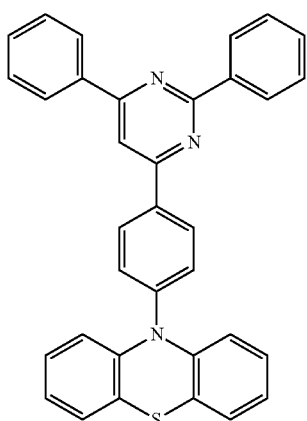
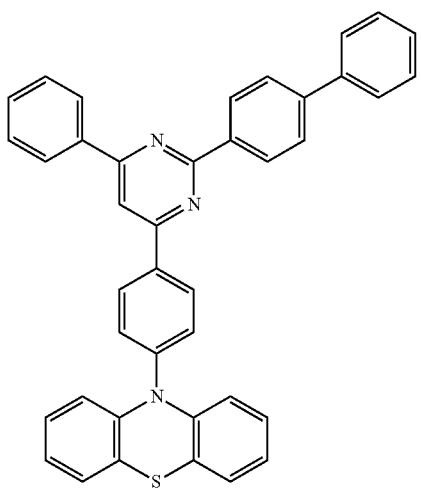
[Formula 142]
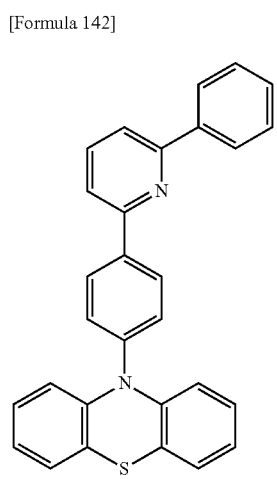
206
-continued
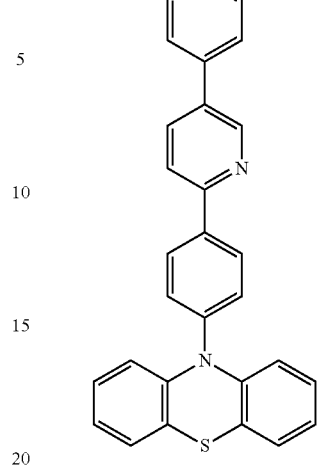
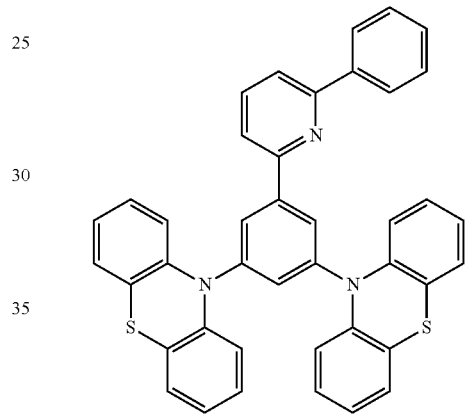
[Formula 143]
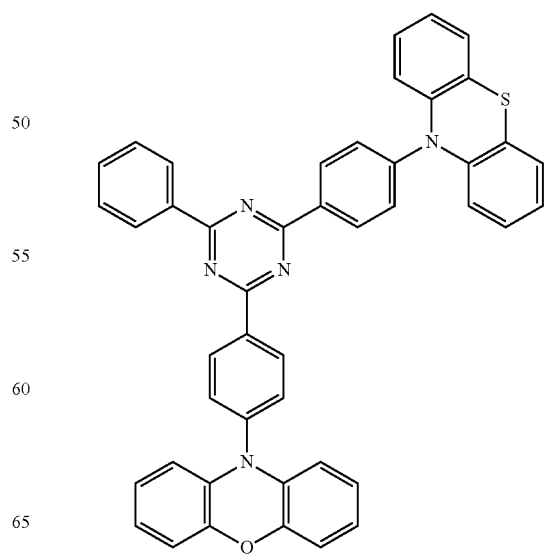

207
-continued
208
-continued
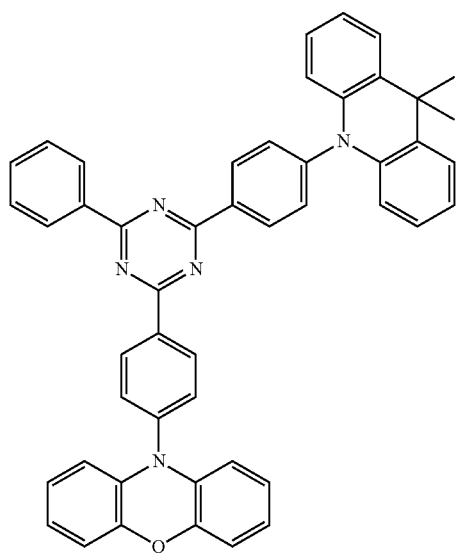
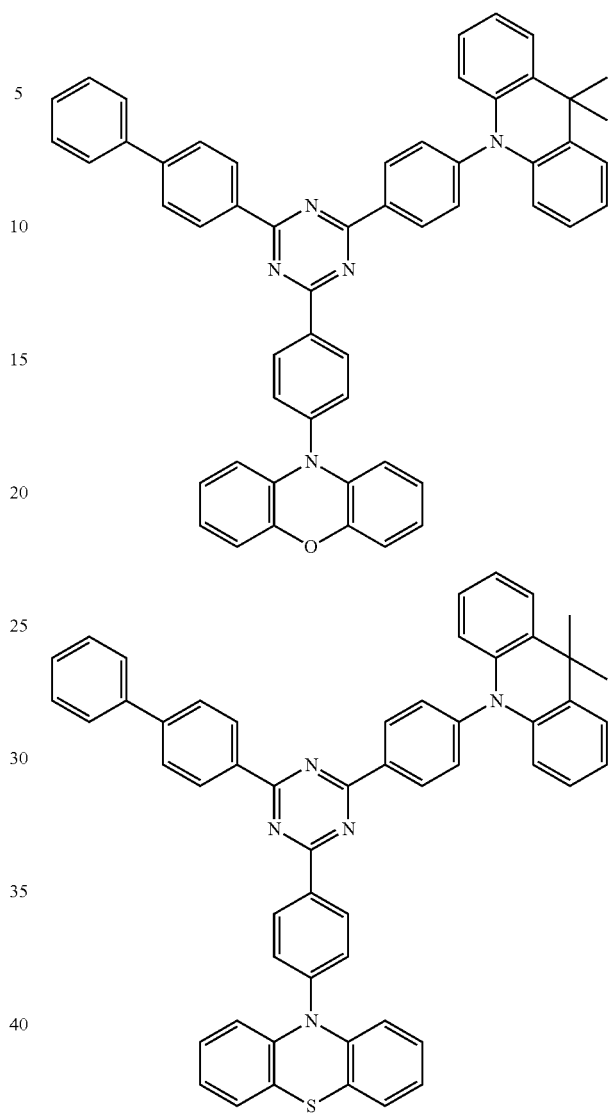
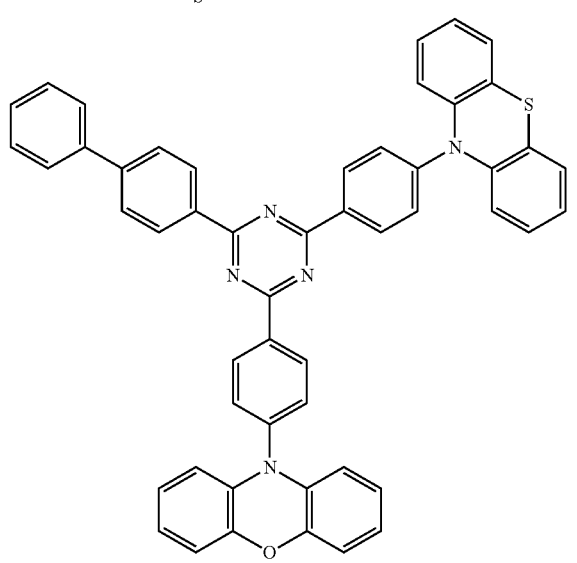
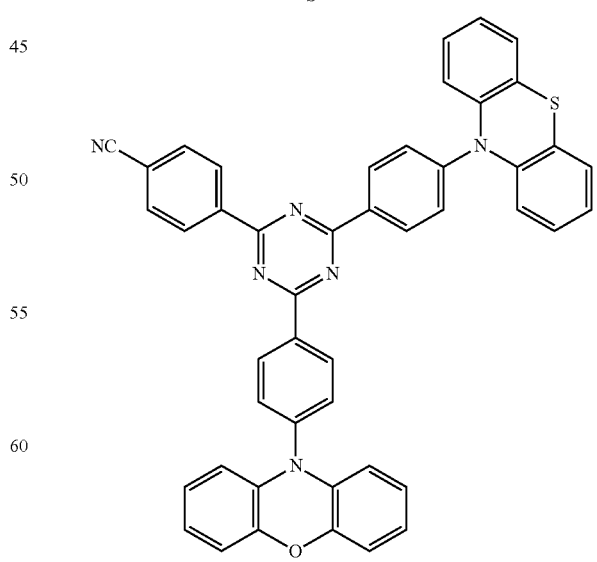

209
-continued
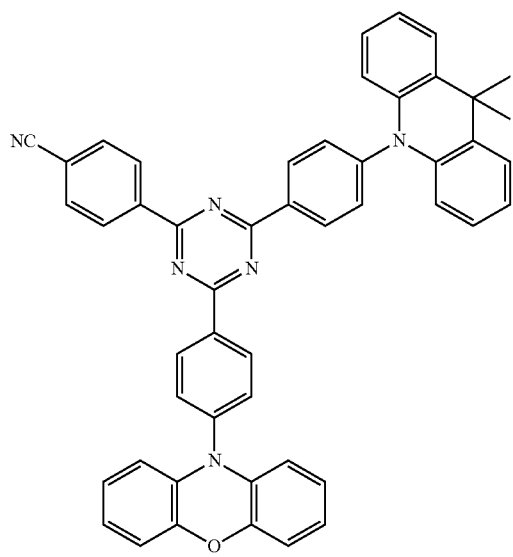
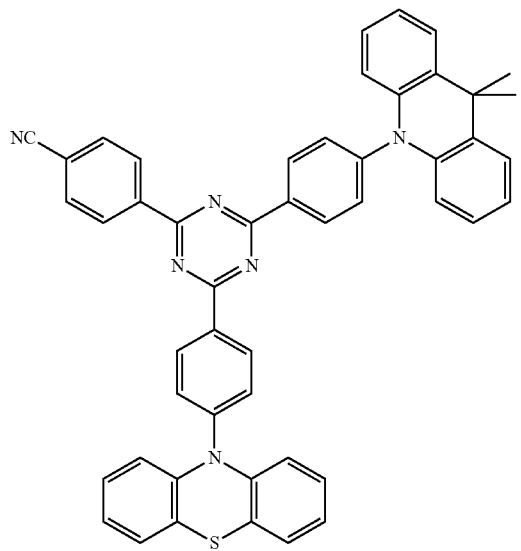
[Formula 144]
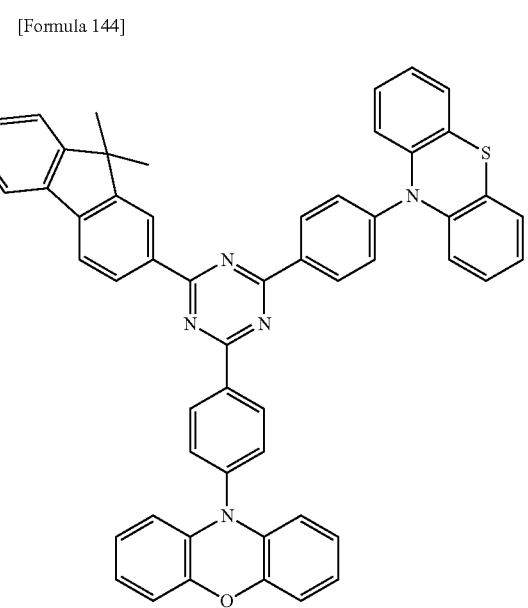
210
-continued
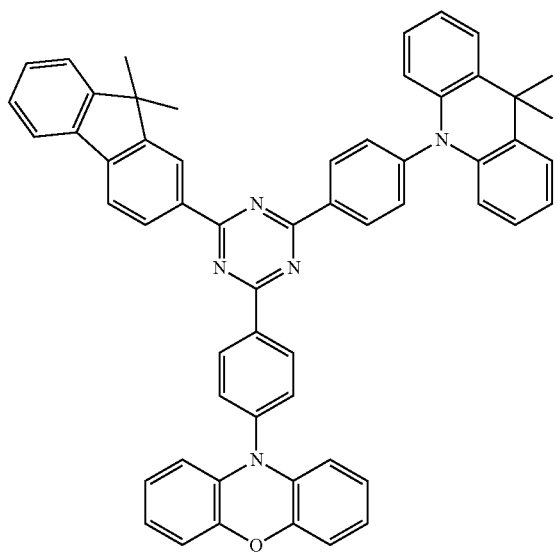
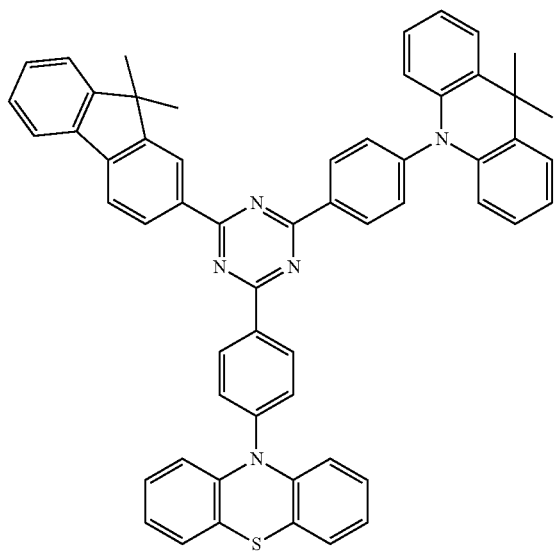
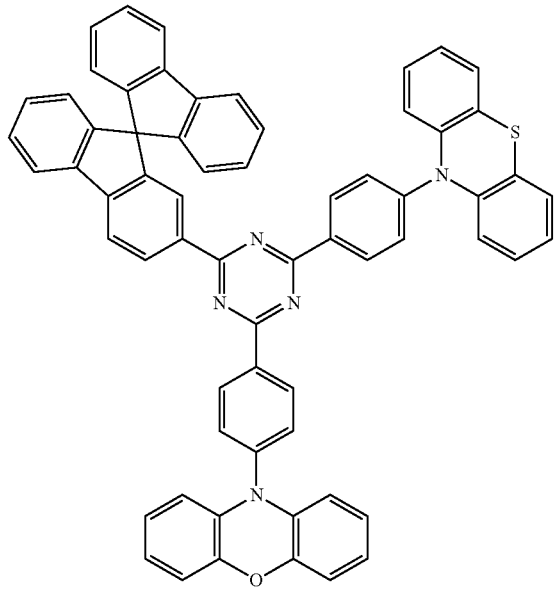

211
-continued
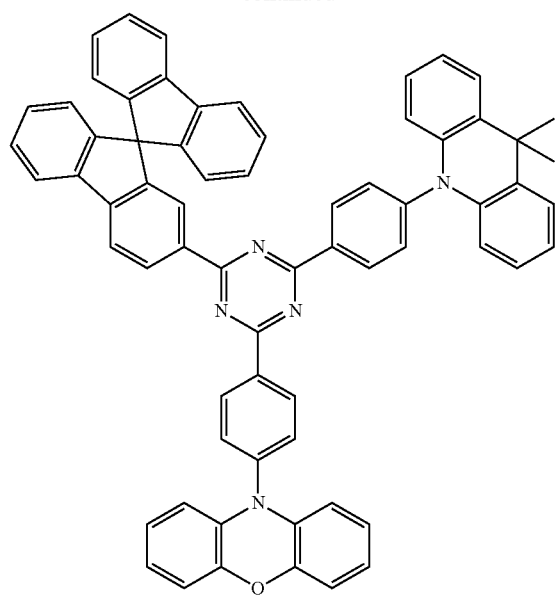
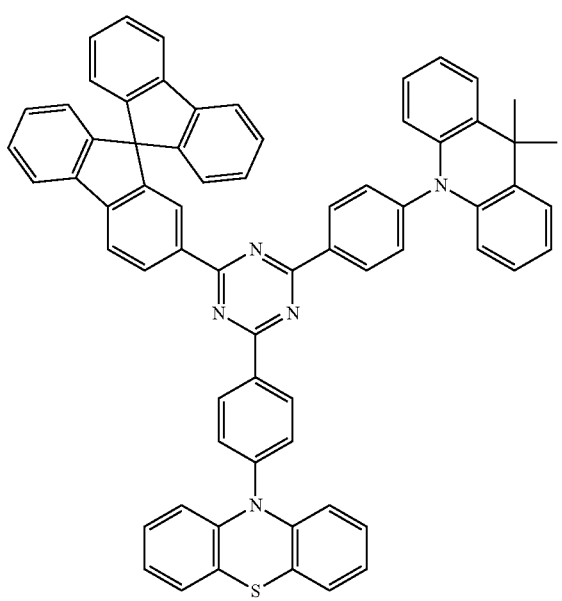
[Formula 145]
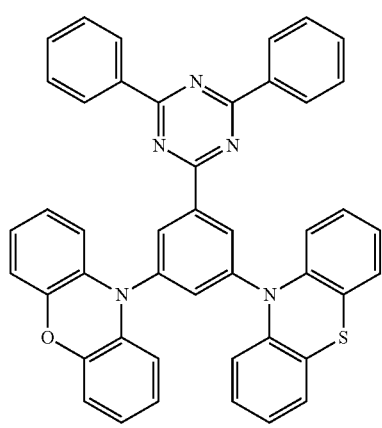
212
-continued
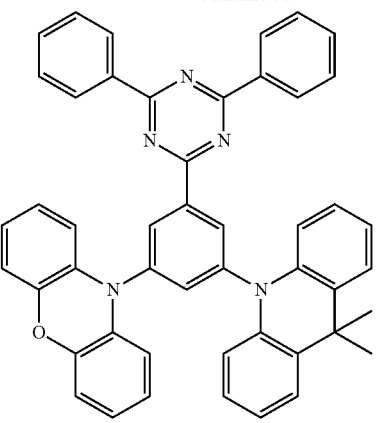
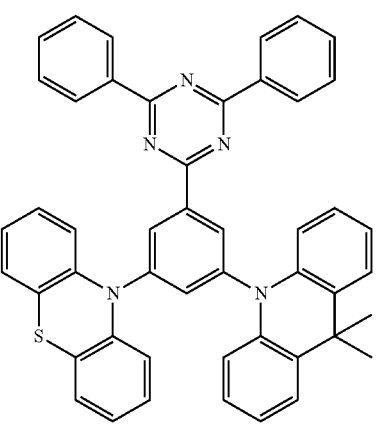
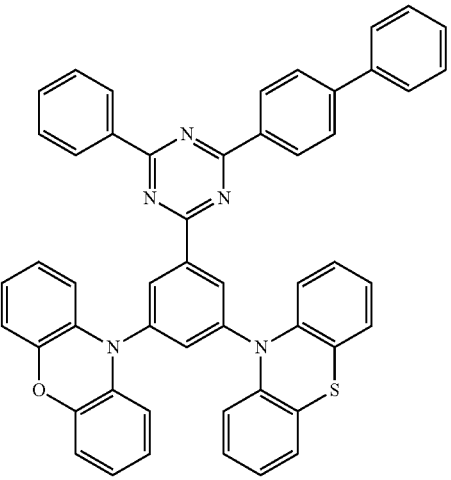

213
-continued
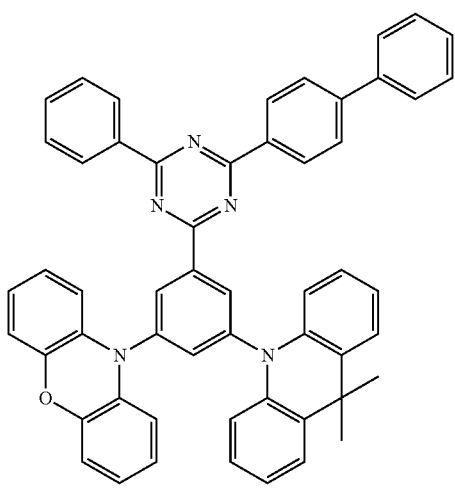
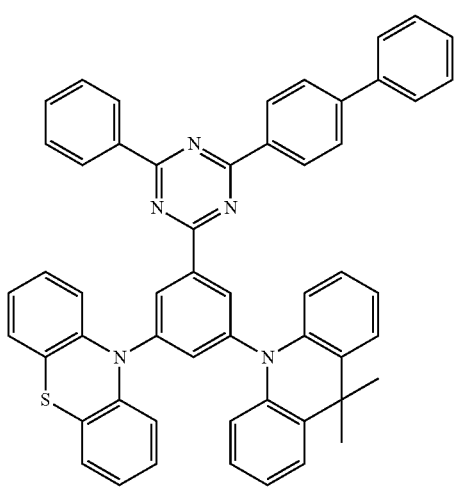
[Formula 146]
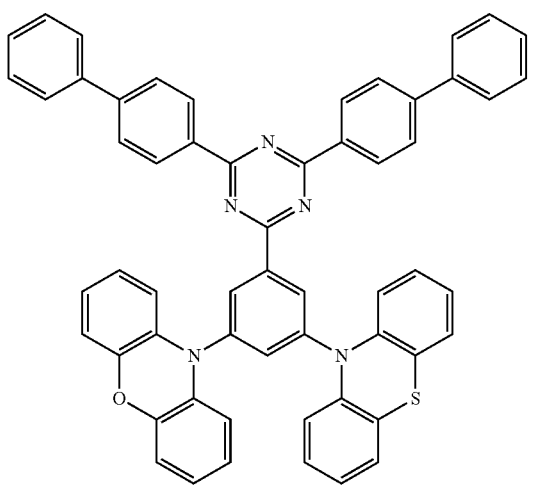
214
-continued
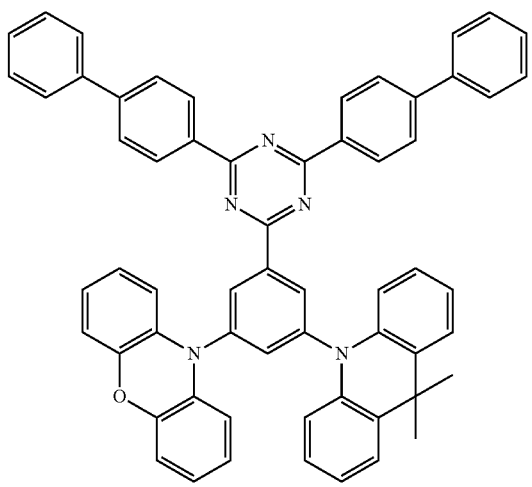
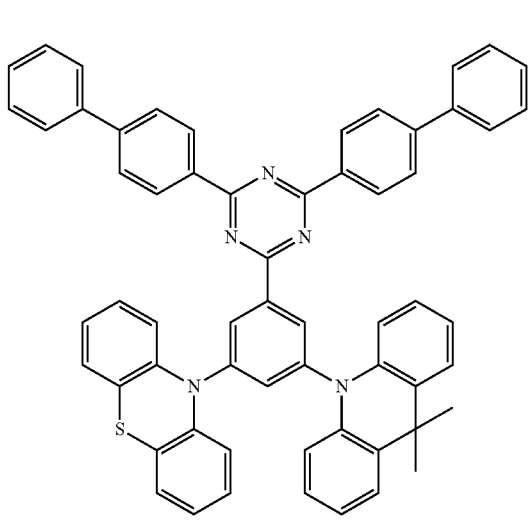
[Formula 147]
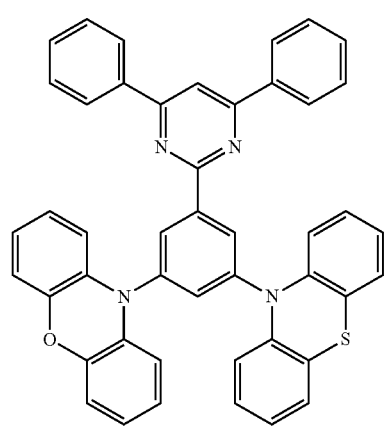

215
-continued
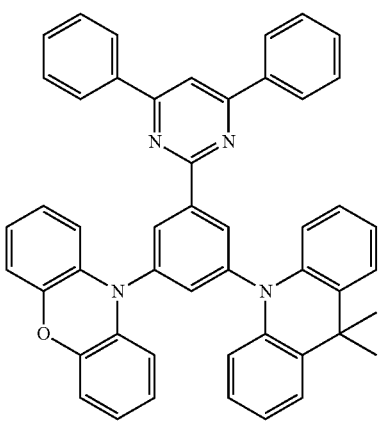
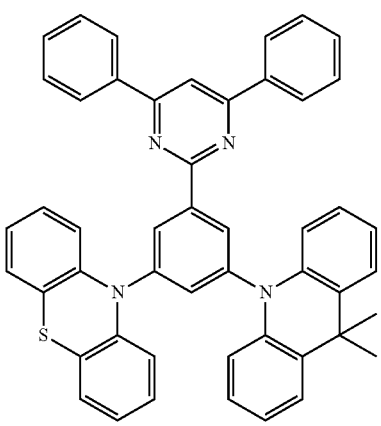
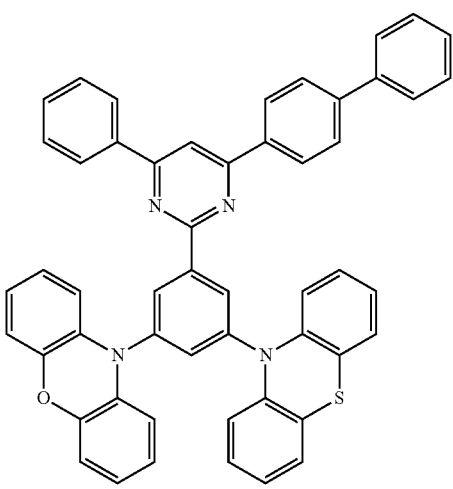
216
-continued
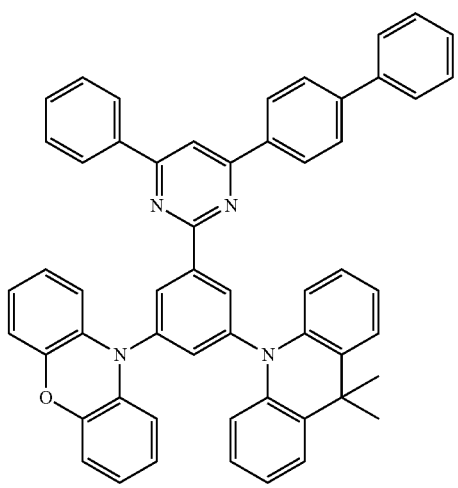
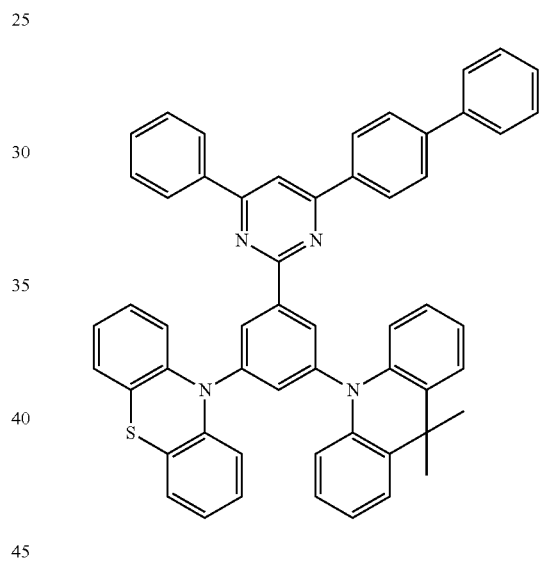
[Formula 148]
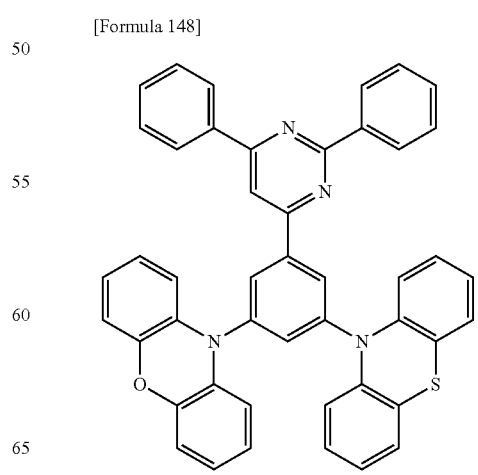

217
-continued
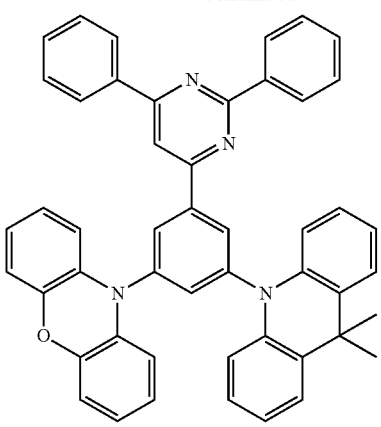
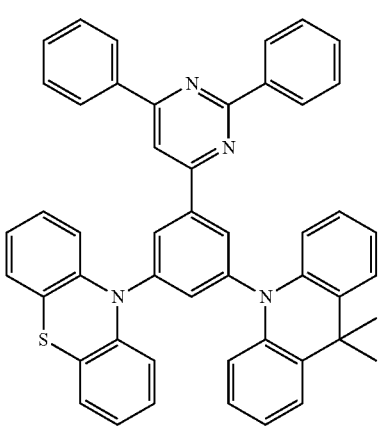
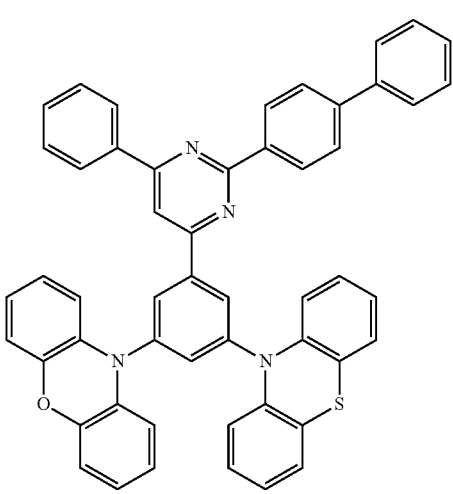
218
-continued
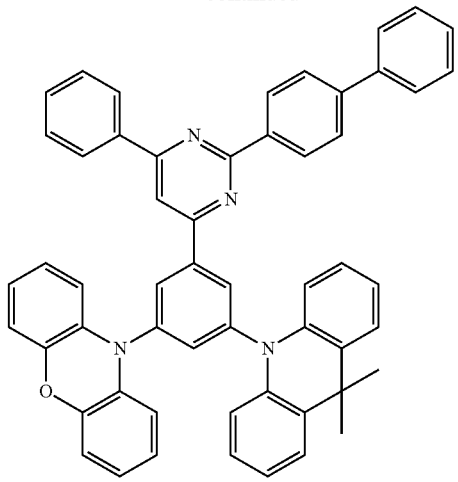
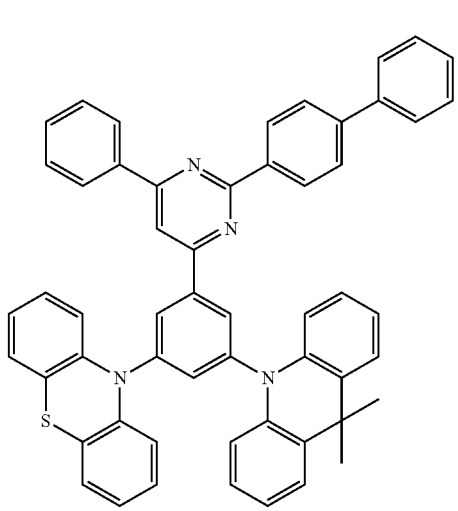
[Formula 149]
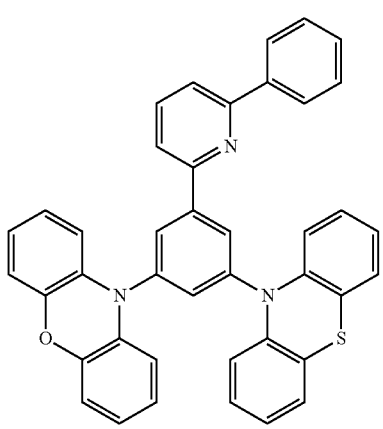

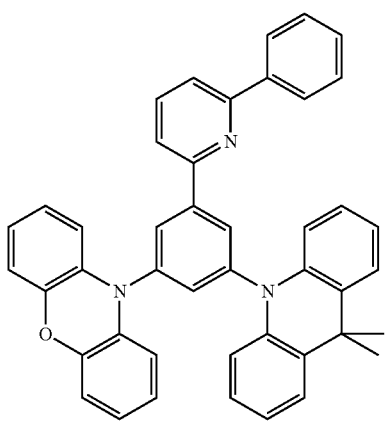
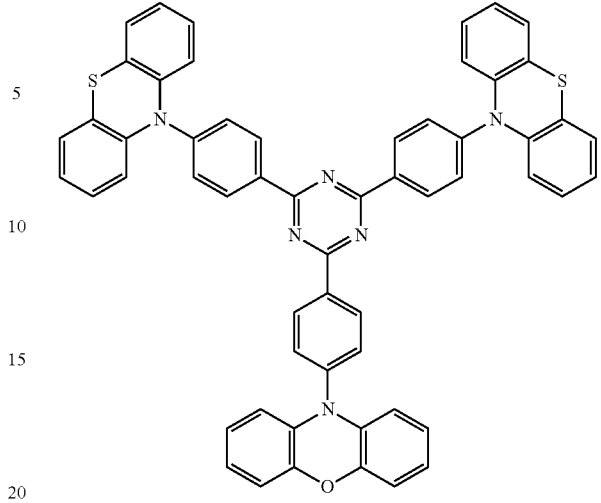
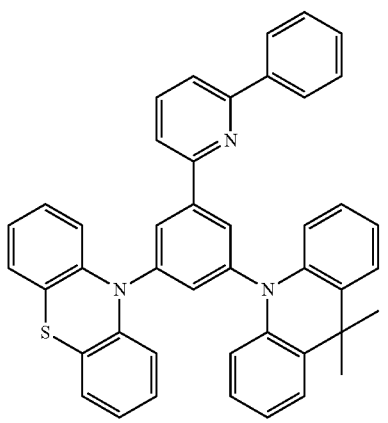
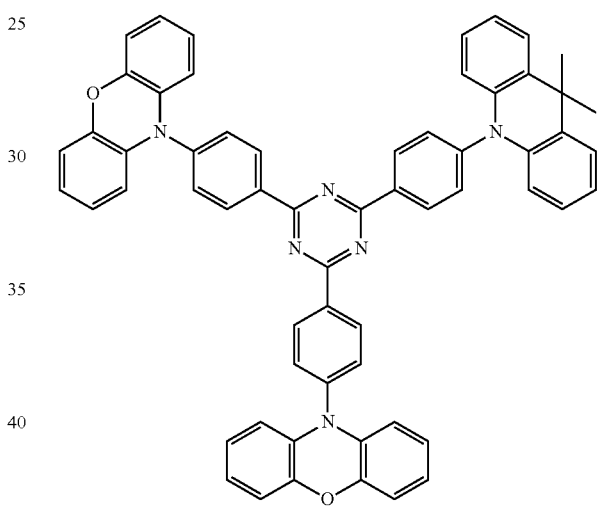
[Formula 150]
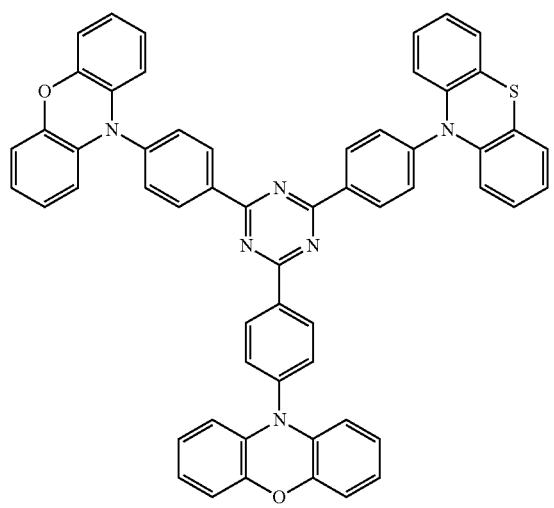
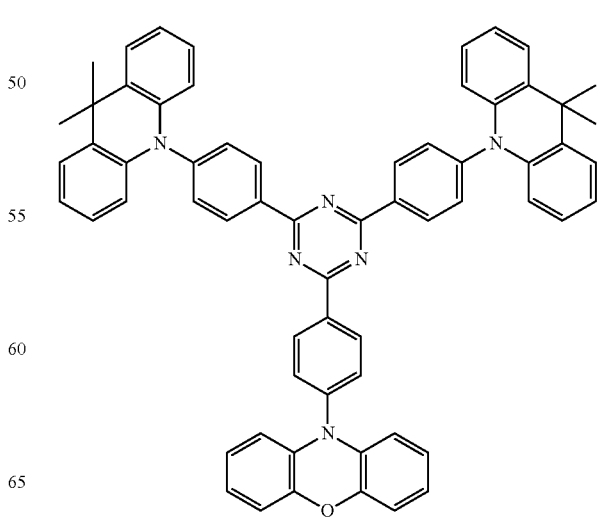

221
-continued
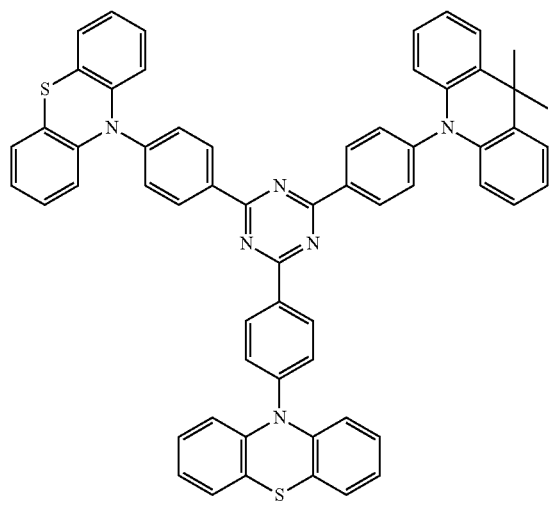
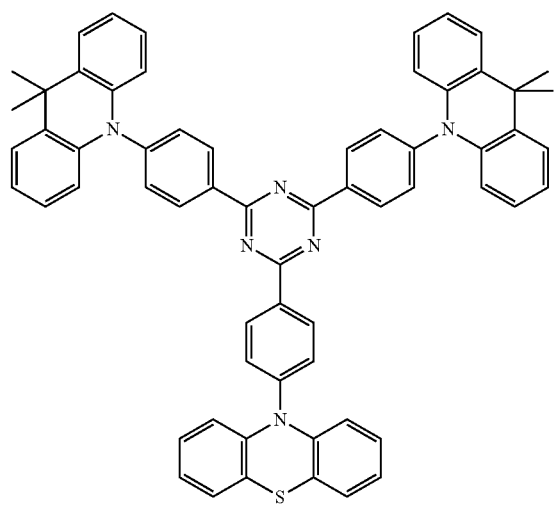
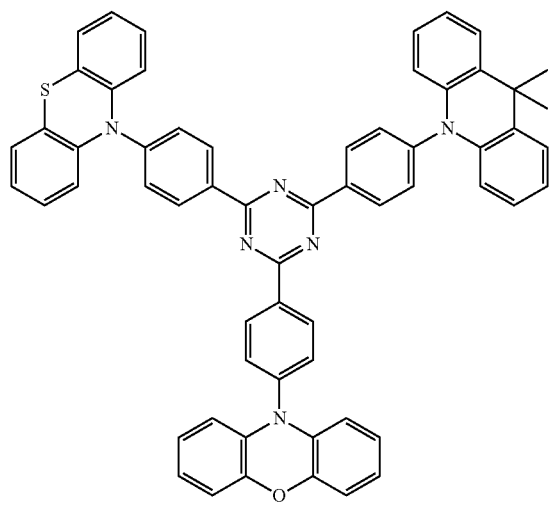
222
-continued
[Formula 151]
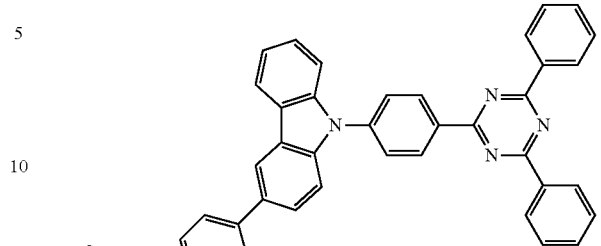
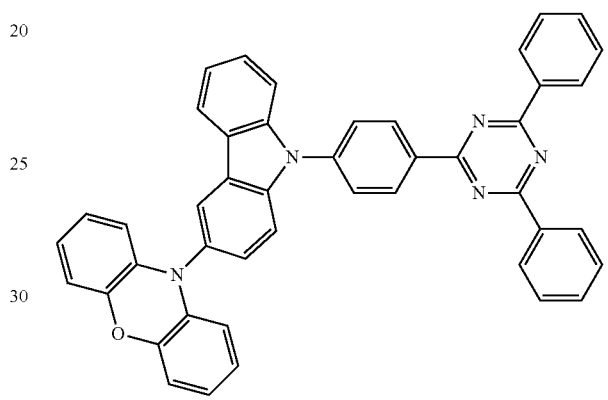
[Formula 152]
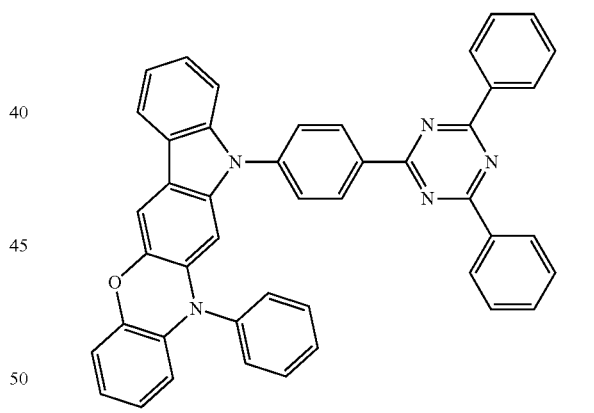
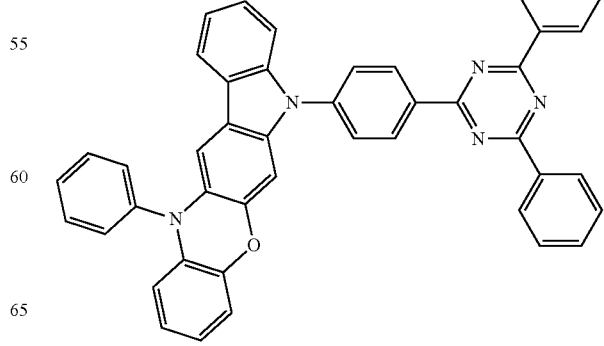

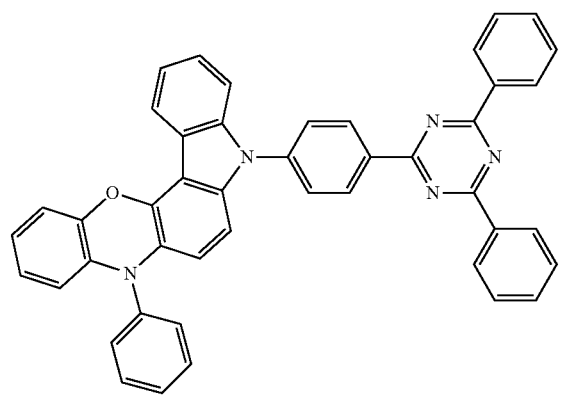
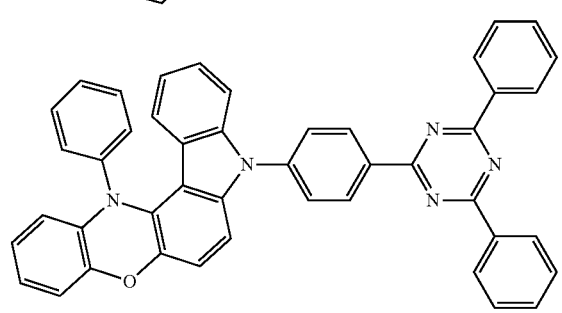
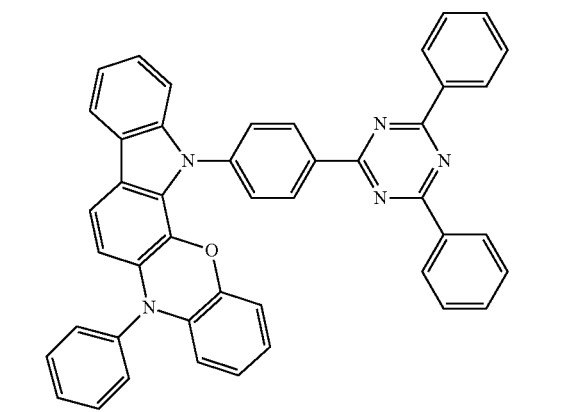
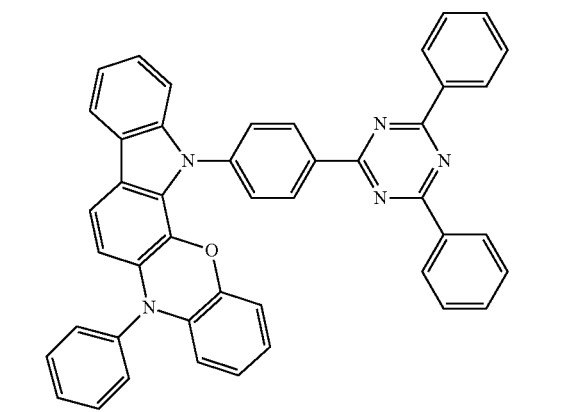
[Formula 153]
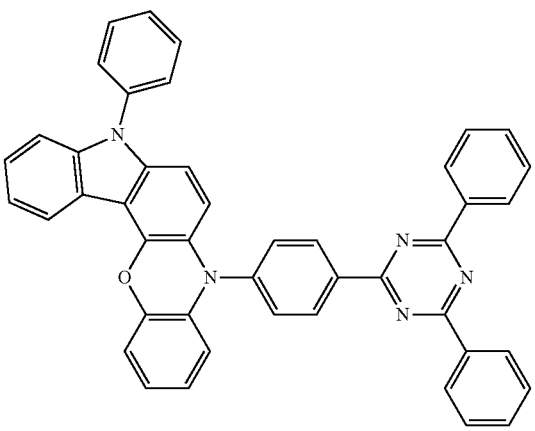
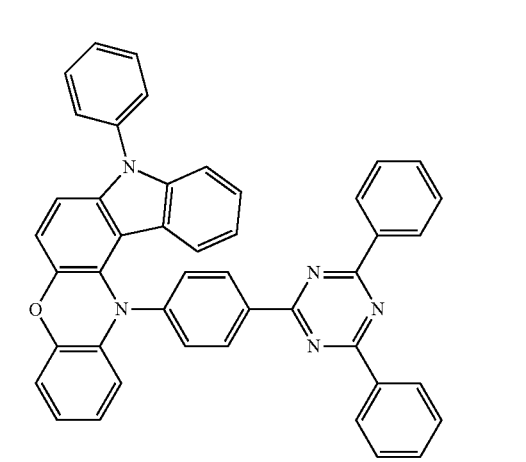
[Formula 154]
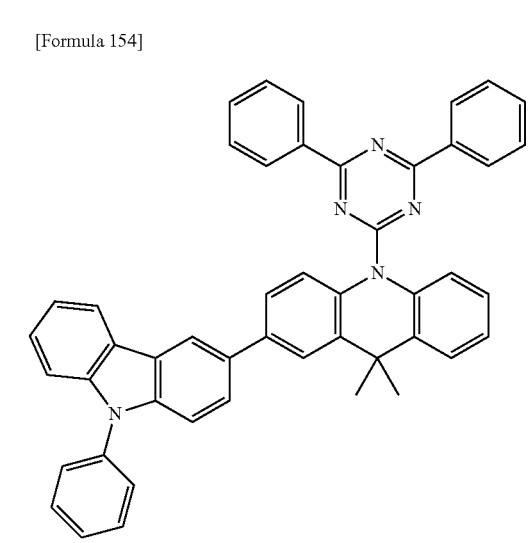

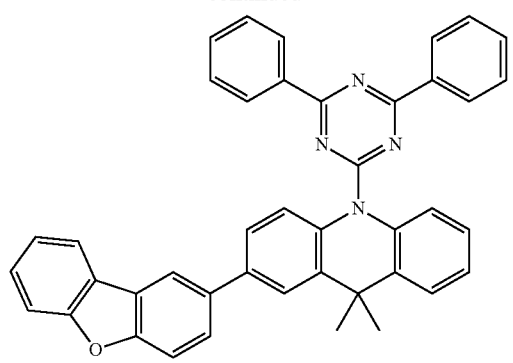
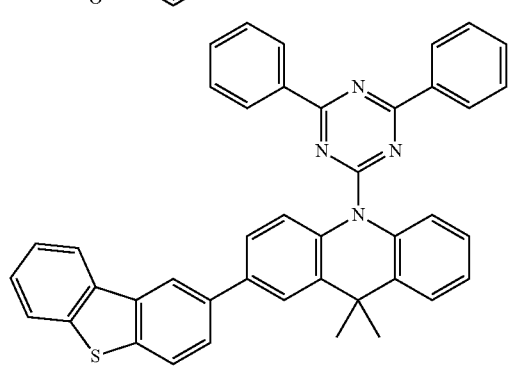
[Formula 155]
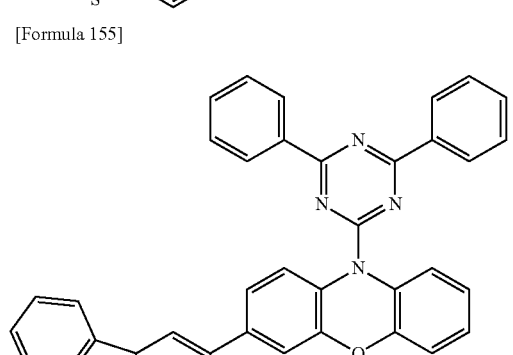
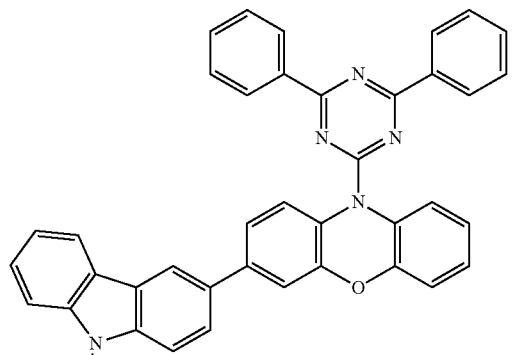
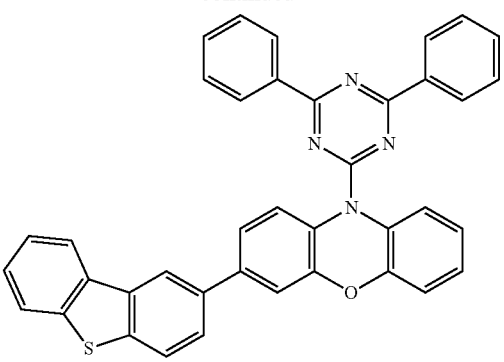
[Formula 156]
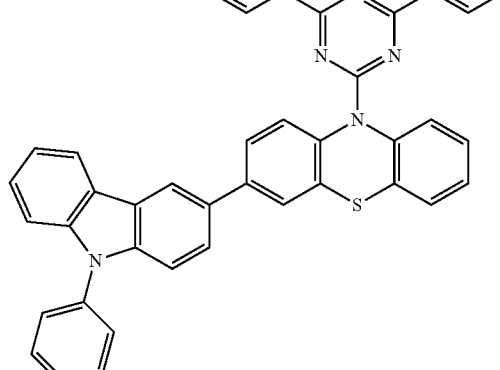
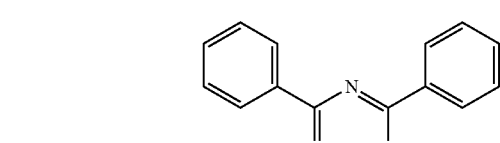
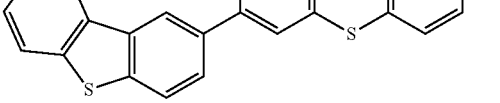

[Formula 157]

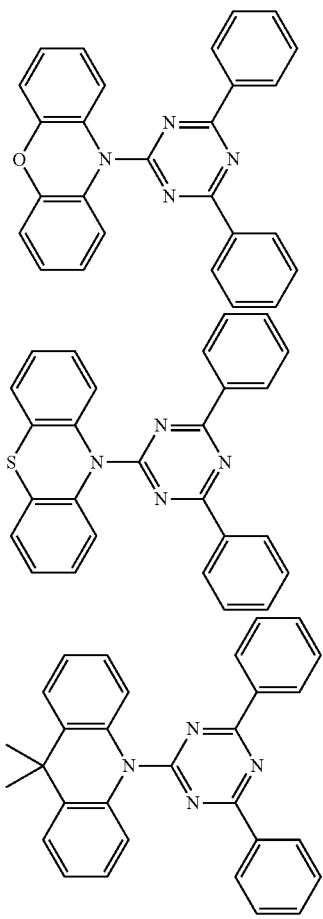

The host material of the first exemplary embodiment can be synthesized by a known synthesizing method.

A film thickness of the emitting layer is preferably in a range of 5 nm to 50 nm, more preferably in a range of 7 nm to 50 nm and most preferably in a range of 10 nm to 50 nm. The thickness of less than 5 nm may cause difficulty in forming the emitting layer and in controlling chromaticity, while the thickness of more than 50 nm may raise drive voltage.

In the emitting layer, a ratio of the host material and the dopant material is preferably in a range of 99:1 to 50:50 at a mass ratio.

Substrate

The organic EL device 2 of the first exemplary embodiment is formed on a light-transmissive substrate (not shown). The light-transmissive substrate supports the anode 21, the organic layer 23, the cathode 22 and the like forming the organic EL device 2. In the first exemplary embodiment, the anode 21 is formed on the substrate. The organic layer 23 and the cathode 22 are sequentially laminated on the anode 21 to form the organic EL device 2. The light-transmissive substrate is preferably a flat and smooth substrate that transmits 50% or more of light in a visible region of 400 nm to 700 nm.

The light-transmissive plate is exemplified by a glass plate and a polymer plate.

The glass plate is particularly formed of soda-lime glass, barium/strontium-containing glass, lead glass, aluminosilicate glass, borosilicate glass, barium borosilicate glass, quartz and the like.

The polymer plate is formed of polycarbonate, acryl, polyethylene terephthalate, polyether sulfide and polysulfone.

Anode and Cathode

The anode 21 of the organic EL device 2 injects holes into the emitting layer 25, so that it is efficient that the anode 21 has a work function of 4.5 eV or higher.

Specific examples of materials for the anode 21 include indium-tin oxide (ITO), tin oxide (NESA), indium zinc oxide, gold, silver, platinum and copper.

When light radiated from the emitting layer 25 is to be extracted through the anode 21, the anode 21 preferably transmits more than 10% of the light in the visible region. In the first exemplary embodiment, the anode 21 is formed of a light-transmissive material so that the light is extracted from the anode 21. Sheet resistance of the anode 21 is preferably several hundreds Ω/sq. or lower. The thickness of the anode 21 is typically in a range of 10 nm to 1 μm, and preferably in a range of 10 nm to 200 nm, though it depends on the material of the anode. The anode can be formed by vapor deposition or sputtering.

The cathode 22 is preferably formed of a material with smaller work function in order to inject electrons into the emitting layer 21.

Although a material for the cathode 22 is not particularly limited, specific examples of the material include indium, aluminium, magnesium, alloy of magnesium and indium, alloy of magnesium and aluminium, alloy of aluminium and lithium, alloy of aluminium, scandium and lithium, 0 and alloy of magnesium and silver.

Like the anode 21, the cathode 22 may be made by forming a thin film on, for instance, the electron transporting layer and the electron injecting layer by a method such as vapor deposition. In addition, light radiated from the emitting layer 25 may be extracted from the cathode 22. When light radiated from the emitting layer 25 is to be emitted through the cathode 22, the cathode 22 preferably transmits more than 10% of the light in the visible region. Note that, when light radiated from the emitting layer 25 is extracted from the cathode 22, the substrate is not limited to a transmissive substrate.

Sheet resistance of the cathode 22 is preferably several hundreds Q/sq. or lower. The thickness of the cathode 22 is typically in the range of 10 nm to 1 nm, and preferably in the range of 50 nm to 200 nm, though it depends on the material of the cathode 22.

Hole Injecting/Transporting Layer

The hole injecting/transporting layer 24 helps injection of holes to the emitting layer 25 and transport the holes to an emitting region. A compound having a large hole mobility and a small ionization energy is used as the hole injection/transport layer 24.

A material for forming the hole injecting/transporting layer 24 is preferably a material for transporting the holes to the emitting layer 25 at a lower electric field intensity. For instance, an aromatic amine compound is preferably used. A material for the hole injecting layer is preferably a porphyrin compound, an aromatic tertiary amine compound or a styryl amine compound, particularly preferably the aromatic tertiary amine compound such as hexacyanohexaazatriphenylene (HAT).

Electron Injecting/Transporting Layer

The electron injecting/transporting layer helps injection of the electrons into the emitting layer 25 and transports the electrons to an emitting region. A compound having a large electron mobility is used as the electron injecting/transporting layer.

A preferable example of the compound used as the electron injecting/transporting layer 26 is an aromatic heterocyclic compound having at least one heteroatom in a molecule. Particularly, a nitrogen-containing cyclic derivative is preferable. The nitrogen-containing cyclic derivative is preferably a heterocyclic compound having a nitrogen-containing six-membered or five-membered ring skeleton, or a fused aromatic cyclic compound having a nitrogen-containing six-membered or five-membered ring skeleton. Moreover, the electron injecting/transporting layer 26 may contain an alkali metal and the like.

In the organic EL device 2 of the first exemplary embodiment, in addition to the aforementioned compounds, any compound selected from compounds to be used in a typical organic EL device is usable as a compound for the organic compound layer 23 other than the emitting layer 25.

Layer Formation Method(s)

A method for forming each layer of the organic EL device 2 is subject to no limitation except for the above particular description. However, known methods of dry film-forming such as vacuum deposition, sputtering, plasma or ion plating and wet film-forming such as spin coating, dipping, flow coating or ink jet are applicable.

Thickness

The thickness of each organic layer 23 of the organic EL device 2 is subject to no limitation except for the thickness particularly described above. However, the thickness is typically preferably in a range of several nanometers to 1 μm because an excessively thin film is likely to entail defects such as a pin hole while an excessively thick film requires high applied voltage and deteriorates efficiency.

With the light-emitting apparatus 1 of the first exemplary embodiment, the following advantages can be obtained.

With the light-emitting apparatus 1, since the dopant material contained in the emitting layer satisfies Numerical Formula 1, the dopant material exhibits emission spectrum having a wide half bandwidth. Accordingly, color light radiated from the emitting layer 25 includes the first color light C1 and the second color light C2 which are luminescence components having a large intensity even in a wavelength region away from a peak of emission spectrum. With the light-emitting apparatus 1, the first color light C1 and the second color light C2 having a large intensity can respectively be transmitted through the first color conversion portion 31 and the second color conversion portion 32. Consequently, with the light-emitting apparatus 1, a luminous efficiency can be improved as compared with an arrangement in which a two-wavelength white emitting device is used as proposed in Patent Literature 1.

Moreover, with the light-emitting apparatus 1, it is only required to form a single emitting layer 25 between the anode 21 and the cathode 22, so that difficulty of a manufacturing procedure can be lowered as compared with an emitting device formed by laminating a plurality of emitting layers, thereby decreasing steps of forming the emitting layer to simplify manufacturing.

Further, when the half bandwidth of the emission spectrum of the dopant material is 60 nm or more, since the first color light C1 and the second color light C2 which each have a larger intensity can be obtained, the luminous efficiency can further be improved.

Moreover, since a quantum yield can be improved and the half bandwidth of the emission spectrum can be expanded by using the compound represented by the formula (1) as the dopant material, the luminous efficiency can further be improved.

Second Exemplary Embodiment

A second exemplary embodiment of the invention will be described below with reference to the drawings. In the description of the second exemplary embodiment, the same components as those in the first exemplary embodiment are denoted by the same reference signs and names to simplify or omit an explanation of the components. In the second exemplary embodiment, the same materials and compounds as described in the first exemplary embodiment are usable.

Arrangement of Light-Emitting Apparatus

FIG. 2 is a cross-sectional view schematically showing an arrangement of a light-emitting apparatus 1A according to the second exemplary embodiment. The light-emitting apparatus 1A includes: an organic EL device 2A; the first color conversion portion 31 that transmits the first color light; the second color conversion portion 32 that transmits the second color light different from the first color light; and a third color conversion portion 33 that transmits a third color light different from the first color light and the second color light.

Arrangement of Color Conversion Portion

In the second exemplary embodiment, the first color conversion portion 31, the second color conversion portion 32 and the third color conversion portion 33 are provided near the anode 21 through which light is extracted from the organic EL device 2A. In the second exemplary embodiment, the first color light C1 and the second color light C2 radiated from a first emitting unit 28 and the third color light C3 radiated from a second emitting unit 29 in the organic EL device 2A are extracted through the anode 21 to transmit through the first color conversion portion 31, the second color conversion portion 32 and the third color conversion portion 33, thereby emitting to the outside of the light-emitting apparatus 1A.

The first color conversion portion 31, the second color conversion portion 32 and the third color conversion portion 33 define a color converter in the second exemplary embodiment. The color converter is exemplified by a color filter. The first color conversion portion 31 transmits the first color light C1 and blocks the second color light C2 and the third color light C3. The second color conversion portion 32 transmits the second color light C2 and blocks the first color light C1 and the third color light C3. The third color conversion portion 33 transmits the third color light C3 and blocks the first color light C1 and the second color light C2. For instance, when the color light radiated from the first emitting unit 28 is a yellow light including a green light and a red light and the color light radiated from the second emitting unit 29 is a blue light, the first color conversion portion 31 transmits the red light, the second color conversion portion 32 transmits the green light, and the third color conversion portion 33 transmits the blue light.

The light-emitting apparatus 1A includes the organic EL device 2A in which the first emitting unit 28 and the second emitting unit 29 are laminated via an intermediate layer 27. Such an organic EL device 2A is occasionally referred to as a tandem organic EL device.

The first emitting unit 28 is provided near the anode 21 and the second emitting unit 29 is provided near the cathode 22.

The first emitting unit 28 includes a first hole injecting/transporting layer 24a, a first emitting layer 25a and a first electron injecting/transporting layer 26a in this order from the anode 21. In the second exemplary embodiment, the first electron injecting/transporting layer 26a is connected to the intermediate layer 27. The first emitting layer 25a includes the host material and the dopant material that emits light including the first color light C1 and the second color light C2, in the same manner as in the first exemplary embodiment. The dopant material contained in the first emitting layer 25a satisfies Numerical Formula 1. A preferable compound for the dopant material is the same as those described in the first exemplary embodiment. In the second exemplary embodiment, the dopant material that emits the yellow light including the red light (the first color light C1) and the green light (the second color light C2) is used for the first emitting layer 25a.

The second emitting unit 29 includes a second hole injecting/transporting layer 24b, a second emitting layer 25b and a second electron injecting/transporting layer 26b in this order from the intermediate layer 27. In the second exemplary embodiment, the second hole injecting/transporting layer 24b is connected to the intermediate layer 27. The second emitting layer 25b includes the host material and the dopant material. In the second exemplary embodiment, the dopant material that emits a blue light (the third color light C3) is used for the second emitting layer 25b. At least one of a fluorescent dopant material and a phosphorescent dopant material is usable as the dopant material contained in the second emitting layer 25b.

The intermediate layer 27 is also referred to as an intermediate conductive layer, a charge generating layer or CGL. The intermediate layer 27 is a source for supplying electrons and holes to be injected to the first emitting unit 28 and the second emitting unit 29. In addition to charge injected from the anode 21 and the cathode 22, charge supplied from the intermediate layer 27 is injected into the first emitting unit 28 and the second emitting unit 29. Accordingly, by providing the intermediate layer 27, luminous efficiency (current efficiency) relative to applied current is improved.

Examples of a material for the intermediate layer 27 include a metal, metal oxide, mixture of metal oxides, composite oxide, and electron-accepting organic compound. Examples of the metal are preferably Mg, Al, and a film formed by co-evaporating Mg and Ag. Examples of the metal oxide include $ZnO$, $WO_3$, $MoO_3$ and $MoO_2$. Examples of the mixture of the metal oxides include ITO and IZO (registered trade mark).

The first electron injecting/transporting layer 26a adjacent to the intermediate layer 27 near the anode 21 is a layer containing an electron-donating material (i.e., a donor-containing layer). The first electron injecting/transporting layer 26a is preferably a layer in which an electron transporting material and a donor represented by an alkali metal are mixed. As the electron-donating material, at least one of a donor metal, donor metal compound and donor metal complex can be used. Examples of the compounds used for the donor metal, donor metal compound and donor metal complex are compounds disclosed in International Publication WO2010/134352.

The second hole injecting/transporting layer 24b adjacent to the intermediate layer 27 near the cathode 22 is a layer containing an electron-accepting material (i.e., an acceptor-containing layer). The second hole injecting/transporting layer 24b preferably contains an electron-accepting organic compound as the electron-accepting material. The electron-accepting organic compound is exemplified by an organic compound having a CN (cyano) group as a substituent. The organic compound having a CN group is preferably a triphenylene derivative, tetracyanoquinodimethane derivative and indenofluorene derivative. The triphenylene derivative is preferably hexacyanohexaazatriphenylene. The tetracyanoquinodimethane derivative is preferably tetrafluoroquinodimethane and dicyanoquinodimethane. The indenofluorene derivative is preferably a compound disclosed in International Publication WO2009/011327, WO2009/069717, or WO2010/064655. The acceptor-containing layer may be provided only by the electron-accepting substance or may be provided in a mixture with other organic compounds.

With the light-emitting apparatus 1A of the second exemplary embodiment, the following advantages can be obtained in addition to the same advantages as those in the light-emitting apparatus 1 of the first exemplary embodiment.

With the light-emitting apparatus 1A, since the dopant material contained in the first emitting layer 25a satisfies Numerical Formula 1, the dopant material exhibits emission spectrum having a wide half bandwidth. Accordingly, with the light-emitting apparatus 1, a luminous efficiency can be improved in the same manner as in the first exemplary embodiment, as compared with the arrangement in which a two-wavelength white emitting device is used as proposed in Patent Literature 1.

The light-emitting apparatus 1A includes a so-called tandem organic EL device 2A. The organic EL device 2A includes the second emitting layer 25b containing the dopant material emitting blue light (the third color light C3). In the light-emitting apparatus 1A, a yellow light including the first color light C1 (red light) and the second color light C2 (green light) is radiated from the first emitting layer 25a and the third color light C3 (blue light) is radiated from the second emitting layer 25b. The color conversion portions 31, 32 and 33 can transmit light in three RGB colors. Accordingly, the light-emitting apparatus 1A can provide a light-emitting apparatus capable of emitting white light with a further improved luminous efficiency as compared with the arrangement in which a two-wavelength white emitting device is used as proposed in Patent Literature 1.

Modifications of Embodiment(s)

The scope of the invention is not limited to the above-described exemplary embodiments but also includes modification(s) and improvement(s) as long as an object of the invention can be achieved.

Representative arrangement examples of the organic EL device are as follows:
(a) anode/emitting layer/cathode;
(b) anode/hole injecting•transporting layer/emitting layer/cathode;
(c) anode/emitting layer/electron injecting•transporting layer/cathode;
(d) anode/hole injecting•transporting layer/emitting layer/electron injecting•transporting layer/cathode;
(e) anode/hole injecting•transporting layer/first emitting layer/second emitting layer/electron injecting•transporting layer/cathode; and
(f) anode/hole injecting•transporting layer/emitting layer/blocking layer/electron injecting•transporting layer/cathode.

In the above exemplary embodiments, an organic EL device having the arrangement (d) among the above arrangements is described as an example. However, the arrangement of the invention is neither limited to the arrangement (d) nor to the arrangements (a) to (f). Any layer applied in a known organic EL device such as a hole injecting layer, a hole transporting layer, an electron injecting layer, an electron transporting layer, a hole blocking layer, and an electron blocking layer may be used.

The electron transporting layer means an organic layer having the highest electron mobility among organic layer(s) providing an electron transporting zone existing between the emitting layer and the cathode. When the electron transporting zone is provided by a single layer, the single layer is the electron transporting layer. Moreover, a blocking layer having an electron mobility that is not always high may be provided as shown in the arrangement (f) between the emitting layer and the electron transporting layer in order to prevent diffusion of excitation energy generated in the emitting layer. Thus, the organic layer adjacent to the emitting layer is not always an electron transporting layer.

The electron blocking layer may be provided to a side of the emitting layer near the anode. With this arrangement, the electrons can be trapped in the emitting layer, thereby enhancing probability of exciton generation in the emitting layer.

The arrangement of the organic EL device is not limited to the arrangement of the tandem organic EL device described in the second exemplary embodiment. For instance, the arrangement of the first emitting unit 28 may be exchanged for the arrangement of the second emitting unit 29. The first emitting unit 28 may have the emitting layer emitting blue light while the second emitting unit 29 may have the emitting layer containing the dopant material satisfying Numerical Formula 1 and emitting yellow light.

In the tandem organic EL device 2A described in the second exemplary embodiment, the dopant material contained in the second emitting layer 25b may also be the compound satisfying Numerical Formula 1.

When a plurality of emitting layers are laminated, the emitting layers may directly be laminated to each other as in the above arrangement (e) instead of the tandem organic EL device described in the second exemplary embodiment. When the organic EL device includes the plurality of emitting layers, it is only required that at least one of the emitting layers includes the dopant material satisfying Numerical Formula 1 and the rest of the emitting layers may be a fluorescent emitting layer or a phosphorescent emitting layer. Alternatively, the plurality of emitting layers may contain the dopant material satisfying Numerical Formula 1.

The color light radiated from the emitting layer containing the dopant material satisfying Numerical Formula 1 is not limited to light in the colors described in the above exemplary embodiments.

In the above exemplary embodiments, the arrangement of the light-emitting device in which the color light radiated from the emitting layer(s) is transmitted through the color conversion portion of the color converter provided near the anode is described as an example. However, the arrangement of the light-emitting device is not limited thereto. For instance, the light-emitting device may have an arrangement in which the cathode is provided by a light-transmissive electrode and the color converter is disposed near the cathode and transmits the color light radiated from the emitting layer.

The host material is not limited to the compounds described in the above exemplary embodiments, but is exemplified by an amine derivative, azine derivative, fused polycyclic aromatic derivative and a fused polycyclic heterocyclic derivative. Examples of the amine derivative include a monoamine compound, diamine compound, triamine compound, tetramine compound and amine compound substituted by a carbazole group. Examples of the azine derivative are a monoazine derivative, diazine derivative and triazine derivative. The fused polycyclic aromatic derivative is exemplified by a compound having a fused polycyclic aromatic hydrocarbon ring skeleton, among which a fused polycyclic aromatic hydrocarbon compound having no heterocyclic skeleton is preferable. Examples of the fused polycyclic aromatic derivative are a fused polycyclic aromatic hydrocarbon compound such as naphthalene, anthracene, phenanthrene, chrysene, fluoranthene and triphenylene, or derivatives thereof. The fused polycyclic heterocyclic derivative is exemplified by a compound having a fused polycyclic heterocyclic skeleton such as a carbazole derivative, a dibenzofuran derivative, and azatriphenylene derivative.

The above exemplary embodiments are described with examples of the compound represented by the formula (1) as the dopant material and the compound represented by the formula (2) as the dopant material. However, the host material and the dopant material are not limited thereto.

For instance, the compound represented by the formula (2) and satisfying Numerical Formula 1 may be used as the dopant material. In this arrangement, it is preferable that $L_{20}$ is a single bond and g is 0 in the formula (2). In other words, the dopant material is preferably a compound in which HAr and $Az_2$ are mutually bonded by a single bond. Further, when the compound represented by the formula (2) is used as the dopant material, the compound represented by the formula (1) is preferably used as the host material.

Electronic Device

The light-emitting apparatus of the invention is applicable to an electronic device such as: a display component of an organic EL panel module and the like; a display device of a television, a mobile phone, a personal computer and the like; and a light-emitting apparatus of an illuminator or a vehicle light.

EXAMPLES

Examples of the invention will be described below. However, the invention is not limited by Examples.

Compounds used in Examples were as follows.

[Formula 158]

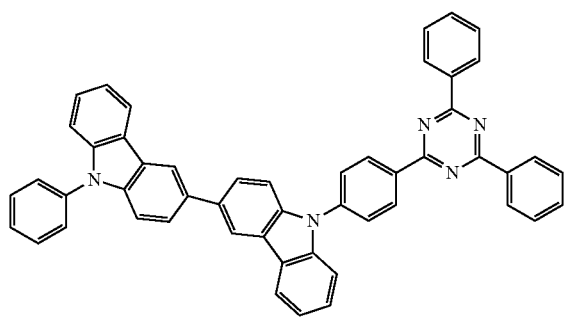

D1

-continued

D2
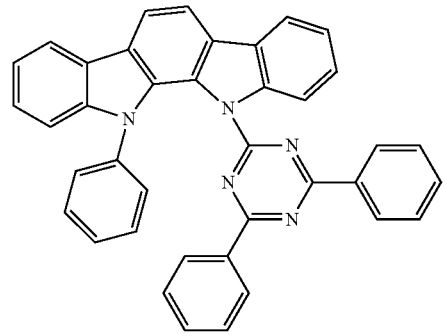

D3
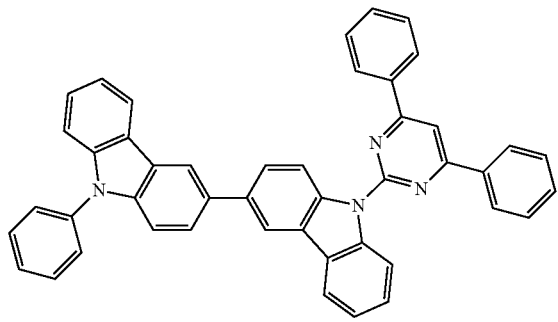

[Formula 159]
D4
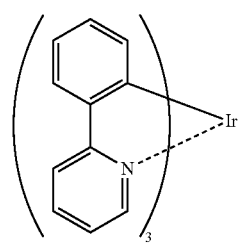

D5
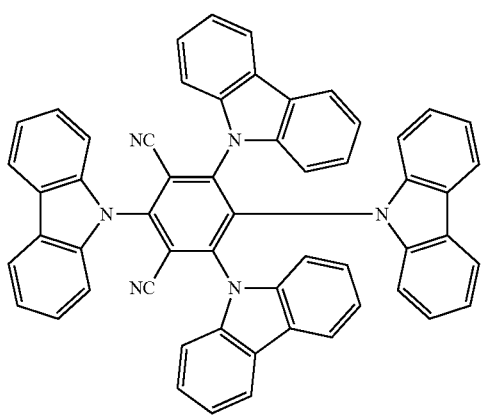

-continued

D6
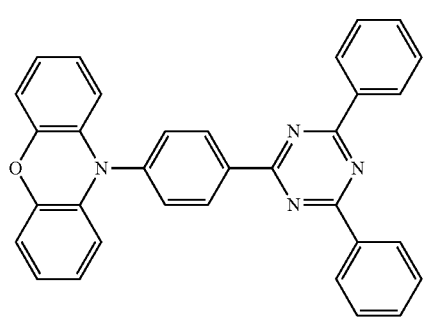

D7
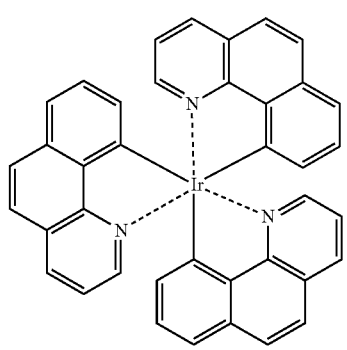

Evaluation of Compounds

Next, properties of the compounds used in Example were measured. A measurement method and a calculation method are described below. Measurement results and calculation results are shown in Table 1.

Evaluation (1) Singlet Energy EgS

Singlet Energy EgS was obtained according to the following method.

The target compound to be measured was deposited by evaporation on a quartz substrate to prepare a sample. An emission spectrum of the sample was measured at a normal temperature (300K). A sample was 100 nm thick. The sample for emission measurement was irradiated with excitation light, so that a luminous intensity was measured while changing a wavelength. The emission spectrum was expressed in coordinates of which ordinate axis indicated the luminous intensity and of which abscissa axis indicated the wavelength. A tangent was drawn to the rise of the emission spectrum on the short-wavelength side, and a wavelength value λedge (nm) at an intersection of the tangent and the abscissa axis was obtained. The wavelength value was converted to an energy value by the following conversion equation. The energy value was defined as EgS.

$$EgS \text{ (eV)} = 1239.85/\lambda\text{edge} \quad \text{Conversion Equation}$$

For the measurement of the emission spectrum, a spectrophotometer (U3310 manufactured by Hitachi, Ltd.) was used.

The tangent to the rise of the emission spectrum on the short-wavelength side was drawn as follows. While moving on a curve of the emission spectrum from the short-wavelength side to the maximum spectral value closest to the short-wavelength side among the maximum spectral values, a tangent is checked at each point on the curve toward the long-wavelength of the emission spectrum. An inclination of the tangent is increased as the curve rises (i.e., a value of the ordinate axis is increased). A tangent drawn at a point of the maximum inclination (i.e., a tangent at an inflection point)

is defined as the tangent to the rise of the emission spectrum on the short-wavelength side.

The maximum with peak intensity being 15% or less of the maximum peak intensity of the spectrum is not included in the above-mentioned maximum closest to the short-wavelength side of the spectrum. The tangent drawn at a point of the maximum spectral value being closest to the short-wavelength side and having the maximum inclination is defined as a tangent to the rise of the emission spectrum on the short-wavelength side.

Evaluation (2) Energy Gap $Eg_{77K}$ $Eg_{77K}$ was obtained by the following method.

A target compound to be measured was deposited on a quartz substrate to prepare a sample. A film thickness was 100 nm. The sample for phosphorescence measurement was put into an NMR tube, cooled to 77K and irradiated with excitation light, so that phosphorescence intensity was measured while changing a wavelength. The phosphorescence spectrum was expressed in coordinates of which ordinate axis indicated phosphorescence intensity and of which abscissa axis indicated the wavelength.

A tangent was drawn to the rise of the phosphorescent spectrum on the short-wavelength side, and a wavelength value λedge (nm) at an intersection of the tangent and the abscissa axis was obtained. The wavelength value was converted to an energy value by the following conversion equation. The energy value was defined as $Eg_{77K}(D)$.

$Eg_{77K}(D)[eV] = 1239.85/\lambda edge$     The conversion equation

The tangent to the rise of the phosphorescence spectrum on the short-wavelength side was drawn as follows. While moving on a curve of the phosphorescence spectrum from the short-wavelength side to the maximum spectral value closest to the short-wavelength side among the maximum spectral values, a tangent was checked at each point on the curve toward the long-wavelength of the phosphorescence spectrum. An inclination of the tangent was increased as the curve rises (i.e., a value of the ordinate axis was increased). A tangent drawn at a point of the maximum inclination (i.e., a tangent at an inflection point) was defined as the tangent to the rise of the emission spectrum on the short-wavelength side.

The maximum with peak intensity being 15% or less of the maximum peak intensity of the spectrum was not included in the above-mentioned maximum closest to the short-wavelength side of the spectrum. The tangent drawn at a point of the maximum spectral value being closest to the short-wavelength side and having the maximum inclination was defined as the tangent to the rise of the phosphorescence spectrum on the short-wavelength side.

For phosphorescence measurement, a spectrophotofluorometer body F-4500 (manufactured by Hitachi High-Technologies Corporation) was used. The measurement instrument is not limited to this arrangement. A combination of a cooling unit, a low temperature container, an excitation light source and a light-receiving unit may be used for measurement.

Evaluation (3) ΔST

ΔST was obtained as a difference between EgS and $Eg_{77K}$ respectively measured in the above (1) and (2) (see the above Numerical Formula 1). The results are shown in Table 1.

Evaluation (4) Half Bandwidth

Each of the compounds was dissolved in a solvent (toluene) to prepare a sample of 10 nmol/liter for fluorescence measurement. The sample for fluorescence measurement was put into a quartz cell and irradiated with excitation light at a room temperature (300 K), so that fluorescence intensity was measured while changing a wavelength. Photoluminescence spectrum was expressed in coordinates of which ordinate axis indicated the fluorescence intensity and of which abscissa axis indicated the wavelength. For fluorescence measurement, a spectrophotofluorometer F-4500 (manufactured by Hitachi High-Technologies Corporation) was used. A half bandwidth (unit: nm) of a main peak of the photoluminescence spectrum was measured.

Compounds D1, D2, D3, D4, D5, D6 and D7 were measured in terms of the half bandwidth. The results are shown in Table 1.

TABLE 1

|  | Target compound | EgS (eV) | $Eg_{77K}$ (eV) | ΔST (eV) | Half Bandwidth (nm) |
|---|---|---|---|---|---|
| Examples | D1 | 2.82 | 2.65 | 0.17 | 67 |
|  | D2 | 2.82 | 2.72 | 0.10 | 85 |
|  | D3 | 2.83 | 2.73 | 0.09 | 89 |
|  | D5 | 2.53 | 2.46 | 0.07 | 68 |
|  | D6 | 2.67 | 2.46 | 0.21 | 67 |
| Comparatives | D4 | — | — | — | 55 |
|  | D7 | — | — | — | 55 |

As shown in Table 1, the target compounds D1 to D3, D5 and D6 in Examples satisfied Numerical Formula 1 and exhibited emission spectrum having a wide half bandwidth. The target compounds D1 to D3, D5 and D6 exhibited a half bandwidth of 67 nm or more. Accordingly, by using the target compounds D1 to D3, D5 and D6 as the dopant material, the first color light and the second color light having a large intensity was obtained even in a wavelength region away from a peak of the emission spectrum, so that the luminous efficiency can be improved.

On the other hand, the target compounds D4 and D7 in Comparatives did not satisfy Numerical Formula 1 and exhibited emission spectrum having a half bandwidth narrower than the half bandwidth (55 nm) of the target compounds D1 to D3, D5 and D6.

Preparation and Evaluation of Organic EL Device

Compounds used in Examples for preparing the organic EL device were as follows.

[Formula 160]

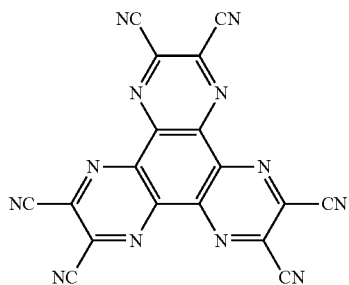

HI

HT-1
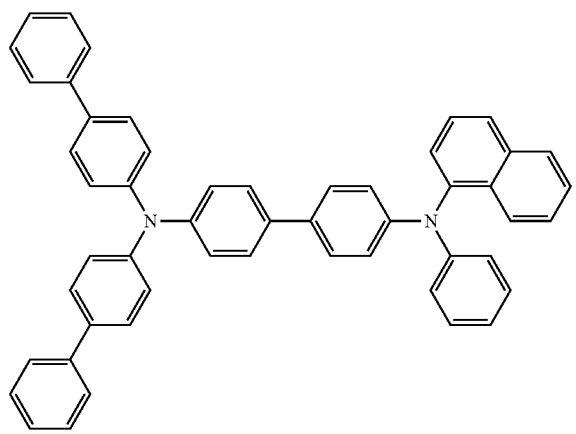
HT-2
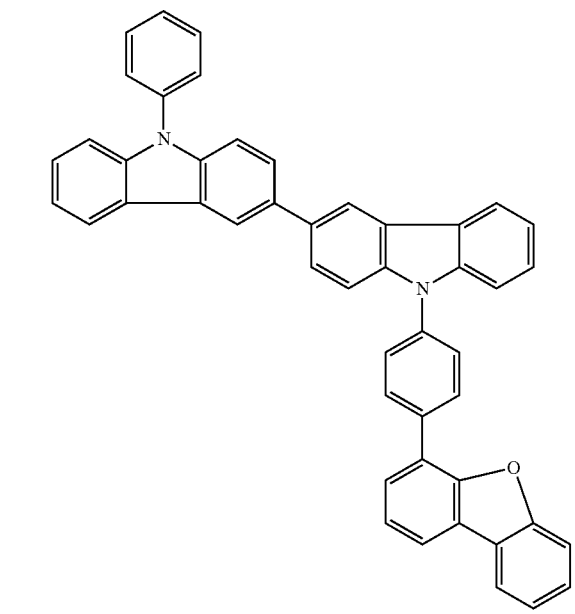
[Formula 161]
CBP
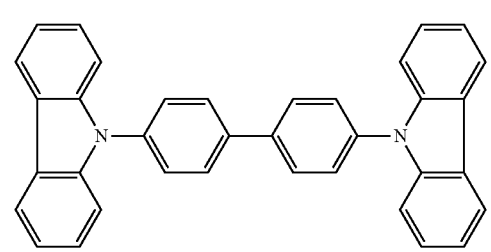
EB-1
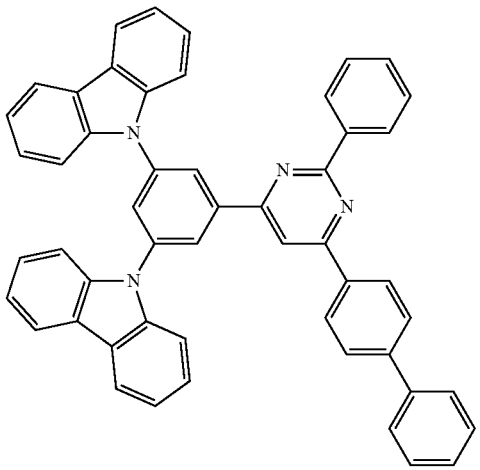
ET-1
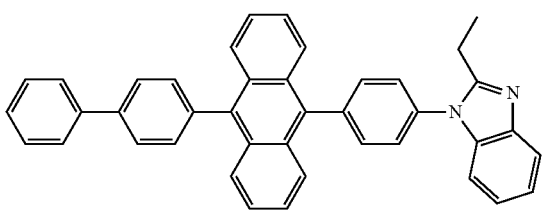
[Formula 162]
H-1
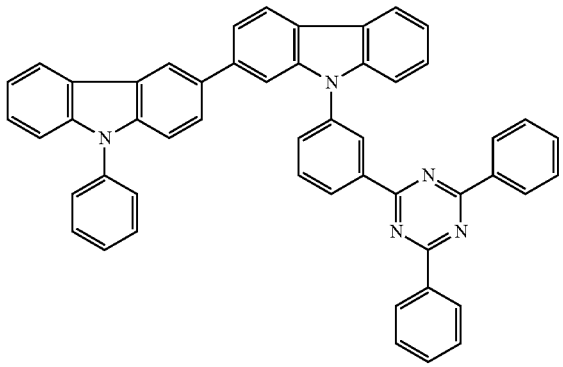
HT-3
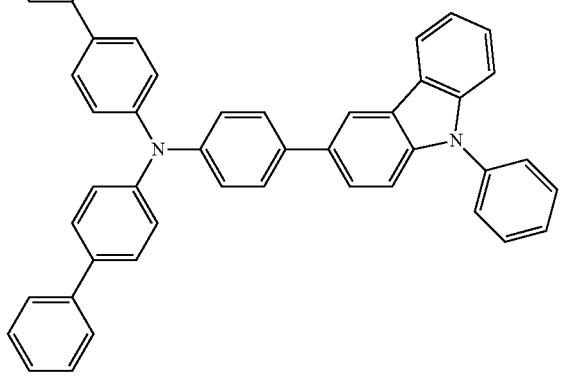

Example 1

In Example, a yellow light is transmitted through a color filter, so that a first color light in red and the second color light in green are extracted.

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 130 nm thick.

After the glass substrate having the transparent electrode line was cleaned, the glass substrate was mounted on a substrate holder of a vacuum evaporation apparatus. Initially, a compound HI was deposited on a surface of the glass substrate where the transparent electrode line was provided in a manner to cover the transparent electrode, thereby forming a 5 nm thick hole injecting layer.

Next, a compound HT-1 was deposited on the hole injecting layer to form a 20 nm thick first hole transporting layer on the HI film.

Next, a compound HT-2 was deposited on the first hole transporting layer to form a 10 nm thick second hole transporting layer.

Next, a compound CBP (the host material) and a compound D-4 (the dopant material) were co-deposited on the second hole transporting layer to form a 25 nm thick emitting layer. A mass ratio between the compound CBP and the compound D-4 was set at 1:1.

Next, a compound EB-1 was deposited on the emitting layer to form a 5 nm thick hole blocking layer.

Next, a compound ET-1 was deposited on the hole blocking layer to form a 50 nm thick electron transporting layer.

Next, lithium fluoride (LiF) was deposited on the electron transporting layer to form a 1 nm thick electron injecting electrode (cathode).

A metal Al was deposited on the electron injecting electrode to form an 80-nm thick metal Al cathode.

A device arrangement of the organic EL device in Example 1 is shown in symbols as follows.

ITO(130)/HI(5)/HT-1(20)/HT-2(10)/CBP:D-4(25, 50%)/EB-1(5)/ET-1(50)/LiF(1)/Al(80)

Numerals in parentheses represent a film thickness (unit: nm). Numerals represented by percentage in the same parentheses represent a ratio (mass %) of an added component such as the dopant material in the emitting layer. Eight devices having the above arrangement were prepared.

Comparative 1

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. A film of ITO was 80 nm thick.

After the glass substrate having the transparent electrode line was cleaned, the glass substrate was mounted on a substrate holder of a vacuum evaporation apparatus. Initially, a compound HI was deposited on a surface of the glass substrate where the transparent electrode line was provided in a manner to cover the transparent electrode, thereby forming a 5 nm thick hole injecting layer.

Next, a compound HT-1 was deposited on the hole injecting layer to form a 65 nm thick first hole transporting layer on the HI film.

Next, a compound HT-3 was deposited on the first hole transporting layer to form a 10 nm thick second hole transporting layer.

Next, a compound H-1 (the host material) and a compound D-7 (the dopant material) were co-deposited on the second hole transporting layer to form a 25 nm thick emitting layer. A mass ratio between the compound H-1 and the compound D-7 was set at 1:1.

Next, a compound ET-1 was deposited on the emitting layer to form a 35 nm thick electron transporting layer.

Next, lithium fluoride (LiF) was deposited on the electron transporting layer to form a 1 nm thick electron injecting electrode (cathode).

A metal Al was deposited on the electron injecting electrode to form an 80-nm thick metal Al cathode.

A device arrangement of the organic EL device in Example 1 is shown in symbols as follows.

ITO(80)/HI(5)/HT-1(65)/HT-3(10)/H-1:D-7(25, 5%)/ET-1(35)/LiF(1)/Al(80)

Numerals in parentheses represent a film thickness (unit: nm). Numerals represented by percentage in the same parentheses represent a ratio (mass %) of an added component such as the dopant material in the emitting layer. Eight devices having the above arrangement were prepared.

Evaluation of Organic EL Devices

The prepared organic EL devices of Example 1 and Comparative 1 were evaluated as follows.

Current Efficiency L/J

Voltage was applied on each of the organic EL devices such that the current density was 10.0 mA/cm$^2$, where spectral radiance spectra were measured by a spectroradiometer CS-1000 (manufactured by Konica Minolta, Inc). Based on the obtained spectral radiance spectra, a main peak wavelength and the half bandwidth were read and the current efficiency (unit: cd/A) was calculated. The main peak wavelength in both Example and Comparative were 553 nm. The half bandwidth of the main peak was 102 nm in Example and 72 nm in Comparative.

Examples 1-1 to 1-7

Next, a color filter in a form of a film was provided to the organic EL device prepared in Example 1 using a transparent adhesive agent. Four kinds of red color filters were used. The four red color filters were respectively denoted by R-CF1, R-CF2, R-CF3 and R-CF4. Three kinds of green color filters were used. The three green color filters were respectively denoted by G-CF1, G-CF2 and G-CF3.

Voltage was again applied on the organic EL device after attached with the color filters such that the current density was 10.0 mA/cm$^2$. At this time, spectral radiance spectra were measured by a spectroradiometer CS-1000 (manufactured by Konica Minolta, Inc). Based on the obtained spectral radiance spectra, the current efficiency L/J (unit: cd/A) was calculated.

Comparatives 1-1 to 1-7

Likewise, a color filter in a form of a film was provided to the organic EL device prepared in Comparative 1 using a transparent adhesive agent. Four kinds of red color filters and three kinds of green color filters were used. All the color filters are the same as the color filters used in Examples 1-1 to 1-7.

Voltage was again applied on the organic EL device provided with the color filters such that the current density was 10.0 mA/cm$^2$. At this time, spectral radiance spectra were measured by a spectroradiometer CS-1000 (manufactured by Konica Minolta, Inc). Based on the obtained spectral radiance spectra, the current efficiency L/J (unit: cd/A) was calculated.

In the measurement, the color filter that transmitted light to have a wavelength (TR10 (nm)) of which a main peak intensity was at a value of 10% of transmittance in Tables 2 to 8 below was selected. When there are a plurality of wavelengths having the main peak intensity at the value of 10% of transmittance, a wavelength closest to the main peak wavelength of the organic EL device before light is transmitted through the color filter is defined as TR10.

In addition, a difference between TR10 and the main peak wavelength of the organic EL device in Example before light is transmitted through the color filter is defined as $\Delta W$.

A ratio of $\Delta W$ to the half bandwidth of the main peak wavelength of the organic EL device in Example before light is transmitted through the color filter is defined as $\Delta W$/half bandwidth.

When the main peak wavelength of the color light extracted through the color filter is larger than the main peak wavelength of the organic EL device before light is transmitted through the color filter, $\Delta W$ is represented as follows:

$$\Delta W = (TR10) - (\text{main peak wavelength of the organic EL device}).$$

When the main peak wavelength of the color light extracted through the color filter is smaller than the main peak wavelength of the organic EL device before light is transmitted through the color filter, $\Delta W$ is represented as follows:

$$\Delta W = (\text{main peak wavelength of the organic EL device}) - (TR10).$$

A ratio $E_2/E_1$ (a current efficiency $E_2$ after light was transmitted through the color filter to a current efficiency $E_1$ of emission before the color filter was provided) in Examples was calculated.

A ratio $E_4/E_3$ (a current efficiency $E_4$ after light was transmitted through the color filter to a current efficiency $E_3$ of emission before the color filter was provided) in Comparatives was calculated.

Further, a ratio $(E_2/E_1)/(E_4/E_3)$ of the ratio $E_2/E_1$ in Examples to the ratio $E_4/E_3$ in Comparatives was calculated. The calculation results are shown as the current efficiency (after the color filter was attached) in Table 2 to 8.

TABLE 2

| | Dopant | Color Filter | TR10 (nm) | $\Delta W$ (nm) | $\Delta W$/Half bandwidth | Current Efficiency (after the color filter was attached) |
|---|---|---|---|---|---|---|
| Example 1-1 | D5 | R-CF1 | 578 | 25 | 25% | 1.06 |
| Comparative 1-1 | D7 | R-CF1 | 578 | 25 | — | 1.00 |

TABLE 3

| | Dopant | Color Filter | TR10 (nm) | $\Delta W$ (nm) | $\Delta W$/Half bandwidth | Current Efficiency (after the color filter was attached) |
|---|---|---|---|---|---|---|
| Example 1-2 | D5 | R-CF2 | 582 | 29 | 28% | 1.08 |
| Comparative 1-2 | D7 | R-CF2 | 582 | 29 | — | 1.00 |

TABLE 4

| | Dopant | Color Filter | TR10 (nm) | $\Delta W$ (nm) | $\Delta W$/Half bandwidth | Current Efficiency (after the color filter was attached) |
|---|---|---|---|---|---|---|
| Example 1-3 | D5 | R-CF3 | 586 | 33 | 32% | 1.09 |
| Comparative 1-3 | D7 | R-CF3 | 586 | 33 | — | 1.00 |

TABLE 5

| | Dopant | Color Filter | TR10 (nm) | $\Delta W$ (nm) | $\Delta W$/Half bandwidth | Current Efficiency (after the color filter was attached) |
|---|---|---|---|---|---|---|
| Example 1-4 | D5 | R-CF4 | 595 | 42 | 41% | 1.13 |
| Comparative 1-4 | D7 | R-CF4 | 595 | 42 | — | 1.00 |

TABLE 6

| | Dopant | Color Filter | TR10 (nm) | $\Delta W$ (nm) | $\Delta W$/Half bandwidth | Current Efficiency (after the color filter was attached) |
|---|---|---|---|---|---|---|
| Example 1-5 | D5 | G-CF1 | 604 | −51 | −50% | 1.00 |
| Comparative 1-5 | D7 | G-CF1 | 604 | −51 | — | 1.00 |

TABLE 7

| | Dopant | Color Filter | TR10 (nm) | $\Delta W$ (nm) | $\Delta W$/Half bandwidth | Current Efficiency (after the color filter was attached) |
|---|---|---|---|---|---|---|
| Example 1-6 | D5 | G-CF2 | 600 | −47 | −46% | 1.00 |
| Comparative 1-6 | D7 | G-CF2 | 600 | −47 | — | 1.00 |

TABLE 8

| | Dopant | Color Filter | TR10 (nm) | $\Delta W$ (nm) | $\Delta W$/Half bandwidth | Current Efficiency (after the color filter was attached) |
|---|---|---|---|---|---|---|
| Example 1-7 | D5 | G-CF3 | 590 | −37 | −36% | 1.02 |
| Comparative 1-7 | D7 | G-CF3 | 590 | −37 | — | 1.00 |

Examples 1-1 to 1-4 show light transmitted through the red color filter, thereby extracting the red color light. TR10 is preferably 570 nm or more. TR10 is more preferably 580 nm or more since the current efficiency is more favorable than that in Comparatives using a typical luminescent material. TR10 is further preferably 590 nm or more.

$\Delta W$ is preferably 17 nm or more. $\Delta W$ is more preferably 27 nm or more since the current efficiency is more favorable than that in Comparatives using a typical luminescent material. $\Delta W$ is further preferably 37 nm or more.

ΔW/half bandwidth is preferably 20% or more. ΔW/half bandwidth is more preferably 30% or more since the current efficiency is more favorable than that in Comparatives using a typical luminescent material. ΔW/half bandwidth is further preferably 40% or more.

Examples 1-5 to 1-7 show light transmitted through the green color filter, thereby extracting the green color light. TR10 is preferably 610 nm or less. TR10 is more preferably 595 nm or less since the current efficiency is more favorable than that in Comparatives using a typical luminescent material.

ΔW is preferably −55 nm or more. ΔW is more preferably −40 nm or more since the current efficiency is more favorable than that in Comparatives using a typical luminescent material.

ΔW/half bandwidth is preferably −55% or more. ΔW/half bandwidth is more preferably −40% or more since the current efficiency is more favorable than that in Comparatives using a typical luminescent material.

The invention claimed is:

1. A light-emitting apparatus comprising:
an organic electroluminescence device;
a first color conversion portion that transmits a first color light; and
a second color conversion portion that transmits a second color light different from the first color light, wherein
the organic electroluminescence device comprises: an anode; a cathode; and one or more organic layers interposed between the anode and the cathode,
the organic layers comprises:
  a hole transporting layer;
  an emitting layer that comprises a host material and a dopant material that emits light comprising the first color light and the second color light; and
  an electron transporting layer,
the emitting layer is in a direct contact with the hole transporting layer and the electron transporting layer,
the organic layer(s) does not comprise an emitting layer other than the emitting layer, the emitting layer does not comprise another dopant material that emits light, and
a difference ΔST(D) between singlet energy EgS(D) of the dopant material and an energy gap $Eg_{77K}(D)$ at 77K of the dopant material satisfies Numerical Formula 1,
the dopant material is a compound represented by a formula (13),
the host material is a carbazole derivative, and
the singlet energy EgS(D) of the dopant material and the singlet energy EgS(H) of the host material satisfy Numerical Formula 3, $\Delta ST(D) = EgS(D) - Eg_{77K}(D) < 0.3$ (eV)  (Numerical Formula 1), $EgS(H) > EgS(D)$  (Numerical Formula 3),

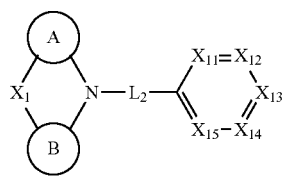

(13)

where: $X_1$ represents a single bond, an oxygen atom, or a sulfur atom,

A and B each independently represent a substituted or unsubstituted cyclic structure, and
when at least one of the cyclic structure A and the cyclic structure B has a plurality of substituents, adjacent ones of the substituents optionally form a ring,
$L_2$ represents a single bond, a substituted or unsubstituted divalent aromatic hydrocarbon group or a substituted or unsubstituted divalent heterocyclic group,
$X_{11}$ to $X_{15}$ each independently represent $CR_8$ or a nitrogen atom and at least one of $X_{11}$ to $X_{15}$ is a nitrogen atom,
$R_8$ are each independently a hydrogen atom, an unsubstituted aryl group having 6 to 30 ring carbon atoms, an unsubstituted heterocyclic group having 5 to 30 ring atoms, or an unsubstituted alkyl group having 1 to 30 carbon atoms, and
a plurality of $R_8$ are optionally mutually the same or different,
wherein
the first color light is a red light and the first color conversion portion transmits the red light,
the second color light is a green light and the second color conversion portion transmits the green light, and
the organic electroluminescence device does not emit blue light.

2. The light-emitting apparatus according to claim 1, wherein the compound represented by the formula (13) is a compound represented by a formula (5) below,

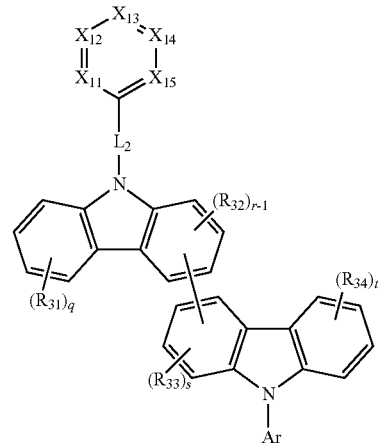

(5)

where: $L_2$ represents the same as $L_2$ of the formula (13); $X_{11}$ to $X_{15}$ each independently represent the same as $X_{11}$ to $X_{15}$ of the formula (13); $R_{31}$ to $R_{34}$ each independently represent the same as $R_8$ described above; $R_{31}$ to $R_{34}$ are respectively bonded to carbon atoms forming the six-membered ring; adjacent ones of $R_{31}$ are optionally mutually bonded to form a ring, adjacent ones of $R_{32}$ are optionally mutually bonded to form a ring, adjacent ones of $R_{33}$ are optionally mutually bonded to form a ring, and adjacent ones of $R_{34}$ are optionally mutually bonded to form a ring; q and r are 4, s is 3 and t is 4; and
Ar represents a substituted or unsubstituted aryl group having 6 to 30 ring carbon atoms or a substituted or unsubstituted heterocyclic group having 5 to 30 ring atoms.

3. The light-emitting apparatus according to claim 1, wherein the compound represented by the formula (13) is a compound represented by a formula (31) below,

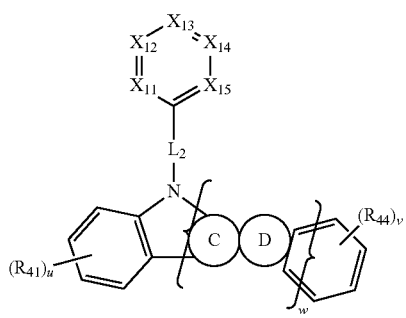

(31)

where: $L_2$ represents the same as $L_2$ of the formula (13);
$X_{11}$ to $X_{15}$ each independently represent the same as $X_{11}$ to $X_{15}$ of the formula (13);
$R_{41}$ and $R_{44}$ each independently represent the same as $R_8$ described above; a plurality of $R_{44}$ are optionally mutually the same or different and a plurality of $R_{44}$, are optionally mutually the same or different; adjacent ones of $R_{41}$ optionally form a ring and adjacent ones of $R_{44}$ optionally form a ring; $R_{41}$ and $R_{44}$ are respectively bonded to carbon atoms forming the six-membered ring;
u and v are 4;
C represents a cyclic structure represented by a formula (32) below and D represents a cyclic structure represented by a formula (33) below; each of the cyclic structure C and the cyclic structure D is fused to an adjacent cyclic structure at any position;
w is an integer of 1 to 4; and
w is a repeating unit of a linking cyclic structure in which the cyclic structure C and the cyclic structure D are fused,

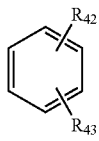

(32)

(33)

where: in the formula (32), $R_{42}$ and $R_{43}$ each independently represent the same as $R_8$ of the formula (13); and when $R_{42}$ and $R_{43}$, are substituents at adjacent positions, $R_{42}$ and $R_{43}$ optionally form a ring, with a proviso that $R_{42}$ and $R_{43}$ are respectively bonded to carbon atoms forming the six-membered ring, and
in the formula (33), $Y_1$ represents $CR_{45}R_{46}$, $NR_{47}$, a sulfur atom, or an oxygen atom; and $R_{45}$ to $R_{47}$ each independently represent the same as $R_8$ described above.

4. The light-emitting apparatus according to claim 1, wherein $L_2$ is a single bond.

5. The light-emitting apparatus according to claim 1, wherein the dopant material has a 60 nm or more of a half bandwidth of emission spectrum.

6. The light-emitting apparatus according to claim 1, wherein the difference $\Delta ST(D)$ is less than 0.2 eV.

7. The light-emitting apparatus according to claim 1, wherein the difference $\Delta ST(D)$ is less than 0.15 eV.

8. The light-emitting apparatus according to claim 1, wherein the difference $\Delta ST(D)$ is less than 0.10 eV.

9. The light-emitting apparatus according to claim 1, wherein in the formula (13) when $X_1$ represents a single bond and at least one of the cyclic structures A and B has a substituted or unsubstituted carbazolyl group as a substituent, a nitrogen atom at a position 9 of the carbazolyl group is bonded to one of atoms forming the cyclic structures A and B, and carbon atoms at positions 1 to 8 of the carbazolyl group are not bonded to the atoms forming the cyclic structures A and B.

10. The light-emitting apparatus according to claim 1, wherein when $X_1$ represents a single bond in the formula (13), both of the cyclic structures A and B do not have a substituted or unsubstituted carbazolyl group as a substituent.

11. The light-emitting apparatus according to claim 9, wherein $X_1$ represents an oxygen atom or a sulfur atom in the formula (13).

12. A light-emitting apparatus comprising:
an organic electroluminescence device;
a first color conversion portion that transmits a first color light; and
a second color conversion portion that transmits a second color light different from the first color light, wherein
the organic electroluminescence device comprises: an anode; a cathode; and one or more organic layers interposed between the anode and the cathode,
the one or more organic layers comprises
a hole transporting layer;
an emitting layer that comprises a host material and a dopant material that emits light comprising the first color light and the second color light; and
an electron transporting layer,
the emitting layer is in a direct contact with the hole transporting layer and the electron transporting layer,
the organic layer(s) does not comprise an emitting layer other than the emitting layer,
the emitting layer does not comprise another dopant material that emits light,
a difference $\Delta ST(D)$ between singlet energy $EgS(D)$ of the dopant material and an energy gap $Eg_{77K}(D)$ at 77K of the dopant material satisfies Numerical Formula 1,
the dopant material is a compound represented by a formula(13),
the host material is a compound represented by a formula (2), and
the singlet energy $EgS(D)$ of the dopant material and the singlet energy $EgS(H)$ of the host material satisfy Numerical Formula 3, $\Delta ST(D) = EgS(D) - Eg_{77K}(D) < 0.3$ (eV)   (Numerical Formula 1), $EgS(H) > EgS(D)$   (Numerical Formula 3), (13)

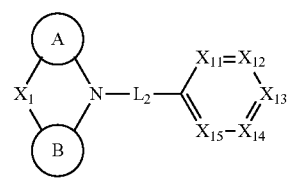

where: $X_1$ represents a single bond, an oxygen atom, or a sulfur atom,

A and B each independently represent a substituted or unsubstituted cyclic structure, and when at least one of the cyclic structure A and the cyclic structure B has a plurality of substituents, adjacent ones of the substituents optionally form a ring, $L_2$ represents a single bond, a substituted or unsubstituted divalent aromatic hydrocarbon group or a substituted or unsubstituted divalent heterocyclic group, $X_{11}$ to $X_{15}$ each independently represent $CR_8$ or a nitrogen atom and at least one of $X_{11}$ to $X_{15}$ is a nitrogen atom, $R_8$ are each independently a hydrogen atom, an unsubstituted aryl group having 6 to 30 ring carbon atoms, an unsubstituted heterocyclic group having 5 to 30 ring atoms, or an unsubstituted alkyl group having 1 to 30 carbon atoms, and a plurality of $R_8$ are optionally mutually the same or different,

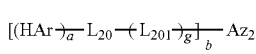
(2)

where: $Az_2$ is represented by formula (2d) below, $L_{20}$ represents a single bond, a substituted or unsubstituted (a+1)-valent aromatic hydrocarbon group or a substituted or unsubstituted (a+1)-valent heterocyclic group, $L_{201}$ is a substituted or unsubstituted divalent aromatic hydrocarbon group or a substituted or unsubstituted divalent heterocyclic group, a is an integer of 1 to 6 and b is an integer of 1 to 3,
  when a is 2 or more, HAr bonded to $L_{20}$ is 2 or more and are mutually the same or different, g is an integer of 0 to 2,
  when g is from 1 to 2, $L_{20}$ and $L_{201}$ are mutually the same or different,
  when g is 2, two $L_{201}$ are mutually the same or different, and
  when b is 2 or more, a plurality of moieties represented by a formula (2-1) to be bonded to $Az_2$ are mutually the same or different,

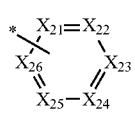
(2d)

where: in the formula (2d),
  $X_{21}$ to $X_{26}$ each independently represent $CR_{16}$ or a nitrogen atom,
  at least one of $X_{21}$ to $X_{26}$ is a nitrogen atom,
  one of $X_{21}$ to $X_{26}$ is a carbon atom to be bonded to $L_{20}$ or $L_{201}$, or two or three of $X_{21}$ to $X_{26}$ are carbon atoms to be bonded to $L_{20}$ or $L_{201}$,
  adjacent ones of $R_{16}$ optionally form a ring,
  $R_{16}$ represents the same as $R_8$ described above,
  * represents a bonding position to $L_{20}$ or $L_{201}$, and
  HAr is a group derived from a structure represented by a formula (20) below,

(2-1)

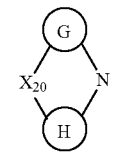
(20)

where: in the formula (20),
  $X_{20}$ represents a single bond, an oxygen atom, a sulfur atom, a carbonyl group, $NR_9$, $CR_{10}R_{11}$, $SiR_{12}R_{13}$ or $GeR_{14}R_{15}$,
  $R_9$ to $R_{15}$ each independently represent the same as $R_8$ described above,
  G and H each independently represent a substituted or unsubstituted cyclic structure,
  when at least one of the cyclic structure G and the cyclic structure H have a plurality of substituents, adjacent ones of the substituents are mutually bonded to form a ring or not bonded to form no ring,
  when adjacent ones of the substituents are mutually bonded to form a ring, the ring to be formed is a saturated ring or an unsaturated ring, and
  when at least one of the cyclic structure G and the cyclic structure H has a substituted or unsubstituted heterocyclic structure, the heterocyclic structure has a partial structure represented by a formula (20-2) below,

(20-2)

the first color light is a red light and the first color conversion portion transmits the red light, the second color light is a green light and the second color conversion portion transmits the green light, and the organic electroluminescence device does not emit blue light.

13. The light-emitting apparatus according to claim 12, wherein the compound represented by the formula (13) is a compound represented by a formula (5) below,

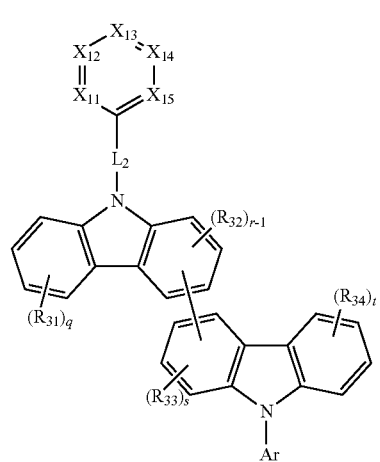
(5)

where: L₂ represents the same as L₂ of the formula (13);

X₁₁ to X₁₅ each independently represent the same as X₁₁ to X₁₅ of the formula (13); R₃₁ to R₃₄ each independently represent the same as R₈ described above; R₃₁ to R₃₄ are respectively bonded to carbon atoms forming the six-membered ring; adjacent ones of R₃₁ are optionally mutually bonded to form a ring, adjacent ones of R₃₂ are optionally mutually bonded to form a ring, adjacent ones of R₃₃ are optionally mutually bonded to form a ring, and adjacent ones of R₃₄ are optionally mutually bonded to form a ring; q and r are 4, s is 3 and t is 4; and Ar represents a substituted or unsubstituted aryl group having 6 to 30 ring carbon atoms or a substituted or unsubstituted heterocyclic group having 5 to 30 ring atoms.

14. The light-emitting apparatus according to claim 12, wherein the compound represented by the formula (13) is a compound represented by a formula (31) below,

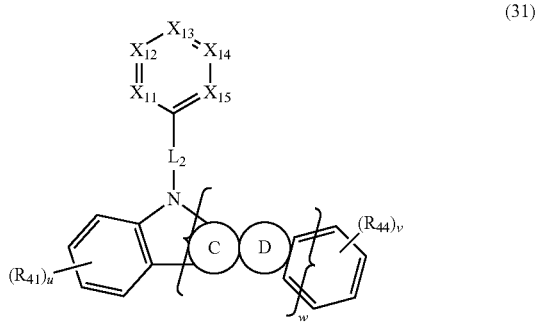

(31)

where: L₂ represents the same as L₁₂ of the formula (13);

X₁₁ to X₁₅ each independently represent the same as X₁₂ to X₁₅ of the formula (13);

R₄₁ and R₄₄ each independently represent the same as R₈ described above; a plurality of R₄₄ are optionally mutually the same or different and a plurality of R₄₄ are optionally mutually the same or different; adjacent ones of R₄ optionally form a ring and adjacent ones of R₄₄ optionally form a ring; R₄₁ and R₄₄ are respectively bonded to carbon atoms forming the six-membered ring;

u and v are 4;

C represents a cyclic structure represented by a formula (32) below and D represents a cyclic structure represented by a formula (33) below; each of the cyclic structure C and the cyclic structure D is fused to an adjacent cyclic structure at any position;

w is an integer of 1 to 4; and w is a repeating unit of a linking cyclic structure in which the cyclic structure C and the cyclic structure D are fused,

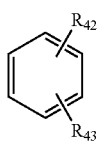

(32)

-continued

(33)

where: in the formula (32), R₄₂ and R₄₃ each independently represent the same as R₈ of the formula (13); and when R₄₂ and R₄₃ are substituents at adjacent positions, R₄₂ and R₄₃ optionally form a ring, with a proviso that R₄₂ and R₄₃ are respectively bonded to carbon atoms forming the six-membered ring, and in the formula (33), Y₁ represents CR₄₅R₄₆, NR₄₇, a sulfur atom, or an oxygen atom; and R₄₅ to R₄₇ each independently represent the same as R₈ described above.

15. The light-emitting apparatus according to claim 12, wherein L₂ is a single bond.

16. The light-emitting apparatus according to claim 12, wherein the dopant material has a 60 nm or more of a half bandwidth of emission spectrum.

17. The light-emitting apparatus according to claim 12, wherein the difference ΔST(D) is less than 0.2 eV.

18. The light-emitting apparatus according to claim 12, wherein the difference ΔST(D) is less than 0.15 eV.

19. The light-emitting apparatus according to claim 12, wherein the difference ΔST(D) is less than 0.10 eV.

20. The light-emitting apparatus according to claim 12, wherein in the formula (13) when X₁ represents a single bond and at least one of the cyclic structures A and B has a substituted or unsubstituted carbazolyl group as a substituent, a nitrogen atom at a position 9 of the carbazolyl group is bonded to one of atoms forming the cyclic structures A and B, and carbon atoms at positions 1 to 8 of the carbazolyl group are not bonded to the atoms forming the cyclic structures A and B.

21. The light-emitting apparatus according to claim 12, wherein when X₁ represents a single bond in the formula (13), both of the cyclic structures A and B do not have a substituted or unsubstituted carbazolyl group as a substituent.

22. The light-emitting apparatus according to claim 12, wherein X₁ represents an oxygen atom or a sulfur atom in the formula (13).

23. The light-emitting apparatus according to claim 1, wherein both of the cyclic structure A and the cyclic structure B are a substituted or unsubstituted benzene ring.

24. The light-emitting apparatus according to claim 12, wherein both of the cyclic structure A and the cyclic structure B are a substituted or unsubstituted benzene ring.

25. The light-emitting apparatus according to claim 1,
at least one of the cyclic structure A and the cyclic structure B has at least one substituent selected from the group consisting of aryl group having 6 to 30 ring carbon atoms, heterocyclic group having 5 to 30 ring atoms and amino group.

26. The light-emitting apparatus according to claim 12,
at least one of the cyclic structure A and the cyclic structure B has at least one substituent selected from the group consisting of aryl group having 6 to 30 ring carbon atoms, heterocyclic group having 5 to 30 ring atoms and amino group.

27. The light-emitting apparatus according to claim 1, wherein the emitting layer does not emit white light.

28. The light-emitting apparatus according to claim 1, wherein the dopant material does not emit white light.

29. The light-emitting apparatus according to claim 1, wherein the emitting layer essentially consists of the host material and the dopant material.

30. The light-emitting apparatus according to claim 1, wherein the emitting layer consists of the host material and the dopant material.

31. The light-emitting apparatus according to claim 1, wherein the dopant material has a 70 nm or more of a half bandwidth of emission spectrum.

* * * * *